US010845364B2

(12) United States Patent
Chu et al.

(10) Patent No.: US 10,845,364 B2
(45) Date of Patent: Nov. 24, 2020

(54) ASSAYS FOR DETECTING T CELL IMMUNE SUBSETS AND METHODS OF USE THEREOF

(71) Applicant: Genentech, Inc., South San Francisco, CA (US)

(72) Inventors: Felix Chu, San Francisco, CA (US); Oded Foreman, Davis, CA (US); James Ziai, Everyville, CA (US)

(73) Assignee: Genentech, Inc., South San Francisco, CA (US)

( * ) Notice: Subject to any disclaimer, the term of this patent is extended or adjusted under 35 U.S.C. 154(b) by 38 days.

(21) Appl. No.: 15/849,805

(22) Filed: Dec. 21, 2017

(65) Prior Publication Data

US 2018/0238878 A1   Aug. 23, 2018

Related U.S. Application Data

(63) Continuation of application No. 14/930,603, filed on Nov. 2, 2015, now abandoned.

(60) Provisional application No. 62/074,594, filed on Nov. 3, 2014.

(51) Int. Cl.
G01N 33/569 (2006.01)
G01N 33/574 (2006.01)
A61K 38/17 (2006.01)
C07K 16/28 (2006.01)
C12Q 1/06 (2006.01)
G01N 33/58 (2006.01)

(52) U.S. Cl.
CPC ..... G01N 33/56972 (2013.01); A61K 38/177 (2013.01); C07K 16/2875 (2013.01); C12Q 1/06 (2013.01); G01N 33/57419 (2013.01); G01N 33/582 (2013.01); C07K 2317/24 (2013.01); C07K 2317/75 (2013.01); G01N 2333/70514 (2013.01); G01N 2800/52 (2013.01); G01N 2800/7028 (2013.01)

(58) Field of Classification Search
CPC ............ G01N 33/56972; A61K 38/177; C07K 16/2875
USPC ...................................... 424/133.1
See application file for complete search history.

(56) References Cited

U.S. PATENT DOCUMENTS

| | | |
|---|---|---|
| 4,676,980 A | 6/1987 | Segal et al. |
| 4,816,567 A | 3/1989 | Cabilly et al. |
| 4,943,533 A | 7/1990 | Mendelsohn et al. |
| 5,208,020 A | 5/1993 | Chari et al. |
| 5,212,290 A | 5/1993 | Vogelstein et al. |
| 5,416,064 A | 5/1995 | Chari et al. |
| 5,457,105 A | 10/1995 | Barker |
| 5,475,001 A | 12/1995 | Barker |
| 5,500,362 A | 3/1996 | Robinson et al. |
| 5,571,894 A | 11/1996 | Wels et al. |
| 5,587,458 A | 12/1996 | King et al. |
| 5,591,828 A | 1/1997 | Bosslet et al. |
| 5,616,582 A | 4/1997 | Barker |
| 5,624,821 A | 4/1997 | Winter et al. |
| 5,635,483 A | 6/1997 | Pettit et al. |
| 5,648,237 A | 7/1997 | Carter |
| 5,648,260 A | 7/1997 | Winter et al. |
| 5,654,307 A | 8/1997 | Bridges et al. |
| 5,679,683 A | 10/1997 | Bridges et al. |
| 5,693,762 A | 12/1997 | Queen |
| 5,712,374 A | 1/1998 | Kuntsmann et al. |
| 5,714,586 A | 2/1998 | Kuntsmann et al. |
| 5,731,168 A | 3/1998 | Carter et al. |
| 5,739,116 A | 4/1998 | Hamann et al. |
| 5,747,498 A | 5/1998 | Schnur et al. |
| 5,750,373 A | 5/1998 | Garrard et al. |
| 5,760,041 A | 6/1998 | Wissner et al. |
| 5,767,285 A | 6/1998 | Hamann et al. |
| 5,770,429 A | 6/1998 | Lonberg et al. |
| 5,770,599 A | 6/1998 | Gibson |
| 5,770,701 A | 6/1998 | Mcgahren et al. |
| 5,770,710 A | 6/1998 | Mcgahren et al. |
| 5,773,001 A | 6/1998 | Hamann et al. |
| 5,780,588 A | 7/1998 | Pettit et al. |

(Continued)

FOREIGN PATENT DOCUMENTS

| | | |
|---|---|---|
| CN | 103221427 A | 7/2013 |
| EP | 0 404 097 A2 | 12/1990 |

(Continued)

OTHER PUBLICATIONS

Andarini, S. et al. (May 1, 2004). "Adenovirus Vector-Mediated in Vivo Gene Transfer of OX40 Ligand to Tumor Cells Enhances Antitumor Immunity of Tumor-Bearing Hosts," Cancer Research 64(9):3281-3287.

(Continued)

Primary Examiner — Yan Xiao
(74) Attorney, Agent, or Firm — Morrison & Foerster LLP

(57) ABSTRACT

The present disclosure provides methods for measuring the number of CD4+ OX40+ Foxp3+ lymphocytes in a sample containing cancer cells and lymphocytes obtained from a subject by labeling lymphocytes that show CD4 expression in the sample, then labeling lymphocytes that show OX40 expression in the sample, then labeling lymphocytes that show Foxp3 expression in the sample, then measuring the number of CD4+ OX40+ Foxp3+ lymphocytes in the sample. Further provided are methods for determining the prognosis of a subject, predicting responsiveness of a subject having cancer to an OX40 agonist treatment, and methods for treating or delaying progression of cancer based on the number of CD4+ OX40+ Foxp3+ lymphocytes in a sample.

12 Claims, 11 Drawing Sheets

Specification includes a Sequence Listing.

(56) References Cited

U.S. PATENT DOCUMENTS

| | | |
|---|---|---|
| 5,789,199 A | 8/1998 | Joly et al. |
| 5,804,396 A | 9/1998 | Plowman |
| 5,821,337 A | 10/1998 | Carter et al. |
| 5,840,523 A | 11/1998 | Simmons et al. |
| 5,866,572 A | 2/1999 | Barker et al. |
| 5,869,046 A | 2/1999 | Presta et al. |
| 5,877,296 A | 3/1999 | Hamann et al. |
| 5,891,996 A | 4/1999 | Mateo de Acosta del Rio et al. |
| 5,959,177 A | 9/1999 | Hein et al. |
| 6,002,008 A | 12/1999 | Wissner et al. |
| 6,040,498 A | 3/2000 | Stomp et al. |
| 6,075,181 A | 6/2000 | Kucherlapati et al. |
| 6,084,095 A | 7/2000 | Bridges et al. |
| 6,140,332 A | 10/2000 | Traxler et al. |
| 6,150,584 A | 11/2000 | Kucherlapati et al. |
| 6,194,551 B1 | 2/2001 | Idusogie et al. |
| 6,235,883 B1 | 5/2001 | Jakobovits et al. |
| 6,248,516 B1 | 6/2001 | Winter et al. |
| 6,265,410 B1 | 7/2001 | Bridges et al. |
| 6,344,455 B1 | 2/2002 | Bridges et al. |
| 6,344,459 B1 | 2/2002 | Bridges et al. |
| 6,391,874 B1 | 5/2002 | Cockerill et al. |
| 6,399,602 B1 | 6/2002 | Barker et al. |
| 6,417,429 B1 | 7/2002 | Hein et al. |
| 6,420,548 B1 | 7/2002 | Vezina et al. |
| 6,455,534 B2 | 9/2002 | Bridges et al. |
| 6,521,620 B1 | 2/2003 | Bridges et al. |
| 6,596,726 B1 | 7/2003 | Bridges et al. |
| 6,602,684 B1 | 8/2003 | Umaña et al. |
| 6,602,863 B1 | 8/2003 | Bridges et al. |
| 6,630,579 B2 | 10/2003 | Chari et al. |
| 6,713,484 B2 | 3/2004 | Bridges et al. |
| 6,737,056 B1 | 5/2004 | Presta |
| 6,982,321 B2 | 1/2006 | Winter |
| 7,041,870 B2 | 5/2006 | Tomizuka et al. |
| 7,087,409 B2 | 8/2006 | Barbas et al. |
| 7,125,978 B1 | 10/2006 | Vezina et al. |
| 7,189,826 B2 | 3/2007 | Rodman |
| 7,332,581 B2 | 2/2008 | Presta |
| 7,371,826 B2 | 5/2008 | Presta |
| 7,498,298 B2 | 3/2009 | Doronina et al. |
| 7,521,541 B2 | 4/2009 | Eigenbrot et al. |
| 7,527,791 B2 | 5/2009 | Adams et al. |
| 7,550,140 B2 | 6/2009 | Bakker et al. |
| 7,696,175 B2 | 4/2010 | Epstein et al. |
| 7,960,515 B2 | 6/2011 | Min et al. |
| 2002/0164328 A1 | 11/2002 | Shinkawa et al. |
| 2003/0115614 A1 | 6/2003 | Kanda et al. |
| 2003/0157108 A1 | 8/2003 | Presta |
| 2004/0093621 A1 | 5/2004 | Shitara et al. |
| 2004/0109865 A1 | 6/2004 | Niwa et al. |
| 2004/0110282 A1 | 6/2004 | Kanda et al. |
| 2004/0110704 A1 | 6/2004 | Yamane et al. |
| 2004/0132140 A1 | 7/2004 | Satoh et al. |
| 2005/0014934 A1 | 1/2005 | Hinton et al. |
| 2005/0079574 A1 | 4/2005 | Bond |
| 2005/0119455 A1 | 6/2005 | Fuh et al. |
| 2005/0123546 A1 | 6/2005 | Umaña et al. |
| 2005/0266000 A1 | 12/2005 | Bond et al. |
| 2006/0025576 A1 | 2/2006 | Miller et al. |
| 2007/0061900 A1 | 3/2007 | Murphy et al. |
| 2007/0117126 A1 | 5/2007 | Sidhu et al. |
| 2007/0160598 A1 | 7/2007 | Dennis et al. |
| 2007/0237764 A1 | 10/2007 | Birtalan et al. |
| 2007/0292936 A1 | 12/2007 | Barthelemy et al. |
| 2008/0069820 A1 | 3/2008 | Fuh et al. |
| 2009/0002360 A1 | 1/2009 | Chen et al. |
| 2012/0141465 A1 | 6/2012 | Croft |
| 2015/0190506 A1 | 7/2015 | Cheung et al. |
| 2015/0307617 A1 | 10/2015 | Du et al. |
| 2016/0152720 A1 | 6/2016 | Kim et al. |
| 2016/0160290 A1 | 6/2016 | Huseni |
| 2016/0161485 A1 | 6/2016 | Chu et al. |
| 2016/0166685 A1 | 6/2016 | Cheung et al. |
| 2016/0355597 A1 | 12/2016 | Rhee et al. |
| 2017/0000885 A1 | 1/2017 | Rhee et al. |
| 2017/0015755 A1 | 1/2017 | Walsh et al. |

FOREIGN PATENT DOCUMENTS

| | | |
|---|---|---|
| EP | 0 659 439 A2 | 6/1995 |
| EP | 0 425 235 B1 | 9/1996 |
| EP | 0 672 141 B1 | 5/2003 |
| WO | WO-1993/01161 A1 | 1/1993 |
| WO | WO-1993/08829 A1 | 5/1993 |
| WO | WO-1993/16185 A2 | 8/1993 |
| WO | WO-1993/16185 A3 | 8/1993 |
| WO | WO-1994/11026 A2 | 5/1994 |
| WO | WO-1994/11026 A3 | 5/1994 |
| WO | WO-1994/29351 A2 | 12/1994 |
| WO | WO-1994/29351 A3 | 12/1994 |
| WO | WO-1996/30347 A1 | 10/1996 |
| WO | WO-1996/33978 A1 | 10/1996 |
| WO | WO-1996/33979 A1 | 10/1996 |
| WO | WO-1996/33980 A1 | 10/1996 |
| WO | WO-1996/40210 A1 | 12/1996 |
| WO | WO-1997/30087 A1 | 8/1997 |
| WO | WO-1997/38983 A1 | 10/1997 |
| WO | WO-1998/14451 A1 | 4/1998 |
| WO | WO-1998/43960 A1 | 10/1998 |
| WO | WO-1998/50038 A1 | 11/1998 |
| WO | WO-1998/50433 A2 | 11/1998 |
| WO | WO-1998/50433 A3 | 11/1998 |
| WO | WO-1998/58964 A1 | 12/1998 |
| WO | WO-1999/06378 A1 | 2/1999 |
| WO | WO-1999/06396 A1 | 2/1999 |
| WO | WO-1999/09016 A1 | 2/1999 |
| WO | WO-1999/22764 A1 | 5/1999 |
| WO | WO-1999/24037 A1 | 5/1999 |
| WO | WO-1999/51642 A1 | 10/1999 |
| WO | WO-2000/42072 A2 | 7/2000 |
| WO | WO-2000/42072 A3 | 7/2000 |
| WO | WO-2000/61739 A1 | 10/2000 |
| WO | WO-2001/29246 A1 | 4/2001 |
| WO | WO-2002/031140 A1 | 4/2002 |
| WO | WO-2003/011878 A2 | 2/2003 |
| WO | WO-2003/011878 A3 | 2/2003 |
| WO | WO-2003/084570 A1 | 10/2003 |
| WO | WO-2003/085107 A1 | 10/2003 |
| WO | WO-2003/085119 A1 | 10/2003 |
| WO | WO-2004/056312 A2 | 7/2004 |
| WO | WO-2004/056312 A3 | 7/2004 |
| WO | WO-2004/92219 A2 | 10/2004 |
| WO | WO-2004/92219 A3 | 10/2004 |
| WO | WO-2005/035586 A1 | 4/2005 |
| WO | WO-2005/035778 A1 | 4/2005 |
| WO | WO-2005/053742 A1 | 6/2005 |
| WO | WO-2005/100402 A1 | 10/2005 |
| WO | WO-2006/029879 A2 | 3/2006 |
| WO | WO-2006/029879 A3 | 3/2006 |
| WO | WO-2006/121168 A1 | 11/2006 |
| WO | WO-2006/121810 A2 | 11/2006 |
| WO | WO-2006/121810 A3 | 11/2006 |
| WO | WO-2007/005874 A2 | 1/2007 |
| WO | WO-2007/005874 A3 | 1/2007 |
| WO | WO-2009/089004 | 7/2009 |
| WO | WO-2009/101611 A1 | 8/2009 |
| WO | WO-2009/114335 A2 | 9/2009 |
| WO | WO-2009/114335 A3 | 9/2009 |
| WO | WO-2010/027827 A2 | 3/2010 |
| WO | WO-2010/027827 A3 | 3/2010 |
| WO | WO-2010/077634 A1 | 7/2010 |
| WO | WO-2011/066342 A2 | 6/2011 |
| WO | WO-2011/066342 A3 | 6/2011 |
| WO | WO-2012/027328 A2 | 3/2012 |
| WO | WO-2012/027328 A3 | 3/2012 |
| WO | WO-2013/028231 A1 | 2/2013 |
| WO | WO-2013/038191 A2 | 3/2013 |
| WO | WO-2013/038191 A3 | 3/2013 |
| WO | WO-2013/119202 A1 | 8/2013 |
| WO | WO-2014/009535 A2 | 1/2014 |
| WO | WO-2014/009535 A3 | 1/2014 |
| WO | WO-2014/148895 A1 | 9/2014 |

(56) References Cited

FOREIGN PATENT DOCUMENTS

| WO | WO-2015/095423 A2 | 6/2015 |
|---|---|---|
| WO | WO-2015/095423 A3 | 6/2015 |
| WO | WO-2015/153513 A1 | 10/2015 |
| WO | WO-2015/153514 A1 | 10/2015 |
| WO | WO-2016/073282 A1 | 5/2016 |
| WO | WO-2016/073378 A1 | 5/2016 |
| WO | WO-2016/073380 A1 | 5/2016 |
| WO | WO-2016/081384 A1 | 5/2016 |
| WO | WO-2016/200835 A1 | 12/2016 |
| WO | WO-2016/200836 A1 | 12/2016 |

OTHER PUBLICATIONS

Deleeuw, R.J. et al. (Jun. 1, 2012). "The Prognostic Value of FoxP3+ Tumor-Infiltrating Lymphocytes in Cancer: A critical Review of the Literature," Clinical Cancer Research 18(11):3022-3029.

Marabelle, A. et al. (Jun. 2013). "Depleting Tumor-Specific Tregs at a Single Site Eradicates Disseminated Tumors," The Journal of Clinical Investigation, vol. 123(6):2447-2463.

Moran, E.A. et al. (2013, e-pub. Feb. 14, 2013). "The TNFRs OX40, 4-1BB, and CD40 as Targets for Cancer Immunotherapy," Current Opinion in Immunology 25:230-237.

Pardee, A.D. et al. (2010, e-pub. Nov. 2, 2010). "A Therapeutic OX40 Agonist Dynamically Alters Dendritic, Endothelial, and T Cell Subsets Within the Established Tumor Microenvironment," Cancer Research 70 (22):9041-9052.

Siddiqui, S.A. et al. (Apr. 1, 2007). "Tumor-Infiltrating Foxp3—CD4+CD25+ T Cells Predict Poor Survival in Renal Cell Carcinoma," Clinical Cancer Research 13(7):2075-2081.

Taraban, V.Y. et al. (2002). "Expression and Costimulatory Effects of the TNF Receptor Superfamily Members CD134 (OX40) and CD137 (4-1BB), and Their role in the Generation of Anti-Tumor Immune Responses," European Journal of Immunology 32:3617-3627.

Zhulikov, Ya. A. et al. (2018). "Mechanisms of Resistance to Anti-PD-1 Therapy in Metastatic Cutaneous Melanoma," Russian Journal of Biotherapy 17:34-46, (English Translation of the Abstract).

Almagro et al. "Humanization of Antibodies," Front. Biosci. 13:1619-1633, (Jan. 1, 2008).

Baca et al., "Antibody Humanization Using Monovalent Phage Display," J. Biol. Chem. 272(16):10678-10684, (Apr. 18, 1997).

Boerner et al. "Production of Antigen-Specific Human Monoclonal Antibodies From in Vitro-Primed Human Splenocytes," J. Immunol. 147(1):86-95, (Jul. 1, 1991).

Brennan et al., "Preparation of Bispecific Antibodies by Chemical Recombination of Monoclonal Immunoglobulin $G_1$ Fragments," Science 229(4708):81-83, (Jul. 5, 1985).

Brodeur et al. "Mouse-Human Myeloma Partners for the Production of Heterohybridomas," Chapter 4 in Monoclonal Antibody Production Techniques and Applications, Marcel-Dekker, Inc., New York, New York, pp. 51-63, (1987).

Brüggemann et al. "Comparison of the Effector Functions of Human Immunoglobulins Using a Matched Set of Chimeric Antibodies," J. Exp. Med. 166(5):1351-1361, (Nov. 1, 1987).

Bulliard et al. "OX40 Engagement Depletes Intratumoral Tregs via Activating FcγRs, Leading to Antitumor Efficacy," Immunol. Cell Biol. 92(6):475-480, (Jul. 2014, e-pub. Apr. 15, 2014).

Burocchi et al. "Intratumor OX40 Stimulation Inhibits IRF1 Expression and IL-10 Production by Treg Cells While Enhancing CD40L Expression by Effector Memory T Cells," Eur. J. Immunol. 41(12):3615-3626, (Dec. 2011).

Capel et al. "Heterogeneity of Human IgG Fc Receptors,"Immunomethods 4(1):25-34, (Feb. 1994).

Carter et al. "Humanization of an Anti-p185$^{HER2}$ Antibody for Human Cancer Therapy," Proc. Natl. Acad. Sci. USA 89(10):4285-4289, (May 1992).

Cha. "S49. Clinical Activity and Development of Biomarkers for an Engineered Anti PDL1 Antibody MPDL3280A," from 1$^{st}$ Immunotherapy of Cancer Conference (ITOC1), Munich, Germany, Mar. 12-14, 2014, Journal for Immunotherapy of Cancer 2(Suppl 2):I21, (2014).

Chari et al., "Immunoconjugates Containing Novel Maytansinoids: Promising Anticancer Drugs," Cancer Res. 52(1):127-131, (Jan. 1, 1992).

Charlton. "Expression and Isolation of Recombinant Antibody Fragments in E. coli," Chapter 14 in Methods in Molecular Biology B.K.C. Lo, ed., Humana Press, Totowa, NJ, 248:245-254, (2003).

Chen et al. "Selection and Analysis of an Optimized Anti-VEGF Antibody: Crystal Structure of an Affinity-matured Fab in Complex with Antigen," J. Mol. Biol. 293(4):856-881, (Nov. 5, 1999).

Chothia et al. "Canonical Structures for the Hypervariable Regions of Immunoglobulins," J. Mal. Biol. 196(4):901-917, (Aug. 20, 1987).

Chowdhury. "Engineering Hot Spots for Affinity Enhancement of Antibodies," Chapter 11 in Methods in Molecular Biology, M. Welschof, ed. et al., Humana Press, Totowa, NJ. 207:179-196, (2003).

Clackson et al. "Making Antibody Fragments Using Phage Display Libraries," Nature 352(6336):624-628, (Aug. 15, 1991).

clinicaltrials.gov. "Her2 and TGFBeta CTLs in Treatment of Her2 Positive Malignancy (HERCREEM)," ClinicalTrails Idenifier: NCT00889954, located at <https:www.clinicaltrials.gov/ct2/sho/studyNCT00889954,>, last visited on Aug. 13, 2015, 4 pages.

Clynes et al. "Fc Receptors are Required in Passive and Active Immunity to Melanoma," Proc. Natl. Acad. Sci. U.S.A. 95(2):652-656, (Jan. 20, 1998).

Cragg et al. "Antibody Specificity Controls in Vivo Effector Mechanisms of Anti-CD20 Reagents," Blood 103(7):2738-2743, (Apr. 1, 2004, e-pub. Oct. 9, 2003).

Cragg et al. "Complement-Mediated Lysis by Anti-CD20 mAb Correlates With Segregation Into Lipid Rafts," Blood 101(3):1045-1052, (Feb. 1, 2003, e-pub. Sep. 19, 2002).

Cunningham et al. "High-Resolution Epitope Mapping of hGH-Receptor Interactions by Alanine-Scanning Mutagenesis," Science 244(4908):1081-1085, (Jun. 2, 1989).

Daëron. "Fc Receptor Biology," Annu. Rev. Immunol. 15:203-234, (1997).

Dall'Acqua et al. "Antibody Humanization by Framework Shuffling," Methods 36(1):43-60, (May 2005).

De Haas et al. "Fcγ Receptors of Phagocytes," J. Lab. Clin. Med. 126(4):330-341, (Oct. 1995).

De Kok et al. "Normalization of Gene Expression Measurements in Tumor Tissues: Comparison of 13 Endogenous Control Genes," Lab Invest. 85(1):154-159, (Jan. 2005, e-pub. Nov. 15, 2004).

Dubowchik et al. "Doxorubicin Immunoconjugates Containing Bivalent, Lysosomally-Cleavable Dipeptide Linkages," Bioorg. & Med. Chem. Letters 12(11):1529-1532, (Jun. 3, 2002).

Duncan et al. "The Binding Site for C1q on IgG,"Nature 332(6166):738-740, (Apr. 21, 1988).

Eisen et al. "Cluster Analysis and Display of Genome-Wide Expression Patterns," Proc. Natl. Acad. Sci. U.S.A 95:14863-14868, (Dec. 8, 1998).

Eisen et al. "Cluster Analysis and Display of Genome-Wide Expression Patterns," Corrections, Proc. Natl. Acad. Sci. U.S.A 95:10943-10944, (1999).

Eisenhauer et al. "New Response Evaluation Criteria in Solid Tumours: Revised RECIST Guideline (Version 1.1)," Eur. J. Cancer 45(2):228-247, (Jan. 2009).

Fellouse et al. "Synthetic Antibodies from a Four-amino-acid Code: A Dominant Role for Tyrosine in Antigen Recognition," Proc. Natl. Acad. Sci. U.S.A. 101(34):12467-12472, (Aug. 24, 2004, e-pub. Aug. 11, 2004).

Flatman et al. "Process Analytics for Purification of Monoclonal Antibodies," J. Chromatogr. B 848(1):79-87, (Mar. 15, 2007, e-pub. Dec. 11, 2006).

Garrison et al. "The Small Moiecule TGF-β Signaling Inhibitor SM16 Synergizes With Agonistic OX40 Antibody to Suppress Established Mammary Tumors and Reduce Spontaneous Metastasis," Cancer Immunology 61(4):511-521, (Apr. 2012. e:-pub. Oct. 5, 2011).

(56) References Cited

OTHER PUBLICATIONS

Gazzano-Santoro et al. "A Non-Radioactive Complement-Dependent Cytotoxicity Assay for Anti-CD20 Monoclonal Antibody," *J. Immunol. Methods* 202(2):163-171, (Mar. 28, 1997).
Gerngross. "Advances in the Production of Human Therapeutic Proteins in Yeasts and Filamentous Fungi," *Nat. Biotech.* 22(11):1409-1414, (Nov. 2004).
Ghetie et al. "FcRn: the MHC Class I-Related Receptor That is More Than an IgG Transporter," *Immunol. Today* 18(12):592-598, (Dec. 1997).
Ghetie et al. "Increasing the Serum Persistence of an IgG Fragment by Random Mutagenesis," *Nature Biotechnology* 15(7):637-640, (Jul. 1997).
Graham et al. "Characteristics of a Human Cell Line Transformed by DNA from Human Adenovirus Type 5," *J. Gen Virol.* 36(1):59-72, (Jul. 1977).
Griffiths et al., "Human Anti-Self Antibodies With High Specificity From Phage Display Libraries," *EMBO J.* 12(2):725-734, (Feb. 1993).
Gruber et al. "Efficient Tumor Cell Lysis Mediated by a Bispecific Single Chain Antibody Expressed in *Escherichia coli*," *J. Immunol.* 152(11):5368-5374, (Jun. 1, 1994).
Guyer et al. "Immunoglobulin Binding by Mouse Intestinal Epithelial Cell Receptors," *J. Immunol.* 117(2):587-593, (Aug. 1976).
Hellström et al. "Antitumor Effects of L6, an IgG2a Antibody That Reacts With Most Human Carcinomas," *Proc. Nat'l Acad. Sci. U.S.A.* 83(18):7059-7063, (Sep. 1986).
Hellström et al. "Strong Antitumor Activities of IgG3 Antibodies to a Human Melanoma-Associated Ganglioside," *Proc. Nat'l Acad. Sci. U.S.A.* 82(5):1499-1502, (Mar. 1985).
Hinman et al. "Preparation and Characterization of Monoclonal Antibody Conjugates of the Calicheamicins: A Novel and Potent Family of Antitumor Antibiotics," *Cancer Res.* 53(14):3336-3342, (Jul. 15, 1993).
Hinton et al. "Engineered Human IgG Antibodies with Longer Serum Half-lives in Primates," *J. Biol. Chem.* 279(8):6213-6216, (Feb. 20, 2004, e-pub. Dec. 29, 2003).
Hollinger et al. "Diabodies": Small Bivalent and Bispecific Antibody Fragments, *Proc. Natl. Acad. Sci. U.S.A.* 90(14):6444-6448, (Jul. 15, 1993).
Hoogenboom et al. "By-passing Immunisation Human Antibodies from Synthetic Repertoires of Germline $V_H$ Gene Segments Rearranged in Vitro," *J. Mol. Biol.* 227:381-388 (1992).
Hoogenboom et al. "Overview of Antibody Phage-Display Technology and Its Applications," Chapter 1 in *Methods in Molecular Biology*, O'Brien et al., ed., Human Press, Totowa, NJ, 178:1-37, (2001).
Huang et al. "Identification of B7-H1 as a Novel Mediator of the Innate Immune/Proinflammatory Response as Well as a Possible Myeloid Cell Prognostic Biomarker in Sepsis," *J. Immunol.* 192(3):1091-1099, (Feb. 1, 2014, e-pub. Dec. 30, 2013).
Huang et al. "Prognostic Value of Tumor-Infiltrating FoxP3+ T Cells in Gastrointestinal Cancers: A Meta Analysis," *Plos One* 9(5)(e94376):1-12, (May 14, 2014).
Hudson et al. "Engineered Antibodies," *Nat. Med.* 9(1):129-134, (Jan. 2003).
Huseni et al. "Anti-Tumor Efficacy and Biomarker Evaluation of Agonistic Anti-OX40 Antibodies in Preclinical Models," *Journal of Immunotherapy of Cancer* 2(Supp. 3):P253, (Nov. 6, 2014).
Idusogie et al. "Mapping of the C1q Binding Site on Rituxan, a Chimeric Antibody with a Human IgG1 Fc," *J. Immunol.* 164:4178-4184, (2000).
Jeffrey et al. "Dipeptide-Based Highly Potent Doxorubicin Antibody Conjugates," *Bioorganic & Med. Chem. Letters* 16(2):358-362, (Jan. 15, 2006, e-pub. Nov. 3, 2005).
Johns et al. "Identification of the Epitope for the Epidermal Growth Factor Receptor-specific Monoclonal Antibody 806 Reveals That It Preferentially Recognizes an Untethered Form of the Receptor," *J. Biol. Chem.* 279(29):30375-30384, (Jul. 16, 2004, e-pub. Apr. 9, 2004).
Kam et al. "Carbon Nanotubes as Multifunctional Biological Transporters and Near-Infrared Agents for Selective Cancer Cell Destruction," *Proc. Natl. Acad. Sci. U.S.A.* 102(33):11600-11605, (Aug. 16, 2005, e-pub. Aug. 8, 2005).
Kanda et al. "Comparison of Cell Lines for Stable Production of Fucose-Negative Antibodies With Enhanced ADCC," *Biotechnol. Bioeng.* 94(4):680-688, (Jul. 5, 2006, e-pub. Apr. 11, 2006).
Kashmiri et al. "SDR Grafting—a New Approach to Antibody Humanization," *Methods* 36:25-34, (2005).
Kim et al. "Localization of the Site of the Murine IgGI Molecule That is Involved in Binding to the Murine Intestinal Fc Receptor," *Eur. J. Immunol.* 24:2429-2434, (1994).
Kindt et al. "Antigens and Antibodies,"Chapter 4 in *Kuby Immunology*, 6th ed., W.H. Freeman and Co., New York, New York, pp. vi-xxii, p. 91, (2007).
King et al., "Monoclonal Antibody Conjugates of Doxorubicin Prepared with Branched Peptide Linkers: Inhibition of Aggregation by Methoxytriethyleneglycol Chains," *J. Med. Chem.* 45(19):4336-4343, (2002, e-pub. Aug. 14, 2002).
Klimka et al. "Human Anti-CD30 Recombinant Antibodies by Guided Phage Antibody Selection Using Cell Panning," *Br. J. Cancer* 83(2):252-260, (2000, e-pub. Dec. 26, 2000).
Kostelny et al. "Formation of a Bispecific Antibody by the use of Leucine Zippers," *J. Immunol.* 148(5):1547-1553, (Mar. 1, 1992).
Kozbor et al. "A Human Hybrid Myeloma for Production of Human Monoclonal Antibodies," *J. Immunol.* 133(6):3001-3005, (Dec. 1984).
Kratz et al. "Prodrugs of Anthracyclines in Cancer Chemotherapy," *Current Med. Chem.* 13(5):477-523, (2006).
Lee et al. "Bivalent Antibody Phage Display Mimics Natural Immunoglobulin," *J. Immunol. Methods* 284:(1-2):119-132, (2004).
Lee et al. "High-affinity Human Antibodies from Phage-displayed Synthetic Fab Libraries with a Single Framework Scaffold," *J. Mol. Biol.* 340(5):1073-1093, (2004).
Li et al. "Human Antibodies for Immunotherapy Development Generated via a Human B Cell Hybridoma Technology," *Proc. Natl. Acad. Sci. U.S.A.* 103(10):3557-3562, (Mar. 7, 2006).
Li et al. "Optimization of Humanized IgGs in Glycoengineered *Pichia pastoris*," *Nat. Biotech.* 24(2):210-215, (Feb. 2006, e-pub. Jan. 22, 2006).
Lode et al. "Targeted Therapy with a Novel Enediyene Antibiotic Calicheamicin $\ominus_1^1$ Effectively Suppresses Growth and Dissemination of Liver Metastases in a Syngeneic Model of Murine Neuroblastoma," *Cancer Res.* 58:2925-2928, (Jul. 15, 1998).
Lonberg. "Fully Human Antibodies From Transgenic Mouse and Phage Display Platforms," *Curr. Opin. Immunol.* 20:450-459, (2008, e-pub. Jul. 21, 2008).
Lonberg. "Human Antibodies From Transgenic Animals," *Nat. Biotech.* 23(9):1117-1125, (Sep. 2005, e-pub. Sep. 7, 2005).
MacCallum et al. "Antibody-Antigen Interactions: Contact Analysis and Binding Site Topography," *J. Mol. Biol.* 262:732-745, (1996).
Marks et al. "By-Passing Immunization Human Antibodies from V-gene Libraries Displayed on Phage," *J. Mol. Biol.* 222: 581-597, (1991).
Marks et al. "Selection of Human Antibodies from Phage Display libraries," Chapter 8 in *Methods in Molecular Biology*, Lo, ed., Humana Press, Totowa, NJ, 248:161-175, (2003).
Mather et al. "Culture of Testicular Cells in Hormone-Supplemented Serum-Free Medium," *Annals N.Y. Acad. Sci.* 383:44-68, (1982).
Mather. "Establishment and Characterization of Two Distinct Mouse Testicular Epithelial Cell Lines," *Biol. Reprod.* 23:243-252, (1980).
McCafferty et al. "Phage Antibodies: Filamentous Phage Displaying Antibody Variable Domains," *Nature* 348:552-554, (Dec. 6, 1990).
Meng et al. "Predictive Biomarkers in PD-1/PD-L1 Checkpoint Blockade Immunotherapy," *Cancer Treat Rev.* 41(10):868-876, (Dec. 2015, e-pub. Nov. 10, 2015).
Milstein et al. "Hybrid Hybridomas and Their use in Immunohistochemistry," *Nature* 305:537-540, (Oct. 6, 1983).
Morrison et al. "Chimeric Human Antibody Molecules: Mouse Antigen-Binding Domains with Human Constant Region Domains," *Proc. Natl. Sci. U.S.A.* 81:6851-6855, (Nov. 1984).

(56) References Cited

OTHER PUBLICATIONS

Murakami et al. "Cell cycle Regulation, Oncogenes, and Antineoplastic Drugs" Chapter 1 in *The Molecular Basis of Cancer*, Mendelsohn and Israel, eds., W.B. Saunders, Philadelphia, PA, p. 13-17, (1995).

Nagy et al. "Stability of Cytotoxic Luteinizing Hormone-Releasing Hormone Conjugate (AN-152) Containing Doxorubicin 14-O-Hemiglutarate in Mouse and Human Serum In vitro: Implications for the Design of Preclinical Studies," *Proc. Natl. Acad. Sci. U.S.A.* 97(2):829-834, (Jan. 18, 2000).

Ni, "Research Progress and Future Perspectives in Antibodomics and Antibodomic Drugs,"*Xiandai Mianyixue* 26(4):265-268, (2006).

Nicolaou et al. "Calicheamicin $\theta_1^I$: A Rationally Designed Molecule with Extremely Potent and Selective DNA Cleaving Properties and Apoptosis Inducing Activity" *Angew. Chem. Int. Ed. Engl.* 33(2):183-186, (1994).

Okazaki et al. "Fucose Depletion from Human IgG1 Oligosaccharide Enhances Binding Enthalpy and Association Rate Between IgG1 and FcγRIIIa," *J. Mol. Biol.* 336:1239-1249, (2004).

Osbourn et al. "From Rodent Reagents to Human Therapeutics Using Antibody Guided Selection," *Methods* 36:61-68, (2005).

Padlan."A Possible Procedure for Reducing the Immunogenicity of Antibody Variable Domains While Preserving Their Ligand-Binding Properties," *Mol. Immunol.* 28(4/5):489-498, (1991).

Petkova et al. "Enhanced Half-Life of Genetically Engineered Human IgG1 Antibodies in a Humanized FcRn Mouse Model: Potential Application in Humorally Mediated Autoimmune Disease," *Intl. Immunol.* 18(12):1759-1769, (2006).

Petty et al. "Survival in Human Colorectal Cancer Correlates with Expression of the T-Cell Costimulatory Molecule OX-40 (CD134)," *Am. J. Surg.* 183(5):512-518, (2002).

Piconese et al. "OX40 Triggering Blocks Suppression by Regulatory T Cells and Facilitates Tumor Rejection," *The Journal of Experimental Medicine* 205(4):825-839, (Apr. 14, 2008, e-pub. Mar. 24, 2008).

Plückthun. "Antibodies from *Escherichia coli*," Chapter 11 in *The Pharmacology of Monoclonal Antibodies*, Rosenburg and Moore eds., Springer-Verlag, New York, 113:269-315, (1994).

Portolano et al. "Lack of Promiscuity in Autoantigen-Specific H and L Chain Combinations as Revealed by Human H and L Chain "Roulette"," *J. Immunol.* 150(3):880-887, (Feb. 1, 1993).

Presta et al. "Humanization of an Antibody Directed Against IgE," *J. Immunol.* 151(5):2623-2632, (Sep. 1, 1993).

Presta et al. "Humanization of an Anti-Vascular Endothelial Growth Factor Monoclonal Antibody for the Therapy of Solid Tumors and Other Disorders," *Cancer Res.* 57:4593-4599, (Oct. 15, 1997).

Queen et al. "A Humanized Antibody That Binds to the Interleukin 2 Receptor," *Proc. Nat'l Acad. Sci. U.S.A.* 86:10029-10033, (Dec. 1989).

Ravetch et al. "Fc Receptors," *Annu. Rev. Immunol.* 9:457-492, (1991).

Riechmann et al. "Reshaping Human Antibodies for Therapy," *Nature* 332:323-329, (Mar. 24, 1988).

Ripka et al. "Two Chinese Hamster Ovary Glycosylation Mutants Affected in the Conversion of GDP-Mannose to GDP-Fucose," *Arch. Biochem. Biophys.* 249(2):533-545, (Sep. 1986).

Rosok et al. "A Combinatorial Library Strategy for the Rapid Humanization of Anticarcinoma BR96 Fab," *J. Biol. Chem.* 271(37):22611-22618, (Sep. 13, 1996).

Sarff et al. "OX40 (CD134) Expression in Sentinel Lymph Nodes Correlates with Prognostic Features of Primary Melanomas," *American Journal of Surgery* 195(5):621-625, (May 2008).

Shah et al. "A Reversed CD4/CD8 Ration of Tumor-Infiltrating Lymphocytes and a High Percentage of CD4$^+$FOXP3$^+$Regulatory T Cells are Significantly Associated with Clinical Outcome in Squamous Cell Carcinoma of the Cervix," *Cellular & Molecular Immunology* 8(1):59-66, (2011, e-pub. Nov. 22, 2010).

Shames et al. "High Heregulin Expression is Associated with Activated HER3 and May Define an Actionable Biomarker in Patients with Squamous Cell Carcinomas of the Head and Neck," *PloS One* 8(2)(e56765):1-10, (Feb. 28, 2013).

Shields et al. "High Resolution Mapping of the Binding Site on Human IgG1 for FcγRI, FcγRII, FcγRIII, and FcRn and Design of IgG1 Variants with Improved Binding to the FcγR," *J. Biol. Chem.* 276(9):6591-6604, (Mar. 2, 2001).

Sidhu et al. "Phage-displayed Antibody Libraries of Synthetic Heavy Chain Complementarity Determining Regions," *J. Mol. Biol.* 338(2):299-310, (2004).

Sims et al. "A Humanized CD18 Antibody can Block Function Without Cell Destruction," *J. Immunol.* 151(4):2296-2308, (Aug. 15, 1993).

Stragliotto et al. "Multiple Infusions of Anti-epidermal Growth Factor Receptor (EGFR) Monoclonal Antibody (EMD 55 900) in Patients with Recurrent Malignant Gliomas,"*Eur. J. Cancer* 32A(4):636-640, (1996).

Therasse et al. "New Guidelines to Evaluate the Response to Treatment in Solid Tumors," *J. Natl. Cancer Inst.* 92(3):205-216, (Feb. 2, 2000).

Topalian et al. "Safety, Activity, and Immune Correlates of Anti-PD-1 Antibody in Cancer," *N. Engl. J. Med.* 366(28):2443-2454, (Jun. 28, 2012).

Torgov et al., "Generation of an Intensely Potent Anthracycline by a Monoclonal Antibody-β-Galactosidase Conjugate," *Bioconj. Chem.* 16(3):717-721, (2005, e-pub. Apr. 27, 2005).

Traunecker et al. "Bispecific Single Chain Molecules (Janusins) Target Cytotoxic Lymphocytes on HIV Infected Cells," *EMBO J.* 10(12):3655-3659, (1991).

Tutt et al. "Trispecific F(ab')$_3$ Derivatives that use Cooperative Signaling via The TCR/CD3 complex and CD2 to Activate and Redirect Resting Cytotoxic T Cells," *J. Immunol.* 147:60-69, (Jul. 1, 1991).

Urlaub et al. "Isolation of Chinese Hamster Cell Mutants Deficient in Dihydrofolate Reductase Activity," *Proc. Natl. Acad. Sci. U.S.A.* 77(7):4216-4220, (Jul. 1980).

Van Dijk et al. "Human Antibodies as Next Generation Therapeutics," *Curr. Opin. Pharmacol.* 5:368-374, (2001).

Veta et al. "Automatic Nuclei Segmentation in H&E Stained Breast Cancer Histopathology Images," *PloS One* 8(7)(e70221):1-12, (Jul. 29, 2013).

Vitetta et al. "Redesigning Nature's Poisons to Create Anti-Tumor Reagents," *Science* 238:1098-1104, (Nov. 20, 1987).

Vollmers et al. "Death by Stress: Natural IgM-Induced Apoptosis," *Methods and Findings in Experimental and Clinical Pharmacology* 27(3):185-191, (2005).

Vollmers et al. "The 'early birds': Natural IgM Antibodies and Immune Surveillance," *Histology and Histopathology* 20(3):927-937, (2005).

Weinberg et al. "Science Gone Translational: the OX40 Agonist Story," *Imunological Reviews* 244(1):218-231, (Nov. 1, 2011).

Winter et al. "Making Antibodies by Phage Display Technology," *Ann. Rev. Immunol.* 12:433-455, (1994).

Wolchok et al. "Guidelines for Evaluation of Immune Therapy Activity in Solid Tumors: Immune-Related Response Criteria," *Clin. Can. Res.* 15(23):7412-7420, (Dec. 1, 2009, e-pub. Nov. 24, 2009).

Wright et al. "Effect of Glycosylation on Antibody Function: Implications for Genetic Engineering," *TIBTECH* 15:26-32, (Jan. 1997).

Yamada et al., "Next-Generation Peptide Vaccines for Advanced Cancer," *Cancer Sci.* 104(1):15-21, (Jan. 2013, e-pub. Dec. 4, 2012).

Yamane-Ohnuki et al. "Establishment of FUT8 Knockout Chinese Hamster Ovary Cells: An Ideal Host Cell line for Producing Completely Defucosylated Antibodies With Enhanced Antibody-Dependent Cellular Cytotoxicity," *Biotech. Bioeng.* 87(5):614-622, (2004, e-pub. Aug. 6, 2004).

Yazaki et al. "Expression of Recombinant Antibodies in Mammalian Cell Lines," Chapter 15 in *Methods in Molecular Biology*, B.K.C. Lo, ed., Humana Press, Totowa, NJ, 248:255-268, (2003).

Zhang et al. "Intratumoral T Cells, Recurrence, and Survival in Epithelial Ovarian Cancer," *N. Engl. J. Med.* 348(3):203-213, (Jan. 16, 2003).

(56) References Cited

OTHER PUBLICATIONS

Ziai et al. "A CD4/Foxp3/OX40 Triple Immunofluorescence Assay Determines Association Between T Cell Immune Subsets and Outcome in Colorectal Cancer," *Journal for Immunotherapy of Cancer* 2(Suppl.3):P133, (Nov. 6, 2014).

International Search Report dated Feb. 5, 2016, for PCT Application No. PCT/US2015/058677, filed on Nov. 2, 2015, 5 pages.

Written Opinion dated Feb. 5, 2016, for PCT Application No. PCT/US2015/058677, filed on Nov. 2, 2015, 7 pages.

International Search Report dated Apr. 4, 2016, for PCT Application No. PCT/US2015/058674, filed on Nov. 2, 2015, 7 pages.

Written Opinion dated Apr. 4, 2016, for PCT Application No. PCT/US2015/058674, filed on Nov. 2, 2015, 12 pages.

Gough, M.J. et al (Jul. 1, 2008). "OX40 Agonist Therapy Enhances CD8 Infiltration and Decreases Immune Suppression in the Tumor," Cancer Res. 68(13):5206-5215.

Ramilo, O. et al. (Mar. 1, 2007). "Gene Expression Patterns in Blood Leukocytes Discriminate Patients With Acute Infections," Blood 109(5):2066-2077.

Subimerb, C. et al (2014). "Transcriptional Profiles of Peripheral Blood Leukocytes Identify Patients with Cholangiocarcinoma and Predict Outcome," Asian Pacific Journal of Cancer Prevention 15:4217-4224.

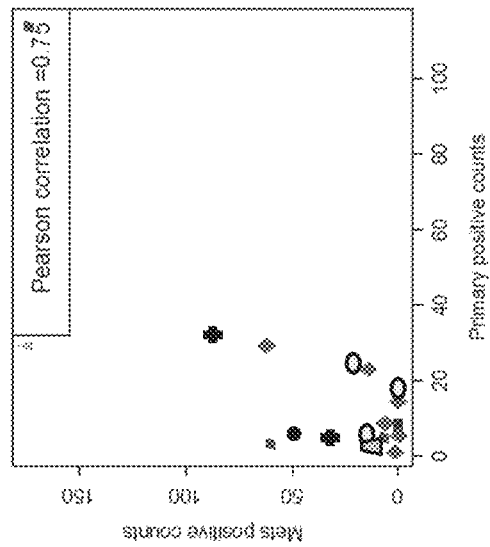
FIG. 10A
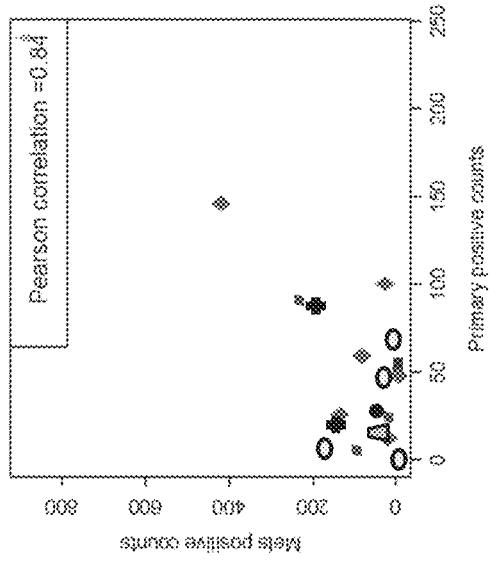
FIG. 10C
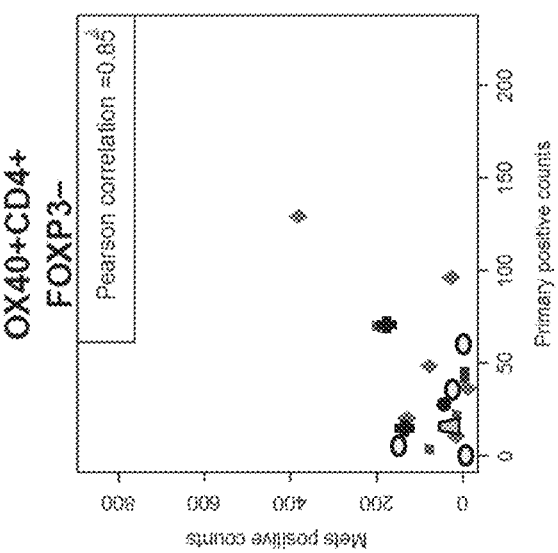
FIG. 10B
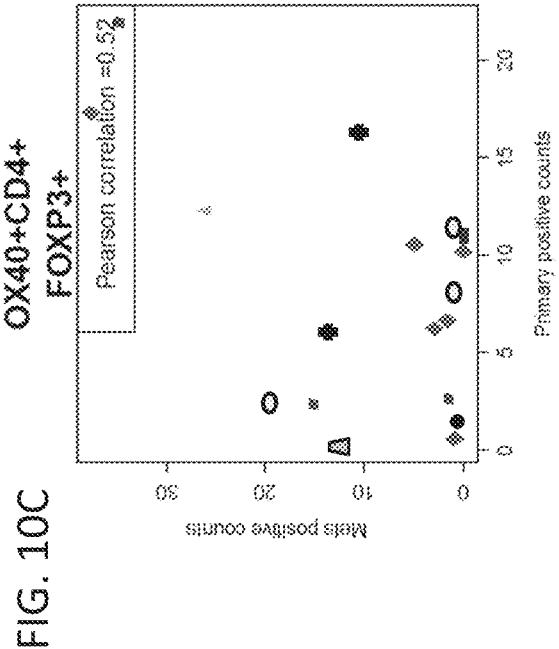
FIG. 10D

SEQUENCE LISTING

```
<160> NUMBER OF SEQ ID NOS: 226

<210> SEQ ID NO 1
<211> LENGTH: 249
<212> TYPE: PRT
<213> ORGANISM: Homo sapiens

<400> SEQUENCE: 1

Leu His Cys Val Gly Asp Thr Tyr Pro Ser Asn Asp Arg Cys Cys His
1               5                   10                  15

Glu Cys Arg Pro Gly Asn Gly Met Val Ser Arg Cys Ser Arg Ser Gln
            20                  25                  30

Asn Thr Val Cys Arg Pro Cys Gly Pro Gly Phe Tyr Asn Asp Val Val
        35                  40                  45

Ser Ser Lys Pro Cys Lys Pro Cys Thr Trp Cys Asn Leu Arg Ser Gly
    50                  55                  60

Ser Glu Arg Lys Gln Leu Cys Thr Ala Thr Gln Asp Thr Val Cys Arg
65                  70                  75                  80

Cys Arg Ala Gly Thr Gln Pro Leu Asp Ser Tyr Lys Pro Gly Val Asp
                85                  90                  95

Cys Ala Pro Cys Pro Pro Gly His Phe Ser Pro Gly Asp Asn Gln Ala
            100                 105                 110

Cys Lys Pro Trp Thr Asn Cys Thr Leu Ala Gly Lys His Thr Leu Gln
        115                 120                 125

Pro Ala Ser Asn Ser Ser Asp Ala Ile Cys Glu Asp Arg Asp Pro Pro
    130                 135                 140

Ala Thr Gln Pro Gln Glu Thr Gln Gly Pro Pro Ala Arg Pro Ile Thr
145                 150                 155                 160
```

```
Val Gln Pro Thr Glu Ala Trp Pro Arg Thr Ser Gln Gly Pro Ser Thr
                165                 170                 175

Arg Pro Val Glu Val Pro Gly Gly Arg Ala Val Ala Ala Ile Leu Gly
            180                 185                 190

Leu Gly Leu Val Leu Gly Leu Leu Gly Pro Leu Ala Ile Leu Leu Ala
        195                 200                 205

Leu Tyr Leu Leu Arg Arg Asp Gln Arg Leu Pro Pro Asp Ala His Lys
    210                 215                 220

Pro Pro Gly Gly Gly Ser Phe Arg Thr Pro Ile Gln Glu Glu Gln Ala
225                 230                 235                 240

Asp Ala His Ser Thr Leu Ala Lys Ile
                245
```

<210> SEQ ID NO 2
<211> LENGTH: 5
<212> TYPE: PRT
<213> ORGANISM: Artificial Sequence
<220> FEATURE:
<223> OTHER INFORMATION: Synthetic Construct

<400> SEQUENCE: 2

```
Asp Ser Tyr Met Ser
1               5
```

<210> SEQ ID NO 3
<211> LENGTH: 17
<212> TYPE: PRT
<213> ORGANISM: Artificial Sequence
<220> FEATURE:
<223> OTHER INFORMATION: Synthetic Construct

<400> SEQUENCE: 3

```
Asp Met Tyr Pro Asp Asn Gly Asp Ser Ser Tyr Asn Gln Lys Phe Arg
1               5                   10                  15

Glu
```

<210> SEQ ID NO 4
<211> LENGTH: 8
<212> TYPE: PRT
<213> ORGANISM: Artificial Sequence
<220> FEATURE:
<223> OTHER INFORMATION: Synthetic Construct

<400> SEQUENCE: 4

```
Ala Pro Arg Trp Tyr Phe Ser Val
1               5
```

<210> SEQ ID NO 5
<211> LENGTH: 11
<212> TYPE: PRT
<213> ORGANISM: Artificial Sequence
<220> FEATURE:
<223> OTHER INFORMATION: Synthetic Construct

<400> SEQUENCE: 5

```
Arg Ala Ser Gln Asp Ile Ser Asn Tyr Leu Asn
1               5                   10
```

<210> SEQ ID NO 6
<211> LENGTH: 7
<212> TYPE: PRT
<213> ORGANISM: Artificial Sequence
<220> FEATURE:
<223> OTHER INFORMATION: Synthetic Construct

```
<400> SEQUENCE: 6

Tyr Thr Ser Arg Leu Arg Ser
1               5

<210> SEQ ID NO 7
<211> LENGTH: 9
<212> TYPE: PRT
<213> ORGANISM: Artificial Sequence
<220> FEATURE:
<223> OTHER INFORMATION: Synthetic Construct

<400> SEQUENCE: 7

Gln Gln Gly His Thr Leu Pro Pro Thr
1               5

<210> SEQ ID NO 8
<211> LENGTH: 5
<212> TYPE: PRT
<213> ORGANISM: Artificial Sequence
<220> FEATURE:
<223> OTHER INFORMATION: Synthetic Construct

<400> SEQUENCE: 8

Asp Ala Tyr Met Ser
1               5

<210> SEQ ID NO 9
<211> LENGTH: 5
<212> TYPE: PRT
<213> ORGANISM: Artificial Sequence
<220> FEATURE:
<223> OTHER INFORMATION: Synthetic Construct

<400> SEQUENCE: 9

Glu Ser Tyr Met Ser
1               5

<210> SEQ ID NO 10
<211> LENGTH: 17
<212> TYPE: PRT
<213> ORGANISM: Artificial Sequence
<220> FEATURE:
<223> OTHER INFORMATION: Synthetic Construct

<400> SEQUENCE: 10

Asp Met Tyr Pro Asp Asn Ala Asp Ser Ser Tyr Asn Gln Lys Phe Arg
1               5                   10                  15

Glu

<210> SEQ ID NO 11
<211> LENGTH: 17
<212> TYPE: PRT
<213> ORGANISM: Artificial Sequence
<220> FEATURE:
<223> OTHER INFORMATION: Synthetic Construct

<400> SEQUENCE: 11

Asp Met Tyr Pro Asp Asn Ala Asp Ala Ser Tyr Asn Gln Lys Phe Arg
1               5                   10                  15

Glu

<210> SEQ ID NO 12
<211> LENGTH: 17
<212> TYPE: PRT
```

<213> ORGANISM: Artificial Sequence
<220> FEATURE:
<223> OTHER INFORMATION: Synthetic Construct

<400> SEQUENCE: 12

Asp Met Tyr Pro Asp Asn Gly Asp Ala Ser Tyr Asn Gln Lys Phe Arg
1               5                   10                  15

Glu

<210> SEQ ID NO 13
<211> LENGTH: 17
<212> TYPE: PRT
<213> ORGANISM: Artificial Sequence
<220> FEATURE:
<223> OTHER INFORMATION: Synthetic Construct

<400> SEQUENCE: 13

Asp Met Tyr Pro Asp Ser Gly Asp Ser Ser Tyr Asn Gln Lys Phe Arg
1               5                   10                  15

Glu

<210> SEQ ID NO 14
<211> LENGTH: 17
<212> TYPE: PRT
<213> ORGANISM: Artificial Sequence
<220> FEATURE:
<223> OTHER INFORMATION: Synthetic Construct

<400> SEQUENCE: 14

Asp Met Tyr Pro Asp Asn Gly Ser Ser Ser Tyr Asn Gln Lys Phe Arg
1               5                   10                  15

Glu

<210> SEQ ID NO 15
<211> LENGTH: 8
<212> TYPE: PRT
<213> ORGANISM: Artificial Sequence
<220> FEATURE:
<223> OTHER INFORMATION: Synthetic Construct

<400> SEQUENCE: 15

Ala Pro Arg Trp Tyr Phe Ser Ala
1               5

<210> SEQ ID NO 16
<211> LENGTH: 8
<212> TYPE: PRT
<213> ORGANISM: Artificial Sequence
<220> FEATURE:
<223> OTHER INFORMATION: Synthetic Construct

<400> SEQUENCE: 16

Ala Pro Arg Trp Tyr Ala Ser Val
1               5

<210> SEQ ID NO 17
<211> LENGTH: 8
<212> TYPE: PRT
<213> ORGANISM: Artificial Sequence
<220> FEATURE:
<223> OTHER INFORMATION: Synthetic Construct

<400> SEQUENCE: 17

Ala Pro Arg Trp Ala Phe Ser Val
1               5

```
<210> SEQ ID NO 18
<211> LENGTH: 8
<212> TYPE: PRT
<213> ORGANISM: Artificial Sequence
<220> FEATURE:
<223> OTHER INFORMATION: Synthetic Construct

<400> SEQUENCE: 18

Ala Pro Ala Trp Tyr Phe Ser Val
1               5

<210> SEQ ID NO 19
<211> LENGTH: 8
<212> TYPE: PRT
<213> ORGANISM: Artificial Sequence
<220> FEATURE:
<223> OTHER INFORMATION: Synthetic Construct

<400> SEQUENCE: 19

Ala Pro Arg Trp Tyr Phe Ala Val
1               5

<210> SEQ ID NO 20
<211> LENGTH: 8
<212> TYPE: PRT
<213> ORGANISM: Artificial Sequence
<220> FEATURE:
<223> OTHER INFORMATION: Synthetic Construct

<400> SEQUENCE: 20

Ala Pro Arg Ala Tyr Phe Ser Val
1               5

<210> SEQ ID NO 21
<211> LENGTH: 8
<212> TYPE: PRT
<213> ORGANISM: Artificial Sequence
<220> FEATURE:
<223> OTHER INFORMATION: Synthetic Construct

<400> SEQUENCE: 21

Ala Ala Arg Trp Tyr Phe Ser Val
1               5

<210> SEQ ID NO 22
<211> LENGTH: 9
<212> TYPE: PRT
<213> ORGANISM: Artificial Sequence
<220> FEATURE:
<223> OTHER INFORMATION: Synthetic Construct

<400> SEQUENCE: 22

Gln Gln Gly His Thr Leu Pro Ala Thr
1               5

<210> SEQ ID NO 23
<211> LENGTH: 9
<212> TYPE: PRT
<213> ORGANISM: Artificial Sequence
<220> FEATURE:
<223> OTHER INFORMATION: Synthetic Construct

<400> SEQUENCE: 23

Gln Gln Gly His Thr Ala Pro Pro Thr
1               5
```

<210> SEQ ID NO 24
<211> LENGTH: 9
<212> TYPE: PRT
<213> ORGANISM: Artificial Sequence
<220> FEATURE:
<223> OTHER INFORMATION: Synthetic Construct

<400> SEQUENCE: 24

Gln Gln Gly Ala Thr Leu Pro Pro Thr
1               5

<210> SEQ ID NO 25
<211> LENGTH: 9
<212> TYPE: PRT
<213> ORGANISM: Artificial Sequence
<220> FEATURE:
<223> OTHER INFORMATION: Synthetic Construct

<400> SEQUENCE: 25

Gln Gln Gly His Ala Leu Pro Pro Thr
1               5

<210> SEQ ID NO 26
<211> LENGTH: 9
<212> TYPE: PRT
<213> ORGANISM: Artificial Sequence
<220> FEATURE:
<223> OTHER INFORMATION: Synthetic Construct

<400> SEQUENCE: 26

Gln Gln Ala His Thr Leu Pro Pro Thr
1               5

<210> SEQ ID NO 27
<211> LENGTH: 9
<212> TYPE: PRT
<213> ORGANISM: Artificial Sequence
<220> FEATURE:
<223> OTHER INFORMATION: Synthetic Construct

<400> SEQUENCE: 27

Gln Gln Gly His Thr Leu Ala Pro Thr
1               5

<210> SEQ ID NO 28
<211> LENGTH: 9
<212> TYPE: PRT
<213> ORGANISM: Artificial Sequence
<220> FEATURE:
<223> OTHER INFORMATION: Synthetic Construct

<400> SEQUENCE: 28

Gln Ala Gly His Thr Leu Pro Pro Thr
1               5

<210> SEQ ID NO 29
<211> LENGTH: 5
<212> TYPE: PRT
<213> ORGANISM: Artificial Sequence
<220> FEATURE:
<223> OTHER INFORMATION: Synthetic Construct

<400> SEQUENCE: 29

Asn Tyr Leu Ile Glu
1               5

```
<210> SEQ ID NO 30
<211> LENGTH: 17
<212> TYPE: PRT
<213> ORGANISM: Artificial Sequence
<220> FEATURE:
<223> OTHER INFORMATION: Synthetic Construct

<400> SEQUENCE: 30

Val Ile Asn Pro Gly Ser Gly Asp Thr Tyr Tyr Ser Glu Lys Phe Lys
1               5                   10                  15

Gly

<210> SEQ ID NO 31
<211> LENGTH: 17
<212> TYPE: PRT
<213> ORGANISM: Artificial Sequence
<220> FEATURE:
<223> OTHER INFORMATION: Synthetic Construct

<400> SEQUENCE: 31

Val Ile Asn Pro Gly Ser Gly Asp Ala Tyr Tyr Ser Glu Lys Phe Lys
1               5                   10                  15

Gly

<210> SEQ ID NO 32
<211> LENGTH: 17
<212> TYPE: PRT
<213> ORGANISM: Artificial Sequence
<220> FEATURE:
<223> OTHER INFORMATION: Synthetic Construct

<400> SEQUENCE: 32

Val Ile Asn Pro Gly Ser Gly Asp Gln Tyr Tyr Ser Glu Lys Phe Lys
1               5                   10                  15

Gly

<210> SEQ ID NO 33
<211> LENGTH: 5
<212> TYPE: PRT
<213> ORGANISM: Artificial Sequence
<220> FEATURE:
<223> OTHER INFORMATION: Synthetic Construct

<400> SEQUENCE: 33

Asp Arg Leu Asp Tyr
1               5

<210> SEQ ID NO 34
<211> LENGTH: 5
<212> TYPE: PRT
<213> ORGANISM: Artificial Sequence
<220> FEATURE:
<223> OTHER INFORMATION: Synthetic Construct

<400> SEQUENCE: 34

Ala Arg Leu Asp Tyr
1               5

<210> SEQ ID NO 35
<211> LENGTH: 5
<212> TYPE: PRT
<213> ORGANISM: Artificial Sequence
<220> FEATURE:
<223> OTHER INFORMATION: Synthetic Construct

<400> SEQUENCE: 35
```

```
Asp Ala Leu Asp Tyr
1               5

<210> SEQ ID NO 36
<211> LENGTH: 5
<212> TYPE: PRT
<213> ORGANISM: Artificial Sequence
<220> FEATURE:
<223> OTHER INFORMATION: Synthetic Construct

<400> SEQUENCE: 36

Asp Arg Ala Asp Tyr
1               5

<210> SEQ ID NO 37
<211> LENGTH: 11
<212> TYPE: PRT
<213> ORGANISM: Artificial Sequence
<220> FEATURE:
<223> OTHER INFORMATION: Synthetic Construct

<400> SEQUENCE: 37

His Ala Ser Gln Asp Ile Ser Ser Tyr Ile Val
1               5                   10

<210> SEQ ID NO 38
<211> LENGTH: 7
<212> TYPE: PRT
<213> ORGANISM: Artificial Sequence
<220> FEATURE:
<223> OTHER INFORMATION: Synthetic Construct

<400> SEQUENCE: 38

His Gly Thr Asn Leu Glu Asp
1               5

<210> SEQ ID NO 39
<211> LENGTH: 7
<212> TYPE: PRT
<213> ORGANISM: Artificial Sequence
<220> FEATURE:
<223> OTHER INFORMATION: Synthetic Construct

<400> SEQUENCE: 39

His Gly Thr Asn Leu Glu Ser
1               5

<210> SEQ ID NO 40
<211> LENGTH: 7
<212> TYPE: PRT
<213> ORGANISM: Artificial Sequence
<220> FEATURE:
<223> OTHER INFORMATION: Synthetic Construct

<400> SEQUENCE: 40

His Gly Thr Asn Leu Glu Glu
1               5

<210> SEQ ID NO 41
<211> LENGTH: 7
<212> TYPE: PRT
<213> ORGANISM: Artificial Sequence
<220> FEATURE:
<223> OTHER INFORMATION: Synthetic Construct

<400> SEQUENCE: 41
```

```
His Gly Thr Asn Leu Glu Gln
1               5

<210> SEQ ID NO 42
<211> LENGTH: 9
<212> TYPE: PRT
<213> ORGANISM: Artificial Sequence
<220> FEATURE:
<223> OTHER INFORMATION: Synthetic Construct

<400> SEQUENCE: 42

Val His Tyr Ala Gln Phe Pro Tyr Thr
1               5

<210> SEQ ID NO 43
<211> LENGTH: 9
<212> TYPE: PRT
<213> ORGANISM: Artificial Sequence
<220> FEATURE:
<223> OTHER INFORMATION: Synthetic Construct

<400> SEQUENCE: 43

Ala His Tyr Ala Gln Phe Pro Tyr Thr
1               5

<210> SEQ ID NO 44
<211> LENGTH: 9
<212> TYPE: PRT
<213> ORGANISM: Artificial Sequence
<220> FEATURE:
<223> OTHER INFORMATION: Synthetic Construct

<400> SEQUENCE: 44

Val Ala Tyr Ala Gln Phe Pro Tyr Thr
1               5

<210> SEQ ID NO 45
<211> LENGTH: 9
<212> TYPE: PRT
<213> ORGANISM: Artificial Sequence
<220> FEATURE:
<223> OTHER INFORMATION: Synthetic Construct

<400> SEQUENCE: 45

Val His Ala Ala Gln Phe Pro Tyr Thr
1               5

<210> SEQ ID NO 46
<211> LENGTH: 9
<212> TYPE: PRT
<213> ORGANISM: Artificial Sequence
<220> FEATURE:
<223> OTHER INFORMATION: Synthetic Construct

<400> SEQUENCE: 46

Val His Tyr Ala Ala Phe Pro Tyr Thr
1               5

<210> SEQ ID NO 47
<211> LENGTH: 9
<212> TYPE: PRT
<213> ORGANISM: Artificial Sequence
<220> FEATURE:
<223> OTHER INFORMATION: Synthetic Construct

<400> SEQUENCE: 47

Val His Tyr Ala Gln Ala Pro Tyr Thr
```

```
1               5

<210> SEQ ID NO 48
<211> LENGTH: 9
<212> TYPE: PRT
<213> ORGANISM: Artificial Sequence
<220> FEATURE:
<223> OTHER INFORMATION: Synthetic Construct

<400> SEQUENCE: 48

Val His Tyr Ala Gln Phe Ala Tyr Thr
1               5

<210> SEQ ID NO 49
<211> LENGTH: 9
<212> TYPE: PRT
<213> ORGANISM: Artificial Sequence
<220> FEATURE:
<223> OTHER INFORMATION: Synthetic Construct

<400> SEQUENCE: 49

Val His Tyr Ala Gln Phe Pro Ala Thr
1               5

<210> SEQ ID NO 50
<211> LENGTH: 5
<212> TYPE: PRT
<213> ORGANISM: Artificial Sequence
<220> FEATURE:
<223> OTHER INFORMATION: Synthetic Construct

<400> SEQUENCE: 50

Asp Tyr Gly Val Leu
1               5

<210> SEQ ID NO 51
<211> LENGTH: 16
<212> TYPE: PRT
<213> ORGANISM: Artificial Sequence
<220> FEATURE:
<223> OTHER INFORMATION: Synthetic Construct

<400> SEQUENCE: 51

Met Ile Trp Ser Gly Gly Thr Thr Asp Tyr Asn Ala Ala Phe Ile Ser
1               5                   10                  15

<210> SEQ ID NO 52
<211> LENGTH: 5
<212> TYPE: PRT
<213> ORGANISM: Artificial Sequence
<220> FEATURE:
<223> OTHER INFORMATION: Synthetic Construct

<400> SEQUENCE: 52

Glu Glu Met Asp Tyr
1               5

<210> SEQ ID NO 53
<211> LENGTH: 11
<212> TYPE: PRT
<213> ORGANISM: Artificial Sequence
<220> FEATURE:
<223> OTHER INFORMATION: Synthetic Construct

<400> SEQUENCE: 53

Arg Ala Ser Gln Asp Ile Ser Asn Phe Leu Asn
1               5                   10
```

<210> SEQ ID NO 54
<211> LENGTH: 7
<212> TYPE: PRT
<213> ORGANISM: Artificial Sequence
<220> FEATURE:
<223> OTHER INFORMATION: Synthetic Construct

<400> SEQUENCE: 54

Tyr Thr Ser Arg Leu His Ser
1               5

<210> SEQ ID NO 55
<211> LENGTH: 9
<212> TYPE: PRT
<213> ORGANISM: Artificial Sequence
<220> FEATURE:
<223> OTHER INFORMATION: Synthetic Construct

<400> SEQUENCE: 55

Gln Gln Gly Asn Thr Leu Pro Trp Thr
1               5

<210> SEQ ID NO 56
<211> LENGTH: 117
<212> TYPE: PRT
<213> ORGANISM: Artificial Sequence
<220> FEATURE:
<223> OTHER INFORMATION: Synthetic Construct

<400> SEQUENCE: 56

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Ser
            20                  25                  30

Tyr Met Ser Trp Val Arg Gln Ala Pro Gly Gln Gly Leu Glu Trp Ile
        35                  40                  45

Gly Asp Met Tyr Pro Asp Asn Gly Asp Ser Ser Tyr Asn Gln Lys Phe
    50                  55                  60

Arg Glu Arg Val Thr Ile Thr Arg Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Val Leu Ala Pro Arg Trp Tyr Phe Ser Val Trp Gly Gln Gly Thr Leu
            100                 105                 110

Val Thr Val Ser Ser
        115

<210> SEQ ID NO 57
<211> LENGTH: 107
<212> TYPE: PRT
<213> ORGANISM: Artificial Sequence
<220> FEATURE:
<223> OTHER INFORMATION: Synthetic Construct

<400> SEQUENCE: 57

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

```
Tyr Tyr Thr Ser Arg Leu Arg Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly His Thr Leu Pro Pro
                85                  90                  95

Thr Phe Gly Gln Gly Thr Lys Val Glu Ile Lys
            100                 105
```

<210> SEQ ID NO 58
<211> LENGTH: 117
<212> TYPE: PRT
<213> ORGANISM: Artificial Sequence
<220> FEATURE:
<223> OTHER INFORMATION: Synthetic Construct

<400> SEQUENCE: 58

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Ser
                20                  25                  30

Tyr Met Ser Trp Val Arg Gln Ala Pro Gly Gln Gly Leu Glu Trp Ile
            35                  40                  45

Gly Asp Met Tyr Pro Asn Gly Asp Ser Ser Tyr Asn Gln Lys Phe
    50                  55                  60

Arg Glu Arg Val Thr Ile Thr Val Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Val Leu Ala Pro Arg Trp Tyr Phe Ser Val Trp Gly Gln Gly Thr Leu
            100                 105                 110

Val Thr Val Ser Ser
        115
```

<210> SEQ ID NO 59
<211> LENGTH: 107
<212> TYPE: PRT
<213> ORGANISM: Artificial Sequence
<220> FEATURE:
<223> OTHER INFORMATION: Synthetic Construct

<400> SEQUENCE: 59

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
                20                  25                  30

Leu Asn Trp Tyr Gln Gln Lys Pro Gly Lys Ala Pro Lys Leu Leu Ile
            35                  40                  45

Tyr Tyr Thr Ser Arg Leu Arg Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly His Thr Leu Pro Pro
                85                  90                  95

Thr Phe Gly Gln Gly Thr Lys Val Glu Ile Lys
            100                 105
```

<210> SEQ ID NO 60
<211> LENGTH: 117
<212> TYPE: PRT
<213> ORGANISM: Artificial Sequence
<220> FEATURE:
<223> OTHER INFORMATION: Synthetic Construct

<400> SEQUENCE: 60

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Ser
            20                  25                  30

Tyr Met Ser Trp Val Arg Gln Ala Pro Gly Gln Gly Leu Glu Trp Ile
        35                  40                  45

Gly Asp Met Tyr Pro Asp Asn Gly Asp Ser Ser Tyr Asn Gln Lys Phe
    50                  55                  60

Arg Glu Arg Val Thr Leu Thr Val Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Val Leu Ala Pro Arg Trp Tyr Phe Ser Val Trp Gly Gln Gly Thr Leu
            100                 105                 110

Val Thr Val Ser Ser
        115
```

<210> SEQ ID NO 61
<211> LENGTH: 107
<212> TYPE: PRT
<213> ORGANISM: Artificial Sequence
<220> FEATURE:
<223> OTHER INFORMATION: Synthetic Construct

<400> SEQUENCE: 61

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu Arg Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly His Thr Leu Pro Pro
                85                  90                  95

Thr Phe Gly Gln Gly Thr Lys Val Glu Ile Lys
            100                 105
```

<210> SEQ ID NO 62
<211> LENGTH: 117
<212> TYPE: PRT
<213> ORGANISM: Artificial Sequence
<220> FEATURE:
<223> OTHER INFORMATION: Synthetic Construct

<400> SEQUENCE: 62

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Ser
            20                  25                  30
```

Tyr Met Ser Trp Val Arg Gln Ala Pro Gly Gln Gly Leu Glu Trp Ile
            35                  40                  45

Gly Asp Met Tyr Pro Asp Asn Gly Asp Ser Ser Tyr Asn Gln Lys Phe
        50                  55                  60

Arg Glu Arg Val Thr Ile Thr Val Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Val Leu Ala Pro Arg Trp Tyr Phe Ser Val Trp Gly Gln Gly Thr Leu
            100                 105                 110

Val Thr Val Ser Ser
        115

<210> SEQ ID NO 63
<211> LENGTH: 107
<212> TYPE: PRT
<213> ORGANISM: Artificial Sequence
<220> FEATURE:
<223> OTHER INFORMATION: Synthetic Construct

<400> SEQUENCE: 63

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Thr Val Lys Leu Leu Ile
            35                  40                  45

Tyr Tyr Thr Ser Arg Leu Arg Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly His Thr Leu Pro Pro
                85                  90                  95

Thr Phe Gly Gln Gly Thr Lys Val Glu Ile Lys
            100                 105

<210> SEQ ID NO 64
<211> LENGTH: 117
<212> TYPE: PRT
<213> ORGANISM: Artificial Sequence
<220> FEATURE:
<223> OTHER INFORMATION: Synthetic Construct

<400> SEQUENCE: 64

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Ser
            20                  25                  30

Tyr Met Ser Trp Val Arg Gln Ala Pro Gly Gln Gly Leu Glu Trp Ile
            35                  40                  45

Gly Asp Met Tyr Pro Asp Asn Gly Asp Ser Ser Tyr Asn Gln Lys Phe
        50                  55                  60

Arg Glu Arg Val Thr Ile Thr Val Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Val Leu Ala Pro Arg Trp Tyr Phe Ser Val Trp Gly Gln Gly Thr Leu

```
                100             105             110

Val Thr Val Ser Ser
            115

<210> SEQ ID NO 65
<211> LENGTH: 107
<212> TYPE: PRT
<213> ORGANISM: Artificial Sequence
<220> FEATURE:
<223> OTHER INFORMATION: Synthetic Construct

<400> SEQUENCE: 65

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Thr Val Lys Leu Leu Ile
        35                  40                  45

Tyr Tyr Thr Ser Arg Leu Arg Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly His Thr Leu Pro Pro
                85                  90                  95

Thr Phe Gly Gln Gly Thr Lys Val Glu Ile Lys
            100                 105

<210> SEQ ID NO 66
<211> LENGTH: 117
<212> TYPE: PRT
<213> ORGANISM: Artificial Sequence
<220> FEATURE:
<223> OTHER INFORMATION: Synthetic Construct

<400> SEQUENCE: 66

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Ser
            20                  25                  30

Tyr Met Ser Trp Val Arg Gln Ala Pro Gly Gln Gly Leu Glu Trp Ile
        35                  40                  45

Gly Asp Met Tyr Pro Asp Asn Gly Asp Ser Ser Tyr Asn Gln Lys Phe
50                  55                  60

Arg Glu Arg Val Thr Ile Thr Val Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Val Leu Ala Pro Arg Trp Tyr Phe Ser Val Trp Gly Gln Gly Thr Leu
            100                 105                 110

Val Thr Val Ser Ser
            115

<210> SEQ ID NO 67
<211> LENGTH: 107
<212> TYPE: PRT
<213> ORGANISM: Artificial Sequence
<220> FEATURE:
<223> OTHER INFORMATION: Synthetic Construct

<400> SEQUENCE: 67
```

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Thr Val Lys Leu Leu Ile
            35                  40                  45

Tyr Tyr Thr Ser Arg Leu Arg Ser Gly Val Pro Ser Arg Phe Ser Gly
50                  55                  60

Ser Gly Ser Gly Lys Asp Tyr Thr Leu Thr Ile Ser Ser Leu Gln Pro
65                  70                  75                  80

Glu Asp Phe Ala Thr Tyr Phe Cys Gln Gln Gly His Thr Leu Pro Pro
                85                  90                  95

Thr Phe Gly Gln Gly Thr Lys Val Glu Ile Lys
            100                 105

<210> SEQ ID NO 68
<211> LENGTH: 117
<212> TYPE: PRT
<213> ORGANISM: Artificial Sequence
<220> FEATURE:
<223> OTHER INFORMATION: Synthetic Construct

<400> SEQUENCE: 68

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Ser
            20                  25                  30

Tyr Met Ser Trp Val Arg Gln Ala Pro Gly Gln Gly Leu Glu Trp Ile
            35                  40                  45

Gly Asp Met Tyr Pro Asp Asn Gly Asp Ser Ser Tyr Asn Gln Lys Phe
50                  55                  60

Arg Glu Arg Val Thr Ile Thr Val Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Val Leu Ala Pro Arg Trp Tyr Phe Ser Val Trp Gly Gln Gly Thr Leu
            100                 105                 110

Val Thr Val Ser Ser
        115

<210> SEQ ID NO 69
<211> LENGTH: 107
<212> TYPE: PRT
<213> ORGANISM: Artificial Sequence
<220> FEATURE:
<223> OTHER INFORMATION: Synthetic Construct

<400> SEQUENCE: 69

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Thr Val Lys Leu Leu Ile
            35                  40                  45

Tyr Tyr Thr Ser Arg Leu Arg Ser Gly Val Pro Ser Arg Phe Ser Gly
50                  55                  60

Ser Gly Ser Gly Lys Asp Tyr Thr Leu Thr Ile Ser Ser Leu Gln Pro

```
                65                  70                  75                  80
Glu Asp Phe Ala Thr Tyr Phe Cys Gln Gln Gly His Thr Leu Pro Pro
                    85                  90                  95

Thr Phe Gly Gln Gly Thr Lys Val Glu Ile Lys
                100                 105

<210> SEQ ID NO 70
<211> LENGTH: 117
<212> TYPE: PRT
<213> ORGANISM: Artificial Sequence
<220> FEATURE:
<223> OTHER INFORMATION: Synthetic Construct

<400> SEQUENCE: 70

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Ala
                20                  25                  30

Tyr Met Ser Trp Val Arg Gln Ala Pro Gly Gln Gly Leu Glu Trp Ile
            35                  40                  45

Gly Asp Met Tyr Pro Asp Asn Gly Asp Ser Ser Tyr Asn Gln Lys Phe
    50                  55                  60

Arg Glu Arg Val Thr Ile Thr Arg Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Val Leu Ala Pro Arg Trp Tyr Phe Ser Val Trp Gly Gln Gly Thr Leu
                100                 105                 110

Val Thr Val Ser Ser
        115

<210> SEQ ID NO 71
<211> LENGTH: 107
<212> TYPE: PRT
<213> ORGANISM: Artificial Sequence
<220> FEATURE:
<223> OTHER INFORMATION: Synthetic Construct

<400> SEQUENCE: 71

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
                20                  25                  30

Leu Asn Trp Tyr Gln Gln Lys Pro Gly Lys Ala Pro Lys Leu Leu Ile
            35                  40                  45

Tyr Tyr Thr Ser Arg Leu Arg Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly His Thr Leu Pro Pro
                85                  90                  95

Thr Phe Gly Gln Gly Thr Lys Val Glu Ile Lys
                100                 105

<210> SEQ ID NO 72
<211> LENGTH: 117
<212> TYPE: PRT
<213> ORGANISM: Artificial Sequence
<220> FEATURE:
```

<223> OTHER INFORMATION: Synthetic Construct

<400> SEQUENCE: 72

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Glu Ser
            20                  25                  30

Tyr Met Ser Trp Val Arg Gln Ala Pro Gly Gln Gly Leu Glu Trp Ile
        35                  40                  45

Gly Asp Met Tyr Pro Asp Asn Gly Asp Ser Ser Tyr Asn Gln Lys Phe
    50                  55                  60

Arg Glu Arg Val Thr Ile Thr Arg Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Val Leu Ala Pro Arg Trp Tyr Phe Ser Val Trp Gly Gln Gly Thr Leu
            100                 105                 110

Val Thr Val Ser Ser
            115

<210> SEQ ID NO 73
<211> LENGTH: 107
<212> TYPE: PRT
<213> ORGANISM: Artificial Sequence
<220> FEATURE:
<223> OTHER INFORMATION: Synthetic Construct

<400> SEQUENCE: 73

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu Arg Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly His Thr Leu Pro Pro
                85                  90                  95

Thr Phe Gly Gln Gly Thr Lys Val Glu Ile Lys
            100                 105

<210> SEQ ID NO 74
<211> LENGTH: 117
<212> TYPE: PRT
<213> ORGANISM: Artificial Sequence
<220> FEATURE:
<223> OTHER INFORMATION: Synthetic Construct

<400> SEQUENCE: 74

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Ser
            20                  25                  30

Tyr Met Ser Trp Val Arg Gln Ala Pro Gly Gln Gly Leu Glu Trp Ile
        35                  40                  45

Gly Asp Met Tyr Pro Asp Asn Ala Asp Ser Ser Tyr Asn Gln Lys Phe

```
            50                  55                  60
Arg Glu Arg Val Thr Ile Thr Arg Asp Thr Ser Thr Ser Thr Ala Tyr
 65                  70                  75                  80

Leu Glu Leu Ser Ser Leu Arg Ser Glu Asp Thr Ala Val Tyr Tyr Cys
                 85                  90                  95

Val Leu Ala Pro Arg Trp Tyr Phe Ser Val Trp Gly Gln Gly Thr Leu
            100                 105                 110

Val Thr Val Ser Ser
            115

<210> SEQ ID NO 75
<211> LENGTH: 107
<212> TYPE: PRT
<213> ORGANISM: Artificial Sequence
<220> FEATURE:
<223> OTHER INFORMATION: Synthetic Construct

<400> SEQUENCE: 75

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Asp Ile Ser Asn Tyr
             20                  25                  30

Leu Asn Trp Tyr Gln Gln Lys Pro Gly Lys Ala Pro Lys Leu Leu Ile
         35                  40                  45

Tyr Tyr Thr Ser Arg Leu Arg Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Gly His Thr Leu Pro Pro
                 85                  90                  95

Thr Phe Gly Gln Gly Thr Lys Val Glu Ile Lys
            100                 105

<210> SEQ ID NO 76
<211> LENGTH: 117
<212> TYPE: PRT
<213> ORGANISM: Artificial Sequence
<220> FEATURE:
<223> OTHER INFORMATION: Synthetic Construct

<400> SEQUENCE: 76

Glu Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Asp Ser
             20                  25                  30

Tyr Met Ser Trp Val Arg Gln Ala Pro Gly Gln Gly Leu Glu Trp Ile
         35                  40                  45

Gly Asp Met Tyr Pro Asp Asn Ala Asp Ala Ser Tyr Asn Gln Lys Phe
 50                  55                  60

Arg Glu Arg Val Thr Ile Thr Arg Asp Thr Ser Thr Ser Thr Ala Tyr
 65                  70                  75                  80

Leu Glu Leu Ser Ser Leu Arg Ser Glu Asp Thr Ala Val Tyr Tyr Cys
                 85                  90                  95

Val Leu Ala Pro Arg Trp Tyr Phe Ser Val Trp Gly Gln Gly Thr Leu
            100                 105                 110

Val Thr Val Ser Ser
            115
```

```
<210> SEQ ID NO 77
<211> LENGTH: 107
<212> TYPE: PRT
<213> ORGANISM: Artificial Sequence
<220> FEATURE:
<223> OTHER INFORMATION: Synthetic Construct

<400> SEQUENCE: 77

Asp Ile Gln Met Thr Gln Ser Pro Ser Leu Ser Ala Ser Val Gly
1               5                   10                  15

Asp Arg Val Thr Ile Thr Cys Arg Ala Ser Gln Asp Ile Ser Asn Tyr
                20                  25                  30

Leu Asn Trp Tyr Gln Gln Lys Pro Gly Lys Ala Pro Lys Leu Leu Ile
            35                  40                  45

Tyr Tyr Thr Ser Arg Leu Arg Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly His Thr Leu Pro Pro
                85                  90                  95

Thr Phe Gly Gln Gly Thr Lys Val Glu Ile Lys
            100                 105

<210> SEQ ID NO 78
<211> LENGTH: 117
<212> TYPE: PRT
<213> ORGANISM: Artificial Sequence
<220> FEATURE:
<223> OTHER INFORMATION: Synthetic Construct

<400> SEQUENCE: 78

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Ser
                20                  25                  30

Tyr Met Ser Trp Val Arg Gln Ala Pro Gly Gln Gly Leu Glu Trp Ile
            35                  40                  45

Gly Asp Met Tyr Pro Asp Asn Gly Asp Ala Ser Tyr Asn Gln Lys Phe
50                  55                  60

Arg Glu Arg Val Thr Ile Thr Arg Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Val Leu Ala Pro Arg Trp Tyr Phe Ser Val Trp Gly Gln Gly Thr Leu
            100                 105                 110

Val Thr Val Ser Ser
            115

<210> SEQ ID NO 79
<211> LENGTH: 107
<212> TYPE: PRT
<213> ORGANISM: Artificial Sequence
<220> FEATURE:
<223> OTHER INFORMATION: Synthetic Construct

<400> SEQUENCE: 79

Asp Ile Gln Met Thr Gln Ser Pro Ser Leu Ser Ala Ser Val Gly
1               5                   10                  15

Asp Arg Val Thr Ile Thr Cys Arg Ala Ser Gln Asp Ile Ser Asn Tyr
```

20                  25                  30

Leu Asn Trp Tyr Gln Gln Lys Pro Gly Lys Ala Pro Lys Leu Leu Ile
            35                  40                  45

Tyr Tyr Thr Ser Arg Leu Arg Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly His Thr Leu Pro Pro
                85                  90                  95

Thr Phe Gly Gln Gly Thr Lys Val Glu Ile Lys
            100                 105

<210> SEQ ID NO 80
<211> LENGTH: 117
<212> TYPE: PRT
<213> ORGANISM: Artificial Sequence
<220> FEATURE:
<223> OTHER INFORMATION: Synthetic Construct

<400> SEQUENCE: 80

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Ser
            20                  25                  30

Tyr Met Ser Trp Val Arg Gln Ala Pro Gly Gln Gly Leu Glu Trp Ile
        35                  40                  45

Gly Asp Met Tyr Pro Asp Ser Gly Asp Ser Ser Tyr Asn Gln Lys Phe
    50                  55                  60

Arg Glu Arg Val Thr Ile Thr Arg Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Val Leu Ala Pro Arg Trp Tyr Phe Ser Val Trp Gly Gln Gly Thr Leu
            100                 105                 110

Val Thr Val Ser Ser
        115

<210> SEQ ID NO 81
<211> LENGTH: 107
<212> TYPE: PRT
<213> ORGANISM: Artificial Sequence
<220> FEATURE:
<223> OTHER INFORMATION: Synthetic Construct

<400> SEQUENCE: 81

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu Arg Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly His Thr Leu Pro Pro
                85                  90                  95

```
Thr Phe Gly Gln Gly Thr Lys Val Glu Ile Lys
            100                 105
```

<210> SEQ ID NO 82
<211> LENGTH: 117
<212> TYPE: PRT
<213> ORGANISM: Artificial Sequence
<220> FEATURE:
<223> OTHER INFORMATION: Synthetic Construct

<400> SEQUENCE: 82

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Ser
            20                  25                  30

Tyr Met Ser Trp Val Arg Gln Ala Pro Gly Gln Gly Leu Glu Trp Ile
        35                  40                  45

Gly Asp Met Tyr Pro Asp Asn Gly Ser Ser Tyr Asn Gln Lys Phe
    50                  55                  60

Arg Glu Arg Val Thr Ile Thr Arg Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Val Leu Ala Pro Arg Trp Tyr Phe Ser Val Trp Gly Gln Gly Thr Leu
            100                 105                 110

Val Thr Val Ser Ser
        115
```

<210> SEQ ID NO 83
<211> LENGTH: 107
<212> TYPE: PRT
<213> ORGANISM: Artificial Sequence
<220> FEATURE:
<223> OTHER INFORMATION: Synthetic Construct

<400> SEQUENCE: 83

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu Arg Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly His Thr Leu Pro Pro
                85                  90                  95

Thr Phe Gly Gln Gly Thr Lys Val Glu Ile Lys
            100                 105
```

<210> SEQ ID NO 84
<211> LENGTH: 117
<212> TYPE: PRT
<213> ORGANISM: Artificial Sequence
<220> FEATURE:
<223> OTHER INFORMATION: Synthetic Construct

<400> SEQUENCE: 84

```
Glu Val Gln Leu Val Gln Ser Gly Ala Glu Val Lys Lys Pro Gly Ala
```

```
                1               5                   10                  15
            Ser Val Lys Val Ser Cys Lys Ala Ser Gly Tyr Thr Phe Thr Asp Ala
                            20                  25                  30

Tyr Met Ser Trp Val Arg Gln Ala Pro Gly Gln Gly Leu Glu Trp Ile
                        35                  40                  45

Gly Asp Met Tyr Pro Asp Asn Ala Asp Ala Ser Tyr Asn Gln Lys Phe
                    50                  55                  60

Arg Glu Arg Val Thr Ile Thr Arg Asp Thr Ser Thr Ser Thr Ala Tyr
             65                 70                  75                  80

Leu Glu Leu Ser Ser Leu Arg Ser Glu Asp Thr Ala Val Tyr Tyr Cys
                            85                  90                  95

Val Leu Ala Pro Arg Trp Tyr Phe Ser Val Trp Gly Gln Gly Thr Leu
                        100                 105                 110

Val Thr Val Ser Ser
                        115

<210> SEQ ID NO 85
<211> LENGTH: 107
<212> TYPE: PRT
<213> ORGANISM: Artificial Sequence
<220> FEATURE:
<223> OTHER INFORMATION: Synthetic Construct

<400> SEQUENCE: 85

Asp Ile Gln Met Thr Gln Ser Pro Ser Ser Leu Ser Ala Ser Val Gly
 1               5                   10                  15

Asp Arg Val Thr Ile Thr Cys Arg Ala Ser Gln Asp Ile Ser Asn Tyr
                20                  25                  30

Leu Asn Trp Tyr Gln Gln Lys Pro Gly Lys Ala Pro Lys Leu Leu Ile
            35                  40                  45

Tyr Tyr Thr Ser Arg Leu Arg Ser Gly Val Pro Ser Arg Phe Ser Gly
        50                  55                  60

Ser Gly Ser Gly Thr Asp Phe Thr Leu Thr Ile Ser Ser Leu Gln Pro
 65                 70                  75                  80

Glu Asp Phe Ala Thr Tyr Tyr Cys Gln Gln Gly His Thr Leu Pro Pro
                85                  90                  95

Thr Phe Gly Gln Gly Thr Lys Val Glu Ile Lys
            100                 105

<210> SEQ ID NO 86
<211> LENGTH: 117
<212> TYPE: PRT
<213> ORGANISM: Artificial Sequence
<220> FEATURE:
<223> OTHER INFORMATION: Synthetic Construct

<400> SEQUENCE: 86

Glu Val Gln Leu Val Gln Ser Gly Ala Glu Val Lys Lys Pro Gly Ala
 1               5                   10                  15

Ser Val Lys Val Ser Cys Lys Ala Ser Gly Tyr Thr Phe Thr Asp Ser
                20                  25                  30

Tyr Met Ser Trp Val Arg Gln Ala Pro Gly Gln Gly Leu Glu Trp Ile
            35                  40                  45

Gly Asp Met Tyr Pro Asp Asn Gly Asp Ser Tyr Asn Gln Lys Phe
        50                  55                  60

Arg Glu Arg Val Thr Ile Thr Arg Asp Thr Ser Thr Ser Thr Ala Tyr
 65                 70                  75                  80
```

```
Leu Glu Leu Ser Ser Leu Arg Ser Glu Asp Thr Ala Val Tyr Tyr Cys
                85                  90                  95

Val Leu Ala Pro Arg Trp Tyr Phe Ser Val Trp Gly Gln Gly Thr Leu
            100                 105                 110

Val Thr Val Ser Ser
            115

<210> SEQ ID NO 87
<211> LENGTH: 107
<212> TYPE: PRT
<213> ORGANISM: Artificial Sequence
<220> FEATURE:
<223> OTHER INFORMATION: Synthetic Construct

<400> SEQUENCE: 87

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu Arg Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly His Thr Leu Pro Ala
                85                  90                  95

Thr Phe Gly Gln Gly Thr Lys Val Glu Ile Lys
            100                 105

<210> SEQ ID NO 88
<211> LENGTH: 117
<212> TYPE: PRT
<213> ORGANISM: Artificial Sequence
<220> FEATURE:
<223> OTHER INFORMATION: Synthetic Construct

<400> SEQUENCE: 88

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Ser
            20                  25                  30

Tyr Met Ser Trp Val Arg Gln Ala Pro Gly Gln Gly Leu Glu Trp Ile
        35                  40                  45

Gly Asp Met Tyr Pro Asp Asn Gly Asp Ser Ser Tyr Asn Gln Lys Phe
50                  55                  60

Arg Glu Arg Val Thr Ile Thr Arg Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Val Leu Ala Pro Arg Trp Tyr Phe Ser Val Trp Gly Gln Gly Thr Leu
            100                 105                 110

Val Thr Val Ser Ser
            115

<210> SEQ ID NO 89
<211> LENGTH: 107
<212> TYPE: PRT
<213> ORGANISM: Artificial Sequence
```

```
<220> FEATURE:
<223> OTHER INFORMATION: Synthetic Construct

<400> SEQUENCE: 89

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu Arg Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Thr Ala Pro Pro
                85                  90                  95

Thr Phe Gly Gln Gly Thr Lys Val Glu Ile Lys
            100                 105

<210> SEQ ID NO 90
<211> LENGTH: 117
<212> TYPE: PRT
<213> ORGANISM: Artificial Sequence
<220> FEATURE:
<223> OTHER INFORMATION: Synthetic Construct

<400> SEQUENCE: 90

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Ser
            20                  25                  30

Tyr Met Ser Trp Val Arg Gln Ala Pro Gly Gln Gly Leu Glu Trp Ile
        35                  40                  45

Gly Asp Met Tyr Pro Asp Asn Gly Asp Ser Ser Tyr Asn Gln Lys Phe
    50                  55                  60

Arg Glu Arg Val Thr Ile Thr Arg Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Val Leu Ala Pro Arg Trp Tyr Phe Ser Val Trp Gly Gln Gly Thr Leu
            100                 105                 110

Val Thr Val Ser Ser
        115

<210> SEQ ID NO 91
<211> LENGTH: 107
<212> TYPE: PRT
<213> ORGANISM: Artificial Sequence
<220> FEATURE:
<223> OTHER INFORMATION: Synthetic Construct

<400> SEQUENCE: 91

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45
```

-continued

Tyr Tyr Thr Ser Arg Leu Arg Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Ala Thr Leu Pro Pro
                85                  90                  95

Thr Phe Gly Gln Gly Thr Lys Val Glu Ile Lys
            100                 105

<210> SEQ ID NO 92
<211> LENGTH: 117
<212> TYPE: PRT
<213> ORGANISM: Artificial Sequence
<220> FEATURE:
<223> OTHER INFORMATION: Synthetic Construct

<400> SEQUENCE: 92

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Ser
                20                  25                  30

Tyr Met Ser Trp Val Arg Gln Ala Pro Gly Gln Gly Leu Glu Trp Ile
            35                  40                  45

Gly Asp Met Tyr Pro Asp Asn Gly Asp Ser Ser Tyr Asn Gln Lys Phe
    50                  55                  60

Arg Glu Arg Val Thr Ile Thr Arg Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Val Leu Ala Pro Arg Trp Tyr Phe Ser Val Trp Gly Gln Gly Thr Leu
            100                 105                 110

Val Thr Val Ser Ser
        115

<210> SEQ ID NO 93
<211> LENGTH: 107
<212> TYPE: PRT
<213> ORGANISM: Artificial Sequence
<220> FEATURE:
<223> OTHER INFORMATION: Synthetic Construct

<400> SEQUENCE: 93

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
                20                  25                  30

Leu Asn Trp Tyr Gln Gln Lys Pro Gly Lys Ala Pro Lys Leu Leu Ile
            35                  40                  45

Tyr Tyr Thr Ser Arg Leu Arg Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly His Ala Leu Pro Pro
                85                  90                  95

Thr Phe Gly Gln Gly Thr Lys Val Glu Ile Lys
            100                 105

<210> SEQ ID NO 94

```
<211> LENGTH: 117
<212> TYPE: PRT
<213> ORGANISM: Artificial Sequence
<220> FEATURE:
<223> OTHER INFORMATION: Synthetic Construct

<400> SEQUENCE: 94

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Ser
            20                  25                  30

Tyr Met Ser Trp Val Arg Gln Ala Pro Gly Gln Gly Leu Glu Trp Ile
        35                  40                  45

Gly Asp Met Tyr Pro Asp Asn Gly Asp Ser Ser Tyr Asn Gln Lys Phe
    50                  55                  60

Arg Glu Arg Val Thr Ile Thr Arg Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Val Leu Ala Pro Arg Trp Tyr Phe Ser Val Trp Gly Gln Gly Thr Leu
            100                 105                 110

Val Thr Val Ser Ser
            115

<210> SEQ ID NO 95
<211> LENGTH: 107
<212> TYPE: PRT
<213> ORGANISM: Artificial Sequence
<220> FEATURE:
<223> OTHER INFORMATION: Synthetic Construct

<400> SEQUENCE: 95

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu Arg Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala His Thr Leu Pro Pro
                85                  90                  95

Thr Phe Gly Gln Gly Thr Lys Val Glu Ile Lys
            100                 105

<210> SEQ ID NO 96
<211> LENGTH: 117
<212> TYPE: PRT
<213> ORGANISM: Artificial Sequence
<220> FEATURE:
<223> OTHER INFORMATION: Synthetic Construct

<400> SEQUENCE: 96

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Ser
            20                  25                  30
```

Tyr Met Ser Trp Val Arg Gln Ala Pro Gly Gln Gly Leu Glu Trp Ile
            35                  40                  45

Gly Asp Met Tyr Pro Asp Asn Gly Asp Ser Ser Tyr Asn Gln Lys Phe
 50                  55                  60

Arg Glu Arg Val Thr Ile Thr Arg Asp Thr Ser Thr Ser Thr Ala Tyr
 65                  70                  75                  80

Leu Glu Leu Ser Ser Leu Arg Ser Glu Asp Thr Ala Val Tyr Tyr Cys
                 85                  90                  95

Val Leu Ala Pro Arg Trp Tyr Phe Ser Val Trp Gly Gln Gly Thr Leu
            100                 105                 110

Val Thr Val Ser Ser
            115

<210> SEQ ID NO 97
<211> LENGTH: 107
<212> TYPE: PRT
<213> ORGANISM: Artificial Sequence
<220> FEATURE:
<223> OTHER INFORMATION: Synthetic Construct

<400> SEQUENCE: 97

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Ala Pro Lys Leu Leu Ile
         35                  40                  45

Tyr Tyr Thr Ser Arg Leu Arg Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Gly His Thr Leu Ala Pro
                 85                  90                  95

Thr Phe Gly Gln Gly Thr Lys Val Glu Ile Lys
            100                 105

<210> SEQ ID NO 98
<211> LENGTH: 117
<212> TYPE: PRT
<213> ORGANISM: Artificial Sequence
<220> FEATURE:
<223> OTHER INFORMATION: Synthetic Construct

<400> SEQUENCE: 98

Glu Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Asp Ser
            20                  25                  30

Tyr Met Ser Trp Val Arg Gln Ala Pro Gly Gln Gly Leu Glu Trp Ile
            35                  40                  45

Gly Asp Met Tyr Pro Asp Asn Gly Asp Ser Ser Tyr Asn Gln Lys Phe
 50                  55                  60

Arg Glu Arg Val Thr Ile Thr Arg Asp Thr Ser Thr Ser Thr Ala Tyr
 65                  70                  75                  80

Leu Glu Leu Ser Ser Leu Arg Ser Glu Asp Thr Ala Val Tyr Tyr Cys
                 85                  90                  95

Val Leu Ala Pro Arg Trp Tyr Phe Ser Val Trp Gly Gln Gly Thr Leu
            100                 105                 110

Val Thr Val Ser Ser
        115

<210> SEQ ID NO 99
<211> LENGTH: 107
<212> TYPE: PRT
<213> ORGANISM: Artificial Sequence
<220> FEATURE:
<223> OTHER INFORMATION: Synthetic Construct

<400> SEQUENCE: 99

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu Arg Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Ala Gly His Thr Leu Pro Pro
                85                  90                  95

Thr Phe Gly Gln Gly Thr Lys Val Glu Ile Lys
            100                 105

<210> SEQ ID NO 100
<211> LENGTH: 117
<212> TYPE: PRT
<213> ORGANISM: Artificial Sequence
<220> FEATURE:
<223> OTHER INFORMATION: Synthetic Construct

<400> SEQUENCE: 100

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Ser
            20                  25                  30

Tyr Met Ser Trp Val Arg Gln Ala Pro Gly Gln Gly Leu Glu Trp Ile
        35                  40                  45

Gly Asp Met Tyr Pro Asp Asn Gly Asp Ser Ser Tyr Asn Gln Lys Phe
    50                  55                  60

Arg Glu Arg Val Thr Ile Thr Arg Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Val Leu Ala Pro Arg Trp Tyr Phe Ser Ala Trp Gly Gln Gly Thr Leu
            100                 105                 110

Val Thr Val Ser Ser
        115

<210> SEQ ID NO 101
<211> LENGTH: 107
<212> TYPE: PRT
<213> ORGANISM: Artificial Sequence
<220> FEATURE:
<223> OTHER INFORMATION: Synthetic Construct

<400> SEQUENCE: 101

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu Arg Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly His Thr Leu Pro Pro
                85                  90                  95

Thr Phe Gly Gln Gly Thr Lys Val Glu Ile Lys
            100                 105
```

<210> SEQ ID NO 102
<211> LENGTH: 117
<212> TYPE: PRT
<213> ORGANISM: Artificial Sequence
<220> FEATURE:
<223> OTHER INFORMATION: Synthetic Construct

<400> SEQUENCE: 102

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Ser
            20                  25                  30

Tyr Met Ser Trp Val Arg Gln Ala Pro Gly Gln Gly Leu Glu Trp Ile
        35                  40                  45

Gly Asp Met Tyr Pro Asn Gly Asp Ser Ser Tyr Asn Gln Lys Phe
50                  55                  60

Arg Glu Arg Val Thr Ile Thr Arg Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Val Leu Ala Pro Arg Trp Tyr Ala Ser Val Trp Gly Gln Gly Thr Leu
            100                 105                 110

Val Thr Val Ser Ser
        115
```

<210> SEQ ID NO 103
<211> LENGTH: 107
<212> TYPE: PRT
<213> ORGANISM: Artificial Sequence
<220> FEATURE:
<223> OTHER INFORMATION: Synthetic Construct

<400> SEQUENCE: 103

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu Arg Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80
```

Glu Asp Phe Ala Thr Tyr Tyr Cys Gln Gln Gly His Thr Leu Pro Pro
                85                  90                  95

Thr Phe Gly Gln Gly Thr Lys Val Glu Ile Lys
            100                 105

<210> SEQ ID NO 104
<211> LENGTH: 117
<212> TYPE: PRT
<213> ORGANISM: Artificial Sequence
<220> FEATURE:
<223> OTHER INFORMATION: Synthetic Construct

<400> SEQUENCE: 104

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Ser
            20                  25                  30

Tyr Met Ser Trp Val Arg Gln Ala Pro Gly Gln Gly Leu Glu Trp Ile
        35                  40                  45

Gly Asp Met Tyr Pro Asp Asn Gly Asp Ser Ser Tyr Asn Gln Lys Phe
    50                  55                  60

Arg Glu Arg Val Thr Ile Thr Arg Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Val Leu Ala Pro Arg Trp Ala Phe Ser Val Trp Gly Gln Gly Thr Leu
            100                 105                 110

Val Thr Val Ser Ser
        115

<210> SEQ ID NO 105
<211> LENGTH: 107
<212> TYPE: PRT
<213> ORGANISM: Artificial Sequence
<220> FEATURE:
<223> OTHER INFORMATION: Synthetic Construct

<400> SEQUENCE: 105

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu Arg Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly His Thr Leu Pro Pro
                85                  90                  95

Thr Phe Gly Gln Gly Thr Lys Val Glu Ile Lys
            100                 105

<210> SEQ ID NO 106
<211> LENGTH: 117
<212> TYPE: PRT
<213> ORGANISM: Artificial Sequence
<220> FEATURE:
<223> OTHER INFORMATION: Synthetic Construct

<400> SEQUENCE: 106

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Ser
            20                  25                  30

Tyr Met Ser Trp Val Arg Gln Ala Pro Gly Gln Gly Leu Glu Trp Ile
        35                  40                  45

Gly Asp Met Tyr Pro Asp Asn Gly Asp Ser Ser Tyr Asn Gln Lys Phe
    50                  55                  60

Arg Glu Arg Val Thr Ile Thr Arg Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Val Leu Ala Pro Ala Trp Tyr Phe Ser Val Trp Gly Gln Gly Thr Leu
                100                 105                 110

Val Thr Val Ser Ser
            115

<210> SEQ ID NO 107
<211> LENGTH: 107
<212> TYPE: PRT
<213> ORGANISM: Artificial Sequence
<220> FEATURE:
<223> OTHER INFORMATION: Synthetic Construct

<400> SEQUENCE: 107

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu Arg Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly His Thr Leu Pro Pro
                85                  90                  95

Thr Phe Gly Gln Gly Thr Lys Val Glu Ile Lys
            100                 105

<210> SEQ ID NO 108
<211> LENGTH: 117
<212> TYPE: PRT
<213> ORGANISM: Artificial Sequence
<220> FEATURE:
<223> OTHER INFORMATION: Synthetic Construct

<400> SEQUENCE: 108

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Ser
            20                  25                  30

Tyr Met Ser Trp Val Arg Gln Ala Pro Gly Gln Gly Leu Glu Trp Ile
        35                  40                  45

Gly Asp Met Tyr Pro Asp Asn Gly Asp Ser Ser Tyr Asn Gln Lys Phe
    50                  55                  60

```
Arg Glu Arg Val Thr Ile Thr Arg Asp Thr Ser Thr Ser Thr Ala Tyr
 65                  70                  75                  80

Leu Glu Leu Ser Ser Leu Arg Ser Glu Asp Thr Ala Val Tyr Tyr Cys
                 85                  90                  95

Val Leu Ala Pro Arg Trp Tyr Phe Ala Val Trp Gly Gln Gly Thr Leu
            100                 105                 110

Val Thr Val Ser Ser
            115

<210> SEQ ID NO 109
<211> LENGTH: 107
<212> TYPE: PRT
<213> ORGANISM: Artificial Sequence
<220> FEATURE:
<223> OTHER INFORMATION: Synthetic Construct

<400> SEQUENCE: 109

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Asp Ile Ser Asn Tyr
             20                  25                  30

Leu Asn Trp Tyr Gln Gln Lys Pro Gly Lys Ala Pro Lys Leu Leu Ile
         35                  40                  45

Tyr Tyr Thr Ser Arg Leu Arg Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Gly His Thr Leu Pro Pro
                 85                  90                  95

Thr Phe Gly Gln Gly Thr Lys Val Glu Ile Lys
            100                 105

<210> SEQ ID NO 110
<211> LENGTH: 117
<212> TYPE: PRT
<213> ORGANISM: Artificial Sequence
<220> FEATURE:
<223> OTHER INFORMATION: Synthetic Construct

<400> SEQUENCE: 110

Glu Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Asp Ser
             20                  25                  30

Tyr Met Ser Trp Val Arg Gln Ala Pro Gly Gln Gly Leu Glu Trp Ile
         35                  40                  45

Gly Asp Met Tyr Pro Asp Asn Gly Asp Ser Ser Tyr Asn Gln Lys Phe
 50                  55                  60

Arg Glu Arg Val Thr Ile Thr Arg Asp Thr Ser Thr Ser Thr Ala Tyr
 65                  70                  75                  80

Leu Glu Leu Ser Ser Leu Arg Ser Glu Asp Thr Ala Val Tyr Tyr Cys
                 85                  90                  95

Val Leu Ala Pro Arg Ala Tyr Phe Ser Val Trp Gly Gln Gly Thr Leu
            100                 105                 110

Val Thr Val Ser Ser
            115
```

```
<210> SEQ ID NO 111
<211> LENGTH: 107
<212> TYPE: PRT
<213> ORGANISM: Artificial Sequence
<220> FEATURE:
<223> OTHER INFORMATION: Synthetic Construct

<400> SEQUENCE: 111
```

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu Arg Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly His Thr Leu Pro Pro
                85                  90                  95

Thr Phe Gly Gln Gly Thr Lys Val Glu Ile Lys
            100                 105

```
<210> SEQ ID NO 112
<211> LENGTH: 117
<212> TYPE: PRT
<213> ORGANISM: Artificial Sequence
<220> FEATURE:
<223> OTHER INFORMATION: Synthetic Construct

<400> SEQUENCE: 112
```

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Ser
            20                  25                  30

Tyr Met Ser Trp Val Arg Gln Ala Pro Gly Gln Gly Leu Glu Trp Ile
        35                  40                  45

Gly Asp Met Tyr Pro Asp Asn Gly Asp Ser Ser Tyr Asn Gln Lys Phe
50                  55                  60

Arg Glu Arg Val Thr Ile Thr Arg Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Val Leu Ala Ala Arg Trp Tyr Phe Ser Val Trp Gly Gln Gly Thr Leu
            100                 105                 110

Val Thr Val Ser Ser
        115

```
<210> SEQ ID NO 113
<211> LENGTH: 107
<212> TYPE: PRT
<213> ORGANISM: Artificial Sequence
<220> FEATURE:
<223> OTHER INFORMATION: Synthetic Construct

<400> SEQUENCE: 113
```

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

```
Leu Asn Trp Tyr Gln Gln Lys Pro Gly Lys Ala Pro Lys Leu Leu Ile
             35                  40                  45

Tyr Tyr Thr Ser Arg Leu Arg Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Gly His Thr Leu Pro Pro
                 85                  90                  95

Thr Phe Gly Gln Gly Thr Lys Val Glu Ile Lys
            100                 105

<210> SEQ ID NO 114
<211> LENGTH: 117
<212> TYPE: PRT
<213> ORGANISM: Artificial Sequence
<220> FEATURE:
<223> OTHER INFORMATION: Synthetic Construct

<400> SEQUENCE: 114

Glu Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Asp Ser
                 20                  25                  30

Tyr Met Ser Trp Val Arg Gln Ala Pro Gly Gln Gly Leu Glu Trp Ile
             35                  40                  45

Gly Asp Met Tyr Pro Asp Asn Gly Asp Ser Ser Tyr Asn Gln Lys Phe
 50                  55                  60

Arg Glu Arg Val Thr Ile Thr Arg Asp Thr Ser Thr Ser Thr Ala Tyr
 65                  70                  75                  80

Leu Glu Leu Ser Ser Leu Arg Ser Glu Asp Thr Ala Val Tyr Tyr Cys
                 85                  90                  95

Ala Leu Ala Pro Arg Trp Tyr Phe Ser Val Trp Gly Gln Gly Thr Leu
                100                 105                 110

Val Thr Val Ser Ser
        115

<210> SEQ ID NO 115
<211> LENGTH: 107
<212> TYPE: PRT
<213> ORGANISM: Artificial Sequence
<220> FEATURE:
<223> OTHER INFORMATION: Synthetic Construct

<400> SEQUENCE: 115

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Asp Ile Ser Asn Tyr
                 20                  25                  30

Leu Asn Trp Tyr Gln Gln Lys Pro Gly Lys Ala Pro Lys Leu Leu Ile
             35                  40                  45

Tyr Tyr Thr Ser Arg Leu Arg Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Gly His Thr Leu Pro Pro
                 85                  90                  95

Thr Phe Gly Gln Gly Thr Lys Val Glu Ile Lys
```

<210> SEQ ID NO 116
<211> LENGTH: 117
<212> TYPE: PRT
<213> ORGANISM: Artificial Sequence
<220> FEATURE:
<223> OTHER INFORMATION: Synthetic Construct

<400> SEQUENCE: 116

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Ser
            20                  25                  30

Tyr Met Ser Trp Val Arg Gln Ala Pro Gly Gln Gly Leu Glu Trp Ile
        35                  40                  45

Gly Asp Met Tyr Pro Asp Asn Gly Asp Ser Ser Tyr Asn Gln Lys Phe
    50                  55                  60

Arg Glu Arg Val Thr Ile Thr Arg Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Val Ala Ala Pro Arg Trp Tyr Phe Ser Val Trp Gly Gln Gly Thr Leu
            100                 105                 110

Val Thr Val Ser Ser
        115

<210> SEQ ID NO 117
<211> LENGTH: 107
<212> TYPE: PRT
<213> ORGANISM: Artificial Sequence
<220> FEATURE:
<223> OTHER INFORMATION: Synthetic Construct

<400> SEQUENCE: 117

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu Arg Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly His Thr Leu Pro Pro
                85                  90                  95

Thr Phe Gly Gln Gly Thr Lys Val Glu Ile Lys
            100                 105

<210> SEQ ID NO 118
<211> LENGTH: 114
<212> TYPE: PRT
<213> ORGANISM: Artificial Sequence
<220> FEATURE:
<223> OTHER INFORMATION: Synthetic Construct

<400> SEQUENCE: 118

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Thr Asn Tyr
            20                  25                  30

Leu Ile Glu Trp Val Arg Gln Ala Pro Gly Gln Gly Leu Glu Trp Ile
        35                  40                  45

Gly Val Ile Asn Pro Gly Ser Gly Asp Thr Tyr Tyr Ser Glu Lys Phe
    50                  55                  60

Lys Gly Arg Val Thr Ile Thr Arg Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Asp Arg Leu Asp Tyr Trp Gly Gln Gly Thr Leu Val Thr Val
                100                 105                 110

Ser Ser

<210> SEQ ID NO 119
<211> LENGTH: 107
<212> TYPE: PRT
<213> ORGANISM: Artificial Sequence
<220> FEATURE:
<223> OTHER INFORMATION: Synthetic Construct

<400> SEQUENCE: 119

Asp Ile Gln Met Thr Gln Ser Pro Ser Ser Leu Ser Ala Ser Val Gly
1               5                   10                  15

Asp Arg Val Thr Ile Thr Cys His Ala Ser Gln Asp Ile Ser Ser Tyr
            20                  25                  30

Ile Val Trp Tyr Gln Gln Lys Pro Gly Lys Ala Pro Lys Leu Leu Ile
        35                  40                  45

Tyr His Gly Thr Asn Leu Glu Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Val His Tyr Ala Gln Phe Pro Tyr
                85                  90                  95

Thr Phe Gly Gln Gly Thr Lys Val Glu Ile Lys
                100                 105

<210> SEQ ID NO 120
<211> LENGTH: 114
<212> TYPE: PRT
<213> ORGANISM: Artificial Sequence
<220> FEATURE:
<223> OTHER INFORMATION: Synthetic Construct

<400> SEQUENCE: 120

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Thr Asn Tyr
            20                  25                  30

Leu Ile Glu Trp Val Arg Gln Ala Pro Gly Gln Gly Leu Glu Trp Ile
        35                  40                  45

Gly Val Ile Asn Pro Gly Ser Gly Asp Thr Tyr Tyr Ser Glu Lys Phe
    50                  55                  60

Lys Gly Arg Val Thr Ile Thr Ala Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Asp Arg Leu Asp Tyr Trp Gly Gln Gly Thr Leu Val Thr Val
            100                 105                 110
Ser Ser

<210> SEQ ID NO 121
<211> LENGTH: 107
<212> TYPE: PRT
<213> ORGANISM: Artificial Sequence
<220> FEATURE:
<223> OTHER INFORMATION: Synthetic Construct

<400> SEQUENCE: 121

Asp Ile Gln Met Thr Gln Ser Pro Ser Ser Leu Ser Ala Ser Val Gly
1               5                   10                  15

Asp Arg Val Thr Ile Thr Cys His Ala Ser Gln Asp Ile Ser Ser Tyr
            20                  25                  30

Ile Val Trp Tyr Gln Gln Lys Pro Gly Lys Ala Pro Lys Leu Leu Ile
        35                  40                  45

Tyr His Gly Thr Asn Leu Glu Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Val His Tyr Ala Gln Phe Pro Tyr
                85                  90                  95

Thr Phe Gly Gln Gly Thr Lys Val Glu Ile Lys
            100                 105

<210> SEQ ID NO 122
<211> LENGTH: 114
<212> TYPE: PRT
<213> ORGANISM: Artificial Sequence
<220> FEATURE:
<223> OTHER INFORMATION: Synthetic Construct

<400> SEQUENCE: 122

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Thr Asn Tyr
            20                  25                  30

Leu Ile Glu Trp Val Arg Gln Ala Pro Gly Gln Gly Leu Glu Trp Ile
        35                  40                  45

Gly Val Ile Asn Pro Gly Ser Gly Asp Thr Tyr Tyr Ser Glu Lys Phe
    50                  55                  60

Lys Gly Arg Val Thr Leu Thr Ala Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Asp Arg Leu Asp Tyr Trp Gly Gln Gly Thr Leu Val Thr Val
            100                 105                 110
Ser Ser

<210> SEQ ID NO 123
<211> LENGTH: 107
<212> TYPE: PRT
<213> ORGANISM: Artificial Sequence
<220> FEATURE:
<223> OTHER INFORMATION: Synthetic Construct

<400> SEQUENCE: 123

```
Asp Ile Gln Met Thr Gln Ser Pro Ser Ser Leu Ser Ala Ser Val Gly
1               5                   10                  15

Asp Arg Val Thr Ile Thr Cys His Ala Ser Gln Asp Ile Ser Ser Tyr
            20                  25                  30

Ile Val Trp Tyr Gln Gln Lys Pro Gly Lys Ala Pro Lys Leu Leu Ile
            35                  40                  45

Tyr His Gly Thr Asn Leu Glu Asp Gly Val Pro Ser Arg Phe Ser Gly
    50                  55                  60

Ser Gly Ser Gly Thr Asp Phe Thr Leu Thr Ile Ser Ser Leu Gln Pro
65              70                  75                  80

Glu Asp Phe Ala Thr Tyr Tyr Cys Val His Tyr Ala Gln Phe Pro Tyr
                85                  90                  95

Thr Phe Gly Gln Gly Thr Lys Val Glu Ile Lys
                100                 105
```

<210> SEQ ID NO 124
<211> LENGTH: 114
<212> TYPE: PRT
<213> ORGANISM: Artificial Sequence
<220> FEATURE:
<223> OTHER INFORMATION: Synthetic Construct

<400> SEQUENCE: 124

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Thr Asn Tyr
            20                  25                  30

Leu Ile Glu Trp Val Arg Gln Ala Pro Gly Gln Gly Leu Glu Trp Ile
            35                  40                  45

Gly Val Ile Asn Pro Gly Ser Gly Asp Thr Tyr Tyr Ser Glu Lys Phe
    50                  55                  60

Lys Gly Arg Val Thr Ile Thr Ala Asp Thr Ser Thr Ser Thr Ala Tyr
65              70                  75                  80

Leu Glu Leu Ser Ser Leu Arg Ser Glu Asp Thr Ala Val Tyr Tyr Cys
                85                  90                  95

Ala Arg Asp Arg Leu Asp Tyr Trp Gly Gln Gly Thr Leu Val Thr Val
                100                 105                 110

Ser Ser
```

<210> SEQ ID NO 125
<211> LENGTH: 107
<212> TYPE: PRT
<213> ORGANISM: Artificial Sequence
<220> FEATURE:
<223> OTHER INFORMATION: Synthetic Construct

<400> SEQUENCE: 125

```
Asp Ile Gln Met Thr Gln Ser Pro Ser Ser Leu Ser Ala Ser Val Gly
1               5                   10                  15

Asp Arg Val Thr Ile Thr Cys His Ala Ser Gln Asp Ile Ser Ser Tyr
            20                  25                  30

Ile Val Trp Tyr Gln Gln Lys Pro Gly Lys Ser Phe Lys Gly Leu Ile
            35                  40                  45

Tyr His Gly Thr Asn Leu Glu Asp Gly Val Pro Ser Arg Phe Ser Gly
    50                  55                  60

Ser Gly Ser Gly Thr Asp Phe Thr Leu Thr Ile Ser Ser Leu Gln Pro
65              70                  75                  80
```

Glu Asp Phe Ala Thr Tyr Tyr Cys Val His Tyr Ala Gln Phe Pro Tyr
                85                  90                  95

Thr Phe Gly Gln Gly Thr Lys Val Glu Ile Lys
                100                 105

<210> SEQ ID NO 126
<211> LENGTH: 114
<212> TYPE: PRT
<213> ORGANISM: Artificial Sequence
<220> FEATURE:
<223> OTHER INFORMATION: Synthetic Construct

<400> SEQUENCE: 126

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Thr Asn Tyr
                20                  25                  30

Leu Ile Glu Trp Val Arg Gln Ala Pro Gly Gln Gly Leu Glu Trp Ile
            35                  40                  45

Gly Val Ile Asn Pro Gly Ser Gly Asp Thr Tyr Tyr Ser Glu Lys Phe
        50                  55                  60

Lys Gly Arg Val Thr Leu Thr Ala Asp Thr Ser Ser Thr Thr Ala Tyr
65                  70                  75                  80

Leu Glu Leu Ser Ser Leu Arg Ser Glu Asp Thr Ala Val Tyr Tyr Cys
                85                  90                  95

Ala Arg Asp Arg Leu Asp Tyr Trp Gly Gln Gly Thr Leu Val Thr Val
                100                 105                 110

Ser Ser

<210> SEQ ID NO 127
<211> LENGTH: 107
<212> TYPE: PRT
<213> ORGANISM: Artificial Sequence
<220> FEATURE:
<223> OTHER INFORMATION: Synthetic Construct

<400> SEQUENCE: 127

Asp Ile Gln Met Thr Gln Ser Pro Ser Ser Leu Ser Ala Ser Val Gly
1               5                   10                  15

Asp Arg Val Thr Ile Thr Cys His Ala Ser Gln Asp Ile Ser Ser Tyr
                20                  25                  30

Ile Val Trp Tyr Gln Gln Lys Pro Gly Lys Ser Phe Lys Gly Leu Ile
            35                  40                  45

Tyr His Gly Thr Asn Leu Glu Asp Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Val His Tyr Ala Gln Phe Pro Tyr
                85                  90                  95

Thr Phe Gly Gln Gly Thr Lys Val Glu Ile Lys
                100                 105

<210> SEQ ID NO 128
<211> LENGTH: 114
<212> TYPE: PRT
<213> ORGANISM: Artificial Sequence
<220> FEATURE:
<223> OTHER INFORMATION: Synthetic Construct

<400> SEQUENCE: 128

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Thr Asn Tyr
            20                  25                  30

Leu Ile Glu Trp Val Arg Gln Ala Pro Gly Gln Gly Leu Glu Trp Ile
        35                  40                  45

Gly Val Ile Asn Pro Gly Ser Gly Asp Thr Tyr Tyr Ser Glu Lys Phe
    50                  55                  60

Lys Gly Arg Val Thr Leu Thr Ala Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Asp Arg Leu Asp Tyr Trp Gly Gln Gly Thr Leu Val Thr Val
            100                 105                 110

Ser Ser

<210> SEQ ID NO 129
<211> LENGTH: 107
<212> TYPE: PRT
<213> ORGANISM: Artificial Sequence
<220> FEATURE:
<223> OTHER INFORMATION: Synthetic Construct

<400> SEQUENCE: 129

Asp Ile Gln Met Thr Gln Ser Pro Ser Ser Leu Ser Ala Ser Val Gly
1               5                   10                  15

Asp Arg Val Thr Ile Thr Cys His Ala Ser Gln Asp Ile Ser Ser Tyr
            20                  25                  30

Ile Val Trp Tyr Gln Gln Lys Pro Gly Lys Ser Phe Lys Gly Leu Ile
        35                  40                  45

Tyr His Gly Thr Asn Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Val His Tyr Ala Gln Phe Pro Tyr
                85                  90                  95

Thr Phe Gly Gln Gly Thr Lys Val Glu Ile Lys
            100                 105

<210> SEQ ID NO 130
<211> LENGTH: 114
<212> TYPE: PRT
<213> ORGANISM: Artificial Sequence
<220> FEATURE:
<223> OTHER INFORMATION: Synthetic Construct

<400> SEQUENCE: 130

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Thr Asn Tyr
            20                  25                  30

Leu Ile Glu Trp Val Arg Gln Ala Pro Gly Gln Gly Leu Glu Trp Ile
        35                  40                  45

Gly Val Ile Asn Pro Gly Ser Gly Asp Thr Tyr Tyr Ser Glu Lys Phe
    50                  55                  60

Lys Gly Arg Val Thr Leu Thr Ala Asp Thr Ser Thr Ser Thr Ala Tyr

```
                65                  70                  75                  80
Leu Glu Leu Ser Ser Leu Arg Ser Glu Asp Thr Ala Val Tyr Tyr Cys
                    85                  90                  95

Ala Arg Asp Arg Leu Asp Tyr Trp Gly Gln Gly Thr Leu Val Thr Val
                100                 105                 110

Ser Ser

<210> SEQ ID NO 131
<211> LENGTH: 107
<212> TYPE: PRT
<213> ORGANISM: Artificial Sequence
<220> FEATURE:
<223> OTHER INFORMATION: Synthetic Construct

<400> SEQUENCE: 131

Asp Ile Gln Met Thr Gln Ser Pro Ser Ser Leu Ser Ala Ser Val Gly
1               5                   10                  15

Asp Arg Val Thr Ile Thr Cys His Ala Ser Gln Asp Ile Ser Ser Tyr
                20                  25                  30

Ile Val Trp Tyr Gln Gln Lys Pro Gly Lys Ser Phe Lys Gly Leu Ile
            35                  40                  45

Tyr His Gly Thr Asn Leu Glu Glu Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Val His Tyr Ala Gln Phe Pro Tyr
                85                  90                  95

Thr Phe Gly Gln Gly Thr Lys Val Glu Ile Lys
                100                 105

<210> SEQ ID NO 132
<211> LENGTH: 114
<212> TYPE: PRT
<213> ORGANISM: Artificial Sequence
<220> FEATURE:
<223> OTHER INFORMATION: Synthetic Construct

<400> SEQUENCE: 132

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Thr Asn Tyr
                20                  25                  30

Leu Ile Glu Trp Val Arg Gln Ala Pro Gly Gln Gly Leu Glu Trp Ile
            35                  40                  45

Gly Val Ile Asn Pro Gly Ser Gly Asp Thr Tyr Tyr Ser Glu Lys Phe
        50                  55                  60

Lys Gly Arg Val Thr Leu Thr Ala Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Asp Arg Leu Asp Tyr Trp Gly Gln Gly Thr Leu Val Thr Val
                100                 105                 110

Ser Ser

<210> SEQ ID NO 133
<211> LENGTH: 107
<212> TYPE: PRT
<213> ORGANISM: Artificial Sequence
```

```
<220> FEATURE:
<223> OTHER INFORMATION: Synthetic Construct

<400> SEQUENCE: 133

Asp Ile Gln Met Thr Gln Ser Pro Ser Ser Leu Ser Ala Ser Val Gly
1               5                   10                  15

Asp Arg Val Thr Ile Thr Cys His Ala Ser Gln Asp Ile Ser Ser Tyr
            20                  25                  30

Ile Val Trp Tyr Gln Gln Lys Pro Gly Lys Ser Phe Lys Gly Leu Ile
        35                  40                  45

Tyr His Gly Thr Asn Leu Glu Gln Gly Val Pro Ser Arg Phe Ser Gly
    50                  55                  60

Ser Gly Ser Gly Thr Asp Phe Thr Leu Thr Ile Ser Ser Leu Gln Pro
65              70                  75                  80

Glu Asp Phe Ala Thr Tyr Tyr Cys Val His Tyr Ala Gln Phe Pro Tyr
                85                  90                  95

Thr Phe Gly Gln Gly Thr Lys Val Glu Ile Lys
            100                 105

<210> SEQ ID NO 134
<211> LENGTH: 114
<212> TYPE: PRT
<213> ORGANISM: Artificial Sequence
<220> FEATURE:
<223> OTHER INFORMATION: Synthetic Construct

<400> SEQUENCE: 134

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Thr Asn Tyr
            20                  25                  30

Leu Ile Glu Trp Val Arg Gln Ala Pro Gly Gln Gly Leu Glu Trp Ile
        35                  40                  45

Gly Val Ile Asn Pro Gly Ser Gly Asp Thr Tyr Tyr Ser Glu Lys Phe
    50                  55                  60

Lys Gly Arg Val Thr Ile Thr Ala Asp Thr Ser Thr Ser Thr Ala Tyr
65              70                  75                  80

Leu Glu Leu Ser Ser Leu Arg Ser Glu Asp Thr Ala Val Tyr Tyr Cys
                85                  90                  95

Ala Arg Asp Arg Leu Asp Tyr Trp Gly Gln Gly Thr Leu Val Thr Val
            100                 105                 110

Ser Ser

<210> SEQ ID NO 135
<211> LENGTH: 107
<212> TYPE: PRT
<213> ORGANISM: Artificial Sequence
<220> FEATURE:
<223> OTHER INFORMATION: Synthetic Construct

<400> SEQUENCE: 135

Asp Ile Gln Met Thr Gln Ser Pro Ser Ser Leu Ser Ala Ser Val Gly
1               5                   10                  15

Asp Arg Val Thr Ile Thr Cys His Ala Ser Gln Asp Ile Ser Ser Tyr
            20                  25                  30

Ile Val Trp Tyr Gln Gln Lys Pro Gly Lys Ser Phe Lys Gly Leu Ile
        35                  40                  45

Tyr His Gly Thr Asn Leu Glu Asp Gly Val Pro Ser Arg Phe Ser Gly
```

```
                    50                  55                  60
Ser Gly Ser Gly Ala Asp Tyr Thr Leu Thr Ile Ser Ser Leu Gln Pro
 65                  70                  75                  80

Glu Asp Phe Ala Thr Tyr Tyr Cys Val His Tyr Ala Gln Phe Pro Tyr
                     85                  90                  95

Thr Phe Gly Gln Gly Thr Lys Val Glu Ile Lys
                100                 105

<210> SEQ ID NO 136
<211> LENGTH: 114
<212> TYPE: PRT
<213> ORGANISM: Artificial Sequence
<220> FEATURE:
<223> OTHER INFORMATION: Synthetic Construct

<400> SEQUENCE: 136

Glu Val Gln Leu Val Gln Ser Gly Ala Glu Val Lys Lys Pro Gly Ala
 1               5                  10                  15

Ser Val Lys Val Ser Cys Lys Ala Ser Gly Tyr Ala Phe Thr Asn Tyr
                20                  25                  30

Leu Ile Glu Trp Val Arg Gln Ala Pro Gly Gln Gly Leu Glu Trp Ile
            35                  40                  45

Gly Val Ile Asn Pro Gly Ser Gly Asp Thr Tyr Tyr Ser Glu Lys Phe
 50                  55                  60

Lys Gly Arg Val Thr Leu Thr Ala Asp Thr Ser Thr Ser Thr Ala Tyr
 65                  70                  75                  80

Leu Glu Leu Ser Ser Leu Arg Ser Glu Asp Thr Ala Val Tyr Tyr Cys
                 85                  90                  95

Ala Arg Asp Arg Leu Asp Tyr Trp Gly Gln Gly Thr Leu Val Thr Val
                100                 105                 110

Ser Ser

<210> SEQ ID NO 137
<211> LENGTH: 107
<212> TYPE: PRT
<213> ORGANISM: Artificial Sequence
<220> FEATURE:
<223> OTHER INFORMATION: Synthetic Construct

<400> SEQUENCE: 137

Asp Ile Gln Met Thr Gln Ser Pro Ser Ser Leu Ser Ala Ser Val Gly
 1               5                  10                  15

Asp Arg Val Thr Ile Thr Cys His Ala Ser Gln Asp Ile Ser Ser Tyr
                20                  25                  30

Ile Val Trp Tyr Gln Gln Lys Pro Gly Lys Ser Phe Lys Gly Leu Ile
            35                  40                  45

Tyr His Gly Thr Asn Leu Glu Asp Gly Val Pro Ser Arg Phe Ser Gly
 50                  55                  60

Ser Gly Ser Gly Ala Asp Tyr Thr Leu Thr Ile Ser Ser Leu Gln Pro
 65                  70                  75                  80

Glu Asp Phe Ala Thr Tyr Tyr Cys Val His Tyr Ala Gln Phe Pro Tyr
                 85                  90                  95

Thr Phe Gly Gln Gly Thr Lys Val Glu Ile Lys
                100                 105

<210> SEQ ID NO 138
<211> LENGTH: 114
<212> TYPE: PRT
```

<213> ORGANISM: Artificial Sequence
<220> FEATURE:
<223> OTHER INFORMATION: Synthetic Construct

<400> SEQUENCE: 138

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Thr Asn Tyr
            20                  25                  30

Leu Ile Glu Trp Val Arg Gln Ala Pro Gly Gln Gly Leu Glu Trp Ile
        35                  40                  45

Gly Val Ile Asn Pro Gly Ser Gly Asp Thr Tyr Tyr Ser Glu Lys Phe
    50                  55                  60

Lys Gly Arg Val Thr Leu Thr Arg Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Asp Arg Leu Asp Tyr Trp Gly Gln Gly Thr Leu Val Thr Val
            100                 105                 110

Ser Ser

<210> SEQ ID NO 139
<211> LENGTH: 107
<212> TYPE: PRT
<213> ORGANISM: Artificial Sequence
<220> FEATURE:
<223> OTHER INFORMATION: Synthetic Construct

<400> SEQUENCE: 139

Asp Ile Gln Met Thr Gln Ser Pro Ser Ser Leu Ser Ala Ser Val Gly
1               5                   10                  15

Asp Arg Val Thr Ile Thr Cys His Ala Ser Gln Asp Ile Ser Ser Tyr
            20                  25                  30

Ile Val Trp Tyr Gln Gln Lys Pro Gly Lys Ser Phe Lys Gly Leu Ile
        35                  40                  45

Tyr His Gly Thr Asn Leu Glu Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Val His Tyr Ala Gln Phe Pro Tyr
                85                  90                  95

Thr Phe Gly Gln Gly Thr Lys Val Glu Ile Lys
            100                 105

<210> SEQ ID NO 140
<211> LENGTH: 114
<212> TYPE: PRT
<213> ORGANISM: Artificial Sequence
<220> FEATURE:
<223> OTHER INFORMATION: Synthetic Construct

<400> SEQUENCE: 140

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Thr Asn Tyr
            20                  25                  30

Leu Ile Glu Trp Val Arg Gln Ala Pro Gly Gln Gly Leu Glu Trp Ile
        35                  40                  45

Gly Val Ile Asn Pro Gly Ser Gly Asp Thr Tyr Tyr Ser Glu Lys Phe
        50                  55                  60

Lys Gly Arg Val Thr Leu Thr Arg Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Asp Arg Leu Asp Tyr Trp Gly Gln Gly Thr Leu Val Thr Val
            100                 105                 110

Ser Ser

<210> SEQ ID NO 141
<211> LENGTH: 107
<212> TYPE: PRT
<213> ORGANISM: Artificial Sequence
<220> FEATURE:
<223> OTHER INFORMATION: Synthetic Construct

<400> SEQUENCE: 141

Asp Ile Gln Met Thr Gln Ser Pro Ser Ser Leu Ser Ala Ser Val Gly
1               5                   10                  15

Asp Arg Val Thr Ile Thr Cys His Ala Ser Gln Asp Ile Ser Ser Tyr
            20                  25                  30

Ile Val Trp Tyr Gln Gln Lys Pro Gly Lys Ser Pro Lys Leu Leu Ile
        35                  40                  45

Tyr His Gly Thr Asn Leu Glu Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Val His Tyr Ala Gln Phe Pro Tyr
                85                  90                  95

Thr Phe Gly Gln Gly Thr Lys Val Glu Ile Lys
            100                 105

<210> SEQ ID NO 142
<211> LENGTH: 114
<212> TYPE: PRT
<213> ORGANISM: Artificial Sequence
<220> FEATURE:
<223> OTHER INFORMATION: Synthetic Construct

<400> SEQUENCE: 142

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Thr Asn Tyr
            20                  25                  30

Leu Ile Glu Trp Val Arg Gln Ala Pro Gly Gln Gly Leu Glu Trp Ile
        35                  40                  45

Gly Val Ile Asn Pro Gly Ser Gly Asp Thr Tyr Tyr Ser Glu Lys Phe
    50                  55                  60

Lys Gly Arg Val Thr Leu Thr Arg Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Asp Arg Leu Asp Tyr Trp Gly Gln Gly Thr Leu Val Thr Val
            100                 105                 110

Ser Ser

```
<210> SEQ ID NO 143
<211> LENGTH: 107
<212> TYPE: PRT
<213> ORGANISM: Artificial Sequence
<220> FEATURE:
<223> OTHER INFORMATION: Synthetic Construct

<400> SEQUENCE: 143
```

Asp Ile Gln Met Thr Gln Ser Pro Ser Ser Leu Ser Ala Ser Val Gly
1               5                   10                  15

Asp Arg Val Thr Ile Thr Cys His Ala Ser Gln Asp Ile Ser Ser Tyr
            20                  25                  30

Ile Val Trp Tyr Gln Gln Lys Pro Gly Lys Ala Phe Lys Leu Leu Ile
        35                  40                  45

Tyr His Gly Thr Asn Leu Glu Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Val His Tyr Ala Gln Phe Pro Tyr
                85                  90                  95

Thr Phe Gly Gln Gly Thr Lys Val Glu Ile Lys
            100                 105

```
<210> SEQ ID NO 144
<211> LENGTH: 114
<212> TYPE: PRT
<213> ORGANISM: Artificial Sequence
<220> FEATURE:
<223> OTHER INFORMATION: Synthetic Construct

<400> SEQUENCE: 144
```

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Thr Asn Tyr
            20                  25                  30

Leu Ile Glu Trp Val Arg Gln Ala Pro Gly Gln Gly Leu Glu Trp Ile
        35                  40                  45

Gly Val Ile Asn Pro Gly Ser Gly Asp Thr Tyr Tyr Ser Glu Lys Phe
    50                  55                  60

Lys Gly Arg Val Thr Leu Thr Arg Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Asp Arg Leu Asp Tyr Trp Gly Gln Gly Thr Leu Val Thr Val
            100                 105                 110

Ser Ser

```
<210> SEQ ID NO 145
<211> LENGTH: 107
<212> TYPE: PRT
<213> ORGANISM: Artificial Sequence
<220> FEATURE:
<223> OTHER INFORMATION: Synthetic Construct

<400> SEQUENCE: 145
```

Asp Ile Gln Met Thr Gln Ser Pro Ser Ser Leu Ser Ala Ser Val Gly
1               5                   10                  15

Asp Arg Val Thr Ile Thr Cys His Ala Ser Gln Asp Ile Ser Ser Tyr
            20                  25                  30

```
Ile Val Trp Tyr Gln Gln Lys Pro Gly Lys Ala Pro Lys Gly Leu Ile
            35                  40                  45

Tyr His Gly Thr Asn Leu Glu Asp Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Val His Tyr Ala Gln Phe Pro Tyr
                 85                  90                  95

Thr Phe Gly Gln Gly Thr Lys Val Glu Ile Lys
            100                 105
```

<210> SEQ ID NO 146
<211> LENGTH: 114
<212> TYPE: PRT
<213> ORGANISM: Artificial Sequence
<220> FEATURE:
<223> OTHER INFORMATION: Synthetic Construct

<400> SEQUENCE: 146

```
Glu Val Gln Leu Val Gln Ser Gly Ala Glu Val Lys Lys Pro Gly Ala
 1               5                  10                  15

Ser Val Lys Val Ser Cys Lys Ala Ser Gly Tyr Ala Phe Thr Asn Tyr
            20                  25                  30

Leu Ile Glu Trp Val Arg Gln Ala Pro Gly Gln Gly Leu Glu Trp Ile
            35                  40                  45

Gly Val Ile Asn Pro Gly Ser Gly Asp Thr Tyr Tyr Ser Glu Lys Phe
 50                  55                  60

Lys Gly Arg Val Thr Leu Thr Ala Asp Thr Ser Thr Ser Thr Ala Tyr
 65                  70                  75                  80

Leu Glu Leu Ser Ser Leu Arg Ser Glu Asp Thr Ala Val Tyr Tyr Cys
                 85                  90                  95

Ala Arg Asp Arg Leu Asp Tyr Trp Gly Gln Gly Thr Leu Val Thr Val
            100                 105                 110

Ser Ser
```

<210> SEQ ID NO 147
<211> LENGTH: 107
<212> TYPE: PRT
<213> ORGANISM: Artificial Sequence
<220> FEATURE:
<223> OTHER INFORMATION: Synthetic Construct

<400> SEQUENCE: 147

```
Asp Ile Gln Met Thr Gln Ser Pro Ser Ser Leu Ser Ala Ser Val Gly
 1               5                  10                  15

Asp Arg Val Thr Ile Thr Cys His Ala Ser Gln Asp Ile Ser Ser Tyr
            20                  25                  30

Ile Val Trp Tyr Gln Gln Lys Pro Gly Lys Ser Phe Lys Gly Leu Ile
            35                  40                  45

Tyr His Gly Thr Asn Leu Glu Asp Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Ala His Tyr Ala Gln Phe Pro Tyr
                 85                  90                  95

Thr Phe Gly Gln Gly Thr Lys Val Glu Ile Lys
            100                 105
```

```
<210> SEQ ID NO 148
<211> LENGTH: 114
<212> TYPE: PRT
<213> ORGANISM: Artificial Sequence
<220> FEATURE:
<223> OTHER INFORMATION: Synthetic Construct

<400> SEQUENCE: 148

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Thr Asn Tyr
            20                  25                  30

Leu Ile Glu Trp Val Arg Gln Ala Pro Gly Gln Gly Leu Glu Trp Ile
        35                  40                  45

Gly Val Ile Asn Pro Gly Ser Gly Asp Thr Tyr Tyr Ser Glu Lys Phe
    50                  55                  60

Lys Gly Arg Val Thr Leu Thr Ala Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Asp Arg Leu Asp Tyr Trp Gly Gln Gly Thr Leu Val Thr Val
            100                 105                 110

Ser Ser

<210> SEQ ID NO 149
<211> LENGTH: 107
<212> TYPE: PRT
<213> ORGANISM: Artificial Sequence
<220> FEATURE:
<223> OTHER INFORMATION: Synthetic Construct

<400> SEQUENCE: 149

Asp Ile Gln Met Thr Gln Ser Pro Ser Ser Leu Ser Ala Ser Val Gly
1               5                   10                  15

Asp Arg Val Thr Ile Thr Cys His Ala Ser Gln Asp Ile Ser Ser Tyr
            20                  25                  30

Ile Val Trp Tyr Gln Gln Lys Pro Gly Lys Ser Phe Lys Gly Leu Ile
        35                  40                  45

Tyr His Gly Thr Asn Leu Glu Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Val Ala Tyr Ala Gln Phe Pro Tyr
                85                  90                  95

Thr Phe Gly Gln Gly Thr Lys Val Glu Ile Lys
            100                 105

<210> SEQ ID NO 150
<211> LENGTH: 114
<212> TYPE: PRT
<213> ORGANISM: Artificial Sequence
<220> FEATURE:
<223> OTHER INFORMATION: Synthetic Construct

<400> SEQUENCE: 150

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Thr Asn Tyr
            20                  25                  30
```

```
Leu Ile Glu Trp Val Arg Gln Ala Pro Gly Gln Gly Leu Glu Trp Ile
            35                  40                  45

Gly Val Ile Asn Pro Gly Ser Gly Asp Thr Tyr Tyr Ser Glu Lys Phe
        50                  55                  60

Lys Gly Arg Val Thr Leu Thr Ala Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Asp Arg Leu Asp Tyr Trp Gly Gln Gly Thr Leu Val Thr Val
                100                 105                 110

Ser Ser
```

<210> SEQ ID NO 151
<211> LENGTH: 107
<212> TYPE: PRT
<213> ORGANISM: Artificial Sequence
<220> FEATURE:
<223> OTHER INFORMATION: Synthetic Construct

<400> SEQUENCE: 151

```
Asp Ile Gln Met Thr Gln Ser Pro Ser Ser Leu Ser Ala Ser Val Gly
1               5                   10                  15

Asp Arg Val Thr Ile Thr Cys His Ala Ser Gln Asp Ile Ser Ser Tyr
                20                  25                  30

Ile Val Trp Tyr Gln Gln Lys Pro Gly Lys Ser Phe Lys Gly Leu Ile
            35                  40                  45

Tyr His Gly Thr Asn Leu Glu Asp Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Val His Ala Ala Gln Phe Pro Tyr
                85                  90                  95

Thr Phe Gly Gln Gly Thr Lys Val Glu Ile Lys
                100                 105
```

<210> SEQ ID NO 152
<211> LENGTH: 114
<212> TYPE: PRT
<213> ORGANISM: Artificial Sequence
<220> FEATURE:
<223> OTHER INFORMATION: Synthetic Construct

<400> SEQUENCE: 152

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Thr Asn Tyr
                20                  25                  30

Leu Ile Glu Trp Val Arg Gln Ala Pro Gly Gln Gly Leu Glu Trp Ile
            35                  40                  45

Gly Val Ile Asn Pro Gly Ser Gly Asp Thr Tyr Tyr Ser Glu Lys Phe
        50                  55                  60

Lys Gly Arg Val Thr Leu Thr Ala Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Asp Arg Leu Asp Tyr Trp Gly Gln Gly Thr Leu Val Thr Val
                100                 105                 110
```

Ser Ser

<210> SEQ ID NO 153
<211> LENGTH: 107
<212> TYPE: PRT
<213> ORGANISM: Artificial Sequence
<220> FEATURE:
<223> OTHER INFORMATION: Synthetic Construct

<400> SEQUENCE: 153

Asp Ile Gln Met Thr Gln Ser Pro Ser Ser Leu Ser Ala Ser Val Gly
1               5                   10                  15

Asp Arg Val Thr Ile Thr Cys His Ala Ser Gln Asp Ile Ser Ser Tyr
            20                  25                  30

Ile Val Trp Tyr Gln Gln Lys Pro Gly Lys Ser Phe Lys Gly Leu Ile
        35                  40                  45

Tyr His Gly Thr Asn Leu Glu Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Val His Tyr Ala Ala Phe Pro Tyr
                85                  90                  95

Thr Phe Gly Gln Gly Thr Lys Val Glu Ile Lys
            100                 105

<210> SEQ ID NO 154
<211> LENGTH: 114
<212> TYPE: PRT
<213> ORGANISM: Artificial Sequence
<220> FEATURE:
<223> OTHER INFORMATION: Synthetic Construct

<400> SEQUENCE: 154

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Thr Asn Tyr
            20                  25                  30

Leu Ile Glu Trp Val Arg Gln Ala Pro Gly Gln Gly Leu Glu Trp Ile
        35                  40                  45

Gly Val Ile Asn Pro Gly Ser Gly Asp Thr Tyr Tyr Ser Glu Lys Phe
    50                  55                  60

Lys Gly Arg Val Thr Leu Thr Ala Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Asp Arg Leu Asp Tyr Trp Gly Gln Gly Thr Leu Val Thr Val
            100                 105                 110

Ser Ser

<210> SEQ ID NO 155
<211> LENGTH: 107
<212> TYPE: PRT
<213> ORGANISM: Artificial Sequence
<220> FEATURE:
<223> OTHER INFORMATION: Synthetic Construct

<400> SEQUENCE: 155

Asp Ile Gln Met Thr Gln Ser Pro Ser Ser Leu Ser Ala Ser Val Gly
1               5                   10                  15

```
Asp Arg Val Thr Ile Thr Cys His Ala Ser Gln Asp Ile Ser Ser Tyr
            20                  25                  30

Ile Val Trp Tyr Gln Gln Lys Pro Gly Lys Ser Phe Lys Gly Leu Ile
        35                  40                  45

Tyr His Gly Thr Asn Leu Glu Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Val His Tyr Ala Gln Ala Pro Tyr
                85                  90                  95

Thr Phe Gly Gln Gly Thr Lys Val Glu Ile Lys
            100                 105
```

<210> SEQ ID NO 156
<211> LENGTH: 114
<212> TYPE: PRT
<213> ORGANISM: Artificial Sequence
<220> FEATURE:
<223> OTHER INFORMATION: Synthetic Construct

<400> SEQUENCE: 156

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Thr Asn Tyr
            20                  25                  30

Leu Ile Glu Trp Val Arg Gln Ala Pro Gly Gln Gly Leu Glu Trp Ile
        35                  40                  45

Gly Val Ile Asn Pro Gly Ser Gly Asp Thr Tyr Tyr Ser Glu Lys Phe
    50                  55                  60

Lys Gly Arg Val Thr Leu Thr Ala Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Asp Arg Leu Asp Tyr Trp Gly Gln Gly Thr Leu Val Thr Val
            100                 105                 110

Ser Ser
```

<210> SEQ ID NO 157
<211> LENGTH: 107
<212> TYPE: PRT
<213> ORGANISM: Artificial Sequence
<220> FEATURE:
<223> OTHER INFORMATION: Synthetic Construct

<400> SEQUENCE: 157

```
Asp Ile Gln Met Thr Gln Ser Pro Ser Ser Leu Ser Ala Ser Val Gly
1               5                   10                  15

Asp Arg Val Thr Ile Thr Cys His Ala Ser Gln Asp Ile Ser Ser Tyr
            20                  25                  30

Ile Val Trp Tyr Gln Gln Lys Pro Gly Lys Ser Phe Lys Gly Leu Ile
        35                  40                  45

Tyr His Gly Thr Asn Leu Glu Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Val His Tyr Ala Gln Phe Ala Tyr
                85                  90                  95
```

Thr Phe Gly Gln Gly Thr Lys Val Glu Ile Lys
            100                 105

<210> SEQ ID NO 158
<211> LENGTH: 114
<212> TYPE: PRT
<213> ORGANISM: Artificial Sequence
<220> FEATURE:
<223> OTHER INFORMATION: Synthetic Construct

<400> SEQUENCE: 158

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Thr Asn Tyr
            20                  25                  30

Leu Ile Glu Trp Val Arg Gln Ala Pro Gly Gln Gly Leu Glu Trp Ile
        35                  40                  45

Gly Val Ile Asn Pro Gly Ser Gly Asp Thr Tyr Tyr Ser Glu Lys Phe
    50                  55                  60

Lys Gly Arg Val Thr Leu Thr Ala Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Asp Arg Leu Asp Tyr Trp Gly Gln Gly Thr Leu Val Thr Val
            100                 105                 110

Ser Ser

<210> SEQ ID NO 159
<211> LENGTH: 107
<212> TYPE: PRT
<213> ORGANISM: Artificial Sequence
<220> FEATURE:
<223> OTHER INFORMATION: Synthetic Construct

<400> SEQUENCE: 159

Asp Ile Gln Met Thr Gln Ser Pro Ser Ser Leu Ser Ala Ser Val Gly
1               5                   10                  15

Asp Arg Val Thr Ile Thr Cys His Ala Ser Gln Asp Ile Ser Ser Tyr
            20                  25                  30

Ile Val Trp Tyr Gln Lys Pro Gly Lys Ser Phe Lys Gly Leu Ile
        35                  40                  45

Tyr His Gly Thr Asn Leu Glu Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Val His Tyr Ala Gln Phe Pro Ala
                85                  90                  95

Thr Phe Gly Gln Gly Thr Lys Val Glu Ile Lys
            100                 105

<210> SEQ ID NO 160
<211> LENGTH: 114
<212> TYPE: PRT
<213> ORGANISM: Artificial Sequence
<220> FEATURE:
<223> OTHER INFORMATION: Synthetic Construct

<400> SEQUENCE: 160

Glu Val Gln Leu Val Gln Ser Gly Ala Glu Val Lys Lys Pro Gly Ala

```
                 1               5                  10                  15
Ser Val Lys Val Ser Cys Lys Ala Ser Gly Tyr Ala Phe Thr Asn Tyr
                    20                  25                  30

Leu Ile Glu Trp Val Arg Gln Ala Pro Gly Gln Gly Leu Glu Trp Ile
            35                  40                  45

Gly Val Ile Asn Pro Gly Ser Gly Asp Thr Tyr Tyr Ser Glu Lys Phe
        50                  55                  60

Lys Gly Arg Val Thr Leu Thr Ala Asp Thr Ser Thr Ser Thr Ala Tyr
 65                 70                  75                  80

Leu Glu Leu Ser Ser Leu Arg Ser Glu Asp Thr Ala Val Tyr Tyr Cys
                85                  90                  95

Ala Arg Ala Arg Leu Asp Tyr Trp Gly Gln Gly Thr Leu Val Thr Val
            100                 105                 110

Ser Ser

<210> SEQ ID NO 161
<211> LENGTH: 107
<212> TYPE: PRT
<213> ORGANISM: Artificial Sequence
<220> FEATURE:
<223> OTHER INFORMATION: Synthetic Construct

<400> SEQUENCE: 161

Asp Ile Gln Met Thr Gln Ser Pro Ser Ser Leu Ser Ala Ser Val Gly
 1               5                  10                  15

Asp Arg Val Thr Ile Thr Cys His Ala Ser Gln Asp Ile Ser Ser Tyr
                20                  25                  30

Ile Val Trp Tyr Gln Gln Lys Pro Gly Lys Ser Phe Lys Gly Leu Ile
            35                  40                  45

Tyr His Gly Thr Asn Leu Glu Asp Gly Val Pro Ser Arg Phe Ser Gly
        50                  55                  60

Ser Gly Ser Gly Thr Asp Phe Thr Leu Thr Ile Ser Ser Leu Gln Pro
 65                 70                  75                  80

Glu Asp Phe Ala Thr Tyr Tyr Cys Val His Tyr Ala Gln Phe Pro Tyr
                85                  90                  95

Thr Phe Gly Gln Gly Thr Lys Val Glu Ile Lys
            100                 105

<210> SEQ ID NO 162
<211> LENGTH: 114
<212> TYPE: PRT
<213> ORGANISM: Artificial Sequence
<220> FEATURE:
<223> OTHER INFORMATION: Synthetic Construct

<400> SEQUENCE: 162

Glu Val Gln Leu Val Gln Ser Gly Ala Glu Val Lys Lys Pro Gly Ala
 1               5                  10                  15

Ser Val Lys Val Ser Cys Lys Ala Ser Gly Tyr Ala Phe Thr Asn Tyr
                20                  25                  30

Leu Ile Glu Trp Val Arg Gln Ala Pro Gly Gln Gly Leu Glu Trp Ile
            35                  40                  45

Gly Val Ile Asn Pro Gly Ser Gly Asp Thr Tyr Tyr Ser Glu Lys Phe
        50                  55                  60

Lys Gly Arg Val Thr Leu Thr Ala Asp Thr Ser Thr Ser Thr Ala Tyr
 65                 70                  75                  80

Leu Glu Leu Ser Ser Leu Arg Ser Glu Asp Thr Ala Val Tyr Tyr Cys
```

```
                    85                  90                  95

Ala Arg Asp Ala Leu Asp Tyr Trp Gly Gln Gly Thr Leu Val Thr Val
                100                 105                 110

Ser Ser

<210> SEQ ID NO 163
<211> LENGTH: 107
<212> TYPE: PRT
<213> ORGANISM: Artificial Sequence
<220> FEATURE:
<223> OTHER INFORMATION: Synthetic Construct

<400> SEQUENCE: 163

Asp Ile Gln Met Thr Gln Ser Pro Ser Ser Leu Ser Ala Ser Val Gly
1               5                   10                  15

Asp Arg Val Thr Ile Thr Cys His Ala Ser Gln Asp Ile Ser Ser Tyr
            20                  25                  30

Ile Val Trp Tyr Gln Gln Lys Pro Gly Lys Ser Phe Lys Gly Leu Ile
        35                  40                  45

Tyr His Gly Thr Asn Leu Glu Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Val His Tyr Ala Gln Phe Pro Tyr
                85                  90                  95

Thr Phe Gly Gln Gly Thr Lys Val Glu Ile Lys
                100                 105

<210> SEQ ID NO 164
<211> LENGTH: 114
<212> TYPE: PRT
<213> ORGANISM: Artificial Sequence
<220> FEATURE:
<223> OTHER INFORMATION: Synthetic Construct

<400> SEQUENCE: 164

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Thr Asn Tyr
            20                  25                  30

Leu Ile Glu Trp Val Arg Gln Ala Pro Gly Gln Gly Leu Glu Trp Ile
        35                  40                  45

Gly Val Ile Asn Pro Gly Ser Gly Asp Thr Tyr Tyr Ser Glu Lys Phe
    50                  55                  60

Lys Gly Arg Val Thr Leu Thr Ala Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Asp Arg Ala Asp Tyr Trp Gly Gln Gly Thr Leu Val Thr Val
                100                 105                 110

Ser Ser

<210> SEQ ID NO 165
<211> LENGTH: 107
<212> TYPE: PRT
<213> ORGANISM: Artificial Sequence
<220> FEATURE:
<223> OTHER INFORMATION: Synthetic Construct
```

<400> SEQUENCE: 165

Asp Ile Gln Met Thr Gln Ser Pro Ser Ser Leu Ser Ala Ser Val Gly
1               5                   10                  15

Asp Arg Val Thr Ile Thr Cys His Ala Ser Gln Asp Ile Ser Ser Tyr
            20                  25                  30

Ile Val Trp Tyr Gln Gln Lys Pro Gly Lys Ser Phe Lys Gly Leu Ile
        35                  40                  45

Tyr His Gly Thr Asn Leu Glu Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Val His Tyr Ala Gln Phe Pro Tyr
                85                  90                  95

Thr Phe Gly Gln Gly Thr Lys Val Glu Ile Lys
            100                 105

<210> SEQ ID NO 166
<211> LENGTH: 113
<212> TYPE: PRT
<213> ORGANISM: Artificial Sequence
<220> FEATURE:
<223> OTHER INFORMATION: Synthetic Construct

<400> SEQUENCE: 166

Glu Val Gln Leu Val Glu Ser Gly Pro Gly Leu Val Lys Pro Ser Glu
1               5                   10                  15

Thr Leu Ser Leu Thr Cys Thr Val Ser Gly Phe Ser Leu Thr Asp Tyr
            20                  25                  30

Gly Val Leu Trp Ile Arg Gln Pro Pro Gly Lys Gly Leu Glu Trp Ile
        35                  40                  45

Gly Met Ile Trp Ser Gly Gly Thr Asp Tyr Asn Ala Ala Phe Ile
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Val
                85                  90                  95

Arg Glu Glu Met Asp Tyr Trp Gly Gln Gly Thr Leu Val Thr Val Ser
            100                 105                 110

Ser

<210> SEQ ID NO 167
<211> LENGTH: 107
<212> TYPE: PRT
<213> ORGANISM: Artificial Sequence
<220> FEATURE:
<223> OTHER INFORMATION: Synthetic Construct

<400> SEQUENCE: 167

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Phe
            20                  25                  30

Leu Asn Trp Tyr Gln Gln Lys Pro Gly Lys Ala Pro Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Phe Thr Leu Thr Ile Ser Ser Leu Gln Pro

```
                65                  70                  75                  80
Glu Asp Phe Ala Thr Tyr Tyr Cys Gln Gln Gly Asn Thr Leu Pro Trp
                    85                  90                  95
Thr Phe Gly Gln Gly Thr Lys Val Glu Ile Lys
            100                 105
```

<210> SEQ ID NO 168
<211> LENGTH: 113
<212> TYPE: PRT
<213> ORGANISM: Artificial Sequence
<220> FEATURE:
<223> OTHER INFORMATION: Synthetic Construct

<400> SEQUENCE: 168

```
Glu Val Gln Leu Val Glu Ser Gly Pro Gly Leu Val Lys Pro Ser Glu
1               5                   10                  15
Thr Leu Ser Leu Thr Cys Thr Val Ser Gly Phe Ser Leu Thr Asp Tyr
                20                  25                  30
Gly Val Leu Trp Ile Arg Gln Pro Pro Gly Lys Gly Leu Glu Trp Ile
            35                  40                  45
Gly Met Ile Trp Ser Gly Gly Thr Thr Asp Tyr Asn Ala Ala Phe Ile
        50                  55                  60
Ser Arg Val Thr Ile Ser Lys Asp Thr Ser Lys Asn Gln Val Ser Leu
65                  70                  75                  80
Lys Leu Ser Ser Val Thr Ala Ala Asp Thr Ala Val Tyr Tyr Cys Val
                85                  90                  95
Arg Glu Glu Met Asp Tyr Trp Gly Gln Gly Thr Leu Val Thr Val Ser
            100                 105                 110
Ser
```

<210> SEQ ID NO 169
<211> LENGTH: 107
<212> TYPE: PRT
<213> ORGANISM: Artificial Sequence
<220> FEATURE:
<223> OTHER INFORMATION: Synthetic Construct

<400> SEQUENCE: 169

```
Asp Ile Gln Met Thr Gln Ser Pro Ser Ser Leu Ser Ala Ser Val Gly
1               5                   10                  15
Asp Arg Val Thr Ile Thr Cys Arg Ala Ser Gln Asp Ile Ser Asn Phe
                20                  25                  30
Leu Asn Trp Tyr Gln Gln Lys Pro Gly Lys Ala Pro Lys Leu Leu Ile
            35                  40                  45
Tyr Tyr Thr Ser Arg Leu His Ser Gly Val Pro Ser Arg Phe Ser Gly
        50                  55                  60
Ser Gly Ser Gly Thr Asp Phe Thr Leu Thr Ile Ser Ser Leu Gln Pro
65                  70                  75                  80
Glu Asp Phe Ala Thr Tyr Tyr Cys Gln Gln Gly Asn Thr Leu Pro Trp
                85                  90                  95
Thr Phe Gly Gln Gly Thr Lys Val Glu Ile Lys
            100                 105
```

<210> SEQ ID NO 170
<211> LENGTH: 113
<212> TYPE: PRT
<213> ORGANISM: Artificial Sequence
<220> FEATURE:
<223> OTHER INFORMATION: Synthetic Construct

<400> SEQUENCE: 170

Glu Val Gln Leu Val Glu Ser Gly Pro Gly Leu Val Lys Pro Ser Glu
1               5                   10                  15

Thr Leu Ser Leu Thr Cys Thr Val Ser Gly Phe Ser Leu Thr Asp Tyr
            20                  25                  30

Gly Val Leu Trp Val Arg Gln Pro Pro Gly Lys Gly Leu Glu Trp Leu
        35                  40                  45

Gly Met Ile Trp Ser Gly Gly Thr Thr Asp Tyr Asn Ala Ala Phe Ile
    50                  55                  60

Ser Arg Leu Thr Ile Ser Lys Asp Thr Ser Lys Asn Gln Val Ser Leu
65                  70                  75                  80

Lys Leu Ser Ser Val Thr Ala Ala Asp Thr Ala Val Tyr Tyr Cys Val
                85                  90                  95

Arg Glu Glu Met Asp Tyr Trp Gly Gln Gly Thr Leu Val Thr Val Ser
            100                 105                 110

Ser

<210> SEQ ID NO 171
<211> LENGTH: 107
<212> TYPE: PRT
<213> ORGANISM: Artificial Sequence
<220> FEATURE:
<223> OTHER INFORMATION: Synthetic Construct

<400> SEQUENCE: 171

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Phe
            20                  25                  30

Leu Asn Trp Tyr Gln Gln Lys Pro Gly Lys Ala Pro Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Asn Thr Leu Pro Trp
                85                  90                  95

Thr Phe Gly Gln Gly Thr Lys Val Glu Ile Lys
            100                 105

<210> SEQ ID NO 172
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = D or E
<220> FEATURE:
<221> NAME/KEY: VARIANT
<222> LOCATION: 2
<223> OTHER INFORMATION: Xaa = S or A

<400> SEQUENCE: 172

Xaa Xaa Tyr Met Ser
1               5

```
<210> SEQ ID NO 173
<211> LENGTH: 17
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 6
<223> OTHER INFORMATION: Xaa = N or S
<220> FEATURE:
<221> NAME/KEY: VARIANT
<222> LOCATION: 7
<223> OTHER INFORMATION: Xaa = A or G
<220> FEATURE:
<221> NAME/KEY: VARIANT
<222> LOCATION: 8
<223> OTHER INFORMATION: Xaa = D or S
<220> FEATURE:
<221> NAME/KEY: VARIANT
<222> LOCATION: 9
<223> OTHER INFORMATION: Xaa = A or S

<400> SEQUENCE: 173

Asp Met Tyr Pro Asp Xaa Xaa Xaa Xaa Ser Tyr Asn Gln Lys Phe Arg
1               5                   10                  15

Glu

<210> SEQ ID NO 174
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 5
<223> OTHER INFORMATION: Xaa = Y or A
<220> FEATURE:
<221> NAME/KEY: VARIANT
<222> LOCATION: 6
<223> OTHER INFORMATION: Xaa = A or F
<220> FEATURE:
<221> NAME/KEY: VARIANT
<222> LOCATION: 7
<223> OTHER INFORMATION: Xaa = S or A
<220> FEATURE:
<221> NAME/KEY: VARIANT
<222> LOCATION: 8
<223> OTHER INFORMATION: Xaa = A or V

<400> SEQUENCE: 174

Ala Pro Arg Trp Xaa Xaa Xaa Xaa
1               5

<210> SEQ ID NO 175
<211> LENGTH: 9
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 2
<223> OTHER INFORMATION: Xaa = A or Q
<220> FEATURE:
<221> NAME/KEY: VARIANT
<222> LOCATION: 3
<223> OTHER INFORMATION: Xaa = A or G
<220> FEATURE:
<221> NAME/KEY: VARIANT
<222> LOCATION: 4
<223> OTHER INFORMATION: Xaa = A or H
<220> FEATURE:
```

```
<221> NAME/KEY: VARIANT
<222> LOCATION: 5
<223> OTHER INFORMATION: Xaa = A or T
<220> FEATURE:
<221> NAME/KEY: VARIANT
<222> LOCATION: 6
<223> OTHER INFORMATION: Xaa = A or L
<220> FEATURE:
<221> NAME/KEY: VARIANT
<222> LOCATION: 7
<223> OTHER INFORMATION: Xaa = A or P
<220> FEATURE:
<221> NAME/KEY: VARIANT
<222> LOCATION: 8
<223> OTHER INFORMATION: Xaa = A or P

<400> SEQUENCE: 175

Gln Xaa Xaa Xaa Xaa Xaa Xaa Xaa Thr
1               5

<210> SEQ ID NO 176
<211> LENGTH: 17
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 9
<223> OTHER INFORMATION: Xaa = T, A or Q

<400> SEQUENCE: 176

Val Ile Asn Pro Gly Ser Gly Asp Xaa Tyr Tyr Ser Glu Lys Phe Lys
1               5                   10                  15

Gly

<210> SEQ ID NO 177
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 7
<223> OTHER INFORMATION: Xaa = S, E, or Q

<400> SEQUENCE: 177

His Gly Thr Asn Leu Glu Xaa
1               5

<210> SEQ ID NO 178
<211> LENGTH: 9
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = V or A
<220> FEATURE:
<221> NAME/KEY: VARIANT
<222> LOCATION: 2
<223> OTHER INFORMATION: Xaa = H or A
<220> FEATURE:
<221> NAME/KEY: VARIANT
<222> LOCATION: 9
<223> OTHER INFORMATION: Xaa = Y or A

<400> SEQUENCE: 178
```

Xaa Xaa Tyr Ala Gln Phe Pro Tyr Xaa
1               5

<210> SEQ ID NO 179
<211> LENGTH: 107
<212> TYPE: PRT
<213> ORGANISM: Artificial Sequence
<220> FEATURE:
<223> OTHER INFORMATION: Synthetic Construct

<400> SEQUENCE: 179

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Arg Leu Arg Ser Gly Val Pro Ser Arg Phe Ser Gly
    50                  55                  60

Ser Gly Ser Gly Lys Asp Tyr Phe Leu Thr Ile Ser Asn Leu Glu Gln
65                  70                  75                  80

Glu Asp Val Ala Ala Tyr Phe Cys Gln Gln Gly His Thr Leu Pro Pro
                85                  90                  95

Thr Phe Gly Gly Gly Thr Lys Leu Glu Ile Lys
            100                 105

<210> SEQ ID NO 180
<211> LENGTH: 117
<212> TYPE: PRT
<213> ORGANISM: Artificial Sequence
<220> FEATURE:
<223> OTHER INFORMATION: Synthetic Construct

<400> SEQUENCE: 180

Glu Val Gln Leu Gln Gln Ser Gly Pro Glu Leu Val Lys Pro Gly Ala
1               5                   10                  15

Ser Val Lys Ile Ser Cys Lys Ala Ser Gly Tyr Thr Phe Thr Asp Ser
            20                  25                  30

Tyr Met Ser Trp Val Lys Gln Ser His Gly Lys Thr Leu Glu Trp Ile
        35                  40                  45

Gly Asp Met Tyr Pro Asp Asn Gly Asp Ser Ser Tyr Asn Gln Lys Phe
    50                  55                  60

Arg Glu Lys Val Thr Leu Thr Val Asp Lys Ser Ser Thr Thr Ala Tyr
65                  70                  75                  80

Met Glu Phe Arg Ser Leu Thr Ser Glu Asp Ser Ala Val Tyr Tyr Cys
                85                  90                  95

Val Leu Ala Pro Arg Trp Tyr Phe Ser Val Trp Gly Thr Gly Thr Thr
            100                 105                 110

Val Thr Val Ser Ser
        115

<210> SEQ ID NO 181
<211> LENGTH: 107
<212> TYPE: PRT
<213> ORGANISM: Artificial Sequence
<220> FEATURE:
<223> OTHER INFORMATION: Synthetic Construct

<400> SEQUENCE: 181

Asp Ile Leu Met Thr Gln Ser Pro Ser Ser Met Ser Val Ser Leu Gly

```
            1               5                  10                 15
Asp Thr Val Ser Ile Thr Cys His Ala Ser Gln Asp Ile Ser Ser Tyr
                    20                  25                  30

Ile Val Trp Leu Gln Gln Lys Pro Gly Lys Ser Phe Arg Gly Leu Ile
            35                  40                  45

Tyr His Gly Thr Asn Leu Glu Asp Gly Ile Pro Ser Arg Phe Ser Gly
        50                  55                  60

Ser Gly Ser Gly Ala Asp Tyr Ser Leu Thr Ile Ser Ser Leu Glu Ser
 65                 70                  75                  80

Glu Asp Phe Ala Asp Tyr Tyr Cys Val His Tyr Ala Gln Phe Pro Tyr
                    85                  90                  95

Thr Phe Gly Gly Gly Thr Lys Leu Glu Ile Lys
                100                 105
```

<210> SEQ ID NO 182
<211> LENGTH: 114
<212> TYPE: PRT
<213> ORGANISM: Artificial Sequence
<220> FEATURE:
<223> OTHER INFORMATION: Synthetic Construct

<400> SEQUENCE: 182

```
Gln Val Gln Leu Gln Gln Ser Gly Ala Glu Leu Val Arg Pro Gly Thr
 1               5                  10                  15

Ser Val Lys Val Ser Cys Lys Ala Ser Gly Tyr Ala Phe Thr Asn Tyr
                    20                  25                  30

Leu Ile Glu Trp Val Lys Gln Arg Pro Gly Gln Gly Leu Glu Trp Ile
            35                  40                  45

Gly Val Ile Asn Pro Gly Ser Gly Asp Thr Tyr Tyr Ser Glu Lys Phe
        50                  55                  60

Lys Gly Lys Val Thr Leu Thr Ala Asp Lys Ser Ser Ser Thr Ala Tyr
 65                 70                  75                  80

Met Gln Leu Ser Ser Leu Thr Ser Glu Asp Ser Ala Val Tyr Phe Cys
                    85                  90                  95

Ala Arg Asp Arg Leu Asp Tyr Trp Gly Gln Gly Thr Thr Leu Thr Val
                100                 105                 110

Ser Ser
```

<210> SEQ ID NO 183
<211> LENGTH: 451
<212> TYPE: PRT
<213> ORGANISM: Artificial Sequence
<220> FEATURE:
<223> OTHER INFORMATION: Synthetic Construct

<400> SEQUENCE: 183

```
Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Asn Tyr
                    20                  25                  30

Thr Met Asn Trp Val Arg Gln Ala Pro Gly Lys Gly Leu Glu Trp Val
            35                  40                  45

Ser Ala Ile Ser Gly Ser Gly Gly Ser Thr Tyr Tyr Ala Asp Ser Val
        50                  55                  60

Lys Gly Arg Phe Thr Ile Ser Arg Asp Asn Ser Lys Asn Thr Leu Tyr
 65                 70                  75                  80

Leu Gln Met Asn Ser Leu Arg Ala Glu Asp Thr Ala Val Tyr Tyr Cys
```

85                  90                  95
Ala Lys Asp Arg Tyr Ser Gln Val His Tyr Ala Leu Asp Tyr Trp Gly
                100                 105                 110

Gln Gly Thr Leu Val Thr Val Ser Ser Ala Ser Thr Lys Gly Pro Ser
            115                 120                 125

Val Phe Pro Leu Ala Pro Ser Ser Lys Ser Thr Ser Gly Gly Thr Ala
        130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 184
<211> LENGTH: 219
<212> TYPE: PRT
<213> ORGANISM: Artificial Sequence
<220> FEATURE:
<223> OTHER INFORMATION: Synthetic Construct

<400> SEQUENCE: 184

Asp Ile Val Met Thr Gln Ser Pro Asp Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Ala Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Gln Gln Tyr
                85                  90                  95

Tyr Asn His Pro Thr Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 185
<211> LENGTH: 219
<212> TYPE: PRT
<213> ORGANISM: Artificial Sequence
<220> FEATURE:
<223> OTHER INFORMATION: Synthetic Construct

<400> SEQUENCE: 185

Asp Ile Gln Met Thr Gln Ser Pro Asp Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Ala Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Gln Gln Tyr
                85                  90                  95

Tyr Asn His Pro Thr Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe

```
            130                 135                 140
Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 186
<211> LENGTH: 450
<212> TYPE: PRT
<213> ORGANISM: Artificial Sequence
<220> FEATURE:
<223> OTHER INFORMATION: Synthetic Construct

<400> SEQUENCE: 186

Glu Val Gln Leu Val Glu Ser Gly Gly Gly Leu Val His Pro Gly Gly
1               5                   10                  15

Ser Leu Arg Leu Ser Cys Ala Gly Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ser Ala Ile Gly Thr Gly Gly Thr Tyr Tyr Ala Asp Ser Val Met
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Tyr Asp Asn Val Met Gly Leu Tyr Trp Phe Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
```

```
                    275                 280                 285
Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 187
<211> LENGTH: 214
<212> TYPE: PRT
<213> ORGANISM: Artificial Sequence
<220> FEATURE:
<223> OTHER INFORMATION: Synthetic Construct

<400> SEQUENCE: 187

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Ala Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
```

```
                    180                 185                 190

Ala Cys Glu Val Thr His Gln Gly Leu Ser Ser Pro Val Thr Lys Ser
                195                 200                 205

Phe Asn Arg Gly Glu Cys
            210
```

<210> SEQ ID NO 188
<211> LENGTH: 118
<212> TYPE: PRT
<213> ORGANISM: Artificial Sequence
<220> FEATURE:
<223> OTHER INFORMATION: Synthetic Construct

<400> SEQUENCE: 188

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Tyr Ile Ser Ser Ser Ser Thr Ile Asp Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Asp Glu Asp Thr Ala Val Tyr Tyr Cys
                85                  90                  95

Ala Arg Glu Ser Gly Trp Tyr Leu Phe Asp Tyr Trp Gly Gln Gly Thr
            100                 105                 110

Leu Val Thr Val Ser Ser
        115
```

<210> SEQ ID NO 189
<211> LENGTH: 107
<212> TYPE: PRT
<213> ORGANISM: Artificial Sequence
<220> FEATURE:
<223> OTHER INFORMATION: Synthetic Construct

<400> SEQUENCE: 189

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Pro
                85                  90                  95

Thr Phe Gly Gly Gly Thr Lys Val Glu Ile Lys
            100                 105
```

<210> SEQ ID NO 190
<211> LENGTH: 124
<212> TYPE: PRT
<213> ORGANISM: Artificial Sequence
<220> FEATURE:

<223> OTHER INFORMATION: Synthetic Construct

<400> SEQUENCE: 190

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp Gln Ser Thr Ala Asp Tyr Tyr Phe Tyr Tyr Gly Met Asp
            100                 105                 110

Val Trp Gly Gln Gly Thr Thr Val Thr Val Ser Ser
        115                 120

<210> SEQ ID NO 191
<211> LENGTH: 106
<212> TYPE: PRT
<213> ORGANISM: Artificial Sequence
<220> FEATURE:
<223> OTHER INFORMATION: Synthetic Construct

<400> SEQUENCE: 191

Glu Ile Val Val Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Thr
                85                  90                  95

Phe Gly Gln Gly Thr Lys Val Glu Ile Lys
            100                 105

<210> SEQ ID NO 192
<211> LENGTH: 122
<212> TYPE: PRT
<213> ORGANISM: Artificial Sequence
<220> FEATURE:
<223> OTHER INFORMATION: Synthetic Construct

<400> SEQUENCE: 192

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asp Tyr
            20                  25                  30

Ser Met His Trp Val Arg Gln Ala Pro Gly Gln Gly Leu Lys Trp Met
        35                  40                  45

Gly Trp Ile Asn Thr Glu Thr Gly Glu Pro Thr Tyr Ala Asp Asp Phe

```
                      50                  55                  60
Lys Gly Arg Phe Val Phe Ser Leu Asp Thr Ser Val Ser Thr Ala Tyr
 65                  70                  75                  80

Leu Gln Ile Ser Ser Leu Lys Ala Glu Asp Thr Ala Val Tyr Tyr Cys
                 85                  90                  95

Ala Asn Pro Tyr Tyr Asp Tyr Val Ser Tyr Tyr Ala Met Asp Tyr Trp
            100                 105                 110

Gly Gln Gly Thr Thr Val Thr Val Ser Ser
            115                 120

<210> SEQ ID NO 193
<211> LENGTH: 107
<212> TYPE: PRT
<213> ORGANISM: Artificial Sequence
<220> FEATURE:
<223> OTHER INFORMATION: Synthetic Construct

<400> SEQUENCE: 193

Asp Ile Gln Met Thr Gln Ser Pro Ser Ser Leu Ser Ala Ser Val Gly
 1               5                  10                  15

Asp Arg Val Thr Ile Thr Cys Lys Ala Ser Gln Asp Val Ser Thr Ala
             20                  25                  30

Val Ala Trp Tyr Gln Gln Lys Pro Gly Lys Ala Pro Lys Leu Leu Ile
         35                  40                  45

Tyr Ser Ala Ser Tyr Leu Tyr Thr Gly Val Pro Ser Arg Phe Ser Gly
     50                  55                  60

Ser Gly Ser Gly Thr Asp Phe Thr Phe Thr Ile Ser Ser Leu Gln Pro
 65                  70                  75                  80

Glu Asp Ile Ala Thr Tyr Tyr Cys Gln Gln His Tyr Ser Thr Pro Arg
                 85                  90                  95

Thr Phe Gly Gln Gly Thr Lys Leu Glu Ile Lys
            100                 105

<210> SEQ ID NO 194
<211> LENGTH: 120
<212> TYPE: PRT
<213> ORGANISM: Artificial Sequence
<220> FEATURE:
<223> OTHER INFORMATION: Synthetic Construct

<400> SEQUENCE: 194

Glu Val Gln Leu Val Glu Ser Gly Gly Gly Leu Val Gln Pro Gly Gly
 1               5                  10                  15

Ser Leu Arg Leu Ser Cys Ala Ala Ser Glu Tyr Glu Phe Pro Ser His
             20                  25                  30

Asp Met Ser Trp Val Arg Gln Ala Pro Gly Lys Gly Leu Glu Leu Val
         35                  40                  45

Ala Ala Ile Asn Ser Asp Gly Gly Ser Thr Tyr Tyr Pro Asp Thr Met
     50                  55                  60

Glu Arg Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg His Tyr Asp Asp Tyr Tyr Ala Trp Phe Ala Tyr Trp Gly Gln
            100                 105                 110

Gly Thr Met Val Thr Val Ser Ser
            115                 120
```

```
<210> SEQ ID NO 195
<211> LENGTH: 111
<212> TYPE: PRT
<213> ORGANISM: Artificial Sequence
<220> FEATURE:
<223> OTHER INFORMATION: Synthetic Construct

<400> SEQUENCE: 195

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Lys Ser Val Ser Thr Ser
            20                  25                  30

Gly Tyr Ser Tyr Met His Trp Tyr Gln Gln Lys Pro Gly Gln Ala Pro
        35                  40                  45

Arg Leu Leu Ile Tyr Leu Ala Ser Asn Leu Glu Ser Gly Val Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys Gln His Ser Arg
                85                  90                  95

Glu Leu Pro Leu Thr Phe Gly Gly Gly Thr Lys Val Glu Ile Lys
            100                 105                 110

<210> SEQ ID NO 196
<211> LENGTH: 469
<212> TYPE: PRT
<213> ORGANISM: Artificial Sequence
<220> FEATURE:
<223> OTHER INFORMATION: Synthetic Construct

<400> SEQUENCE: 196

Met Tyr Leu Gly Leu Asn Tyr Val Phe Ile Val Phe Leu Leu Asn Gly
1               5                   10                  15

Val Gln Ser Glu Val Lys Leu Glu Glu Ser Gly Gly Gly Leu Val Gln
            20                  25                  30

Pro Gly Gly Ser Met Lys Leu Ser Cys Ala Ala Ser Gly Phe Thr Phe
        35                  40                  45

Ser Asp Ala Trp Met Asp Trp Val Arg Gln Ser Pro Glu Lys Gly Leu
    50                  55                  60

Glu Trp Val Ala Glu Ile Arg Ser Lys Ala Asn Asn His Ala Thr Tyr
65                  70                  75                  80

Tyr Ala Glu Ser Val Asn Gly Arg Phe Thr Ile Ser Arg Asp Asp Ser
                85                  90                  95

Lys Ser Ser Val Tyr Leu Gln Met Asn Ser Leu Arg Ala Glu Asp Thr
            100                 105                 110

Gly Ile Tyr Tyr Cys Thr Trp Gly Glu Val Phe Tyr Phe Asp Tyr Trp
        115                 120                 125

Gly Gln Gly Thr Thr Leu Thr Val Ser Ser Ala Ser Thr Lys Gly Pro
    130                 135                 140

Ser Val Phe Pro Leu Ala Pro Ser Ser Lys Ser Thr Ser Gly Gly Thr
145                 150                 155                 160

Ala Ala Leu Gly Cys Leu Val Lys Asp Tyr Phe Pro Glu Pro Val Thr
                165                 170                 175

Val Ser Trp Asn Ser Gly Ala Leu Thr Ser Gly Val His Thr Phe Pro
            180                 185                 190

Ala Val Leu Gln Ser Ser Gly Leu Tyr Ser Leu Ser Ser Val Val Thr
        195                 200                 205
```

Val Pro Ser Ser Ser Leu Gly Thr Gln Thr Tyr Ile Thr Cys Asn Val
    210                 215                 220

Asn His Lys Pro Ser Asn Thr Lys Val Asp Lys Val Glu Pro Lys
225                 230                 235                 240

Ser Cys Asp Lys Thr His Thr Cys Pro Pro Cys Pro Ala Pro Glu Leu
                245                 250                 255

Leu Gly Gly Pro Ser Val Phe Leu Phe Pro Pro Lys Pro Lys Asp Thr
                260                 265                 270

Leu Met Ile Ser Arg Thr Pro Glu Val Thr Cys Val Val Val Asp Val
            275                 280                 285

Ser His Glu Asp Pro Glu Val Lys Phe Asn Trp Tyr Val Asp Gly Val
290                 295                 300

Glu Val His Asn Ala Lys Thr Lys Pro Arg Glu Glu Gln Tyr Asn Ser
305                 310                 315                 320

Thr Tyr Arg Val Val Ser Val Leu Thr Val Leu His Gln Asp Trp Leu
                325                 330                 335

Asn Gly Lys Glu Tyr Lys Cys Lys Val Ser Asn Lys Ala Leu Pro Ala
                340                 345                 350

Pro Ile Glu Lys Thr Ile Ser Lys Ala Lys Gly Gln Pro Arg Glu Pro
            355                 360                 365

Gln Val Tyr Thr Leu Pro Pro Ser Arg Asp Glu Leu Thr Lys Asn Gln
370                 375                 380

Val Ser Leu Thr Cys Leu Val Lys Gly Phe Tyr Pro Ser Asp Ile Ala
385                 390                 395                 400

Val Glu Trp Glu Ser Asn Gly Gln Pro Glu Asn Asn Tyr Lys Thr Thr
                405                 410                 415

Pro Pro Val Leu Asp Ser Asp Gly Ser Phe Phe Leu Tyr Ser Lys Leu
                420                 425                 430

Thr Val Asp Lys Ser Arg Trp Gln Gln Gly Asn Val Phe Ser Cys Ser
            435                 440                 445

Val Met His Glu Ala Leu His Asn His Tyr Thr Gln Lys Ser Leu Ser
450                 455                 460

Leu Ser Pro Gly Lys
465

<210> SEQ ID NO 197
<211> LENGTH: 233
<212> TYPE: PRT
<213> ORGANISM: Artificial Sequence
<220> FEATURE:
<223> OTHER INFORMATION: Synthetic Construct

<400> SEQUENCE: 197

Met Arg Pro Ser Ile Gln Phe Leu Gly Leu Leu Leu Phe Trp Leu His
1               5                   10                  15

Gly Ala Gln Cys Asp Ile Gln Met Thr Gln Ser Pro Ser Ser Leu Ser
                20                  25                  30

Ala Ser Leu Gly Gly Lys Val Thr Ile Thr Cys Lys Ser Ser Gln Asp
            35                  40                  45

Ile Asn Lys Tyr Ile Ala Trp Tyr Gln His Lys Pro Gly Lys Gly Pro
        50                  55                  60

Arg Leu Leu Ile His Tyr Thr Ser Thr Leu Gln Pro Gly Ile Pro Ser
65                  70                  75                  80

Arg Phe Ser Gly Ser Gly Ser Gly Arg Asp Tyr Ser Phe Ser Ile Ser
                85                  90                  95

```
Asn Leu Glu Pro Glu Asp Ile Ala Thr Tyr Tyr Cys Leu Gln Tyr Asp
            100                 105                 110

Asn Leu Leu Thr Phe Gly Ala Gly Thr Lys Leu Glu Leu Lys Arg Thr
        115                 120                 125

Val Ala Ala Pro Ser Val Phe Ile Phe Pro Pro Ser Asp Glu Gln Leu
130                 135                 140

Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly
                165                 170                 175

Asn Ser Gln Glu Ser Val Thr Glu Gln Asp Ser Lys Asp Ser Thr Tyr
            180                 185                 190

Ser Leu Ser Ser Thr Leu Thr Leu Ser Lys Ala Asp Tyr Glu Lys His
        195                 200                 205

Lys Val Tyr Ala Cys Glu Val Thr His Gln Gly Leu Ser Ser Pro Val
210                 215                 220

Thr Lys Ser Phe Asn Arg Gly Glu Cys
225                 230

<210> SEQ ID NO 198
<211> LENGTH: 138
<212> TYPE: PRT
<213> ORGANISM: Artificial Sequence
<220> FEATURE:
<223> OTHER INFORMATION: Synthetic Construct

<400> SEQUENCE: 198

Met Tyr Leu Gly Leu Asn Tyr Val Phe Ile Val Phe Leu Leu Asn Gly
1               5                   10                  15

Val Gln Ser Glu Val Lys Leu Glu Glu Ser Gly Gly Gly Leu Val Gln
            20                  25                  30

Pro Gly Gly Ser Met Lys Leu Ser Cys Ala Ala Ser Gly Phe Thr Phe
        35                  40                  45

Ser Asp Ala Trp Met Asp Trp Val Arg Gln Ser Pro Glu Lys Gly Leu
50                  55                  60

Glu Trp Val Ala Glu Ile Arg Ser Lys Ala Asn Asn His Ala Thr Tyr
65                  70                  75                  80

Tyr Ala Glu Ser Val Asn Gly Arg Phe Thr Ile Ser Arg Asp Asp Ser
                85                  90                  95

Lys Ser Ser Val Tyr Leu Gln Met Asn Ser Leu Arg Ala Glu Asp Thr
            100                 105                 110

Gly Ile Tyr Tyr Cys Thr Trp Gly Glu Val Pro Tyr Phe Asp Tyr Trp
        115                 120                 125

Gly Gln Gly Thr Thr Leu Thr Val Ser Ser
        130                 135

<210> SEQ ID NO 199
<211> LENGTH: 126
<212> TYPE: PRT
<213> ORGANISM: Artificial Sequence
<220> FEATURE:
<223> OTHER INFORMATION: Synthetic Construct

<400> SEQUENCE: 199

Met Arg Pro Ser Ile Gln Phe Leu Gly Leu Leu Leu Phe Trp Leu His
1               5                   10                  15

Gly Ala Gln Cys Asp Ile Gln Met Thr Gln Ser Pro Ser Ser Leu Ser
```

```
                    20                  25                  30
Ala Ser Leu Gly Gly Lys Val Thr Ile Thr Cys Lys Ser Ser Gln Asp
            35                  40                  45
Ile Asn Lys Tyr Ile Ala Trp Tyr Gln His Lys Pro Gly Lys Gly Pro
         50                  55                  60
Arg Leu Leu Ile His Tyr Thr Ser Thr Leu Gln Pro Gly Ile Pro Ser
65                  70                  75                  80
Arg Phe Ser Gly Ser Gly Ser Gly Arg Asp Tyr Ser Phe Ser Ile Ser
                85                  90                  95
Asn Leu Glu Pro Glu Asp Ile Ala Thr Tyr Tyr Cys Leu Gln Tyr Asp
            100                 105                 110
Asn Leu Leu Thr Phe Gly Ala Gly Thr Lys Leu Glu Leu Lys
        115                 120                 125

<210> SEQ ID NO 200
<211> LENGTH: 119
<212> TYPE: PRT
<213> ORGANISM: Artificial Sequence
<220> FEATURE:
<223> OTHER INFORMATION: Synthetic Construct

<400> SEQUENCE: 200

Glu Val Gln Leu Gln Gln Ser Gly Pro Glu Leu Val Lys Pro Gly Ala
1               5                   10                  15
Ser Val Lys Met Ser Cys Lys Ala Ser Gly Tyr Thr Phe Thr Ser Tyr
            20                  25                  30
Val Met His Trp Val Lys Gln Lys Pro Gly Gln Gly Leu Glu Trp Ile
        35                  40                  45
Gly Tyr Ile Asn Pro Tyr Asn Asp Gly Thr Lys Tyr Asn Glu Lys Phe
    50                  55                  60
Lys Gly Lys Ala Thr Leu Thr Ser Asp Lys Ser Ser Ser Thr Ala Tyr
65                  70                  75                  80
Met Glu Leu Ser Ser Leu Thr Ser Glu Asp Ser Ala Val Tyr Tyr Cys
                85                  90                  95
Ala Asn Tyr Tyr Gly Ser Ser Leu Ser Met Asp Tyr Trp Gly Gln Gly
            100                 105                 110
Thr Ser Val Thr Val Ser Ser
        115

<210> SEQ ID NO 201
<211> LENGTH: 108
<212> TYPE: PRT
<213> ORGANISM: Artificial Sequence
<220> FEATURE:
<223> OTHER INFORMATION: Synthetic Construct

<400> SEQUENCE: 201

Asp Ile Gln Met Thr Gln Thr Thr Ser Ser Leu Ser Ala Ser Leu Gly
1               5                   10                  15
Asp Arg Val Thr Ile Ser Cys Arg Ala Ser Gln Asp Ile Ser Asn Tyr
            20                  25                  30
Leu Asn Trp Tyr Gln Gln Lys Pro Asp Gly Thr Val Lys Leu Leu Ile
        35                  40                  45
Tyr Tyr Thr Ser Arg Leu His Ser Gly Val Pro Ser Arg Phe Ser Gly
    50                  55                  60
Ser Gly Ser Gly Thr Asp Tyr Ser Leu Thr Ile Ser Asn Leu Glu Gln
65                  70                  75                  80
```

Glu Asp Ile Ala Thr Tyr Phe Cys Gln Gln Gly Asn Thr Leu Pro Trp
            85                  90                  95

Thr Phe Gly Gly Gly Thr Lys Leu Glu Ile Lys Arg
            100                 105

<210> SEQ ID NO 202
<211> LENGTH: 121
<212> TYPE: PRT
<213> ORGANISM: Artificial Sequence
<220> FEATURE:
<223> OTHER INFORMATION: Synthetic Construct

<400> SEQUENCE: 202

Glu Val Gln Leu Gln Gln Ser Gly Pro Glu Leu Val Lys Pro Gly Ala
1               5                   10                  15

Ser Val Lys Ile Ser Cys Lys Thr Ser Gly Tyr Thr Phe Lys Asp Tyr
            20                  25                  30

Thr Met His Trp Val Lys Gln Ser His Gly Lys Ser Leu Glu Trp Ile
        35                  40                  45

Gly Gly Ile Tyr Pro Asn Asn Gly Gly Ser Thr Tyr Asn Gln Asn Phe
    50                  55                  60

Lys Asp Lys Ala Thr Leu Thr Val Asp Lys Ser Ser Ser Thr Ala Tyr
65                  70                  75                  80

Met Glu Phe Arg Ser Leu Thr Ser Glu Asp Ser Ala Val Tyr Tyr Cys
                85                  90                  95

Ala Arg Met Gly Tyr His Gly Pro His Leu Asp Phe Asp Val Trp Gly
            100                 105                 110

Ala Gly Thr Thr Val Thr Val Ser Pro
        115                 120

<210> SEQ ID NO 203
<211> LENGTH: 108
<212> TYPE: PRT
<213> ORGANISM: Artificial Sequence
<220> FEATURE:
<223> OTHER INFORMATION: Synthetic Construct

<400> SEQUENCE: 203

Asp Ile Val Met Thr Gln Ser His Lys Phe Met Ser Thr Ser Leu Gly
1               5                   10                  15

Asp Arg Val Ser Ile Thr Cys Lys Ala Ser Gln Asp Val Gly Ala Ala
            20                  25                  30

Val Ala Trp Tyr Gln Gln Lys Pro Gly Gln Ser Pro Lys Leu Leu Ile
        35                  40                  45

Tyr Trp Ala Ser Thr Arg His Thr Gly Val Pro Asp Arg Phe Thr Gly
    50                  55                  60

Gly Gly Ser Gly Thr Asp Phe Thr Leu Thr Ile Ser Asn Val Gln Ser
65                  70                  75                  80

Glu Asp Leu Thr Asp Tyr Phe Cys Gln Gln Tyr Ile Asn Tyr Pro Leu
                85                  90                  95

Thr Phe Gly Gly Gly Thr Lys Leu Glu Ile Lys Arg
            100                 105

<210> SEQ ID NO 204
<211> LENGTH: 119
<212> TYPE: PRT
<213> ORGANISM: Artificial Sequence
<220> FEATURE:
<223> OTHER INFORMATION: Synthetic Construct

```
<400> SEQUENCE: 204

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Val Met His Trp Val Arg Gln Ala Pro Gly Gln Arg Leu Glu Trp Met
        35                  40                  45

Gly Tyr Ile Asn Pro Tyr Asn Asp Gly Thr Lys Tyr Asn Glu Lys Phe
    50                  55                  60

Lys Gly Arg Val Thr Ile Thr Ser Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Asn Tyr Tyr Gly Ser Ser Leu Ser Met Asp Tyr Trp Gly Gln Gly
            100                 105                 110

Thr Leu Val Thr Val Ser Ser
        115

<210> SEQ ID NO 205
<211> LENGTH: 108
<212> TYPE: PRT
<213> ORGANISM: Artificial Sequence
<220> FEATURE:
<223> OTHER INFORMATION: Synthetic Construct

<400> SEQUENCE: 205

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Gly Asn Thr Leu Pro Trp
                85                  90                  95

Thr Phe Gly Gln Gly Thr Lys Val Glu Ile Lys Arg
            100                 105

<210> SEQ ID NO 206
<211> LENGTH: 108
<212> TYPE: PRT
<213> ORGANISM: Artificial Sequence
<220> FEATURE:
<223> OTHER INFORMATION: Synthetic Construct

<400> SEQUENCE: 206

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Ala Val Lys Leu Leu Ile
        35                  40                  45

Tyr Tyr Thr Ser Arg Leu His Ser Gly Val Pro Ser Arg Phe Ser Gly
    50                  55                  60
```

-continued

Ser Gly Ser Gly Thr Asp Tyr Thr Leu Thr Ile Ser Ser Leu Gln Pro
 65                  70                  75                  80

Glu Asp Phe Ala Thr Tyr Phe Cys Gln Gln Gly Asn Thr Leu Pro Trp
                 85                  90                  95

Thr Phe Gly Gln Gly Thr Lys Val Glu Ile Lys Arg
            100                 105

<210> SEQ ID NO 207
<211> LENGTH: 119
<212> TYPE: PRT
<213> ORGANISM: Artificial Sequence
<220> FEATURE:
<223> OTHER INFORMATION: Synthetic Construct

<400> SEQUENCE: 207

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Val Met His Trp Val Arg Gln Ala Pro Gly Gln Arg Leu Glu Trp Ile
            35                  40                  45

Gly Tyr Ile Asn Pro Tyr Asn Asp Gly Thr Lys Tyr Asn Glu Lys Phe
    50                  55                  60

Lys Gly Arg Ala Thr Ile Thr Ser Asp Thr Ser Ala Ser Thr Ala Tyr
 65                  70                  75                  80

Met Glu Leu Ser Ser Leu Arg Ser Glu Asp Thr Ala Val Tyr Tyr Cys
                 85                  90                  95

Ala Asn Tyr Tyr Gly Ser Ser Leu Ser Met Asp Tyr Trp Gly Gln Gly
            100                 105                 110

Thr Leu Val Thr Val Ser Ser
        115

<210> SEQ ID NO 208
<211> LENGTH: 119
<212> TYPE: PRT
<213> ORGANISM: Artificial Sequence
<220> FEATURE:
<223> OTHER INFORMATION: Synthetic Construct

<400> SEQUENCE: 208

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Val Met His Trp Val Arg Gln Ala Pro Gly Gln Arg Leu Glu Trp Ile
            35                  40                  45

Gly Tyr Ile Asn Pro Tyr Asn Asp Gly Thr Lys Tyr Asn Glu Lys Phe
    50                  55                  60

Lys Gly Arg Ala Thr Leu Thr Ser Asp Lys Ser Ala Ser Thr Ala Tyr
 65                  70                  75                  80

Met Glu Leu Ser Ser Leu Arg Ser Glu Asp Thr Ala Val Tyr Tyr Cys
                 85                  90                  95

Ala Asn Tyr Tyr Gly Ser Ser Leu Ser Met Asp Tyr Trp Gly Gln Gly
            100                 105                 110

Thr Leu Val Thr Val Ser Ser
        115

<210> SEQ ID NO 209

-continued

```
<211> LENGTH: 121
<212> TYPE: PRT
<213> ORGANISM: Artificial Sequence
<220> FEATURE:
<223> OTHER INFORMATION: Synthetic Construct

<400> SEQUENCE: 209

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Lys Asp Tyr
            20                  25                  30

Thr Met His Trp Val Arg Gln Ala Pro Gly Gln Gly Leu Glu Trp Met
        35                  40                  45

Gly Gly Ile Tyr Pro Asn Asn Gly Gly Ser Thr Tyr Asn Gln Asn Phe
    50                  55                  60

Lys Asp Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Met Gly Tyr His Gly Pro His Leu Asp Phe Asp Val Trp Gly
            100                 105                 110

Gln Gly Thr Thr Val Thr Val Ser Ser
        115                 120

<210> SEQ ID NO 210
<211> LENGTH: 108
<212> TYPE: PRT
<213> ORGANISM: Artificial Sequence
<220> FEATURE:
<223> OTHER INFORMATION: Synthetic Construct

<400> SEQUENCE: 210

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Gly Ala Ala
            20                  25                  30

Val Ala Trp Tyr Gln Gln Lys Pro Gly Lys Ala Pro Lys Leu Leu Ile
        35                  40                  45

Tyr Trp Ala Ser Thr Arg His Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ile Asn Tyr Pro Leu
                85                  90                  95

Thr Phe Gly Gly Gly Thr Lys Val Glu Ile Lys Arg
            100                 105

<210> SEQ ID NO 211
<211> LENGTH: 108
<212> TYPE: PRT
<213> ORGANISM: Artificial Sequence
<220> FEATURE:
<223> OTHER INFORMATION: Synthetic Construct

<400> SEQUENCE: 211

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Gly Ala Ala
            20                  25                  30
```

-continued

Val Ala Trp Tyr Gln Gln Lys Pro Gly Lys Ala Pro Lys Leu Leu Ile
         35                  40                  45

Tyr Trp Ala Ser Thr Arg His Thr Gly Val Pro Asp Arg Phe Ser Gly
 50                  55                  60

Gly Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Ile Asn Tyr Pro Leu
             85                  90                  95

Thr Phe Gly Gly Gly Thr Lys Val Glu Ile Lys Arg
            100                 105

<210> SEQ ID NO 212
<211> LENGTH: 121
<212> TYPE: PRT
<213> ORGANISM: Artificial Sequence
<220> FEATURE:
<223> OTHER INFORMATION: Synthetic Construct

<400> SEQUENCE: 212

Gln Val Gln Leu Val Gln Ser Gly Ala Glu Val Lys Lys Pro Gly Ser
 1               5                  10                  15

Ser Val Lys Val Ser Cys Lys Ala Ser Gly Tyr Thr Phe Lys Asp Tyr
             20                  25                  30

Thr Met His Trp Val Arg Gln Ala Pro Gly Gln Gly Leu Glu Trp Ile
         35                  40                  45

Gly Gly Ile Tyr Pro Asn Asn Gly Gly Ser Thr Tyr Asn Gln Asn Phe
 50                  55                  60

Lys Asp Arg Val Thr Leu Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
             85                  90                  95

Ala Arg Met Gly Tyr His Gly Pro His Leu Asp Phe Asp Val Trp Gly
            100                 105                 110

Gln Gly Thr Thr Val Thr Val Ser Ser
        115                 120

<210> SEQ ID NO 213
<211> LENGTH: 121
<212> TYPE: PRT
<213> ORGANISM: Artificial Sequence
<220> FEATURE:
<223> OTHER INFORMATION: Synthetic Construct

<400> SEQUENCE: 213

Gln Val Gln Leu Val Gln Ser Gly Ala Glu Val Lys Lys Pro Gly Ser
 1               5                  10                  15

Ser Val Lys Val Ser Cys Lys Ala Ser Gly Tyr Thr Phe Lys Asp Tyr
             20                  25                  30

Thr Met His Trp Val Arg Gln Ala Pro Gly Gln Gly Leu Glu Trp Ile
         35                  40                  45

Gly Gly Ile Tyr Pro Asn Asn Gly Gly Ser Thr Tyr Asn Gln Asn Phe
 50                  55                  60

Lys Asp Arg Ala Thr Leu Thr Val Asp Lys Ser Thr Ser Thr Ala Tyr
 65                  70                  75                  80

Met Glu Leu Ser Ser Leu Arg Ser Glu Asp Thr Ala Val Tyr Tyr Cys
             85                  90                  95

Ala Arg Met Gly Tyr His Gly Pro His Leu Asp Phe Asp Val Trp Gly
            100                 105                 110

Gln Gly Thr Thr Val Thr Val Ser Ser
        115                 120

<210> SEQ ID NO 214
<211> LENGTH: 25
<212> TYPE: PRT
<213> ORGANISM: Artificial Sequence
<220> FEATURE:
<223> OTHER INFORMATION: Synthetic Construct

<400> SEQUENCE: 214

Glu Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 215
<211> LENGTH: 13
<212> TYPE: PRT
<213> ORGANISM: Artificial Sequence
<220> FEATURE:
<223> OTHER INFORMATION: Synthetic Construct

<400> SEQUENCE: 215

Trp Val Arg Gln Ala Pro Gly Lys Gly Leu Glu Trp Val
1               5                   10

<210> SEQ ID NO 216
<211> LENGTH: 30
<212> TYPE: PRT
<213> ORGANISM: Artificial Sequence
<220> FEATURE:
<223> OTHER INFORMATION: Synthetic Construct

<400> SEQUENCE: 216

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys
            20                  25                  30

<210> SEQ ID NO 217
<211> LENGTH: 11
<212> TYPE: PRT
<213> ORGANISM: Artificial Sequence
<220> FEATURE:
<223> OTHER INFORMATION: Synthetic Construct

<400> SEQUENCE: 217

Trp Gly Gln Gly Thr Leu Val Thr Val Ser Ser
1               5                   10

<210> SEQ ID NO 218
<211> LENGTH: 23
<212> TYPE: PRT
<213> ORGANISM: Artificial Sequence
<220> FEATURE:
<223> OTHER INFORMATION: Synthetic Construct

<400> SEQUENCE: 218

Asp Ile Gln Met Thr Gln Ser Pro Ser Ser Leu Ser Ala Ser Val Gly
1               5                   10                  15

Asp Arg Val Thr Ile Thr Cys
            20

```
<210> SEQ ID NO 219
<211> LENGTH: 15
<212> TYPE: PRT
<213> ORGANISM: Artificial Sequence
<220> FEATURE:
<223> OTHER INFORMATION: Synthetic Construct

<400> SEQUENCE: 219

Trp Tyr Gln Gln Lys Pro Gly Lys Ala Pro Lys Leu Leu Ile Tyr
1               5                   10                  15

<210> SEQ ID NO 220
<211> LENGTH: 32
<212> TYPE: PRT
<213> ORGANISM: Artificial Sequence
<220> FEATURE:
<223> OTHER INFORMATION: Synthetic Construct

<400> SEQUENCE: 220

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
            20                  25                  30

<210> SEQ ID NO 221
<211> LENGTH: 10
<212> TYPE: PRT
<213> ORGANISM: Artificial Sequence
<220> FEATURE:
<223> OTHER INFORMATION: Synthetic Construct

<400> SEQUENCE: 221

Phe Gly Gln Gly Thr Lys Val Glu Ile Lys
1               5                   10

<210> SEQ ID NO 222
<211> LENGTH: 17
<212> TYPE: PRT
<213> ORGANISM: Artificial Sequence
<220> FEATURE:
<223> OTHER INFORMATION: Synthetic Construct

<400> SEQUENCE: 222

Asp Met Tyr Pro Asp Ala Ala Ala Ala Ser Tyr Asn Gln Lys Phe Arg
1               5                   10                  15

Glu

<210> SEQ ID NO 223
<211> LENGTH: 8
<212> TYPE: PRT
<213> ORGANISM: Artificial Sequence
<220> FEATURE:
<223> OTHER INFORMATION: Synthetic Construct

<400> SEQUENCE: 223

Ala Pro Arg Trp Ala Ala Ala Ala
1               5

<210> SEQ ID NO 224
<211> LENGTH: 9
<212> TYPE: PRT
<213> ORGANISM: Artificial Sequence
<220> FEATURE:
<223> OTHER INFORMATION: Synthetic Construct

<400> SEQUENCE: 224
```

```
<210> SEQ ID NO 225
<211> LENGTH: 117
<212> TYPE: PRT
<213> ORGANISM: Artificial Sequence
<220> FEATURE:
<223> OTHER INFORMATION: Synthetic Construct

<400> SEQUENCE: 225

Gln Ala Ala Ala Ala Ala Ala Thr
1               5

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Ser
                20                  25                  30

Tyr Met Ser Trp Val Arg Gln Ala Pro Gly Gln Gly Leu Glu Trp Ile
            35                  40                  45

Gly Asp Met Tyr Pro Asp Asn Gly Asp Ser Ser Tyr Asn Gln Lys Phe
        50                  55                  60

Arg Glu Arg Val Thr Leu Thr Val Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Val Leu Ala Pro Arg Trp Tyr Phe Ser Val Trp Gly Gln Gly Thr Leu
                100                 105                 110

Val Thr Val Ser Ser
            115

<210> SEQ ID NO 226
<211> LENGTH: 117
<212> TYPE: PRT
<213> ORGANISM: Artificial Sequence
<220> FEATURE:
<223> OTHER INFORMATION: Synthetic Construct

<400> SEQUENCE: 226

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Ser
                20                  25                  30

Tyr Met Ser Trp Val Arg Gln Ala Pro Gly Gln Gly Leu Glu Trp Ile
            35                  40                  45

Gly Asp Met Tyr Pro Asp Asn Gly Asp Ser Ser Tyr Asn Gln Lys Phe
        50                  55                  60

Arg Glu Arg Val Thr Leu Thr Val Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Val Leu Ala Pro Arg Trp Tyr Phe Ser Val Trp Gly Gln Gly Thr Leu
                100                 105                 110

Val Thr Val Ser Ser
            115
```

ASSAYS FOR DETECTING T CELL IMMUNE SUBSETS AND METHODS OF USE THEREOF

REFERENCE TO RELATED APPLICATIONS

This application is a Continuation of U.S. patent application Ser. No. 14/930,603, filed Nov. 2, 2015, now abandoned, which claims the priority benefit of U.S. Provisional Application Ser. No. 62/074,594, filed Nov. 3, 2014, each of which is incorporated herein by reference in its entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 146392029001SEQLIST.TXT, date recorded: Dec. 14, 2017, size: 185 KB).

FIELD

The present disclosure relates to assays for detecting T cell immune subsets, as well as methods for determining prognosis, predicting responsiveness to treatment, and methods of treatment related thereto.

BACKGROUND

OX40 (also known as CD134, TNFRSF4 and ACT35) is a member of the tumor necrosis factor receptor superfamily. OX40 is not constitutively expressed on naïve T cells, but is induced after engagement of the T cell receptor (TCR). The ligand for OX40, OX40L, is predominantly expressed on antigen presenting cells. OX40 is highly expressed by activated CD4+ T cells, activated CD8+ T cells, memory T cells, and regulatory T cells. OX40 signaling can provide costimulatory signals to CD4 and CD8 T cells, leading to enhanced cell proliferation, survival, effector function and migration. OX40 signaling also enhances memory T cell development and function.

Regulatory T cells (Treg) cells are highly enriched in tumors and tumor draining lymph nodes derived from multiple cancer indications, including melanoma, NSCLC, renal, ovarian, colon, pancreatic, hepatocellular, and breast cancer. In a subset of these indications, increased intratumoral T reg cell densities are associated with poor patient prognosis, suggesting that these cells play an important role in suppressing antitumor immunity. OX40 positive tumor infiltrating lymphocytes have been described.

It is clear that there continues to be a need for diagnostic, prognostic, and predictive methods to identify patients that are more likely to benefit from anti-tumor treatments that modulate OX40 activity. The invention described herein meets this need and provides other benefits.

All references cited herein, including patent applications, patent publications, and UniProtKB/Swiss-Prot Accession numbers are herein incorporated by reference in their entirety, as if each individual reference were specifically and individually indicated to be incorporated by reference.

BRIEF SUMMARY

The present disclosure describes assays for detecting T cell immune subsets, as well as methods of using these assays to determine prognosis, predict responsiveness, and/or treating or delay progress of cancer.

In certain aspects, the present disclosure provides a method for determining prognosis of a subject having cancer, comprising: (a) measuring the number of CD4+ OX40+ Foxp3+ lymphocytes in a sample comprising cancer cells and lymphocytes obtained from the subject; and (b) determining the prognosis of the subject based on the number of CD4+ OX40+ Foxp3+ lymphocytes in the sample, as compared with a reference, wherein an increased number of CD4+ OX40+ Foxp3+ lymphocytes in the sample indicates that the subject may have an improved prognosis. In some embodiments, the improved prognosis comprises increased overall survival. In some embodiments, the improved prognosis comprises increased progression-free survival.

In certain aspects, the present disclosure provides a method for treating or delaying progression of cancer in a subject, comprising: (a) measuring the number of CD4+ OX40+ Foxp3+ lymphocytes in a sample comprising cancer cells and lymphocytes obtained from the subject; (b) determining the number of CD4+ OX40+ Foxp3+ lymphocytes in the sample, as compared with a reference; and (c) if the number of CD4+ OX40+ Foxp3+ lymphocytes in the sample is higher than the reference, administering to the subject an effective amount of an OX40 agonist.

In certain aspects, the present disclosure provides a method for treating or delaying progression of cancer in a subject, comprising administering to the subject an effective amount of an OX40 agonist, wherein a sample comprising cancer cells and lymphocytes obtained from the subject has an increased number of CD4+ OX40+ Foxp3+ lymphocytes, as compared with a reference. In some embodiments, the subject has been tested to determine if a sample comprising cancer cells and lymphocytes obtained from the subject has an increased number of CD4+ OX40+ Foxp3+ lymphocytes as compared with a reference before treatment or is selected for treatment based on a sample comprising cancer cells and lymphocytes obtained from the subject has an increased number of CD4+ OX40+ Foxp3+ lymphocytes as compared with a reference.

In certain aspects, the present disclosure provides a method for predicting responsiveness of a subject having cancer to an OX40 agonist treatment, comprising: (a) measuring the number of CD4+ OX40+ Foxp3+ lymphocytes in a sample comprising cancer cells and lymphocytes obtained from the subject; and (b) classifying the subject as a responsive or non-responsive subject based on the number of CD4+ OX40+ Foxp3+ lymphocytes in the sample, as compared with a reference, wherein an increased number of CD4+ OX40+ Foxp3+ lymphocytes in the sample indicates the subject may be responsive to the OX40 agonist treatment.

In some embodiments, the number of CD4+ OX40+ Foxp3+ lymphocytes in one or more regions of interest in the sample of a subject is measured. In some embodiments, the region of interest includes tumor cells and stroma. In some embodiments, the number of CD4+ OX40+ Foxp3+ lymphocytes is a median, mean or average number of CD4+ OX40+ Foxp3+ lymphocytes in different regions of interest of the sample from the subject. In some embodiments, the number of CD4+ OX40+ Foxp3+ lymphocytes is normalized to total cells in the region of interest of the sample. In some embodiments, the reference is based on the number of CD4+ OX40+ Foxp3+ lymphocytes in a sample comprising cancer cells and lymphocytes obtained from a cancer having the same type and/or stage as the cancer of the subject. In some embodiments, the reference is a median, mean, or average number of CD4+ OX40+ Foxp3+ lymphocytes in samples obtained from cancers having the same type and/or stage as the cancer of the subject. In some embodiments, the OX40 agonist is an agonist anti-human OX40 antibody. In some embodiments, the antibody is a monoclonal antibody. In some embodiments, the antibody is a humanized or human antibody. In some embodiments, the antibody comprises an IgG1 Fc region. In some embodiments, the antibody comprises an IgG4 Fc region. In some embodiments, the antibody comprises an Fc region comprising a mutation that decreases binding to an Fc receptor. In some embodiments, the antibody comprises (a) HVR-H1 comprising the amino acid sequence of SEQ ID NO:2, 8 or 9; (b) HVR-H2 comprising the amino acid sequence of SEQ ID NO:3, 10, 11, 12, 13, or 14; (c) HVR-H3 comprising the amino acid sequence of SEQ ID NO:4, 15 or 19; (d) HVR-L1 comprising the amino acid sequence of SEQ ID NO:5; (e) HVR-L2 comprising the amino acid sequence of SEQ ID NO:6; and (f) HVR-L3 comprising an amino acid sequence selected from SEQ ID NO:7, 22, 23, 24, 25, 26, 27 or 28. In some embodiments, the antibody comprises (a) HVR-H1 comprising the amino acid sequence of SEQ ID NO:2; (b) HVR-H2 comprising the amino acid sequence of SEQ ID NO:3; (c) HVR-H3 comprising the amino acid sequence of SEQ ID NO:4; (d) HVR-L1 comprising the amino acid sequence of SEQ ID NO:5; (e) HVR-L2 comprising the amino acid sequence of SEQ ID NO:6; and (f) HVR-L3 comprising an amino acid sequence selected from SEQ ID NO:7. In some embodiments, the antibody comprises (a) HVR-H1 comprising the amino acid sequence of SEQ ID NO:2; (b) HVR-H2 comprising the amino acid sequence of SEQ ID NO:3; (c) HVR-H3 comprising the amino acid sequence of SEQ ID NO:4; (d) HVR-L1 comprising the amino acid sequence of SEQ ID NO:5; (e) HVR-L2 comprising the amino acid sequence of SEQ ID NO:6; and (f) HVR-L3 comprising an amino acid sequence selected from SEQ ID NO:26. In some embodiments, the antibody comprises (a) HVR-H1 comprising the amino acid sequence of SEQ ID NO:2; (b) HVR-H2 comprising the amino acid sequence of SEQ ID NO:3; (c) HVR-H3 comprising the amino acid sequence of SEQ ID NO:4; (d) HVR-L1 comprising the amino acid sequence of SEQ ID NO:5; (e) HVR-L2 comprising the amino acid sequence of SEQ ID NO:6; and (f) HVR-L3 comprising an amino acid sequence selected from SEQ ID NO:27. In some embodiments, the antibody is MEDI6469 or MEDI0562. In some embodiments, the OX40 agonist comprises one or more extracellular domains of OX40L. In some embodiments, the OX40 agonist is MEDI6383. In some embodiments, measuring the number of CD4+ OX40+ Foxp3+ lymphocytes in the sample comprises: (a) labeling lymphocytes that show CD4 expression in the sample; (b) labeling lymphocytes that show OX40 expression in the sample after step (a); (c) labeling lymphocytes that show Foxp3 expression in the sample after step (b); and (d) measuring the number of CD4+ OX40+ Foxp3+ lymphocytes in the sample after step (c).

In certain aspects, the present disclosure provides a method for measuring the number of CD4+ OX40+ Foxp3+ lymphocytes in a sample comprising cancer cells and lymphocytes obtained from a subject, comprising the steps of: (a) labeling lymphocytes that show CD4 expression in the sample; (b) labeling lymphocytes that show OX40 expression in the sample after step (a); (c) labeling lymphocytes that show Foxp3 expression in the sample after step (b); and (d) measuring the number of CD4+ OX40+ Foxp3+ lymphocytes in the sample after step (c). In some embodiments, the sample is treated with a solution comprising EDTA or citrate buffer between steps (a) and (b) and/or between steps (b) and (c). In some embodiments, lymphocytes showing CD4 expression, OX40 expression, and Foxp3 expression are labeled by immunofluorescence staining. In some embodiments, lymphocytes showing OX40 expression are labeled using an antibody comprising (a) HVR-H1 comprising the amino acid sequence of SEQ ID NO:2; (b) HVR-H2 comprising the amino acid sequence of SEQ ID NO:3; (c) HVR-H3 comprising the amino acid sequence of SEQ ID NO:4; (d) HVR-L1 comprising the amino acid sequence of SEQ ID NO:5; (e) HVR-L2 comprising the amino acid sequence of SEQ ID NO:6; and (f) HVR-L3 comprising an amino acid sequence selected from SEQ ID NO:7, 26 or 27. In some embodiments, quantifying the number of CD4+ OX40+ Foxp3+ lymphocytes in the sample comprises imaging said immunofluorescence staining.

In some embodiments, the cancer is colorectal cancer. In some embodiments, the cancer is selected from the group consisting of non-small cell lung cancer, renal cell carcinoma, bladder cancer, ovarian cancer, glioblastoma, neuroblastoma, melanoma, breast carcinoma, gastric cancer, and hepatocellular carcinoma. In some embodiments, the breast carcinoma is triple-negative breast carcinoma. In some embodiments, the sample comprising cancer cells and lymphocytes, wherein said cancer cells are from a primary tumor. In some embodiments, the sample comprising cancer cells and lymphocytes, wherein said cancer cells are from a metastasis. In some embodiments, the CD4+ OX40+ Foxp3+ lymphocytes are tumor-infiltrating lymphocytes.

In certain aspects, the present disclosure provides a method for determining prognosis of a subject having cancer, comprising: (a) measuring the number of OX40+, CD4+ OX40+ Foxp3+, or CD4+ OX40+ Foxp3− lymphocytes in a sample comprising metastatic cancer cells and lymphocytes obtained from the subject; and (b) determining the prognosis of the subject based on the number of OX40+, CD4+ OX40+ Foxp3+, or CD4+ OX40+ Foxp3− lymphocytes in the sample, as compared with a reference, wherein an increased number of OX40+, CD4+ OX40+ Foxp3+, or CD4+ OX40+ Foxp3− lymphocytes in the sample indicates that the subject may have an improved prognosis. In some embodiments, the improved prognosis comprises increased overall survival. In some embodiments, the improved prognosis comprises increased progression-free survival.

In certain aspects, the present disclosure provides a method for treating or delaying progression of cancer in a subject, comprising: (a) measuring the number of OX40+, CD4+ OX40+ Foxp3+, or CD4+ OX40+ Foxp3− lymphocytes in a sample comprising metastatic cancer cells and lymphocytes obtained from the subject; (b) determining the number of OX40+, CD4+ OX40+ Foxp3+, or CD4+ OX40+ Foxp3− lymphocytes in the sample, as compared with a reference; and (c) if the number of OX40+, CD4+ OX40+ Foxp3+, or CD4+ OX40+ Foxp3− lymphocytes in the sample is higher than the reference, administering to the subject an effective amount of an OX40 agonist.

In certain aspects, the present disclosure provides a method for treating or delaying progression of cancer in a subject, comprising administering to the subject an effective amount of an OX40 agonist, wherein a sample comprising metastatic cancer cells and lymphocytes obtained from the subject has an increased number of OX40+, CD4+ OX40+ Foxp3+, or CD4+ OX40+ Foxp3− lymphocytes, as compared with a reference.

In certain aspects, the present disclosure provides a method for predicting responsiveness of a subject having cancer to an OX40 agonist treatment, comprising: (a) measuring the number of OX40+, CD4+ OX40+ Foxp3+, or CD4+ OX40+ Foxp3− lymphocytes in a sample comprising metastatic cancer cells and lymphocytes obtained from the subject; and (b) classifying the subject as a responsive or non-responsive subject based on the number of OX40+, CD4+ OX40+ Foxp3+, or CD4+ OX40+ Foxp3− lymphocytes in the sample, as compared with a reference, wherein an increased number of OX40+, CD4+ OX40+ Foxp3+, or CD4+ OX40+ Foxp3− lymphocytes in the sample indicates the subject may be responsive to the OX40 agonist treatment.

In some embodiments, the number of OX40+, CD4+ OX40+ Foxp3+, or CD4+ OX40+ Foxp3− lymphocytes in one or more regions of interest in the sample of a subject is measured. In some embodiments, the region of interest includes metastatic cancer cells and stroma. In some embodiments, the number of OX40+, CD4+ OX40+ Foxp3+, or CD4+ OX40+ Foxp3− lymphocytes is a median, mean or average number of OX40+, CD4+ OX40+ Foxp3+, or CD4+ OX40+ Foxp3-lymphocytes in different regions of interest in the sample from the subject. In some embodiments, the number of OX40+, CD4+ OX40+ Foxp3+, or CD4+ OX40+ Foxp3− lymphocytes is normalized to total cells in the region of interest in the sample. In some embodiments, the reference is based on the number of OX40+, CD4+ OX40+ Foxp3+, or CD4+ OX40+ Foxp3− lymphocytes in a sample comprising metastatic cancer cells and lymphocytes obtained from a cancer having the same type and/or stage as the cancer of the subject. In some embodiments, the reference is a median, mean, or average number of CD4+ OX40+ Foxp3+ lymphocytes in samples obtained from cancers having the same type and/or stage as the cancer of the subject. In some embodiments, the OX40 agonist is an agonist anti-human OX40 antibody. In some embodiments, the antibody is a monoclonal antibody. In some embodiments, the antibody is a humanized or human antibody. In some embodiments, the antibody comprises an IgG1 Fc region. In some embodiments, the antibody comprises an IgG4 Fc region. In some embodiments, the antibody comprises an Fc region comprising a mutation that decreases binding to an Fc receptor. In some embodiments, the antibody comprises (a) HVR-H1 comprising the amino acid sequence of SEQ ID NO:2, 8 or 9; (b) HVR-H2 comprising the amino acid sequence of SEQ ID NO:3, 10, 11, 12, 13, or 14; (c) HVR-H3 comprising the amino acid sequence of SEQ ID NO:4, 15 or 19; (d) HVR-L1 comprising the amino acid sequence of SEQ ID NO:5; (e) HVR-L2 comprising the amino acid sequence of SEQ ID NO:6; and (f) HVR-L3 comprising an amino acid sequence selected from SEQ ID NO:7, 22, 23, 24, 25, 26, 27 or 28. In some embodiments, the antibody comprises (a) HVR-H1 comprising the amino acid sequence of SEQ ID NO:2; (b) HVR-H2 comprising the amino acid sequence of SEQ ID NO:3; (c) HVR-H3 comprising the amino acid sequence of SEQ ID NO:4; (d) HVR-L1 comprising the amino acid sequence of SEQ ID NO:5; (e) HVR-L2 comprising the amino acid sequence of SEQ ID NO:6; and (f) HVR-L3 comprising an amino acid sequence selected from SEQ ID NO:7. In some embodiments, the antibody comprises (a) HVR-H1 comprising the amino acid sequence of SEQ ID NO:2; (b) HVR-H2 comprising the amino acid sequence of SEQ ID NO:3; (c) HVR-H3 comprising the amino acid sequence of SEQ ID NO:4; (d) HVR-L1 comprising the amino acid sequence of SEQ ID NO:5; (e) HVR-L2 comprising the amino acid sequence of SEQ ID NO:6; and (f) HVR-L3 comprising an amino acid sequence selected from SEQ ID NO:26. In some embodiments, the antibody comprises (a) HVR-H1 comprising the amino acid sequence of SEQ ID NO:2; (b) HVR-H2 comprising the amino acid sequence of SEQ ID NO:3; (c) HVR-H3 comprising the amino acid sequence of SEQ ID NO:4; (d) HVR-L1 comprising the amino acid sequence of SEQ ID NO:5; (e) HVR-L2 comprising the amino acid sequence of SEQ ID NO:6; and (f) HVR-L3 comprising an amino acid sequence selected from SEQ ID NO:27. In some embodiments, the antibody is MEDI6469 or MEDI0562. In some embodiments, the OX40 agonist comprises one or more extracellular domains of OX40L. In some embodiments, the OX40 agonist is MEDI6383. In some embodiments, the cancer is colorectal cancer. In some embodiments, the cancer is selected from the group consisting of non-small cell lung cancer, renal cell carcinoma, bladder cancer, ovarian cancer, glioblastoma, neuroblastoma, melanoma, breast carcinoma, gastric cancer, and hepatocellular carcinoma. In some embodiments, the breast carcinoma is triple-negative breast carcinoma. In some embodiments, the OX40+, CD4+ OX40+ Foxp3+, or CD4+ OX40+ Foxp3− lymphocytes are tumor-infiltrating lymphocytes.

It is to be understood that one, some, or all of the properties of the various embodiments described above and herein may be combined to form other embodiments of the present invention. These and other aspects of the invention will become apparent to one of skill in the art. These and other embodiments of the invention are further described by the detailed description that follows.

P values reflecting the difference between overall survival of patients whose samples showed cell counts above and below the median are indicated for each cell type.

Figure 8A:
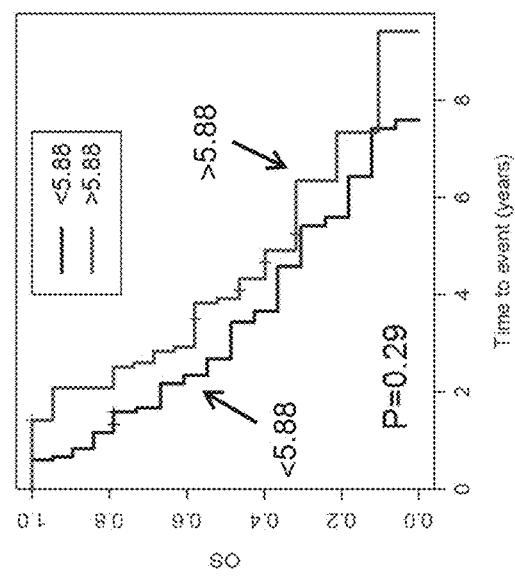
Figure 8B:
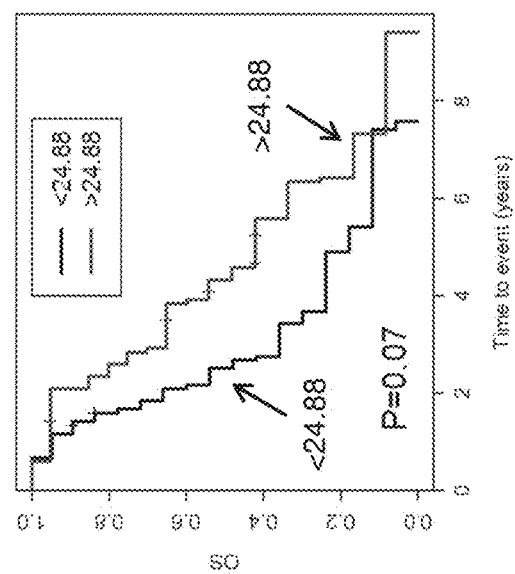
Figure 8C:
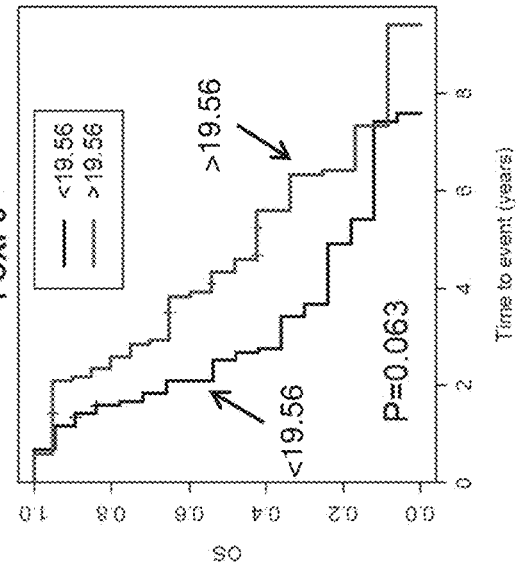
Figure 8D:
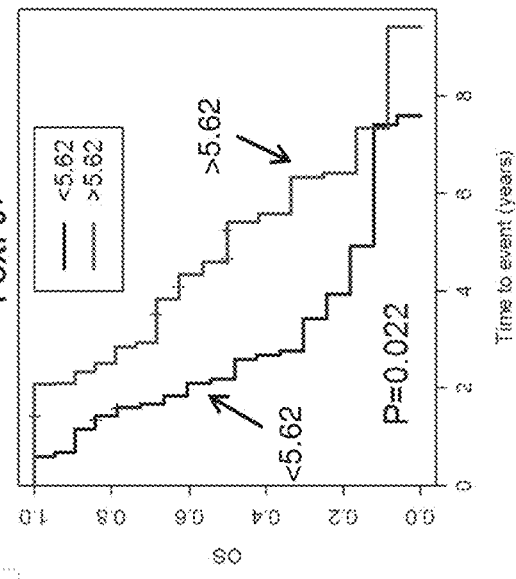

FIGS. 8A-8D show the correlation between overall survival and the number of cells in a sample showing expression of specific marker(s). Overall survival is shown for patients whose samples contained greater than or less than the median count (as labeled) of the following cell types: OX40+CD4+ (FIG. 8A), OX40+CD4− (FIG. 8B), OX40+CD4+ Foxp3+ (FIG. 8C), and OX40+CD4+ Foxp3− (FIG. 8D). P values reflecting the difference between overall survival of patients whose samples showed cell counts above and below the median are indicated for each cell type.

Figure 9A:
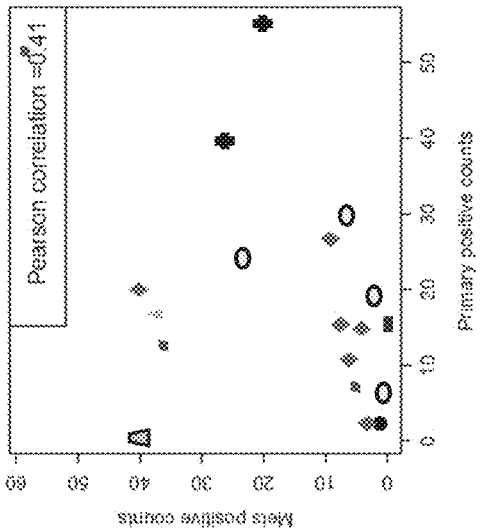
Figure 9B:
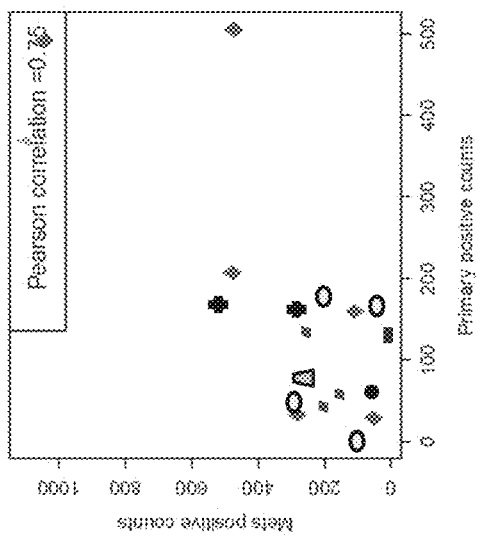
Figure 9C:
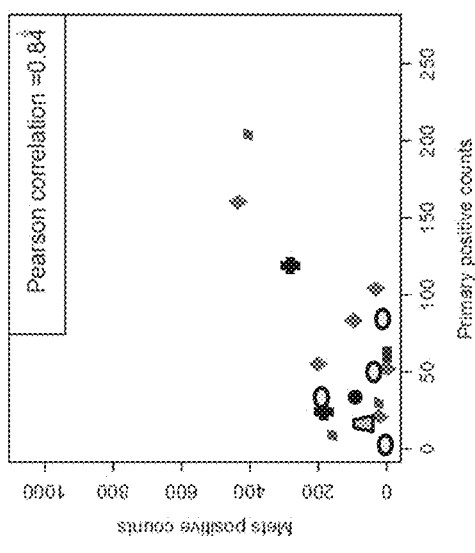

FIGS. 9A-9C show the correlation between the number of cells showing expression of specific marker(s) in paired primary and metastatic samples (n=19). Mean counts of cells that are positive for expression of specific markers, normalized to total number of cells, are provided as follows: CD4+ (FIG. 9A), Foxp3+ (FIG. 9B), and OX40+ (FIG. 9C). Tissue types are as labeled: Brain (BN), Bone (BO-Rib), Lymph node (LN), Lung (LU), Liver (LV), Omentum (OM), Ovary (OV), and Soft tissue/retroperitoneum (SOT-Ret).

FIGS. 10A-10D show the correlation between the number of cells showing expression of specific marker(s) in paired primary and metastatic samples (n=19). Mean counts of cells that are positive for expression of specific markers, normalized to total number of cells, are provided as follows: OX40+CD4+ (FIG. 10A), OX40+CD4− (FIG. 10B), OX40+CD4+ Foxp3+ (FIG. 10C), and OX40+CD4+ Foxp3− (FIG. 10D). Tissue types are as labeled: Brain (BN), Bone (BO-Rib), Lymph node (LN), Lung (LU), Liver (LV), Omentum (OM), Ovary (OV), and Soft tissue/retroperitoneum (SOT-Ret).

FIGS. 11A-11D provide the results of multivariate Cox model analyses of CD4 expression (FIG. 11A), OX40 expression (FIG. 11B), Foxp3 expression (FIG. 11C), and the ratio of OX40+ Teff cells to OX40+ Treg cells (OX40 Teff/Treg) (FIG. 11D) adjusted for age, gender and stage (n=32/39).

DETAILED DESCRIPTION

I. General Techniques

The techniques and procedures described or referenced herein are generally well understood and commonly employed using conventional methodology by those skilled in the art, such as, for example, the widely utilized methodologies described in Sambrook et al., *Molecular Cloning: A Laboratory Manual* 3d edition (2001) Cold Spring Harbor Laboratory Press, Cold Spring Harbor, N.Y.; *Current Protocols in Molecular Biology* (F. M. Ausubel, et al. eds., (2003)); the series *Methods in Enzymology* (Academic Press, Inc.): *PCR 2: A Practical Approach* (M. J. MacPherson, B. D. Hames and G. R. Taylor eds. (1995)), Harlow and Lane, eds. (1988) *Antibodies, A Laboratory Manual, and Animal Cell Culture* (R. I. Freshney, ed. (1987)); *Oligonucleotide Synthesis* (M. J. Gait, ed., 1984); *Methods in Molecular Biology*, Humana Press; *Cell Biology: A Laboratory Notebook* (J. E. Cellis, ed., 1998) Academic Press; *Animal Cell Culture* (R. I. Freshney), ed., 1987); *Introduction to Cell and Tissue Culture* (J. P. Mather and P. E. Roberts, 1998) Plenum Press; *Cell and Tissue Culture: Laboratory Procedures* (A. Doyle, J. B. Griffiths, and D. G. Newell, eds., 1993-8) J. Wiley and Sons; *Handbook of Experimental Immunology* (D. M. Weir and C. C. Blackwell, eds.); *Gene Transfer Vectors for Mammalian Cells* (J. M. Miller and M. P. Calos, eds., 1987); *PCR: The Polymerase Chain Reaction*, (Mullis et al., eds., 1994); *Current Protocols in Immunology* (J. E. Coligan et al., eds., 1991); *Short Protocols in Molecular Biology* (Wiley and Sons, 1999); *Immunobiology* (C. A. Janeway and P. Travers, 1997); *Antibodies* (P. Finch, 1997); *Antibodies: A Practical Approach* (D. Catty., ed., IRL Press, 1988-1989); *Monoclonal Antibodies: A Practical Approach* (P. Shepherd and C. Dean, eds., Oxford University Press, 2000); *Using Antibodies: A Laboratory Manual* (E. Harlow and D. Lane (Cold Spring Harbor Laboratory Press, 1999); *The Antibodies* (M. Zanetti and J. D. Capra, eds., Harwood Academic Publishers, 1995); and *Cancer: Principles and Practice of Oncology* (V. T. DeVita et al., eds., J.B. Lippincott Company, 1993).

II. Definitions

Before describing the invention in detail, it is to be understood that this invention is not limited to particular compositions or biological systems, which can, of course, vary. It is also to be understood that the terminology used herein is for the purpose of describing particular embodiments only, and is not intended to be limiting.

As used herein and in the appended claims, the singular forms "a," "or," and "the" include plural referents unless the context clearly dictates otherwise.

Reference to "about" a value or parameter herein includes (and describes) variations that are directed to that value or parameter per se. For example, description referring to "about X" includes description of "X".

It is understood that aspects and variations of the invention described herein include "consisting" and/or "consisting essentially of" aspects and variations.

The term "dysfunction" in the context of immune dysfunction, refers to a state of reduced immune responsiveness to antigenic stimulation.

The term "dysfunctional", as used herein, also includes refractory or unresponsive to antigen recognition, specifically, impaired capacity to translate antigen recognition into downstream T-cell effector functions, such as proliferation, cytokine production (e.g., gamma interferon) and/or target cell killing.

"Enhancing T cell function" means to induce, cause or stimulate an effector or memory T cell to have a renewed, sustained or amplified biological function. Examples of enhancing T-cell function include: increased secretion of γ-interferon from $CD8^+$ effector T cells, increased secretion of γ-interferon from CD4+ memory and/or effector T-cells, increased proliferation of CD4+ effector and/or memory T cells, increased proliferation of $CD8^+$ effector T-cells, increased antigen responsiveness (e.g., clearance), relative to such levels before the intervention. In one embodiment, the level of enhancement is at least 50%, alternatively 60%, 70%, 80%, 90%, 100%, 120%, 150%, 200%. The manner of measuring this enhancement is known to one of ordinary skill in the art.

"Tumor immunity" refers to the process in which tumors evade immune recognition and clearance. Thus, as a therapeutic concept, tumor immunity is "treated" when such evasion is attenuated, and the tumors are recognized and attacked by the immune system. Examples of tumor recognition include tumor binding, tumor shrinkage and tumor clearance.

"Immunogenicity" refers to the ability of a particular substance to provoke an immune response. Tumors are immunogenic and enhancing tumor immunogenicity aids in the clearance of the tumor cells by the immune response.

An "acceptor human framework" for the purposes herein is a framework comprising the amino acid sequence of a light chain variable domain (VL) framework or a heavy chain variable domain (VH) framework derived from a human immunoglobulin framework or a human consensus framework, as defined below. An acceptor human framework "derived from" a human immunoglobulin framework or a human consensus framework may comprise the same amino acid sequence thereof, or it may contain amino acid sequence changes. In some embodiments, the number of amino acid changes are 10 or less, 9 or less, 8 or less, 7 or less, 6 or less, 5 or less, 4 or less, 3 or less, or 2 or less. In some embodiments, the VL acceptor human framework is identical in sequence to the VL human immunoglobulin framework sequence or human consensus framework sequence.

"Affinity" refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). Affinity can be measured by common methods known in the art, including those described herein. Specific illustrative and exemplary embodiments for measuring binding affinity are described in the following.

An "agonist antibody," as used herein, is an antibody which activates a biological activity of the antigen it binds.

An "anti-angiogenic agent" refers to a compound which blocks, or interferes with to some degree, the development of blood vessels. An anti-angiogenic agent may, for instance, be a small molecule or antibody that binds to a growth factor or growth factor receptor involved in promoting angiogenesis. In one embodiment, an anti-angiogenic agent is an antibody that binds to vascular endothelial growth factor (VEGF), such as bevacizumab (AVASTIN).

"Antibody-dependent cell-mediated cytotoxicity" or "ADCC" refers to a form of cytotoxicity in which secreted immunoglobulin bound onto Fc receptors (FcRs) present on certain cytotoxic cells (e.g. NK cells, neutrophils, and macrophages) enable these cytotoxic effector cells to bind specifically to an antigen-bearing target cell and subsequently kill the target cell with cytotoxins. The primary cells for mediating ADCC, NK cells, express FcγRIII only, whereas monocytes express FcγRI, FcγRII, and FcγRIII. FcR expression on hematopoietic cells is summarized in Table 3 on page 464 of Ravetch and Kinet, *Annu. Rev. Immunol* 9:457-92 (1991). To assess ADCC activity of a molecule of interest, an in vitro ADCC assay, such as that described in U.S. Pat. No. 5,500,362 or 5,821,337 or U.S. Pat. No. 6,737,056 (Presta), may be performed. Useful effector cells for such assays include PBMC and NK cells. Alternatively, or additionally, ADCC activity of the molecule of interest may be assessed in vivo, e.g., in an animal model such as that disclosed in Clynes et al. *PNAS (USA)* 95:652-656 (1998). An exemplary assay for assessing ADCC activity is provided in the examples herein.

The terms "anti-OX40 antibody" and "an antibody that binds to OX40" refer to an antibody that is capable of binding OX40 with sufficient affinity such that the antibody is useful as a diagnostic and/or therapeutic agent in targeting OX40. In one embodiment, the extent of binding of an anti-OX40 antibody to an unrelated, non-OX40 protein is less than about 10% of the binding of the antibody to OX40 as measured, e.g., by a radioimmunoassay (RIA). In certain embodiments, an antibody that binds to OX40 has a dissociation constant (Kd) of ≤1 µM, ≤100 nM, ≤10 nM, ≤1 nM, ≤0.1 nM, ≤0.01 nM, or ≤0.001 nM (e.g. $10^{-8}$M or less, e.g. from $10^{-8}$M to $10^{-13}$M, e.g., from $10^{-9}$ M to $10^{-13}$ M). In certain embodiments, an anti-OX40 antibody binds to an epitope of OX40 that is conserved among OX40 from different species.

As use herein, the term "binds", "specifically binds to" or is "specific for" refers to measurable and reproducible interactions such as binding between a target and an antibody, which is determinative of the presence of the target in the presence of a heterogeneous population of molecules including biological molecules. For example, an antibody that binds to or specifically binds to a target (which can be an epitope) is an antibody that binds this target with greater affinity, avidity, more readily, and/or with greater duration than it binds to other targets. In one embodiment, the extent of binding of an antibody to an unrelated target is less than about 10% of the binding of the antibody to the target as measured, e.g., by a radioimmunoassay (RIA). In certain embodiments, an antibody that specifically binds to a target has a dissociation constant (Kd) of ≤1 µM, ≤100 nM, ≤10 nM, ≤1 nM, or ≤0.1 nM. In certain embodiments, an antibody specifically binds to an epitope on a protein that is conserved among the protein from different species. In another embodiment, specific binding can include, but does not require exclusive binding.

The term "antibody" herein is used in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity.

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')$_2$; diabodies; linear antibodies; single-chain antibody molecules (e.g. scFv); and multispecific antibodies formed from antibody fragments.

An "antibody that binds to the same epitope" as a reference antibody refers to an antibody that blocks binding of the reference antibody to its antigen in a competition assay by 50% or more, and conversely, the reference antibody blocks binding of the antibody to its antigen in a competition assay by 50% or more. An exemplary competition assay is provided herein.

The term "binding domain" refers to the region of a polypeptide that binds to another molecule. In the case of an FcR, the binding domain can comprise a portion of a polypeptide chain thereof (e.g. the alpha chain thereof) which is responsible for binding an Fc region. One useful binding domain is the extracellular domain of an FcR alpha chain.

A polypeptide with a variant IgG Fc with "altered" FcR, ADCC or phagocytosis activity is one which has either enhanced or diminished FcR binding activity (e.g, FcγR) and/or ADCC activity and/or phagocytosis activity compared to a parent polypeptide or to a polypeptide comprising a native sequence Fc region.

The term "OX40," as used herein, refers to any native OX40 from any vertebrate source, including mammals such as primates (e.g. humans) and rodents (e.g., mice and rats), unless otherwise indicated. The term encompasses "full-length," unprocessed OX40 as well as any form of OX40 that results from processing in the cell. The term also encompasses naturally occurring variants of OX40, e.g., splice variants or allelic variants. The amino acid sequence of an exemplary human OX40 is shown in SEQ ID NO:1.

"OX40 activation" refers to activation, of the OX40 receptor. Generally, OX40 activation results in signal transduction.

The terms "cancer" and "cancerous" refer to or describe the physiological condition in mammals that is typically characterized by unregulated cell growth. Examples of cancer include but are not limited to, carcinoma, lymphoma, blastoma, sarcoma, and leukemia or lymphoid malignancies. More particular examples of such cancers include, but not limited to, squamous cell cancer (e.g., epithelial squamous cell cancer), lung cancer including small-cell lung cancer, non-small cell lung cancer, adenocarcinoma of the lung and squamous carcinoma of the lung, cancer of the peritoneum, hepatocellular cancer, gastric or stomach cancer including gastrointestinal cancer and gastrointestinal stromal cancer, pancreatic cancer, glioblastoma, cervical cancer, ovarian cancer, liver cancer, bladder cancer, cancer of the urinary tract, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, melanoma, superficial spreading melanoma, lentigo maligna melanoma, acral lentiginous melanomas, nodular melanomas, multiple myeloma and B-cell lymphoma; chronic lymphocytic leukemia (CLL); acute lymphoblastic leukemia (ALL); hairy cell leukemia; chronic myeloblastic leukemia; and post-transplant lymphoproliferative disorder (PTLD), as well as abnormal vascular proliferation associated with phakomatoses, edema (such as that associated with brain tumors), Meigs' syndrome, brain, as well as head and neck cancer, and associated metastases. In certain embodiments, cancers that are amenable to treatment by the antibodies of the invention include breast cancer, colorectal cancer, rectal cancer, non-small cell lung cancer, glioblastoma, non-Hodgkins lymphoma (NHL), renal cell cancer, prostate cancer, liver cancer, pancreatic cancer, soft-tissue sarcoma, kaposi's sarcoma, carcinoid carcinoma, head and neck cancer, ovarian cancer, mesothelioma, and multiple myeloma. In some embodiments, the cancer is selected from: non-small cell lung cancer, glioblastoma, neuroblastoma, melanoma, breast carcinoma (e.g. triple-negative breast cancer), gastric cancer, colorectal cancer (CRC), and hepatocellular carcinoma. Yet, in some embodiments, the cancer is selected from: non-small cell lung cancer, colorectal cancer, glioblastoma and breast carcinoma (e.g. triple-negative breast cancer), including metastatic forms of those cancers.

The term "tumor" refers to all neoplastic cell growth and proliferation, whether malignant or benign, and all pre-cancerous and cancerous cells and tissues. The terms "cancer," "cancerous," "cell proliferative disorder," "proliferative disorder" and "tumor" are not mutually exclusive as referred to herein.

The terms "cell proliferative disorder" and "proliferative disorder" refer to disorders that are associated with some degree of abnormal cell proliferation. In one embodiment, the cell proliferative disorder is cancer.

The term "chimeric" antibody refers to an antibody in which a portion of the heavy and/or light chain is derived from a particular source or species, while the remainder of the heavy and/or light chain is derived from a different source or species.

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g., $IgG_1$, $IgG_2$, $IgG_3$, $IgG_4$, $IgA_1$, and $IgA_2$. The heavy chain constant domains that correspond to the different classes of immunoglobulins are called α, δ, ε, γ, and μ, respectively.

"Complement dependent cytotoxicity" or "CDC" refers to the lysis of a target cell in the presence of complement. Activation of the classical complement pathway is initiated by the binding of the first component of the complement system (C1q) to antibodies (of the appropriate subclass), which are bound to their cognate antigen. To assess complement activation, a CDC assay, e.g., as described in Gazzano-Santoro et al., *J. Immunol. Methods* 202:163 (1996), may be performed. Polypeptide variants with altered Fc region amino acid sequences (polypeptides with a variant Fc region) and increased or decreased C1q binding capability are described, e.g., in U.S. Pat. No. 6,194,551 B1 and WO 1999/51642. See also, e.g., Idusogie et al. *J. Immunol.* 164: 4178-4184 (2000).

The term "cytostatic agent" refers to a compound or composition which arrests growth of a cell either in vitro or in vivo. Thus, a cytostatic agent may be one which significantly reduces the percentage of cells in S phase. Further examples of cytostatic agents include agents that block cell cycle progression by inducing G0/G1 arrest or M-phase arrest. The humanized anti-Her2 antibody trastuzumab (HERCEPTIN®) is an example of a cytostatic agent that induces G0/G1 arrest. Classical M-phase blockers include the vincas (vincristine and vinblastine), taxanes, and topoisomerase II inhibitors such as doxorubicin, epirubicin, daunorubicin, etoposide, and bleomycin. Certain agents that arrest G1 also spill over into S-phase arrest, for example, DNA alkylating agents such as tamoxifen, prednisone, dacarbazine, mechlorethamine, cisplatin, methotrexate, 5-fluorouracil, and ara-C. Further information can be found in Mendelsohn and Israel, eds., *The Molecular Basis of Cancer*, Chapter 1, entitled "Cell cycle regulation, oncogenes, and antineoplastic drugs" by Murakami et al. (W.B. Saunders, Philadelphia, 1995), e.g., p. 13. The taxanes (paclitaxel and docetaxel) are anticancer drugs both derived from the yew tree. Docetaxel (TAXOTERE®, Rhone-Poulenc Rorer), derived from the European yew, is a semisynthetic analogue of paclitaxel (TAXOL®, Bristol-Myers Squibb). Paclitaxel and docetaxel promote the assembly of microtubules from tubulin dimers and stabilize microtubules by preventing depolymerization, which results in the inhibition of mitosis in cells.

The term "cytotoxic agent" as used herein refers to a substance that inhibits or prevents a cellular function and/or causes cell death or destruction. Cytotoxic agents include, but are not limited to, radioactive isotopes (e.g., $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu); chemotherapeutic agents or drugs (e.g., methotrexate, adriamicin, vinca alkaloids (vincristine, vinblastine, etoposide), doxorubicin, melphalan, mitomycin C, chlorambucil, daunorubicin or other intercalating agents); growth inhibitory agents; enzymes and fragments thereof such as nucleolytic enzymes; antibiotics; toxins such as small molecule toxins or enzymatically active toxins of bacterial, fungal, plant or animal origin, including fragments and/or variants thereof; and the various antitumor or anti-cancer agents disclosed below.

A "depleting anti-OX40 antibody," is an anti-OX40 antibody that kills or depletes OX40-expressing cells. Depletion of OX40 expressing cells can be achieved by various mechanisms, such as antibody-dependent cell-mediated cytotoxicity and/or phagocytosis. Depletion of OX40-expressing cells may be assayed in vitro, and exemplary methods for in vitro ADCC and phagocytosis assays are provided herein. In some embodiments, the OX40-expressing cell is a human CD4+ effector T cell. In some embodiments, the OX40-expressing cell is a transgenic BT474 cell that expresses human OX40.

"Effector functions" refer to those biological activities attributable to the Fc region of an antibody, which vary with the antibody isotype. Examples of antibody effector functions include: C1q binding and complement dependent cytotoxicity (CDC); Fc receptor binding; antibody-dependent cell-mediated cytotoxicity (ADCC); phagocytosis; down regulation of cell surface receptors (e.g. B cell receptor); and B cell activation.

An "effective amount" of an agent, e.g., a pharmaceutical formulation, refers to an amount effective, at dosages and for periods of time necessary, to achieve the desired therapeutic or prophylactic result.

"Fc receptor" or "FcR" describes a receptor that binds to the Fc region of an antibody. In some embodiments, an FcR is a native human FcR. In some embodiments, an FcR is one which binds an IgG antibody (a gamma receptor) and includes receptors of the FcγRI, FcγRII, and FcγRIII subclasses, including allelic variants and alternatively spliced forms of those receptors. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain. (see, e.g., Daëron, *Annu. Rev. Immunol.* 15:203-234 (1997)). FcRs are reviewed, for example, in Ravetch and Kinet, *Annu. Rev. Immunol* 9:457-92 (1991); Capel et al., *Immunomethods* 4:25-34 (1994); and de Haas et al., *J. Lab. Clin. Med.* 126:330-41 (1995). Other FcRs, including those to be identified in the future, are encompassed by the term "FcR" herein. The term "Fc receptor" or "FcR" also includes the neonatal receptor, FcRn, which is responsible for the transfer of maternal IgGs to the fetus (Guyer et al., *J. Immunol.* 117:587 (1976) and Kim et al., *J. Immunol.* 24:249 (1994)) and regulation of homeostasis of immunoglobulins. Methods of measuring binding to FcRn are known (see, e.g., Ghetie and Ward., *Immunol. Today* 18(12):592-598 (1997); Ghetie et al., *Nature Biotechnology*, 15(7):637-640 (1997); Hinton et al., *J. Biol. Chem.* 279(8): 6213-6216 (2004); WO 2004/92219 (Hinton et al.). Binding to human FcRn in vivo and serum half life of human FcRn high affinity binding polypeptides can be assayed, e.g., in transgenic mice or transfected human cell lines expressing human FcRn, or in primates to which the polypeptides with a variant Fc region are administered. WO 2000/42072 (Presta) describes antibody variants with improved or diminished binding to FcRs. See also, e.g., Shields et al. *J. Biol. Chem.* 9(2):6591-6604 (2001).

The term "Fc region" herein is used to define a C-terminal region of an immunoglobulin heavy chain that contains at least a portion of the constant region. The term includes native sequence Fc regions and variant Fc regions. In one embodiment, a human IgG heavy chain Fc region extends from Cys226, or from Pro230, to the carboxyl-terminus of the heavy chain. However, the C-terminal lysine (Lys447) of the Fc region may or may not be present. Unless otherwise specified herein, numbering of amino acid residues in the Fc region or constant region is according to the EU numbering system, also called the EU index, as described in Kabat et al., *Sequences of Proteins of Immunological Interest,* 5th Ed. Public Health Service, National Institutes of Health, Bethesda, Md., 1991.

A "functional Fc region" possesses an "effector function" of a native sequence Fc region. Exemplary "effector functions" include C1q binding; CDC; Fc receptor binding; ADCC; phagocytosis; down regulation of cell surface receptors (e.g. B cell receptor; BCR), etc. Such effector functions generally require the Fc region to be combined with a binding domain (e.g., an antibody variable domain) and can be assessed using various assays as disclosed, for example, in definitions herein.

"Human effector cells" refer to leukocytes that express one or more FcRs and perform effector functions. In certain embodiments, the cells express at least FcγRIII and perform ADCC effector function(s). Examples of human leukocytes which mediate ADCC include peripheral blood mononuclear cells (PBMC), natural killer (NK) cells, monocytes, cytotoxic T cells, and neutrophils. The effector cells may be isolated from a native source, e.g., from blood.

"Framework" or "FR" refers to variable domain residues other than hypervariable region (HVR) residues. The FR of a variable domain generally consists of four FR domains: FR1, FR2, FR3, and FR4. Accordingly, the HVR and FR sequences generally appear in the following sequence in VH (or VL): FR1-H1(L1)-FR2-H2(L2)-FR3-H3(L3)-FR4.

The terms "full length antibody," "intact antibody," and "whole antibody" are used herein interchangeably to refer to an antibody having a structure substantially similar to a native antibody structure or having heavy chains that contain an Fc region as defined herein.

The terms "host cell," "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

A "human antibody" is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

A "human consensus framework" is a framework which represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat et al., *Sequences of Proteins of Immunological Interest*, Fifth Edition, NIH Publication 91-3242, Bethesda Md. (1991), vols. 1-3. In one embodiment, for the VL, the subgroup is subgroup kappa I as in Kabat et al., supra. In one embodiment, for the VH, the subgroup is subgroup III as in Kabat et al., supra.

A "humanized" antibody refers to a chimeric antibody comprising amino acid residues from non-human HVRs and amino acid residues from human FRs. In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

The term "hypervariable region" or "HVR" as used herein refers to each of the regions of an antibody variable domain which are hypervariable in sequence ("complementarity determining regions" or "CDRs") and/or form structurally defined loops ("hypervariable loops") and/or contain the antigen-contacting residues ("antigen contacts"). Generally, antibodies comprise six HVRs: three in the VH (H1, H2, H3), and three in the VL (L1, L2, L3). Exemplary HVRs herein include:

(a) hypervariable loops occurring at amino acid residues 26-32 (L1), 50-52 (L2), 91-96 (L3), 26-32 (H1), 53-55 (H2), and 96-101 (H3) (Chothia and Lesk, *J. Mol. Biol.* 196:901-917 (1987));

(b) CDRs occurring at amino acid residues 24-34 (L1), 50-56 (L2), 89-97 (L3), 31-35b (H1), 50-65 (H2), and 95-102 (H3) (Kabat et al., *Sequences of Proteins of Immunological Interest*, 5th Ed. Public Health Service, National Institutes of Health, Bethesda, Md. (1991));

(c) antigen contacts occurring at amino acid residues 27c-36 (L1), 46-55 (L2), 89-96 (L3), 30-35b (H1), 47-58 (H2), and 93-101 (H3) (MacCallum et al. *J. Mol. Biol.* 262: 732-745 (1996)); and (d) combinations of (a), (b), and/or (c), including HVR amino acid residues 46-56 (L2), 47-56 (L2), 48-56 (L2), 49-56 (L2), 26-35 (H1), 26-35b (H1), 49-65 (H2), 93-102 (H3), and 94-102 (H3).

Unless otherwise indicated, HVR residues and other residues in the variable domain (e.g., FR residues) are numbered herein according to Kabat et al., supra.

An "immunoconjugate" is an antibody conjugated to one or more heterologous molecule(s), including but not limited to a cytotoxic agent.

An "individual" or "subject" is a mammal. Mammals include, but are not limited to, domesticated animals (e.g., cows, sheep, cats, dogs, and horses), primates (e.g., humans and non-human primates such as monkeys), rabbits, and rodents (e.g., mice and rats). In certain embodiments, the individual or subject is a human.

"Promoting cell growth or proliferation" means increasing a cell's growth or proliferation by at least 10%, 20%, 30%, 40%, 50%, 60%, 70%, 80%, 90%, 95%, or 100%.

An "isolated" antibody is one which has been separated from a component of its natural environment. In some embodiments, an antibody is purified to greater than 95% or 99% purity as determined by, for example, electrophoretic (e.g., SDS-PAGE, isoelectric focusing (IEF), capillary electrophoresis) or chromatographic (e.g., ion exchange or reverse phase HPLC). For review of methods for assessment of antibody purity, see, e.g., Flatman et al., *J. Chromatogr. B* 848:79-87 (2007).

An "isolated" nucleic acid refers to a nucleic acid molecule that has been separated from a component of its natural environment. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

"Isolated nucleic acid encoding an anti-OX40 antibody" refers to one or more nucleic acid molecules encoding antibody heavy and light chains (or fragments thereof), including such nucleic acid molecule(s) in a single vector or separate vectors, and such nucleic acid molecule(s) present at one or more locations in a host cell.

The term "monoclonal antibody" as used herein refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

A "naked antibody" refers to an antibody that is not conjugated to a heterologous moiety (e.g., a cytotoxic moiety) or radiolabel. The naked antibody may be present in a pharmaceutical formulation.

"Native antibodies" refer to naturally occurring immunoglobulin molecules with varying structures. For example, native IgG antibodies are heterotetrameric glycoproteins of about 150,000 daltons, composed of two identical light chains and two identical heavy chains that are disulfide-bonded. From N- to C-terminus, each heavy chain has a variable region (VH), also called a variable heavy domain or a heavy chain variable domain, followed by three constant domains (CHL CH2, and CH3). Similarly, from N- to C-terminus, each light chain has a variable region (VL), also called a variable light domain or a light chain variable domain, followed by a constant light (CL) domain. The light chain of an antibody may be assigned to one of two types, called kappa (κ) and lambda (λ), based on the amino acid sequence of its constant domain. A "native sequence Fc region" comprises an amino acid sequence identical to the amino acid sequence of an Fc region found in nature. Native sequence human Fc regions include a native sequence human IgG1 Fc region (non-A and A allotypes); native sequence human IgG2 Fc region; native sequence human IgG3 Fc region; and native sequence human IgG4 Fc region as well as naturally occurring variants thereof.

The term "package insert" is used to refer to instructions customarily included in commercial packages of therapeutic products, that contain information about the indications, usage, dosage, administration, combination therapy, contraindications and/or warnings concerning the use of such therapeutic products.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, Calif., or may be compiled from the source code. The ALIGN-2 program should be compiled for use on a UNIX operating system, including digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the fraction X/Y where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

The term "pharmaceutical formulation" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

As used herein, "treatment" (and grammatical variations thereof such as "treat" or "treating") refers to clinical intervention in an attempt to alter the natural course of the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, antibodies of the invention are used to delay development of a disease or to slow the progression of a disease.

The term "tumor" refers to all neoplastic cell growth and proliferation, whether malignant or benign, and all precancerous and cancerous cells and tissues. The terms "cancer," "cancerous," "cell proliferative disorder," "proliferative disorder" and "tumor" are not mutually exclusive as referred to herein.

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three hypervariable regions (HVRs). (See, e.g., Kindt et al. *Kuby Immunology*, 6$^{th}$ ed., W.H. Freeman and Co., page 91 (2007).) A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively. See, e.g., Portolano et al., *J. Immunol.* 150:880-887 (1993); Clarkson et al., *Nature* 352:624-628 (1991).

A "variant Fc region" comprises an amino acid sequence which differs from that of a native sequence Fc region by virtue of at least one amino acid modification, preferably one or more amino acid substitution(s). Preferably, the variant Fc region has at least one amino acid substitution compared to a native sequence Fc region or to the Fc region of a parent polypeptide, e.g. from about one to about ten amino acid substitutions, and preferably from about one to about five amino acid substitutions in a native sequence Fc region or in the Fc region of the parent polypeptide. The variant Fc region herein will preferably possess at least about 80% homology with a native sequence Fc region and/or with an Fc region of a parent polypeptide, and most preferably at least about 90% homology therewith, more preferably at least about 95% homology therewith.

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors."

A "VH subgroup III consensus framework" comprises the consensus sequence obtained from the amino acid sequences in variable heavy subgroup III of Kabat et al. In one embodiment, the VH subgroup III consensus framework amino acid sequence comprises at least a portion or all of each of the following sequences:

(SEQ ID NO: 214)
EVQLVESGGGLVQPGGSLRLSCAAS-H1-

(SEQ ID NO: 215)
WVRQAPGKGLEWV-H2-

(SEQ ID NO: 216)
RFTISRDNSKNTLYLQMNSLRAEDTAVYYC-H3-

(SEQ ID NO: 217)
WGQGTLVTVSS.

A "VL subgroup I consensus framework" comprises the consensus sequence obtained from the amino acid sequences in variable light kappa subgroup I of Kabat et al. In one embodiment, the VH subgroup I consensus framework amino acid sequence comprises at least a portion or all of each of the following sequences:

DIQMTQSPSSLSASVGDRVTITC-L1- (SEQ ID NO: 218)

WYQQKPGKAPKLLIY-L2- (SEQ ID NO: 219)

GVPSRFSGSGSGTDFTLTISSLQPEDFATYYC-L3- (SEQ ID NO: 220)

FGQGTKVEIK. (SEQ ID NO: 221)

The term "cytotoxic agent" as used herein refers to a substance that inhibits or prevents a cellular function and/or causes cell death or destruction. Cytotoxic agents include, but are not limited to, radioactive isotopes (e.g., At211, I131, I125, Y90, Re186, Re188, Sm153, Bi212, P32, Pb212 and radioactive isotopes of Lu); chemotherapeutic agents; growth inhibitory agents; enzymes and fragments thereof such as nucleolytic enzymes; and toxins such as small molecule toxins or enzymatically active toxins of bacterial, fungal, plant or animal origin, including fragments and/or variants thereof. Exemplary cytotoxic agents can be selected from anti-microtubule agents, platinum coordination complexes, alkylating agents, antibiotic agents, topoisomerase II inhibitors, antimetabolites, topoisomerase I inhibitors, hormones and hormonal analogues, signal transduction pathway inhibitors, non-receptor tyrosine kinase angiogenesis inhibitors, immunotherapeutic agents, proapoptotic agents, inhibitors of LDH-A; inhibitors of fatty acid biosynthesis; cell cycle signalling inhibitors; HDAC inhibitors, proteasome inhibitors; and inhibitors of cancer metabolism.

In one embodiment the cytotoxic agent is selected from anti-microtubule agents, platinum coordination complexes, alkylating agents, antibiotic agents, topoisomerase II inhibitors, antimetabolites, topoisomerase I inhibitors, hormones and hormonal analogues, signal transduction pathway inhibitors, non-receptor tyrosine kinase angiogenesis inhibitors, immunotherapeutic agents, proapoptotic agents, inhibitors of LDH-A, inhibitors of fatty acid biosynthesis, cell cycle signalling inhibitors, HDAC inhibitors, proteasome inhibitors, and inhibitors of cancer metabolism. In one embodiment the cytotoxic agent is a taxane. In one embodiment the taxane is paclitaxel or docetaxel. In one embodiment the cytotoxic agent is a platinum agent. In one embodiment the cytotoxic agent is an antagonist of EGFR. In one embodiment the antagonist of EGFR is N-(3-ethynylphenyl)-6,7-bis(2-methoxyethoxy)quinazolin-4-amine (e.g., erlotinib). In one embodiment the cytotoxic agent is a RAF inhibitor. In one embodiment, the RAF inhibitor is a BRAF and/or CRAF inhibitor. In one embodiment the RAF inhibitor is vemurafenib. In one embodiment the cytotoxic agent is a PI3K inhibitor.

"Chemotherapeutic agent" includes chemical compounds useful in the treatment of cancer. Examples of chemotherapeutic agents include erlotinib (TARCEVA®, Genentech/OSI Pharm.), bortezomib (VELCADE®, Millennium Pharm.), disulfiram, epigallocatechin gallate, salinosporamide A, carfilzomib, 17-AAG (geldanamycin), radicicol, lactate dehydrogenase A (LDH-A), fulvestrant (FASLODEX®, AstraZeneca), sunitib (SUTENT®, Pfizer/Sugen), letrozole (FEMARA®, Novartis), imatinib mesylate (GLEEVEC®, Novartis), finasunate (VATALANIB®, Novartis), oxaliplatin (ELOXATIN®, Sanofi), 5-FU (5-fluorouracil), leucovorin, Rapamycin (Sirolimus, RAPAMUNE®, Wyeth), Lapatinib (TYKERB®, GSK572016, Glaxo Smith Kline), Lonafamib (SCH 66336), sorafenib (NEXAVAR®, Bayer Labs), gefitinib (IRESSA®, AstraZeneca), AG1478, alkylating agents such as thiotepa and CYTOXAN® cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); a camptothecin (including topotecan and irinotecan); bryostatin; callystatin; CC-1065 (including its adozelesin, carzelesin and bizelesin synthetic analogs); cryptophycins (particularly cryptophycin 1 and cryptophycin 8); adrenocorticosteroids (including prednisone and prednisolone); cyproterone acetate; 5α-reductases including finasteride and dutasteride); vorinostat, romidepsin, panobinostat, valproic acid, mocetinostat dolastatin; aldesleukin, talc duocarmycin (including the synthetic analogs, KW-2189 and CB1-TM1); eleutherobin; pancratistatin; a sarcodictyin; spongistatin; nitrogen mustards such as chlorambucil, chlomaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, and ranimnustine; antibiotics such as the enediyne antibiotics (e.g., calicheamicin, especially calicheamicin γ1I and calicheamicin ω1I (Angew Chem. Intl. Ed. Engl. 1994 33:183-186); dynemicin, including dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® (doxorubicin), morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfomithine; elliptinium acetate; an epothilone; etoglucid; gallium nitrate; hydroxyurea; lentinan; lonidainine; maytansinoids such as maytansine and ansamitocins; mitoguazone; mitoxantrone; mopidamnol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane;

rhizoxin; sizofuran; spirogermanium; tenuazonic acid; triaziquone; 2,2',2''-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL (paclitaxel; Bristol-Myers Squibb Oncology, Princeton, N.J.), ABRAXANE® (Cremophor-free), albumin-engineered nanoparticle formulations of paclitaxel (American Pharmaceutical Partners, Schaumberg, Ill.), and TAXOTERE® (docetaxel, doxetaxel; Sanofi-Aventis); chloranmbucil; GEMZAR® (gemcitabine); 6-thioguanine; mercaptopurine; methotrexate; platinum analogs such as cisplatin and carboplatin; vinblastine; etoposide (VP-16); Ifosfamide; mitoxantrone; vincristine; NAVELBINE® (vinorelbine); novantrone; teniposide; edatrexate; daunomycin; aminopterin; capecitabine (XELODA®); ibandronate; CPT-11; topoisomerase inhibitor RFS 2000; difluoromethylornithine (DMFO); retinoids such as retinoic acid; and pharmaceutically acceptable salts, acids and derivatives of any of the above.

Chemotherapeutic agent also includes (i) anti-hormonal agents that act to regulate or inhibit hormone action on tumors such as anti-estrogens and selective estrogen receptor modulators (SERMs), including, for example, tamoxifen (including NOLVADEX®; tamoxifen citrate), raloxifene, droloxifene, iodoxyfene, 4-hydroxytamoxifen, trioxifene, keoxifene, LY117018, onapristone, and FARESTON® (toremifine citrate); (ii) aromatase inhibitors that inhibit the enzyme aromatase, which regulates estrogen production in the adrenal glands, such as, for example, 4(5)-imidazoles, aminoglutethimide, MEGASE® (megestrol acetate), AROMASIN® (exemestane; Pfizer), formestanie, fadrozole, RIVISOR® (vorozole), FEMARA® (letrozole; Novartis), and ARIMIDEX® (anastrozole; AstraZeneca); (iii) anti-androgens such as flutamide, nilutamide, bicalutamide, leuprolide and goserelin; buserelin, tripterelin, medroxyprogesterone acetate, diethylstilbestrol, premarin, fluoxymesterone, all transretionic acid, fenretinide, as well as troxacitabine (a 1,3-dioxolane nucleoside cytosine analog); (iv) protein kinase inhibitors; (v) lipid kinase inhibitors; (vi) antisense oligonucleotides, particularly those which inhibit expression of genes in signaling pathways implicated in aberrant cell proliferation, such as, for example, PKC-alpha, Ralf and H-Ras; (vii) ribozymes such as VEGF expression inhibitors (e.g., ANGIOZYME®) and HER2 expression inhibitors; (viii) vaccines such as gene therapy vaccines, for example, ALLOVECTIN®, LEUVECTIN®, and VAXID®; PROLEUKIN®, rIL-2; a topoisomerase 1 inhibitor such as LURTOTECAN®; ABARELIX® rmRH; and (ix) pharmaceutically acceptable salts, acids and derivatives of any of the above.

Chemotherapeutic agent also includes antibodies such as alemtuzumab (Campath), bevacizumab (AVAS TIN®, Genentech); cetuximab (ERBITUX®, Imclone); panitumumab (VECTIBIX®, Amgen), rituximab (RITUXAN®, Genentech/Biogen Idec), pertuzumab (OMNITARG®, 2C4, Genentech), trastuzumab (HERCEPTIN®, Genentech), tositumomab (Bexxar, Corixia), and the antibody drug conjugate, gemtuzumab ozogamicin (MYLOTARG®, Wyeth). Additional humanized monoclonal antibodies with therapeutic potential as agents in combination with the compounds of the invention include: apolizumab, aselizumab, atlizumab, bapineuzumab, bivatuzumab mertansine, cantuzumab mertansine, cedelizumab, certolizumab pegol, cidfusituzumab, cidtuzumab, daclizumab, eculizumab, efalizumab, epratuzumab, erlizumab, felvizumab, fontolizumab, gemtuzumab ozogamicin, inotuzumab ozogamicin, ipilimumab, labetuzumab, lintuzumab, matuzumab, mepolizumab, motavizumab, motovizumab, natalizumab, nimotuzumab, nolovizumab, numavizumab, ocrelizumab, omalizumab, palivizumab, pascolizumab, pecfusituzumab, pectuzumab, pexelizumab, ralivizumab, ranibizumab, reslivizumab, reslizumab, resyvizumab, rovelizumab, ruplizumab, sibrotuzumab, siplizumab, sontuzumab, tacatuzumab tetraxetan, tadocizumab, talizumab, tefibazumab, tocilizumab, toralizumab, tucotuzumab celmoleukin, tucusituzumab, umavizumab, urtoxazumab, ustekinumab, visilizumab, and the anti-interleukin-12 (ABT-874/J695, Wyeth Research and Abbott Laboratories) which is a recombinant exclusively human-sequence, full-length IgG1λ antibody genetically modified to recognize interleukin-12 p40 protein.

Chemotherapeutic agent also includes "EGFR inhibitors," which refers to compounds that bind to or otherwise interact directly with EGFR and prevent or reduce its signaling activity, and is alternatively referred to as an "EGFR antagonist." Examples of such agents include antibodies and small molecules that bind to EGFR. Examples of antibodies which bind to EGFR include MAb 579 (ATCC CRL HB 8506), MAb 455 (ATCC CRL HB8507), MAb 225 (ATCC CRL 8508), MAb 528 (ATCC CRL 8509) (see, U.S. Pat. No. 4,943,533, Mendelsohn et al.) and variants thereof, such as chimerized 225 (C225 or Cetuximab; ERBUTIX®) and reshaped human 225 (H225) (see, WO 96/40210, Imclone Systems Inc.); IMC-11F8, a fully human, EGFR-targeted antibody (Imclone); antibodies that bind type II mutant EGFR (U.S. Pat. No. 5,212,290); humanized and chimeric antibodies that bind EGFR as described in U.S. Pat. No. 5,891,996; and human antibodies that bind EGFR, such as ABX-EGF or Panitumumab (see WO98/50433, Abgenix/Amgen); EMD 55900 (Stragliotto et al. Eur. J. Cancer 32A:636-640 (1996)); EMD7200 (matuzumab) a humanized EGFR antibody directed against EGFR that competes with both EGF and TGF-alpha for EGFR binding (EMD/Merck); human EGFR antibody, HuMax-EGFR (GenMab); fully human antibodies known as E1.1, E2.4, E2.5, E6.2, E6.4, E2.11, E6.3 and E7.6.3 and described in U.S. Pat. No. 6,235,883; MDX-447 (Medarex Inc); and mAb 806 or humanized mAb 806 (Johns et al., J. Biol. Chem. 279(29): 30375-30384 (2004)). The anti-EGFR antibody may be conjugated with a cytotoxic agent, thus generating an immunoconjugate (see, e.g., EP659,439A2, Merck Patent GmbH). EGFR antagonists include small molecules such as compounds described in U.S. Pat. Nos. 5,616,582, 5,457,105, 5,475,001, 5,654,307, 5,679,683, 6,084,095, 6,265,410, 6,455,534, 6,521,620, 6,596,726, 6,713,484, 5,770,599, 6,140,332, 5,866,572, 6,399,602, 6,344,459, 6,602,863, 6,391,874, 6,344,455, 5,760,041, 6,002,008, and 5,747,498, as well as the following PCT publications: WO98/14451, WO98/50038, WO99/09016, and WO99/24037. Particular small molecule EGFR antagonists include OSI-774 (CP-358774, erlotinib, TARCEVA® Genentech/OSI Pharmaceuticals); PD 183805 (CI 1033, 2-propenamide, N-[4-[(3-chloro-4-fluorophenyl)amino]-7-[3-(4-morpholinyl) propoxy]-6-quinazolinyl]-, dihydrochloride, Pfizer Inc.); ZD1839, gefitinib (IRESSA®) 4-(3'-Chloro-4'-fluoroanilino)-7-methoxy-6-(3-morpholinopropoxy)quinazoline, AstraZeneca); ZM 105180 ((6-amino-4-(3-methylphenyl-amino)-quinazoline, Zeneca); BIBX-1382 (N8-(3-chloro-4-fluoro-phenyl)-N2-(1-methyl-piperidin-4-yl)-pyrimido[5,4-d]pyrimidine-2,8-diamine, Boehringer Ingelheim); PKI-166 ((R)-4-[4-[(1-phenylethy)amino]-1H-pyrrolo[2,3-d]pyrimidin-6-yl]-phenol); (R)-6-(4-hydroxyphenyl)-4-[(1-phenylethy)amino]-7H-pyrrolo[2,3-d]pyrimidine); CL-387785 (N-

[4-[(3-bromophenyl)amino]-6-quinazolinyl]-2-butynamide); EKB-569 (N-[4-[(3-chloro-4-fluorophenyl)amino]-3-cyano-7-ethoxy-6-quinolinyl]-4-(dimethylamino)-2-butenamide) (Wyeth); AG1478 (Pfizer); AG1571 (SU 5271; Pfizer); dual EGFR/HER2 tyrosine kinase inhibitors such as lapatinib (TYKERB®, GSK572016 or N-[3-chloro-4-[(3 fluorophenyl)methoxy]phenyl]-6[5[[[2methylsulfonyl)ethyl]amino]methyl]-2-furanyl]-4-quinazolinamine).

Chemotherapeutic agents also include "tyrosine kinase inhibitors" including the EGFR-targeted drugs noted in the preceding paragraph; small molecule HER2 tyrosine kinase inhibitor such as TAK165 available from Takeda; CP-724,714, an oral selective inhibitor of the ErbB2 receptor tyrosine kinase (Pfizer and OSI); dual-HER inhibitors such as EKB-569 (available from Wyeth) which preferentially binds EGFR but inhibits both HER2 and EGFR-overexpressing cells; lapatinib (GSK572016; available from Glaxo-SmithKline), an oral HER2 and EGFR tyrosine kinase inhibitor; PKI-166 (available from Novartis); pan-HER inhibitors such as canertinib (CI-1033; Pharmacia); Raf-1 inhibitors such as antisense agent ISIS-5132 available from ISIS Pharmaceuticals which inhibit Raf-1 signaling; non-HER targeted TK inhibitors such as imatinib mesylate (GLEEVEC®, available from Glaxo SmithKline); multi-targeted tyrosine kinase inhibitors such as sunitinib (SUTENT®, available from Pfizer); VEGF receptor tyrosine kinase inhibitors such as vatalanib (PTK787/ZK222584, available from Novartis/Schering AG); MAPK extracellular regulated kinase I inhibitor CI-1040 (available from Pharmacia); quinazolines, such as PD 153035, 4-(3-chloroanilino) quinazoline; pyridopyrimidines; pyrimidopyrimidines; pyrrolopyrimidines, such as CGP 59326, CGP 60261 and CGP 62706; pyrazolopyrimidines, 4-(phenylamine)-7H-pyrrolo[2,3-d] pyrimidines; curcumin (diferuloyl methane, 4,5-bis (4-fluoroanilino)phthalimide); tyrphostines containing nitrothiophene moieties; PD-0183805 (Warner-Lamber); antisense molecules (e.g. those that bind to HER-encoding nucleic acid); quinoxalines (U.S. Pat. No. 5,804,396); tryphostins (U.S. Pat. No. 5,804,396); ZD6474 (Astra Zeneca); PTK-787 (Novartis/Schering AG); pan-HER inhibitors such as CI-1033 (Pfizer); Affinitac (ISIS 3521; Isis/Lilly); imatinib mesylate (GLEEVEC®); PKI 166 (Novartis); GW2016 (Glaxo SmithKline); CI-1033 (Pfizer); EKB-569 (Wyeth); Semaxinib (Pfizer); ZD6474 (AstraZeneca); PTK-787 (Novartis/Schering AG); INC-1C11 (Imclone), rapamycin (sirolimus, RAPAMUNE®); or as described in any of the following patent publications: U.S. Pat. No. 5,804,396; WO 1999/09016 (American Cyanamid); WO 1998/43960 (American Cyanamid); WO 1997/38983 (Warner Lambert); WO 1999/06378 (Warner Lambert); WO 1999/06396 (Warner Lambert); WO 1996/30347 (Pfizer, Inc); WO 1996/33978 (Zeneca); WO 1996/3397 (Zeneca) and WO 1996/33980 (Zeneca).

Chemotherapeutic agents also include dexamethasone, interferons, colchicine, metoprine, cyclosporine, amphotericin, metronidazole, alemtuzumab, alitretinoin, allopurinol, amifostine, arsenic trioxide, asparaginase, BCG live, bevacuzimab, bexarotene, cladribine, clofarabine, darbepoetin alfa, denileukin, dexrazoxane, epoetin alfa, elotinib, filgrastim, histrelin acetate, ibritumomab, interferon alfa-2a, interferon alfa-2b, lenalidomide, levamisole, mesna, methoxsalen, nandrolone, nelarabine, nofetumomab, oprelvekin, palifermin, pamidronate, pegademase, pegaspargase, pegfilgrastim, pemetrexed disodium, plicamycin, porfimer sodium, quinacrine, rasburicase, sargramostim, temozolomide, VM-26, 6-TG, toremifene, tretinoin, ATRA, valrubicin, zoledronate, and zoledronic acid, and pharmaceutically acceptable salts thereof.

Chemotherapeutic agents also include hydrocortisone, hydrocortisone acetate, cortisone acetate, tixocortol pivalate, triamcinolone acetonide, triamcinolone alcohol, mometasone, amcinonide, budesonide, desonide, fluocinonide, fluocinolone acetonide, betamethasone, betamethasone sodium phosphate, dexamethasone, dexamethasone sodium phosphate, fluocortolone, hydrocortisone-17-butyrate, hydrocortisone-17-valerate, aclometasone dipropionate, betamethasone valerate, betamethasone dipropionate, prednicarbate, clobetasone-17-butyrate, clobetasol-17-propionate, fluocortolone caproate, fluocortolone pivalate and fluprednidene acetate; immune selective anti-inflammatory peptides (ImSAIDs) such as phenylalanine-glutamine-glycine (FEG) and its D-isomeric form (feG) (IMULAN Bio-Therapeutics, LLC); anti-rheumatic drugs such as azathioprine, ciclosporin (cyclosporine A), D-penicillamine, gold salts, hydroxychloroquine, leflunomideminocycline, sulfasalazine, tumor necrosis factor alpha (TNFα) blockers such as etanercept (Enbrel), infliximab (Remicade), adalimumab (Humira), certolizumab pegol (Cimzia), golimumab (Simponi), Interleukin 1 (IL-1) blockers such as anakinra (Kineret), T cell costimulation blockers such as abatacept (Orencia), Interleukin 6 (IL-6) blockers such as tocilizumab (ACTEMERA®); Interleukin 13 (IL-13) blockers such as lebrikizumab; Interferon alpha (IFN) blockers such as Rontalizumab; Beta 7 integrin blockers such as rhuMAb Beta7; IgE pathway blockers such as Anti-M1 prime; Secreted homotrimeric LTa3 and membrane bound heterotrimer LTa1/β2 blockers such as Anti-lymphotoxin alpha (LTa); radioactive isotopes (e.g., At211, 1131, 1125, Y90, Re186, Re188, Sm153, Bi212, P32, Pb212 and radioactive isotopes of Lu); miscellaneous investigational agents such as thioplatin, PS-341, phenylbutyrate, ET-18-OCH3, or farnesyl transferase inhibitors (L-739749, L-744832); polyphenols such as quercetin, resveratrol, piceatannol, epigallocatechine gallate, theaflavins, flavanols, procyanidins, betulinic acid and derivatives thereof; autophagy inhibitors such as chloroquine; delta-9-tetrahydrocannabinol (dronabinol, MARINOL®); beta-lapachone; lapachol; colchicines; betulinic acid; acetylcamptothecin, scopolectin, and 9-aminocamptothecin); podophyllotoxin; tegafur (UFTORAL®); bexarotene (TARGRETIN®); bisphosphonates such as clodronate (for example, BONEFOS® or OSTAC®), etidronate (DIDROCAL®), NE-58095, zoledronic acid/zoledronate (ZOMETA®), alendronate (FOSAMAX®), pamidronate (AREDIA®), tiludronate (SKELID®), or risedronate (ACTONEL®); and epidermal growth factor receptor (EGF-R); vaccines such as THERATOPE® vaccine; perifosine, COX-2 inhibitor (e.g. celecoxib or etoricoxib), proteosome inhibitor (e.g. PS341); CCI-779; tipifarnib (R11577); orafenib, ABT510; Bcl-2 inhibitor such as oblimersen sodium (GENASENSE®); pixantrone; farnesyltransferase inhibitors such as lonafarnib (SCH 6636, SARASAR™); and pharmaceutically acceptable salts, acids or derivatives of any of the above; as well as combinations of two or more of the above such as CHOP, an abbreviation for a combined therapy of cyclophosphamide, doxorubicin, vincristine, and prednisolone; and FOLFOX, an abbreviation for a treatment regimen with oxaliplatin (ELOXATIN™) combined with 5-FU and leucovorin.

Chemotherapeutic agents also include non-steroidal anti-inflammatory drugs with analgesic, antipyretic and anti-inflammatory effects. NSAIDs include non-selective inhibitors of the enzyme cyclooxygenase. Specific examples of NSAIDs include aspirin, propionic acid derivatives such as ibuprofen, fenoprofen, ketoprofen, flurbiprofen, oxaprozin and naproxen, acetic acid derivatives such as indomethacin, sulindac, etodolac, diclofenac, enolic acid derivatives such as piroxicam, meloxicam, tenoxicam, droxicam, lornoxicam and isoxicam, fenamic acid derivatives such as mefenamic acid, meclofenamic acid, flufenamic acid, tolfenamic acid, and COX-2 inhibitors such as celecoxib, etoricoxib, lumiracoxib, parecoxib, rofecoxib, rofecoxib, and valdecoxib. NSAIDs can be indicated for the symptomatic relief of conditions such as rheumatoid arthritis, osteoarthritis, inflammatory arthropathies, ankylosing spondylitis, psoriatic arthritis, Reiter's syndrome, acute gout, dysmenorrhoea, metastatic bone pain, headache and migraine, postoperative pain, mild-to-moderate pain due to inflammation and tissue injury, pyrexia, ileus, and renal colic.

The term "cytokine" is a generic term for proteins released by one cell population that act on another cell as intercellular mediators. Examples of such cytokines are lymphokines, monokines; interleukins (ILs) such as IL-1, IL-1a, IL-2, IL-3, IL-4, IL-5, IL-6, IL-7, IL-8, IL-9, IL-11, IL-12, IL-15; a tumor necrosis factor such as TNF-α or TNF-β; and other polypeptide factors including LIF and kit ligand (KL) and gamma interferon. As used herein, the term cytokine includes proteins from natural sources or from recombinant cell culture and biologically active equivalents of the native-sequence cytokines, including synthetically produced small-molecule entities and pharmaceutically acceptable derivatives and salts thereof.

The term "PD-1 axis binding antagonist" is a molecule that inhibits the interaction of a PD-1 axis binding partner with either one or more of its binding partner, so as to remove T-cell dysfunction resulting from signaling on the PD-1 signaling axis—with a result being to restore or enhance T-cell function (e.g., proliferation, cytokine production, target cell killing). As used herein, a PD-1 axis binding antagonist includes a PD-1 binding antagonist, a PD-L1 binding antagonist and a PD-L2 binding antagonist.

The term "PD-1 binding antagonists" is a molecule that decreases, blocks, inhibits, abrogates or interferes with signal transduction resulting from the interaction of PD-1 with one or more of its binding partners, such as PD-L1, PD-L2. In some embodiments, the PD-1 binding antagonist is a molecule that inhibits the binding of PD-1 to its binding partners. In a specific aspect, the PD-1 binding antagonist inhibits the binding of PD-1 to PD-L1 and/or PD-L2. For example, PD-1 binding antagonists include anti-PD-1 antibodies, antigen binding fragments thereof, immunoadhesins, fusion proteins, oligopeptides and other molecules that decrease, block, inhibit, abrogate or interfere with signal transduction resulting from the interaction of PD-1 with PD-L1 and/or PD-L2. In one embodiment, a PD-1 binding antagonist reduces the negative co-stimulatory signal mediated by or through cell surface proteins expressed on T lymphocytes mediated signaling through PD-1 so as render a dysfunctional T-cell less dysfunctional (e.g., enhancing effector responses to antigen recognition). In some embodiments, the PD-1 binding antagonist is an anti-PD-1 antibody. In a specific aspect, a PD-1 binding antagonist is MDX-1 106 described herein. In another specific aspect, a PD-1 binding antagonist is Merck 3745 described herein. In another specific aspect, a PD-1 binding antagonist is CT-011 described herein.

The term "PD-L1 binding antagonists" is a molecule that decreases, blocks, inhibits, abrogates or interferes with signal transduction resulting from the interaction of PD-L1 with either one or more of its binding partners, such as PD-1, B7-1. In some embodiments, a PD-L1 binding antagonist is a molecule that inhibits the binding of PD-L1 to its binding partners. In a specific aspect, the PD-L1 binding antagonist inhibits binding of PD-L1 to PD-1 and/or B7-1. In some embodiments, the PD-L1 binding antagonists include anti-PD-L1 antibodies, antigen binding fragments thereof, immunoadhesins, fusion proteins, oligopeptides and other molecules that decrease, block, inhibit, abrogate or interfere with signal transduction resulting from the interaction of PD-L1 with one or more of its binding partners, such as PD-1, B7-1. In one embodiment, a PD-L1 binding antagonist reduces the negative co-stimulatory signal mediated by or through cell surface proteins expressed on T lymphocytes mediated signaling through PD-L1 so as to render a dysfunctional T-cell less dysfunctional (e.g., enhancing effector responses to antigen recognition). In some embodiments, a PD-L1 binding antagonist is an anti-PD-L1 antibody. In a specific aspect, an anti-PD-L1 antibody is YW243.55.S70 described herein. In another specific aspect, an anti-PD-L1 antibody is MDX-1 105 described herein. In still another specific aspect, an anti-PD-L1 antibody is MPDL3280A described herein.

The term "PD-L2 binding antagonists" is a molecule that decreases, blocks, inhibits, abrogates or interferes with signal transduction resulting from the interaction of PD-L2 with either one or more of its binding partners, such as PD-1. In some embodiments, a PD-L2 binding antagonist is a molecule that inhibits the binding of PD-L2 to its binding partners. In a specific aspect, the PD-L2 binding antagonist inhibits binding of PD-L2 to PD-1. In some embodiments, the PD-L2 antagonists include anti-PD-L2 antibodies, antigen binding fragments thereof, immunoadhesins, fusion proteins, oligopeptides and other molecules that decrease, block, inhibit, abrogate or interfere with signal transduction resulting from the interaction of PD-L2 with either one or more of its binding partners, such as PD-1. In one embodiment, a PD-L2 binding antagonist reduces the negative co-stimulatory signal mediated by or through cell surface proteins expressed on T lymphocytes mediated signaling through PD-L2 so as render a dysfunctional T-cell less dysfunctional (e.g., enhancing effector responses to antigen recognition). In some embodiments, a PD-L2 binding antagonist is an immunoadhesin.

The term "phagocytosis" means the internalization of cells or particulate matter by cells. In some embodiments, the phagocytic cells or phagocytes are macrophages or neutrophils. In some embodiments, the cells are cells that express human OX40. Methods for assaying phagocytosis are known in the art and include use of microscopy to detect the presence of cells internalized within another cells. In other embodiments, phagocytosis is detected using FACS, e.g., by detecting presence of a detectably labeled cell within another cell (which may be detectably labeled, e.g., with a different label than the first cell).

The phrase "does not possess substantial activity" or "substantially no activity" with respect to an antibody, as used herein, means the antibody does not exhibit an activity that is above background level (in some embodiments, that is above background level that is statistically significant). The phrase "little to no activity" with respect to an antibody, as used herein, means the antibody does not display a biologically meaningful amount of a function. The function can be measured or detected according to any assay or technique known in the art, including, e.g., those described herein. In some embodiments, antibody function is stimulation of effector T cell proliferation and/or cytokine secretion.

The term "biomarker" or "marker" as used herein refers generally to a molecule, including a gene, mRNA, protein, carbohydrate structure, or glycolipid, the expression of which in or on a tissue or cell or secreted can be detected by known methods (or methods disclosed herein) and is predictive or can be used to predict (or aid prediction) for a cell, tissue, or patient's responsiveness to treatment regimes. In some embodiments, a biomarker may refer to a gene or protein, e.g., the level of expression of the gene or protein detected in one or more cells. In some embodiments, a biomarker may refer to a cell type of interest, e.g., the number of a cell type of interest detected in one or more samples.

By "patient sample" is meant a collection of cells or fluids obtained from a cancer patient. The source of the tissue or cell sample may be solid tissue as from a fresh, frozen and/or preserved organ or tissue sample or biopsy or aspirate; blood or any blood constituents; bodily fluids such as cerebrospinal fluid, amniotic fluid, peritoneal fluid, or interstitial fluid; cells from any time in gestation or development of the subject. The tissue sample may contain compounds which are not naturally intermixed with the tissue in nature such as preservatives, anticoagulants, buffers, fixatives, nutrients, antibiotics, or the like. Examples of tumor samples herein include, but are not limited to, tumor biopsy, fine needle aspirate, bronchiolar lavage, pleural fluid, sputum, urine, a surgical specimen, circulating tumor cells, serum, plasma, circulating plasma proteins, ascitic fluid, primary cell cultures or cell lines derived from tumors or exhibiting tumor-like properties, as well as preserved tumor samples, such as formalin-fixed, paraffin-embedded tumor samples or frozen tumor samples.

The phrase "based on expression of" when used herein means that information about expression level or presence or absence of expression (e.g., presence or absence or prevalence of (e.g., percentage of cells displaying) of the one or more biomarkers herein (e.g., presence or absence of or amount or prevalence of FcR-expressing cells, or e.g., presence or absence or amount or prevalence of human effector cells) is used to inform a treatment decision, information provided on a package insert, or marketing/promotional guidance etc.

A cancer or biological sample which "has human effector cells" is one which, in a diagnostic test, has human effector cells present in the sample (e.g., infiltrating human effector cells).

A cancer or biological sample which "has FcR-expressing cells" is one which, in a diagnostic test, has FcR-expressing present in the sample (e.g., infiltrating FcR-expressing cells). In some embodiments, FcR is FcγR. In some embodiments, FcR is an activating FcγR.

The phrase "recommending a treatment" as used herein refers to using the information or data generated relating to the level or presence of c-met in a sample of a patient to identify the patient as suitably treated or not suitably treated with a therapy. In some embodiments the therapy may comprise c-met antibody (e.g., onartuzumab). In some embodiments, the therapy may comprise VEGF antagonist (e.g., bevacizumab). In some embodiments, the therapy may comprise anti-human OX40 agonist antibody. The information or data may be in any form, written, oral or electronic. In some embodiments, using the information or data generated includes communicating, presenting, reporting, storing, sending, transferring, supplying, transmitting, delivering, dispensing, or combinations thereof. In some embodiments, communicating, presenting, reporting, storing, sending, transferring, supplying, transmitting, delivering, dispensing, or combinations thereof are performed by a computing device, analyzer unit or combination thereof. In some further embodiments, communicating, presenting, reporting, storing, sending, transferring, supplying, transmitting, dispensing, or combinations thereof are performed by an individual (e.g., a laboratory or medical professional). In some embodiments, the information or data includes a comparison of the amount or prevalence of FcR expressing cells to a reference level. In some embodiments, the information or data includes a comparison of the amount or prevalence of human effector cells to a reference level. In some embodiments, the information or data includes an indication that human effector cells or FcR-expressing cells are present or absent in the sample. In some embodiments, the information or data includes an indication that FcR-expressing cells and/or human effector cells are present in a particular percentage of cells (e.g., high prevalence). In some embodiments, the information or data includes an indication that the patient is suitably treated or not suitably treated with a therapy comprising anti-human OX40 agonist antibody.

The term "detection" includes any means of detecting, including direct and indirect detection.

The "amount" or "level" of a biomarker associated with an increased clinical benefit to an individual is a detectable level in a biological sample. These can be measured by methods known to one skilled in the art and also disclosed herein. The expression level or amount of biomarker assessed can be used to determine the response to the treatment.

"Elevated expression," "elevated expression levels," or "elevated levels" refers to an increased expression or increased levels of a biomarker in an individual relative to a control, such as an individual or individuals who are not suffering from the disease or disorder (e.g., cancer), a tumor with a known responsiveness to a treatment (e.g., with an OX40 agonist), an internal control (e.g., housekeeping biomarker), or a reference number (e.g., a set threshold amount, such as a threshold based on clinical outcome data).

"Reduced expression," "reduced expression levels," or "reduced levels" refers to a decrease expression or decreased levels of a biomarker in an individual relative to a control, such as an individual or individuals who are not suffering from the disease or disorder (e.g., cancer), a tumor with a known responsiveness to a treatment (e.g., with an OX40 agonist), an internal control (e.g., housekeeping biomarker), or a reference number (e.g., a set threshold amount, such as a threshold based on clinical outcome data). In some embodiments, reduced expression is little or no expression.

The term "diagnosis" is used herein to refer to the identification or classification of a molecular or pathological state, disease or condition (e.g., cancer). For example, "diagnosis" may refer to identification of a particular type of cancer. "Diagnosis" may also refer to the classification of a particular subtype of cancer, e.g., by histopathological criteria, or by molecular features (e.g., a subtype characterized by expression of one or a combination of biomarkers (e.g., particular genes or proteins encoded by said genes)).

The term "aiding diagnosis" is used herein to refer to methods that assist in making a clinical determination regarding the presence, or nature, of a particular type of symptom or condition of a disease or disorder (e.g., cancer). For example, a method of aiding diagnosis of a disease or condition (e.g., cancer) can comprise measuring certain biomarkers in a biological sample from an individual.

The term "sample," as used herein, refers to a composition that is obtained or derived from a subject and/or individual of interest that contains a cellular and/or other molecular entity that is to be characterized and/or identified, for example based on physical, biochemical, chemical and/or physiological characteristics. For example, the phrase "disease sample" and variations thereof refers to any sample obtained from a subject of interest that would be expected or is known to contain the cellular and/or molecular entity that is to be characterized. Samples include, but are not limited to, primary or cultured cells or cell lines, cell supernatants, cell lysates, platelets, serum, plasma, vitreous fluid, lymph fluid, synovial fluid, follicular fluid, seminal fluid, amniotic fluid, milk, whole blood, blood-derived cells, urine, cerebrospinal fluid, saliva, sputum, tears, perspiration, mucus, tumor lysates, and tissue culture medium, tissue extracts such as homogenized tissue, tumor tissue, cellular extracts, and combinations thereof.

By "tissue sample" or "cell sample" is meant a collection of similar cells obtained from a tissue of a subject or individual. The source of the tissue or cell sample may be solid tissue as from a fresh, frozen and/or preserved organ, tissue sample, biopsy, and/or aspirate; blood or any blood constituents such as plasma; bodily fluids such as cerebral spinal fluid, amniotic fluid, peritoneal fluid, or interstitial fluid; cells from any time in gestation or development of the subject. The tissue sample may also be primary or cultured cells or cell lines. Optionally, the tissue or cell sample is obtained from a disease tissue/organ. The tissue sample may contain compounds which are not naturally intermixed with the tissue in nature such as preservatives, anticoagulants, buffers, fixatives, nutrients, antibiotics, or the like.

As used herein, a "section" of a tissue sample is meant a single part or piece of a tissue sample, e.g. a thin slice of tissue or cells cut from a tissue sample. It is understood that multiple sections of tissue samples may be taken and subjected to analysis according to the present invention, provided that it is understood that the present invention comprises a method whereby the same section of tissue sample is analyzed at both morphological and molecular levels, or is analyzed with respect to protein or nucleic acid.

By "correlate" or "correlating" is meant comparing, in any way, the performance and/or results of a first analysis or protocol with the performance and/or results of a second analysis or protocol. For example, one may use the results of a first analysis or protocol in carrying out a second protocols and/or one may use the results of a first analysis or protocol to determine whether a second analysis or protocol should be performed. With respect to the embodiment of polypeptide analysis or protocol, one may use the results of the polypeptide expression analysis or protocol to determine whether a specific therapeutic regimen should be performed. With respect to the embodiment of polynucleotide analysis or protocol, one may use the results of the polynucleotide expression analysis or protocol to determine whether a specific therapeutic regimen should be performed.

"Individual response" or "response" can be assessed using any endpoint indicating a benefit to the individual, including, without limitation, (1) inhibition, to some extent, of disease progression (e.g., cancer progression), including slowing down and complete arrest; (2) a reduction in tumor size; (3) inhibition (i.e., reduction, slowing down or complete stopping) of cancer cell infiltration into adjacent peripheral organs and/or tissues; (4) inhibition (i.e. reduction, slowing down or complete stopping) of metastasis; (5) relief, to some extent, of one or more symptoms associated with the disease or disorder (e.g., cancer); (6) increase or extend in the length of survival, including overall survival and progression free survival; and/or (9) decreased mortality at a given point of time following treatment.

An "effective response" of a patient or a patient's "responsiveness" to treatment with a medicament and similar wording refers to the clinical or therapeutic benefit imparted to a patient at risk for, or suffering from, a disease or disorder, such as cancer. In one embodiment, such benefit includes any one or more of: extending survival (including overall survival and progression free survival); resulting in an objective response (including a complete response or a partial response); or improving signs or symptoms of cancer.

By "extending survival" is meant increasing overall or progression free survival in a treated patient relative to an untreated patient (i.e. relative to a patient not treated with the medicament), or relative to a patient who does not express a biomarker at the designated level, and/or relative to a patient treated with an approved anti-tumor agent. An objective response refers to a measurable response, including complete response (CR) or partial response (PR).

III. OX40 Agonists

Provided herein are methods for predicting responsiveness of a subject having cancer to an OX40 agonist treatment. These methods are based in part on the discovery described herein that the number of CD4+ OX40+ Foxp3+ lymphocytes in a sample containing cancer cells and lymphocytes obtained from a subject having cancer may be used to classify the subject as responsive or non-responsive to an OX40 agonist treatment. It is a further discovery of the present disclosure that the number of CD4+ OX40+ Foxp3+ lymphocytes in a sample containing cancer cells and lymphocytes obtained from a subject having cancer may also be used to determine prognosis of the subject and/or select a subject for treatment with an OX40 agonist of the present disclosure. It is a further discovery of the present disclosure that the number of CD4+, OX40+, CD4+ OX40+ Foxp3+, or CD4+ OX40+ Foxp3− lymphocytes in a sample containing metastatic cancer cells and lymphocytes obtained from a subject having cancer may also be used to determine prognosis of the subject and/or select a subject for treatment with an OX40 agonist of the present disclosure. Additionally, as described herein, OX40 agonist antibodies may further find use in methods for quantifying OX40+, CD4+ OX40+ Foxp3+, or CD4+ OX40+ Foxp3− lymphocytes in a sample comprising cancer cells (including primary and metastatic cancer cells) and lymphocytes obtained from a subject.

Antibodies suitable for use in the methods of the invention include antibodies that bind to human OX40. In some embodiments, the anti-OX40 antibody is an agonist antibody. Descriptions of anti-OX40 antibodies (e.g., anti-human OX40 agonist antibodies) may be found in US PG Pub. No. US2015/0307617 and International Publication No. WO/2015/153513, which are each incorporated by reference herein in their entirety.

In some embodiments, the anti-human OX40 agonist antibody binds human OX40 with an affinity of less than or equal to about 0.45 nM. In some embodiments, the anti-human OX40 antibody binds human OX40 with an affinity of less than or equal to about 0.4 nM. In some embodiments, the anti-human OX40 antibody binds human OX40 with an affinity of less than or equal to about 0.5 nM. In some embodiments, the binding affinity is determined using radioimmunoassay.

In some embodiments, the anti-human OX40 agonist antibody binds human OX40 and cynomolgus OX40. In some embodiments, binding is determined using a FACS assay. In some embodiments, binding to human OX40 has an EC50 of about 0.2 ug/ml. In some embodiments, binding to human OX40 has an EC50 of about 0.3 ug/ml or lower. In some embodiments, binding to cynomolgus OX40 has an EC50 of about 1.5 ug/ml. In some embodiments, binding to cynomolgus OX40 has an EC50 of about 1.4 ug/ml.

In some embodiments, the anti-human OX40 agonist antibody does not bind to rat OX40 or mouse OX40.

In some embodiments, the anti-human OX40 agonist antibody is a depleting anti-human OX40 antibody (e.g., depletes cells that express human OX40). In some embodiments, the human OX40 expressing cells are CD4+ effector T cells. In some embodiments, the human OX40 expressing cells are Treg cells. In some embodiments, depleting is by ADCC and/or phagocytosis. In some embodiments, the antibody mediates ADCC by binding FcγR expressed by a human effector cell and activating the human effector cell function. In some embodiments, the antibody mediates phagocytosis by binding FcγR expressed by a human effector cell and activating the human effector cell function. Exemplary human effector cells include, e.g., macrophage, natural killer (NK) cells, monocytes, neutrophils. In some embodiments, the human effector cell is macrophage. In some embodiments, the human effector cell is NK cells. In some embodiments, depletion is not by apoptosis.

In some embodiments, the anti-human OX40 agonist antibody has a functional Fc region. In some embodiments, effector function of a functional Fc region is ADCC. In some embodiments, effector function of a functional Fc region is phagocytosis. In some embodiments, effector function of a functional Fc region is ADCC and phagocytosis. In some embodiments, the Fc region is human IgG1. In some embodiments, the Fc region is human IgG4.

In some embodiments, the anti-human OX40 agonist antibody does not induce apoptosis in OX40-expressing cells (e.g., Treg). In some embodiments, apoptosis is assayed using an antibody concentration of 30 ug/ml, e.g., by determining whether apoptosis has occurred using annexin V and proprodium iodide stained Treg.

In some embodiments, the anti-human OX40 agonist antibody enhances CD4+ effector T cell function, for example, by increasing CD4+ effector T cell proliferation and/or increasing gamma interferon production by the CD4+ effector T cell (for example, as compared to proliferation and/or cytokine production prior to treatment with anti-human OX40 agonist antibody). In some embodiments, the cytokine is gamma interferon. In some embodiments, the anti-human OX40 agonist antibody increases number of intratumoral (infiltrating) CD4+ effector T cells (e.g., total number of CD4+ effector T cells, or e.g., percentage of CD4+ cells in CD45+ cells), e.g., as compared to number of intratumoral (infiltrating) CD4+ T cells prior to treatment with anti-human OX40 agonist antibody. In some embodiments, the anti-human OX40 agonist antibody increases number of intratumoral (infiltrating) CD4+ effector T cells that express gamma interferon (e.g., total gamma interferon expressing CD4+ cells, or e.g., percentage of gamma interferon expressing CD4+ cells in total CD4+ cells), e.g., as compared to number of intratumoral (infiltrating) CD4+ T cells that express gamma interferon prior to treatment with anti-human OX40 agonist antibody.

In some embodiments, the anti-human OX40 agonist antibody increases number of intratumoral (infiltrating) CD8+ effector T cells (e.g., total number of CD8+ effector T cells, or e.g., percentage of CD8+ in CD45+ cells), e.g., as compared to number of intratumoral (infiltrating) CD8+ T effector cells prior to treatment with anti-human OX40 agonist antibody. In some embodiments, the anti-human OX40 agonist antibody increases number of intratumoral (infiltrating) CD8+ effector T cells that express gamma interferon (e.g., percentage of CD8+ cells that express gamma interferon in total CD8+ cells), e.g., compared to number of intratumoral (infiltrating) CD8+ T cells that express gamma interferon prior to treatment with anti-human OX40 agonist antibody.

In some embodiments, the anti-human OX40 agonist antibody enhances memory T cell function, for example by increasing memory T cell proliferation and/or increasing cytokine production by the memory cell. In some embodiments, the cytokine is gamma interferon.

In some embodiments, the anti-human OX40 agonist antibody inhibits Treg function, for example, by decreasing Treg suppression of effector T cell function (e.g., effector T cell proliferation and/or effector T cell cytokine secretion). In some embodiments, the effector T cell is a CD4+ effector T cell. In some embodiments, the anti-human OX40 agonist antibody reduces the number of intratumoral (infiltrating) Treg (e.g., total number of Treg or e.g., percentage of Fox3p+ cells in CD4+ cells).

In some embodiments, the anti-human OX40 agonist antibody is engineered to increase effector function (e.g., compared to effector function in a wild-type IgG1). In some embodiments, the antibody has increased binding to a Fcγ receptor. In some embodiments, the antibody lacks fucose attached (directly or indirectly) to the Fc region. For example, the amount of fucose in such antibody may be from 1% to 80%, from 1% to 65%, from 5% to 65% or from 20% to 40%. In some embodiments, the Fc region comprises bisected oligosaccharides, e.g., in which a biantennary oligosaccharide attached to the Fc region of the antibody is bisected by GlcNAc. In some embodiments, the antibody comprises an Fc region with one or more amino acid substitutions which improve ADCC, e.g., substitutions at positions 298, 333, and/or 334 of the Fc region (EU numbering of residues).

In some embodiments, the anti-human OX40 agonist antibody increases OX40 signal transduction in a target cell that expresses OX40. In some embodiments, OX40 signal transduction is detected by monitoring NFkB downstream signaling.

In some embodiments, the anti-human OX40 agonist antibody is stable after treatment at 40 C for two weeks.

In some embodiments, the anti-human OX40 agonist antibody binds human effector cells, e.g., binds FcγR (e.g., an activating FcγR) expressed by human effector cells. In some embodiments, the human effector cell performs (is capable of performing) ADCC effector function. In some embodiments, the human effector cell performs (is capable of performing) phagocytosis effector function.

In some embodiments, the anti-human OX40 agonist antibody comprising a variant IgG1 Fc polypeptide comprising a mutation that eliminates binding to human effector cells (e.g., a DANA mutation) has diminished activity (e.g., CD4+ effector T cell function, e.g., proliferation), relative to anti-human OX40 agonist antibody comprising native sequence IgG1 Fc portion. In some embodiment, the anti-human OX40 agonist antibody comprising a variant IgG1 Fc polypeptide comprising a mutation that eliminates binding to human effector cells (e.g., a DANA mutation) does not possess substantial activity (e.g., CD4+ effector T cell function, e.g., proliferation).

In some embodiments, antibody cross-linking is required for anti-human OX40 agonist antibody function. In some embodiments, function is stimulation of CD4+ effector T cell proliferation. In some embodiments, antibody cross-linking is determined by providing anti-human OX40 agonist antibody adhered on a solid surface (e.g., a cell culture plate). In some embodiments, antibody cross-linking is determined by introducing a mutation in the antibody's IgG1 Fc portion (e.g., a DANA mutation) and testing function of the mutant antibody.

In some embodiments, the anti-human OX40 agonist antibody competes for binding to human OX40 with OX40L. In some embodiments, addition of OX40L does not enhance anti-human OX40 antibody function in an in vitro assay.

According to another embodiment, the anti-human OX40 agonist antibodies include any one, any combination, or all of the following properties: (1) binds human OX40 with an affinity of less than or equal to about 0.45 nM, in some embodiments, binds human OX40 with an affinity of less than or equal to about 0.4 nM, in some embodiments, binds human OX40 with an affinity of less than or equal to about 0.5 nM, in some embodiments, the binding affinity is determined using radioimmunoassay; (2) binds human OX40 and cynomolgus OX40, in some embodiments, binding is determined using a FACS assay, (3) binds human OX40 with an EC50 of about 0.2 ug/ml, in some embodiments, binds to human OX40 has an EC50 of about 0.3 ug/ml or lower, in some embodiments, binds to cynomolgus OX40 with an EC50 of about 1.5 ug/ml, in some embodiments, binds to cynomolgus OX40 has an EC50 of about 1.4 ug/ml, (4) does not substantially bind to rat OX40 or mouse OX40, (6) is a depleting anti-human OX40 antibody (e.g., depletes cells that express human OX40), in some embodiments, the cells are CD4+ effector T cells and/or Treg cells, (7) enhances CD4+ effector T cell function, for example, by increasing CD4+ effector T cell proliferation and/or increasing gamma interferon production by the CD4+ effector T cell (for example, as compared to proliferation and/or cytokine production prior to treatment with anti-human OX40 agonist antibody), (8) enhances memory T cell function, for example by increasing memory T cell proliferation and/or increasing cytokine production by the memory cell, (9) inhibits Treg function, for example, by decreasing Treg suppression of effector T cell function (e.g., effector T cell proliferation and/or effector T cell cytokine secretion). In some embodiments, the effector T cell is a CD4+ effector T cell, (10) increases OX40 signal transduction in a target cell that expresses OX40 (in some embodiments, OX40 signal transduction is detected by monitoring NFkB downstream signaling), (11) is stable after treatment at 40 C for two weeks, (12) binds human effector cells, e.g., binds FcγR expressed by human effector cells, (13) anti-human OX40 agonist antibody comprising a variant IgG1 Fc polypeptide comprising a mutation that eliminates binding to human effector cells (e.g., N297G) has diminished activity (e.g., CD4+ effector T cell function, e.g., proliferation), relative to anti-human OX40 agonist antibody comprising native sequence IgG1 Fc portion, in some embodiment, the anti-human OX40 agonist antibody comprising a variant IgG1 Fc polypeptide comprising a mutation that eliminates binding to human effector cells (e.g., N297G) does not possess substantial activity (e.g., CD4+ effector T cell function, e.g., proliferation), (14) antibody cross-linking (e.g., by Fc receptor binding) is required for anti-human OX40 agonist antibody function.

In one aspect, the invention provides an anti-human OX40 agonist antibody comprising at least one, two, three, four, five, or six HVRs selected from (a) HVR-H1 comprising the amino acid sequence of SEQ ID NO:2; (b) HVR-H2 comprising the amino acid sequence of SEQ ID NO:3; (c) HVR-H3 comprising the amino acid sequence of SEQ ID NO:4; (d) HVR-L1 comprising the amino acid sequence of SEQ ID NO:5; (e) HVR-L2 comprising the amino acid sequence of SEQ ID NO:6; and (f) HVR-L3 comprising the amino acid sequence of SEQ ID NO:7.

In one aspect, the invention provides an anti-human OX40 agonist antibody comprising at least one, at least two, or all three VH HVR sequences selected from (a) HVR-H1 comprising the amino acid sequence of SEQ ID NO:2; (b) HVR-H2 comprising the amino acid sequence of SEQ ID NO:3; and (c) HVR-H3 comprising the amino acid sequence of SEQ ID NO:4. In one embodiment, the antibody comprises HVR-H3 comprising the amino acid sequence of SEQ ID NO:4. In another embodiment, the antibody comprises HVR-H3 comprising the amino acid sequence of SEQ ID NO:4 and HVR-L3 comprising the amino acid sequence of SEQ ID NO:7. In a further embodiment, the antibody comprises HVR-H3 comprising the amino acid sequence of SEQ ID NO:4, HVR-L3 comprising the amino acid sequence of SEQ ID NO:7, and HVR-H2 comprising the amino acid sequence of SEQ ID NO:3. In a further embodiment, the antibody comprises (a) HVR-H1 comprising the amino acid sequence of SEQ ID NO:2; (b) HVR-H2 comprising the amino acid sequence of SEQ ID NO:3; and (c) HVR-H3 comprising the amino acid sequence of SEQ ID NO:4.

In another aspect, the invention provides an anti-human OX40 agonist antibody comprising at least one, at least two, or all three VL HVR sequences selected from (a) HVR-L1 comprising the amino acid sequence of SEQ ID NO:5; (b) HVR-L2 comprising the amino acid sequence of SEQ ID NO:6; and (c) HVR-L3 comprising the amino acid sequence of SEQ ID NO:7. In one embodiment, the antibody comprises (a) HVR-L1 comprising the amino acid sequence of SEQ ID NO:5; (b) HVR-L2 comprising the amino acid sequence of SEQ ID NO:6; and (c) HVR-L3 comprising the amino acid sequence of SEQ ID NO:7.

In another aspect, an anti-human OX40 agonist antibody of the invention comprises (a) a VH domain comprising at least one, at least two, or all three VH HVR sequences selected from (i) HVR-H1 comprising the amino acid sequence of SEQ ID NO:2, (ii) HVR-H2 comprising the amino acid sequence of SEQ ID NO:3, and (iii) HVR-H3 comprising an amino acid sequence selected from SEQ ID NO:4; and (b) a VL domain comprising at least one, at least two, or all three VL HVR sequences selected from (i) HVR-L1 comprising the amino acid sequence of SEQ ID NO:5, (ii) HVR-L2 comprising the amino acid sequence of SEQ ID NO:6, and (c) HVR-L3 comprising the amino acid sequence of SEQ ID NO:7.

In another aspect, the invention provides an anti-human OX40 agonist antibody comprising (a) HVR-H1 comprising the amino acid sequence of SEQ ID NO:2; (b) HVR-H2 comprising the amino acid sequence of SEQ ID NO:3; (c) HVR-H3 comprising the amino acid sequence of SEQ ID NO:4; (d) HVR-L1 comprising the amino acid sequence of SEQ ID NO:5; (e) HVR-L2 comprising the amino acid sequence of SEQ ID NO:6; and (f) HVR-L3 comprising an amino acid sequence selected from SEQ ID NO:7.

In one aspect, the invention provides an anti-human OX40 agonist antibody comprising at least one, two, three, four, five, or six HVRs selected from (a) HVR-H1 comprising the amino acid sequence of SEQ ID NO:2; (b) HVR-H2 comprising the amino acid sequence of SEQ ID NO:3; (c) HVR-H3 comprising the amino acid sequence of SEQ ID NO:4; (d) HVR-L1 comprising the amino acid sequence of SEQ ID NO:5; (e) HVR-L2 comprising the amino acid sequence of SEQ ID NO:6; and (f) HVR-L3 comprising the amino acid sequence of SEQ ID NO:26.

In another embodiment, the antibody comprises HVR-H3 comprising the amino acid sequence of SEQ ID NO:4 and HVR-L3 comprising the amino acid sequence of SEQ ID NO:26. In a further embodiment, the antibody comprises HVR-H3 comprising the amino acid sequence of SEQ ID NO:4, HVR-L3 comprising the amino acid sequence of SEQ ID NO:26, and HVR-H2 comprising the amino acid sequence of SEQ ID NO:3.

In another aspect, an antibody of the invention comprises (a) a VH domain comprising at least one, at least two, or all three VH HVR sequences selected from (i) HVR-H1 comprising the amino acid sequence of SEQ ID NO:2, (ii) HVR-H2 comprising the amino acid sequence of SEQ ID NO:3, and (iii) HVR-H3 comprising an amino acid sequence selected from SEQ ID NO:4; and (b) a VL domain comprising at least one, at least two, or all three VL HVR sequences selected from (i) HVR-L1 comprising the amino acid sequence of SEQ ID NO:5, (ii) HVR-L2 comprising the amino acid sequence of SEQ ID NO:6, and (c) HVR-L3 comprising the amino acid sequence of SEQ ID NO:26.

In another aspect, the invention provides an antibody comprising (a) HVR-H1 comprising the amino acid sequence of SEQ ID NO:2; (b) HVR-H2 comprising the amino acid sequence of SEQ ID NO:3; (c) HVR-H3 comprising the amino acid sequence of SEQ ID NO:4; (d) HVR-L1 comprising the amino acid sequence of SEQ ID NO:5; (e) HVR-L2 comprising the amino acid sequence of SEQ ID NO:6; and (f) HVR-L3 comprising an amino acid sequence selected from SEQ ID NO:26.

In one aspect, the invention provides an anti-human OX40 agonist antibody comprising at least one, two, three, four, five, or six HVRs selected from (a) HVR-H1 comprising the amino acid sequence of SEQ ID NO:2; (b) HVR-H2 comprising the amino acid sequence of SEQ ID NO:3; (c) HVR-H3 comprising the amino acid sequence of SEQ ID NO:4; (d) HVR-L1 comprising the amino acid sequence of SEQ ID NO:5; (e) HVR-L2 comprising the amino acid sequence of SEQ ID NO:6; and (f) HVR-L3 comprising the amino acid sequence of SEQ ID NO:27.

In another embodiment, the antibody comprises HVR-H3 comprising the amino acid sequence of SEQ ID NO:4 and HVR-L3 comprising the amino acid sequence of SEQ ID NO:27. In a further embodiment, the antibody comprises HVR-H3 comprising the amino acid sequence of SEQ ID NO:4, HVR-L3 comprising the amino acid sequence of SEQ ID NO:27, and HVR-H2 comprising the amino acid sequence of SEQ ID NO:3.

In another aspect, an antibody of the invention comprises (a) a VH domain comprising at least one, at least two, or all three VH HVR sequences selected from (i) HVR-H1 comprising the amino acid sequence of SEQ ID NO:2, (ii) HVR-H2 comprising the amino acid sequence of SEQ ID NO:3, and (iii) HVR-H3 comprising an amino acid sequence selected from SEQ ID NO:4; and (b) a VL domain comprising at least one, at least two, or all three VL HVR sequences selected from (i) HVR-L1 comprising the amino acid sequence of SEQ ID NO:5, (ii) HVR-L2 comprising the amino acid sequence of SEQ ID NO:6, and (c) HVR-L3 comprising the amino acid sequence of SEQ ID NO:27.

In another aspect, the invention provides an antibody comprising (a) HVR-H1 comprising the amino acid sequence of SEQ ID NO:2; (b) HVR-H2 comprising the amino acid sequence of SEQ ID NO:3; (c) HVR-H3 comprising the amino acid sequence of SEQ ID NO:4; (d) HVR-L1 comprising the amino acid sequence of SEQ ID NO:5; (e) HVR-L2 comprising the amino acid sequence of SEQ ID NO:6; and (f) HVR-L3 comprising an amino acid sequence selected from SEQ ID NO:27.

In one aspect, the invention provides an anti-human OX40 agonist antibody comprising at least one, two, three, four, five, or six HVRs selected from (a) HVR-H1 comprising the amino acid sequence of SEQ ID NO:2, 8 or 9; (b) HVR-H2 comprising the amino acid sequence of SEQ ID NO:3, 10, 11, 12, 13 or 14; (c) HVR-H3 comprising the amino acid sequence of SEQ ID NO:4, 15, or 19; (d) HVR-L1 comprising the amino acid sequence of SEQ ID NO:5; (e) HVR-L2 comprising the amino acid sequence of SEQ ID NO:6; and (f) HVR-L3 comprising the amino acid sequence of SEQ ID NO:7, 22, 23, 24, 25, 26, 27, or 28.

In one aspect, the invention provides an antibody comprising at least one, at least two, or all three VH HVR sequences selected from (a) HVR-H1 comprising the amino acid sequence of SEQ ID NO: 2, 8 or 9; (b) HVR-H2 comprising the amino acid sequence of SEQ ID NO: 3, 10, 11, 12, 13 or 14; and (c) HVR-H3 comprising the amino acid sequence of SEQ ID NO: 4, 15, or 19. In one embodiment, the antibody comprises HVR-H3 comprising the amino acid sequence of SEQ ID NO: 4, 15, or 19. In another embodiment, the antibody comprises HVR-H3 comprising the amino acid sequence of SEQ ID NO:4, 15, or 19 and HVR-L3 comprising the amino acid sequence of SEQ ID NO: 7, 22, 23, 24, 25, 26, 27, or 28. In a further embodiment, the antibody comprises HVR-H3 comprising the amino acid sequence of SEQ ID NO: 4, 15, or 19, HVR-L3 comprising the amino acid sequence of SEQ ID NO: 7, 22, 23, 24, 25, 26, 27, or 28, and HVR-H2 comprising the amino acid sequence of SEQ ID NO: 3, 10, 11, 12, 13 or 14. In a further embodiment, the antibody comprises (a) HVR-H1 comprising the amino acid sequence of SEQ ID NO: 2, 8 or 9; (b) HVR-H2 comprising the amino acid sequence of SEQ ID NO: 3, 10, 11, 12, 13 or 14; and (c) HVR-H3 comprising the amino acid sequence of SEQ ID NO: 4, 15, or 19.

In another aspect, the invention provides an antibody comprising at least one, at least two, or all three VL HVR sequences selected from (a) HVR-L1 comprising the amino acid sequence of SEQ ID NO: 5; (b) HVR-L2 comprising the amino acid sequence of SEQ ID NO:6; and (c) HVR-L3 comprising the amino acid sequence of SEQ ID NO: 7, 22, 23, 24, 25, 26, 27, or 28. In one embodiment, the antibody comprises (a) HVR-L1 comprising the amino acid sequence of SEQ ID NO:5; (b) HVR-L2 comprising the amino acid sequence of SEQ ID NO:6; and (c) HVR-L3 comprising the amino acid sequence of SEQ ID NO: 7, 22, 23, 24, 25, 26, 27, or 28.

In another aspect, an antibody of the invention comprises (a) a VH domain comprising at least one, at least two, or all three VH HVR sequences selected from (i) HVR-H1 comprising the amino acid sequence of SEQ ID NO: 2, 8 or 9, (ii) HVR-H2 comprising the amino acid sequence of SEQ ID NO: 3, 10, 11, 12, 13 or 14, and (iii) HVR-H3 comprising an amino acid sequence selected from SEQ ID NO: 4, 15, or 19; and (b) a VL domain comprising at least one, at least two, or all three VL HVR sequences selected from (i) HVR-L1 comprising the amino acid sequence of SEQ ID NO:5, (ii) HVR-L2 comprising the amino acid sequence of SEQ ID NO:6, and (c) HVR-L3 comprising the amino acid sequence of SEQ ID NO: 7, 22, 23, 24, 25, 26, 27, or 28.

In another aspect, the invention provides an antibody comprising (a) HVR-H1 comprising the amino acid sequence of SEQ ID NO: 2, 8 or 9; (b) HVR-H2 comprising the amino acid sequence of SEQ ID NO: 3, 10, 11, 12, 13 or 14; (c) HVR-H3 comprising the amino acid sequence of SEQ ID NO: 4, 15, or 19; (d) HVR-L1 comprising the amino acid sequence of SEQ ID NO:5; (e) HVR-L2 comprising the amino acid sequence of SEQ ID NO:6; and (f) HVR-L3 comprising an amino acid sequence selected from SEQ ID NO: 7, 22, 23, 24, 25, 26, 27, or 28.

In one aspect, the invention provides an anti-human OX40 agonist antibody comprising at least one, two, three, four, five, or six HVRs selected from (a) HVR-H1 comprising the amino acid sequence of SEQ ID NO:172; (b) HVR-H2 comprising the amino acid sequence of SEQ ID NO:173; (c) HVR-H3 comprising the amino acid sequence of SEQ ID NO:174; (d) HVR-L1 comprising the amino acid sequence of SEQ ID NO:5; (e) HVR-L2 comprising the amino acid sequence of SEQ ID NO:6; and (f) HVR-L3 comprising the amino acid sequence of SEQ ID NO:175. In some embodiment, HVR-H2 is not DMYPDAAAASYNQKFRE (SEQ ID NO:222). In some embodiments, HVR-H3 is not APRWAAAA (SEQ ID NO:223). In some embodiments, HVR-L3 is not QAAAAAAAT (SEQ ID NO:224).

In one aspect, the invention provides an antibody comprising at least one, at least two, or all three VH HVR sequences selected from (a) HVR-H1 comprising the amino acid sequence of SEQ ID NO:172; (b) HVR-H2 comprising the amino acid sequence of SEQ ID NO:173; and (c) HVR-H3 comprising the amino acid sequence of SEQ ID NO:174. In one embodiment, the antibody comprises HVR-H3 comprising the amino acid sequence of SEQ ID NO:174. In another embodiment, the antibody comprises HVR-H3 comprising the amino acid sequence of SEQ ID NO:174 and HVR-L3 comprising the amino acid sequence of SEQ ID NO:175. In a further embodiment, the antibody comprises HVR-H3 comprising the amino acid sequence of SEQ ID NO:174, HVR-L3 comprising the amino acid sequence of SEQ ID NO:175, and HVR-H2 comprising the amino acid sequence of SEQ ID NO:173. In a further embodiment, the antibody comprises (a) HVR-H1 comprising the amino acid sequence of SEQ ID NO:172; (b) HVR-H2 comprising the amino acid sequence of SEQ ID NO:173; and (c) HVR-H3 comprising the amino acid sequence of SEQ ID NO:174. In some embodiment, HVR-H2 is not DMYPDAAAASYNQKFRE (SEQ ID NO:222). In some embodiments, HVR-H3 is not APRWAAAA (SEQ ID NO:223). In some embodiments, HVR-L3 is not QAAAAAAAT (SEQ ID NO:224).

In another aspect, the invention provides an antibody comprising (a) HVR-L1 comprising the amino acid sequence of SEQ ID NO:5; (b) HVR-L2 comprising the amino acid sequence of SEQ ID NO:6; and (c) HVR-L3 comprising the amino acid sequence of SEQ ID NO:175. In some embodiments, HVR-L3 is not QAAAAAAAT (SEQ ID NO:224).

In another aspect, an antibody of the invention comprises (a) a VH domain comprising at least one, at least two, or all three VH HVR sequences selected from (i) HVR-H1 comprising the amino acid sequence of SEQ ID NO:172, (ii) HVR-H2 comprising the amino acid sequence of SEQ ID NO:173, and (iii) HVR-H3 comprising an amino acid sequence selected from SEQ ID NO:174; and (b) a VL domain comprising at least one, at least two, or all three VL HVR sequences selected from (i) HVR-L1 comprising the amino acid sequence of SEQ ID NO:5, (ii) HVR-L2 comprising the amino acid sequence of SEQ ID NO:6, and (c) HVR-L3 comprising the amino acid sequence of SEQ ID NO:175.

In another aspect, the invention provides an antibody comprising (a) HVR-H1 comprising the amino acid sequence of SEQ ID NO:172; (b) HVR-H2 comprising the amino acid sequence of SEQ ID NO:173; (c) HVR-H3 comprising the amino acid sequence of SEQ ID NO:174; (d) HVR-L1 comprising the amino acid sequence of SEQ ID NO:5; (e) HVR-L2 comprising the amino acid sequence of SEQ ID NO:6; and (f) HVR-L3 comprising an amino acid sequence selected from SEQ ID NO:175. In some embodiment, HVR-H2 is not DMYPDAAAASYNQKFRE (SEQ ID NO:222). In some embodiments, HVR-H3 is not APRWAAAA (SEQ ID NO:223). In some embodiments, HVR-L3 is not QAAAAAAAT (SEQ ID NO:224).

All possible combinations of the above substitutions are encompassed by the consensus sequences of SEQ ID NO:172, 173, 174 and 175.

In one aspect, the invention provides an anti-human OX40 agonist antibody comprising at least one, two, three, four, five, or six HVRs selected from (a) HVR-H1 comprising the amino acid sequence of SEQ ID NO:29; (b) HVR-H2 comprising the amino acid sequence of SEQ ID NO:30; (c) HVR-H3 comprising the amino acid sequence of SEQ ID NO:33; (d) HVR-L1 comprising the amino acid sequence of SEQ ID NO:37; (e) HVR-L2 comprising the amino acid sequence of SEQ ID NO:39; and (f) HVR-L3 comprising the amino acid sequence of SEQ ID NO:42.

In one aspect, the invention provides an antibody comprising at least one, at least two, or all three VH HVR sequences selected from (a) HVR-H1 comprising the amino acid sequence of SEQ ID NO:29; (b) HVR-H2 comprising the amino acid sequence of SEQ ID NO:30; and (c) HVR-H3 comprising the amino acid sequence of SEQ ID NO:33. In one embodiment, the antibody comprises HVR-H3 comprising the amino acid sequence of SEQ ID NO:33. In another embodiment, the antibody comprises HVR-H3 comprising the amino acid sequence of SEQ ID NO:33 and HVR-L3 comprising the amino acid sequence of SEQ ID NO:42. In a further embodiment, the antibody comprises HVR-H3 comprising the amino acid sequence of SEQ ID NO:33, HVR-L3 comprising the amino acid sequence of SEQ ID NO:42, and HVR-H2 comprising the amino acid sequence of SEQ ID NO:30. In a further embodiment, the antibody comprises (a) HVR-H1 comprising the amino acid sequence of SEQ ID NO:29; (b) HVR-H2 comprising the amino acid sequence of SEQ ID NO:30; and (c) HVR-H3 comprising the amino acid sequence of SEQ ID NO:33.

In another aspect, the invention provides an antibody comprising at least one, at least two, or all three VL HVR sequences selected from (a) HVR-L1 comprising the amino acid sequence of SEQ ID NO:37; (b) HVR-L2 comprising the amino acid sequence of SEQ ID NO:39; and (c) HVR-L3 comprising the amino acid sequence of SEQ ID NO:42. In one embodiment, the antibody comprises (a) HVR-L1 comprising the amino acid sequence of SEQ ID NO:37; (b) HVR-L2 comprising the amino acid sequence of SEQ ID NO:39; and (c) HVR-L3 comprising the amino acid sequence of SEQ ID NO:42.

In another aspect, an antibody of the invention comprises (a) a VH domain comprising at least one, at least two, or all three VH HVR sequences selected from (i) HVR-H1 comprising the amino acid sequence of SEQ ID NO:29, (ii) HVR-H2 comprising the amino acid sequence of SEQ ID NO:30, and (iii) HVR-H3 comprising an amino acid sequence selected from SEQ ID NO:33; and (b) a VL domain comprising at least one, at least two, or all three VL HVR sequences selected from (i) HVR-L1 comprising the amino acid sequence of SEQ ID NO:37, (ii) HVR-L2 comprising the amino acid sequence of SEQ ID NO:39, and (c) HVR-L3 comprising the amino acid sequence of SEQ ID NO:42.

In another aspect, the invention provides an antibody comprising (a) HVR-H1 comprising the amino acid sequence of SEQ ID NO:29; (b) HVR-H2 comprising the amino acid sequence of SEQ ID NO:30; (c) HVR-H3 comprising the amino acid sequence of SEQ ID NO:33; (d) HVR-L1 comprising the amino acid sequence of SEQ ID NO:37; (e) HVR-L2 comprising the amino acid sequence of SEQ ID NO:39; and (f) HVR-L3 comprising an amino acid sequence selected from SEQ ID NO:42.

In one aspect, the invention provides an anti-human OX40 agonist antibody comprising at least one, two, three, four, five, or six HVRs selected from (a) HVR-H1 comprising the amino acid sequence of SEQ ID NO:29; (b) HVR-H2 comprising the amino acid sequence of SEQ ID NO:30; (c) HVR-H3 comprising the amino acid sequence of SEQ ID NO:33; (d) HVR-L1 comprising the amino acid sequence of SEQ ID NO:37; (e) HVR-L2 comprising the amino acid sequence of SEQ ID NO:40; and (f) HVR-L3 comprising the amino acid sequence of SEQ ID NO:42.

In another aspect, the invention provides an antibody comprising at least one, at least two, or all three VL HVR sequences selected from (a) HVR-L1 comprising the amino acid sequence of SEQ ID NO:37; (b) HVR-L2 comprising the amino acid sequence of SEQ ID NO:40; and (c) HVR-L3 comprising the amino acid sequence of SEQ ID NO:42. In one embodiment, the antibody comprises (a) HVR-L1 comprising the amino acid sequence of SEQ ID NO:37; (b) HVR-L2 comprising the amino acid sequence of SEQ ID NO:40; and (c) HVR-L3 comprising the amino acid sequence of SEQ ID NO:42.

In another aspect, an antibody of the invention comprises (a) a VH domain comprising at least one, at least two, or all three VH HVR sequences selected from (i) HVR-H1 comprising the amino acid sequence of SEQ ID NO:29, (ii) HVR-H2 comprising the amino acid sequence of SEQ ID NO:30, and (iii) HVR-H3 comprising an amino acid sequence selected from SEQ ID NO:33; and (b) a VL domain comprising at least one, at least two, or all three VL HVR sequences selected from (i) HVR-L1 comprising the amino acid sequence of SEQ ID NO:37, (ii) HVR-L2 comprising the amino acid sequence of SEQ ID NO:40, and (c) HVR-L3 comprising the amino acid sequence of SEQ ID NO:42.

In another aspect, the invention provides an antibody comprising (a) HVR-H1 comprising the amino acid sequence of SEQ ID NO:29; (b) HVR-H2 comprising the amino acid sequence of SEQ ID NO:30; (c) HVR-H3 comprising the amino acid sequence of SEQ ID NO:33; (d) HVR-L1 comprising the amino acid sequence of SEQ ID NO:37; (e) HVR-L2 comprising the amino acid sequence of SEQ ID NO:40; and (f) HVR-L3 comprising an amino acid sequence selected from SEQ ID NO:42.

In one aspect, the invention provides an anti-human OX40 agonist antibody comprising at least one, two, three, four, five, or six HVRs selected from (a) HVR-H1 comprising the amino acid sequence of SEQ ID NO:29; (b) HVR-H2 comprising the amino acid sequence of SEQ ID NO:30, 31, or 32; (c) HVR-H3 comprising the amino acid sequence of SEQ ID NO:33; (d) HVR-L1 comprising the amino acid sequence of SEQ ID NO:37; (e) HVR-L2 comprising the amino acid sequence of SEQ ID NO:39, 40 or 41; and (f) HVR-L3 comprising the amino acid sequence of SEQ ID NO:42, 43, or 44.

In one aspect, the invention provides an antibody comprising at least one, at least two, or all three VH HVR sequences selected from (a) HVR-H1 comprising the amino acid sequence of SEQ ID NO:29; (b) HVR-H2 comprising the amino acid sequence of SEQ ID NO: 30, 31, or 32; and (c) HVR-H3 comprising the amino acid sequence of SEQ ID NO:33. In another embodiment, the antibody comprises HVR-H3 comprising the amino acid sequence of SEQ ID NO:33 and HVR-L3 comprising the amino acid sequence of SEQ ID NO: 42, 43, or 44. In a further embodiment, the antibody comprises HVR-H3 comprising the amino acid sequence of SEQ ID NO:33, HVR-L3 comprising the amino acid sequence of SEQ ID NO: 42, 43, or 44, and HVR-H2 comprising the amino acid sequence of SEQ ID NO: 39, 40 or 41. In a further embodiment, the antibody comprises (a) HVR-H1 comprising the amino acid sequence of SEQ ID NO:29; (b) HVR-H2 comprising the amino acid sequence of SEQ ID NO:30, 31, or 32; and (c) HVR-H3 comprising the amino acid sequence of SEQ ID NO:33.

In another aspect, the invention provides an antibody comprising at least one, at least two, or all three VL HVR sequences selected from (a) HVR-L1 comprising the amino acid sequence of SEQ ID NO:37; (b) HVR-L2 comprising the amino acid sequence of SEQ ID NO: 39, 40 or 41; and (c) HVR-L3 comprising the amino acid sequence of SEQ ID NO: 42, 43, or 44. In one embodiment, the antibody comprises (a) HVR-L1 comprising the amino acid sequence of SEQ ID NO:37; (b) HVR-L2 comprising the amino acid sequence of SEQ ID NO: 39, 40 or 41; and (c) HVR-L3 comprising the amino acid sequence of SEQ ID NO: 42, 43, or 44.

In another aspect, an antibody of the invention comprises (a) a VH domain comprising at least one, at least two, or all three VH HVR sequences selected from (i) HVR-H1 comprising the amino acid sequence of SEQ ID NO:29, (ii) HVR-H2 comprising the amino acid sequence of SEQ ID NO: 30, 31, or 32, and (iii) HVR-H3 comprising an amino acid sequence selected from SEQ ID NO:33; and (b) a VL domain comprising at least one, at least two, or all three VL HVR sequences selected from (i) HVR-L1 comprising the amino acid sequence of SEQ ID NO:37, (ii) HVR-L2 comprising the amino acid sequence of SEQ ID NO: 39, 40 or 41, and (c) HVR-L3 comprising the amino acid sequence of SEQ ID NO: 42, 43, or 44.

In another aspect, the invention provides an antibody comprising (a) HVR-H1 comprising the amino acid sequence of SEQ ID NO:29; (b) HVR-H2 comprising the amino acid sequence of SEQ ID NO: 30, 31, or 32; (c) HVR-H3 comprising the amino acid sequence of SEQ ID NO:33; (d) HVR-L1 comprising the amino acid sequence of SEQ ID NO:37; (e) HVR-L2 comprising the amino acid sequence of SEQ ID NO: 39, 40 or 41; and (f) HVR-L3 comprising an amino acid sequence selected from SEQ ID NO: 42, 43, or 44.

In one aspect, the invention provides an anti-human OX40 agonist antibody comprising at least one, two, three, four, five, or six HVRs selected from (a) HVR-H1 comprising the amino acid sequence of SEQ ID NO:29; (b) HVR-H2 comprising the amino acid sequence of SEQ ID NO:175; (c) HVR-H3 comprising the amino acid sequence of SEQ ID NO:33; (d) HVR-L1 comprising the amino acid sequence of SEQ ID NO:37; (e) HVR-L2 comprising the amino acid sequence of SEQ ID NO:177; and (f) HVR-L3 comprising the amino acid sequence of SEQ ID NO:178.

In one aspect, the invention provides an antibody comprising at least one, at least two, or all three VH HVR sequences selected from (a) HVR-H1 comprising the amino acid sequence of SEQ ID NO:29; (b) HVR-H2 comprising the amino acid sequence of SEQ ID NO:175; and (c) HVR-H3 comprising the amino acid sequence of SEQ ID NO:33. In another embodiment, the antibody comprises HVR-H3 comprising the amino acid sequence of SEQ ID NO:33 and HVR-L3 comprising the amino acid sequence of SEQ ID NO:177. In a further embodiment, the antibody comprises HVR-H3 comprising the amino acid sequence of SEQ ID NO:33, HVR-L3 comprising the amino acid sequence of SEQ ID NO:178, and HVR-H2 comprising the amino acid sequence of SEQ ID NO:176. In a further embodiment, the antibody comprises (a) HVR-H1 comprising the amino acid sequence of SEQ ID NO:29; (b) HVR-H2 comprising the amino acid sequence of SEQ ID NO:176; and (c) HVR-H3 comprising the amino acid sequence of SEQ ID NO:33.

In another aspect, the invention provides an antibody comprising at least one, at least two, or all three VL HVR sequences selected from (a) HVR-L1 comprising the amino acid sequence of SEQ ID NO:37; (b) HVR-L2 comprising the amino acid sequence of SEQ ID NO:177; and (c) HVR-L3 comprising the amino acid sequence of SEQ ID NO:177. In one embodiment, the antibody comprises (a) HVR-L1 comprising the amino acid sequence of SEQ ID NO:37; (b) HVR-L2 comprising the amino acid sequence of SEQ ID NO:177; and (c) HVR-L3 comprising the amino acid sequence of SEQ ID NO:178.

In another aspect, an antibody of the invention comprises (a) a VH domain comprising at least one, at least two, or all three VH HVR sequences selected from (i) HVR-H1 comprising the amino acid sequence of SEQ ID NO:29, (ii) HVR-H2 comprising the amino acid sequence of SEQ ID NO:176, and (iii) HVR-H3 comprising an amino acid sequence selected from SEQ ID NO:33; and (b) a VL domain comprising at least one, at least two, or all three VL HVR sequences selected from (i) HVR-L1 comprising the amino acid sequence of SEQ ID NO:37, (ii) HVR-L2 comprising the amino acid sequence of SEQ ID NO:177, and (c) HVR-L3 comprising the amino acid sequence of SEQ ID NO:178.

In another aspect, the invention provides an antibody comprising (a) HVR-H1 comprising the amino acid sequence of SEQ ID NO:29; (b) HVR-H2 comprising the amino acid sequence of SEQ ID NO:176; (c) HVR-H3 comprising the amino acid sequence of SEQ ID NO:33; (d) HVR-L1 comprising the amino acid sequence of SEQ ID NO:37; (e) HVR-L2 comprising the amino acid sequence of SEQ ID NO:177; and (f) HVR-L3 comprising an amino acid sequence selected from SEQ ID NO:178.

In any of the above embodiments, an anti-OX40 agonist antibody is humanized. In one embodiment, an anti-OX40 antibody comprises HVRs as in any of the above embodiments or for any of the embodiments in FIG. 11, and further comprises an acceptor human framework, e.g. a human immunoglobulin framework or a human consensus framework. In another embodiment, an anti-OX40 antibody comprises HVRs as in any of the above embodiments, and further comprises a VH and/or VL comprising an FR sequence shown in FIG. 11.

In another aspect, an anti-human OX40 agonist antibody comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO:56, 58, 60, 62, 64, 66, 68, 70, 72, 74, 76, 78, 80, 82, 84, 86, 88, 90, 92, 94, 96, 98, 100, 108, 114 or 116. In certain embodiments, a VH sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-human OX40 agonist antibody comprising that sequence retains the ability to bind to OX40. In certain embodiments, a total of 1 to 10 amino acids have been substituted, inserted and/or deleted in SEQ ID NO:56, 58, 60, 62, 64, 66, 68, 70, 72, 74, 76, 78, 80, 82, 84, 86, 88, 90, 92, 94, 96, 98, 100, 108, 114 or 116. In certain embodiments, substitutions, insertions, or deletions occur in regions outside the HVRs (i.e., in the FRs). Optionally, the anti-human OX40 agonist antibody comprises the VH sequence in SEQ ID NO: SEQ ID NO:56, 58, 60, 62, 64, 66, 68, 70, 72, 74, 76, 78, 80, 82, 84, 86, 88, 90, 92, 94, 96, 98, 100, 108, 114 or 116, including post-translational modifications of that sequence. In a particular embodiment, the VH comprises one, two or three HVRs selected from: (a) HVR-H1 comprising the amino acid sequence of SEQ ID NO:2, (b) HVR-H2 comprising the amino acid sequence of SEQ ID NO:3, and (c) HVR-H3 comprising the amino acid sequence of SEQ ID NO:4.

In another aspect, an anti-human OX40 agonist antibody is provided, wherein the antibody comprises a light chain variable domain (VL) having at least 90%, 91%, 92%, 93%, 94%, 95%, 96%, 97%, 98%, 99%, or 100% sequence identity to the amino acid sequence of SEQ ID NO:57, 59, 61, 63, 65, 67, 69, 71, 73, 75, 77, 79, 81, 83, 85, 87, 89, 91, 93, 95, 97, 99, 101, 109, 115 or 117. In certain embodiments, a VL sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-human OX40 agonist antibody comprising that sequence retains the ability to bind to OX40. In certain embodiments, a total of 1 to 10 amino acids have been substituted, inserted and/or deleted in SEQ ID NO: 57, 59, 61, 63, 65, 67, 69, 71, 73, 75, 77, 79, 81, 83, 85, 87, 89, 91, 93, 95, 97, 99, 101, 109, 115 or 117. In certain embodiments, the substitutions, insertions, or deletions occur in regions outside the HVRs (i.e., in the FRs). Optionally, the anti-human OX40 agonist antibody comprises the VL sequence in SEQ ID NO: 57, 59, 61, 63, 65, 67, 69, 71, 73, 75, 77, 79, 81, 83, 85, 87, 89, 91, 93, 95, 97, 99, 101, 109, 115 or 117, including post-translational modifications of that sequence. In a particular embodiment, the VL comprises one, two or three HVRs selected from (a) HVR-L1 comprising the amino acid sequence of SEQ ID NO:5; (b) HVR-L2 comprising the amino acid sequence of SEQ ID NO:6; and (c) HVR-L3 comprising the amino acid sequence of SEQ ID NO:7.

In another aspect, an anti-human OX40 agonist antibody comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO:56. In certain embodiments, a VH sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-human OX40 agonist antibody comprising that sequence retains the ability to bind to OX40. In certain embodiments, a total of 1 to 10 amino acids have been substituted, inserted and/or deleted in SEQ ID NO:56. In certain embodiments, substitutions, insertions, or deletions occur in regions outside the HVRs (i.e., in the FRs). Optionally, the anti-human OX40 agonist antibody comprises the VH sequence in SEQ ID NO:56, including post-translational modifications of that sequence. In a particular embodiment, the VH comprises one, two or three HVRs selected from: (a) HVR-H1 comprising the amino acid sequence of SEQ ID NO:2, (b) HVR-H2 comprising the amino acid sequence of SEQ ID NO:3, and (c) HVR-H3 comprising the amino acid sequence of SEQ ID NO:4.

In another aspect, an anti-human OX40 agonist antibody is provided, wherein the antibody comprises a light chain variable domain (VL) having at least 90%, 91%, 92%, 93%, 94%, 95%, 96%, 97%, 98%, 99%, or 100% sequence identity to the amino acid sequence of SEQ ID NO:57. In certain embodiments, a VL sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-human OX40 agonist antibody comprising that sequence retains the ability to bind to OX40. In certain embodiments, a total of 1 to 10 amino acids have been substituted, inserted and/or deleted in SEQ ID NO: 57. In certain embodiments, the substitutions, insertions, or deletions occur in regions outside the HVRs (i.e., in the FRs). Optionally, the anti-human OX40 agonist antibody comprises the VL sequence in SEQ ID NO: 57, including post-translational modifications of that sequence. In a particular embodiment, the VL comprises one, two or three HVRs selected from (a) HVR-L1 comprising the amino acid sequence of SEQ ID NO:5; (b) HVR-L2 comprising the amino acid sequence of SEQ ID NO:6; and (c) HVR-L3 comprising the amino acid sequence of SEQ ID NO:7.

In another aspect, an anti-human OX40 agonist antibody comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO:94. In certain embodiments, a VH sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-human OX40 agonist antibody comprising that sequence retains the ability to bind to OX40. In certain embodiments, a total of 1 to 10 amino acids have been substituted, inserted and/or deleted in SEQ ID NO:94. In certain embodiments, substitutions, insertions, or deletions occur in regions outside the HVRs (i.e., in the FRs). Optionally, the anti-human OX40 agonist antibody comprises the VH sequence in SEQ ID NO:94, including post-translational modifications of that sequence. In a particular embodiment, the VH comprises one, two or three HVRs selected from: (a) HVR-H1 comprising the amino acid sequence of SEQ ID NO:2, (b) HVR-H2 comprising the amino acid sequence of SEQ ID NO:3, and (c) HVR-H3 comprising the amino acid sequence of SEQ ID NO:4.

In another aspect, an anti-human OX40 agonist antibody is provided, wherein the antibody comprises a light chain variable domain (VL) having at least 90%, 91%, 92%, 93%, 94%, 95%, 96%, 97%, 98%, 99%, or 100% sequence identity to the amino acid sequence of SEQ ID NO:95. In certain embodiments, a VL sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-human OX40 agonist antibody comprising that sequence retains the ability to bind to OX40. In certain embodiments, a total of 1 to 10 amino acids have been substituted, inserted and/or deleted in SEQ ID NO:95. In certain embodiments, the substitutions, insertions, or deletions occur in regions outside the HVRs (i.e., in the FRs). Optionally, the anti-human OX40 agonist antibody comprises the VL sequence in SEQ ID NO:95, including post-translational modifications of that sequence. In a particular embodiment, the VL comprises one, two or three HVRs selected from (a) HVR-L1 comprising the amino acid sequence of SEQ ID NO:5; (b) HVR-L2 comprising the amino acid sequence of SEQ ID NO:6; and (c) HVR-L3 comprising the amino acid sequence of SEQ ID NO:26.

In another aspect, an anti-human OX40 agonist antibody comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO:96. In certain embodiments, a VH sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-human OX40 agonist antibody comprising that sequence retains the ability to bind to OX40. In certain embodiments, a total of 1 to 10 amino acids have been substituted, inserted and/or deleted in SEQ ID NO:96. In certain embodiments, substitutions, insertions, or deletions occur in regions outside the HVRs (i.e., in the FRs). Optionally, the anti-human OX40 agonist antibody comprises the VH sequence in SEQ ID NO:96, including post-translational modifications of that sequence. In a particular embodiment, the VH comprises one, two or three HVRs selected from: (a) HVR-H1 comprising the amino acid sequence of SEQ ID NO:2, (b) HVR-H2 comprising the amino acid sequence of SEQ ID NO:3, and (c) HVR-H3 comprising the amino acid sequence of SEQ ID NO:4.

In another aspect, an anti-human OX40 agonist antibody is provided, wherein the antibody comprises a light chain variable domain (VL) having at least 90%, 91%, 92%, 93%, 94%, 95%, 96%, 97%, 98%, 99%, or 100% sequence identity to the amino acid sequence of SEQ ID NO:97. In certain embodiments, a VL sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-human OX40 agonist antibody comprising that sequence retains the ability to bind to OX40. In certain embodiments, a total of 1 to 10 amino acids have been substituted, inserted and/or deleted in SEQ ID NO:97. In certain embodiments, the substitutions, insertions, or deletions occur in regions outside the HVRs (i.e., in the FRs). Optionally, the anti-human OX40 agonist antibody comprises the VL sequence in SEQ ID NO:97, including post-translational modifications of that sequence. In a particular embodiment, the VL comprises one, two or three HVRs selected from (a) HVR-L1 comprising the amino acid sequence of SEQ ID NO:5; (b) HVR-L2 comprising the amino acid sequence of SEQ ID NO:6; and (c) HVR-L3 comprising the amino acid sequence of SEQ ID NO:27.

In another aspect, an anti-human OX40 agonist antibody comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO: 118, 120, 122, 124, 126, 128, 130, 132, 134, 136, 138, 140, 142, 144, 146, 148. In certain embodiments, a VH sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-human OX40 agonist antibody comprising that sequence retains the ability to bind to OX40. In certain embodiments, a total of 1 to 10 amino acids have been substituted, inserted and/or deleted in SEQ ID NO: 118, 120, 122, 124, 126, 128, 130, 132, 134, 136, 138, 140, 142, 144, 146, 148. In certain embodiments, substitutions, insertions, or deletions occur in regions outside the HVRs (i.e., in the FRs). Optionally, the anti-human OX40 agonist antibody comprises the VH sequence in SEQ ID NO: SEQ ID NO: 118, 120, 122, 124, 126, 128, 130, 132, 134, 136, 138, 140, 142, 144, 146, 148, including post-translational modifications of that sequence. In a particular embodiment, the VH comprises one, two or three HVRs selected from: (a) HVR-H1 comprising the amino acid sequence of SEQ ID NO: 29, (b) HVR-H2 comprising the amino acid sequence of SEQ ID NO:30, and (c) HVR-H3 comprising the amino acid sequence of SEQ ID NO:33.

In another aspect, an anti-human OX40 agonist antibody is provided, wherein the antibody comprises a light chain variable domain (VL) having at least 90%, 91%, 92%, 93%, 94%, 95%, 96%, 97%, 98%, 99%, or 100% sequence identity to the amino acid sequence of SEQ ID NO: 119, 121, 123, 125, 127, 129, 131, 133, 135, 137, 139, 141, 143, 145, 147, 149. In certain embodiments, a VL sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-human OX40 agonist antibody comprising that sequence retains the ability to bind to OX40. In certain embodiments, a total of 1 to 10 amino acids have been substituted, inserted and/or deleted in SEQ ID NO: 119, 121, 123, 125, 127, 129, 131, 133, 135, 137, 139, 141, 143, 145, 147, 149. In certain embodiments, the substitutions, insertions, or deletions occur in regions outside the HVRs (i.e., in the FRs). Optionally, the anti-human OX40 agonist antibody comprises the VL sequence in SEQ ID NO: 119, 121, 123, 125, 127, 129, 131, 133, 135, 137, 139, 141, 143, 145, 147, 149, including post-translational modifications of that sequence. In a particular embodiment, the VL comprises one, two or three HVRs selected from (a) HVR-L1 comprising the amino acid sequence of SEQ ID NO:37; (b) HVR-L2 comprising the amino acid sequence of SEQ ID NO:39; and (c) HVR-L3 comprising the amino acid sequence of SEQ ID NO:42.

In one embodiment, the antibody comprises the VH and VL sequences in SEQ ID NO:56 and SEQ ID NO:57, respectively, including post-translational modifications of those sequences. In one embodiment, the antibody comprises the VH and VL sequences in SEQ ID NO:58 and SEQ ID NO:59, respectively, including post-translational modifications of those sequences. In one embodiment, the antibody comprises the VH and VL sequences in SEQ ID NO:60 and SEQ ID NO:61, respectively, including post-translational modifications of those sequences. In one embodiment, the antibody comprises the VH and VL sequences in SEQ ID NO:62 and SEQ ID NO:63, respectively, including post-translational modifications of those sequences. In one embodiment, the antibody comprises the VH and VL sequences in SEQ ID NO:64 and SEQ ID NO:65, respectively, including post-translational modifications of those sequences. In one embodiment, the antibody comprises the VH and VL sequences in SEQ ID NO:66 and SEQ ID NO:67, respectively, including post-translational modifications of those sequences. In one embodiment, the antibody comprises the VH and VL sequences in SEQ ID NO:68 and SEQ ID NO:69, respectively, including post-translational modifications of those sequences. In one embodiment, the antibody comprises the VH and VL sequences in SEQ ID NO:70 and SEQ ID NO:71, respectively, including post-translational modifications of those sequences. In one embodiment, the antibody comprises the VH and VL sequences in SEQ ID NO:72 and SEQ ID NO:73, respectively, including post-translational modifications of those sequences. In one embodiment, the antibody comprises the VH and VL sequences in SEQ ID NO:74 and SEQ ID NO:75, respectively, including post-translational modifications of those sequences. In one embodiment, the antibody comprises the VH and VL sequences in SEQ ID NO:76 and SEQ ID NO:77, respectively, including post-translational modifications of those sequences. In one embodiment, the antibody comprises the VH and VL sequences in SEQ ID NO:78 and SEQ ID NO:79, respectively, including post-translational modifications of those sequences. In one embodiment, the antibody comprises the VH and VL sequences in SEQ ID NO:80 and SEQ ID NO:81, respectively, including post-translational modifications of those sequences. In one embodiment, the antibody comprises the VH and VL sequences in SEQ ID NO:82 and SEQ ID NO:83, respectively, including post-translational modifications of those sequences. In one embodiment, the antibody comprises the VH and VL sequences in SEQ ID NO:84 and SEQ ID NO:85, respectively, including post-translational modifications of those sequences. In one embodiment, the antibody comprises the VH and VL sequences in SEQ ID NO:86 and SEQ ID NO:87, respectively, including post-translational modifications of those sequences. In one embodiment, the antibody comprises the VH and VL sequences in SEQ ID NO:88 and SEQ ID NO:89, respectively, including post-translational modifications of those sequences. In one embodiment, the antibody comprises the VH and VL sequences in SEQ ID NO:90 and SEQ ID NO:91, respectively, including post-translational modifications of those sequences. In one embodiment, the antibody comprises the VH and VL sequences in SEQ ID NO:92 and SEQ ID NO:93, respectively, including post-translational modifications of those sequences. In one embodiment, the antibody comprises the VH and VL sequences in SEQ ID NO:94 and SEQ ID NO:95, respectively, including post-translational modifications of those sequences. In one embodiment, the antibody comprises the VH and VL sequences in SEQ ID NO:96 and SEQ ID NO:97, respectively, including post-translational modifications of those sequences. In one embodiment, the antibody comprises the VH and VL sequences in SEQ ID NO:98 and SEQ ID NO:99, respectively, including post-translational modifications of those sequences. In one embodiment, the antibody comprises the VH and VL sequences in SEQ ID NO:100 and SEQ ID NO:101, respectively, including post-translational modifications of those sequences. In one embodiment, the antibody comprises the VH and VL sequences in SEQ ID NO:108 and SEQ ID NO:109, respectively, including post-translational modifications of those sequences. In one embodiment, the antibody comprises the VH and VL sequences in SEQ ID NO:114 and SEQ ID NO:115, respectively, including post-translational modifications of those sequences. In one embodiment, the antibody comprises the VH and VL sequences in SEQ ID NO:116 and SEQ ID NO:117, respectively, including post-translational modifications of those sequences.

In one embodiment, the antibody comprises the VH and VL sequences in SEQ ID NO:118 and SEQ ID NO:119, respectively, including post-translational modifications of those sequences. In one embodiment, the antibody comprises the VH and VL sequences in SEQ ID NO:120 and SEQ ID NO:121, respectively, including post-translational modifications of those sequences. In one embodiment, the antibody comprises the VH and VL sequences in SEQ ID NO:122 and SEQ ID NO:123, respectively, including post-translational modifications of those sequences. In one embodiment, the antibody comprises the VH and VL sequences in SEQ ID NO:124 and SEQ ID NO:125, respectively, including post-translational modifications of those sequences. In one embodiment, the antibody comprises the VH and VL sequences in SEQ ID NO:126 and SEQ ID NO:127, respectively, including post-translational modifications of those sequences. In one embodiment, the antibody comprises the VH and VL sequences in SEQ ID NO:128 and SEQ ID NO:129, respectively, including post-translational modifications of those sequences. In one embodiment, the antibody comprises the VH and VL sequences in SEQ ID NO:130 and SEQ ID NO:131, respectively, including post-translational modifications of those sequences. In one embodiment, the antibody comprises the VH and VL sequences in SEQ ID NO:132 and SEQ ID NO:133, respectively, including post-translational modifications of those sequences. In one embodiment, the antibody comprises the VH and VL sequences in SEQ ID NO:134 and SEQ ID NO:135, respectively, including post-translational modifications of those sequences. In one embodiment, the antibody comprises the VH and VL sequences in SEQ ID NO:136 and SEQ ID NO:137, respectively, including post-translational modifications of those sequences. In one embodiment, the antibody comprises the VH and VL sequences in SEQ ID NO:138 and SEQ ID NO:139, respectively, including post-translational modifications of those sequences. In one embodiment, the antibody comprises the VH and VL sequences in SEQ ID NO:140 and SEQ ID NO:141, respectively, including post-translational modifications of those sequences. In one embodiment, the antibody comprises the VH and VL sequences in SEQ ID NO:142 and SEQ ID NO:143, respectively, including post-translational modifications of those sequences. In one embodiment, the antibody comprises the VH and VL sequences in SEQ ID NO:144 and SEQ ID NO:145, respectively, including post-translational modifications of those sequences. In one embodiment, the antibody comprises the VH and VL sequences in SEQ ID NO:146 and SEQ ID NO:147, respectively, including post-translational modifications of those sequences.

In another aspect, an anti-human OX40 agonist antibody is provided, wherein the antibody comprises a VH as in any of the embodiments provided above, and a VL as in any of the embodiments provided above.

In some embodiments, the OX40 agonist antibody is MEDI6469. In some embodiments, the OX40 agonist antibody is MEDI0562.

In a further aspect, the invention provides an antibody that binds to the same epitope as an anti-human OX40 antibody provided herein. In some embodiments, the antibody is an anti-human OX40 agonist antibody.

In a further aspect of the invention, an anti-OX40 antibody according to any of the above embodiments is a monoclonal antibody, including a chimeric, humanized or human antibody. In one embodiment, an anti-OX40 antibody is an antibody fragment, e.g., a Fv, Fab, Fab', scFv, diabody, or F(ab')2 fragment. In another embodiment, the antibody is a full length antibody, e.g., an intact IgG1 antibody or other antibody class or isotype as defined herein. In some embodiments, the antibody is a full length intact IgG4 antibody.

Exemplary amino acid sequences corresponding to OX40 polypeptides and OX40 antibodies are provided below.

TABLE 2

Amino acid sequences

| Name | SEQUENCE | SEQ ID NO: |
|---|---|---|
| Human OX40 (lacking the signal peptide) | LHCVGDTYPSNDRCCHECRPGNGMVSRCSRSQNTVCRPCGPGFY NDVVSSKPCKPCTWCNLRSGSERKQLCTATQDTVCRCRAGTQPL DSYKPGVDCAPCPPGHFSPGDNQACKPWTNCTLAGKHTLQPASN SSDAICEDRDPPATQPQETQGPPARPITVQPTEAWPRTSQGPSTRP VEVPGGRAVAAILGLGLVLGLLGPLAILLALYLLRRDQRLPPDAH KPPGGGSFRTPIQEEQADAHSTLAKI | 1 |
| HVR-H1-<br>1A7.gr.1<br>1A7.gr.2<br>1A7.gr.3<br>1A7.gr.4<br>1A7.gr.5<br>1A7.gr.6<br>1A7.gr.7<br>1A7.gr.NADS<br>1A7.gr.NADA<br>1A7.gr.NGDA<br>1A7.gr.SGDS<br>1A7.gr.NGSS<br>1A7.Ala.1<br>1A7.Ala.2<br>1A7.Ala.3<br>1A7.Ala.4<br>1A7.Ala.5<br>1A7.Ala.6<br>1A7.Ala.7<br>1A7.Ala.8<br>1A7.Ala.9<br>1A7.Ala.10<br>1A7.Ala.11<br>1A7.Ala.12<br>1A7.Ala.13<br>1A7.Ala.14<br>1A7.Ala.15<br>1A7.Ala.16 | DSYMS | 2 |

TABLE 2-continued

Amino acid sequences

| Name | SEQUENCE | SEQ ID NO: |
|---|---|---|
| HVR-H2-<br>1A7.gr.1<br>1A7.gr.2<br>1A7.gr.3<br>1A7.gr.4<br>1A7.gr.5<br>1A7.gr.6<br>1A7.gr.7<br>1A7.gr.DA<br>1A7.gr.ES<br>1A7.Ala.1<br>1A7.Ala.2<br>1A7.Ala.3<br>1A7.Ala.4<br>1A7.Ala.5<br>1A7.Ala.6<br>1A7.Ala.7<br>1A7.Ala.8<br>1A7.Ala.9<br>1A7.Ala.10<br>1A7.Ala.11<br>1A7.Ala.12<br>1A7.Ala.13<br>1A7.Ala.14<br>1A7.Ala.15<br>1A7.Ala.16 | DMYPDNGDSSYNQKFRE | 3 |
| HVR-H3-<br>1A7.gr.1<br>1A7.gr.2<br>1A7.gr.3<br>1A7.gr.4<br>1A7.gr.5<br>1A7.gr.6<br>1A7.gr.7<br>1A7.gr.DA<br>1A7.gr.ES<br>1A7.gr.NADS<br>1A7.gr.NADA<br>1A7.gr.NGDA<br>1A7.gr.SGDS<br>1A7.gr.NGSS<br>1A7.gr.DANADA<br>1A7.Ala.1<br>1A7.Ala.2<br>1A7.Ala.3<br>1A7.Ala.4<br>1A7.Ala.5<br>1A7.Ala.6<br>1A7.Ala.7<br>1A7-Ala.15<br>1A7.Ala.16 | APRWYFSV | 4 |
| HVR-L1-<br>1A7.gr.1<br>1A7.gr.2<br>1A7.gr.3<br>1A7.gr.4<br>1A7.gr.5<br>1A7.gr.6<br>1A7.gr.7<br>1A7.gr.DA<br>1A7.gr.ES<br>1A7.gr.NADS<br>1A7.gr.NADA<br>1A7.gr.NGDA<br>1A7.gr.SGDS<br>1A7.gr.NGSS<br>1A7.gr.DANADA<br>1A7.Ala.1<br>1A7.Ala.2<br>1A7.Ala.3<br>1A7.Ala.4<br>1A7.Ala.5 | RASQDISNYLN | 5 |

TABLE 2-continued

Amino acid sequences

| Name | SEQUENCE | SEQ ID NO: |
|---|---|---|
| 1A7.Ala.6 | | |
| 1A7.Ala.7 | | |
| 1A7.Ala.8 | | |
| 1A7.Ala.9 | | |
| 1A7.Ala.10 | | |
| 1A7.Ala.11 | | |
| 1A7.Ala.12 | | |
| 1A7.Ala.13 | | |
| 1A7.Ala.14 | | |
| 1A7.Ala.15 | | |
| 1A7.Ala.16 | | |
| HVR-L2-1A7.gr.1 | YTSRLRS | 6 |
| 1A7.gr.2 | | |
| 1A7.gr.3 | | |
| 1A7.gr.4 | | |
| 1A7.gr.5 | | |
| 1A7.gr.6 | | |
| 1A7.gr.7 | | |
| 1A7.gr.DA | | |
| 1A7.gr.ES | | |
| 1A7.gr.NADS | | |
| 1A7.gr.NADA | | |
| 1A7.gr.NGDA | | |
| 1A7.gr.SGDS | | |
| 1A7.gr.NGSS | | |
| 1A7.gr.DANADA | | |
| 1A7.Ala.1 | | |
| 1A7.Ala.2 | | |
| 1A7.Ala.3 | | |
| 1A7.Ala.4 | | |
| 1A7.Ala.5 | | |
| 1A7.Ala.6 | | |
| 1A7.Ala.7 | | |
| 1A7.Ala.8 | | |
| 1A7.Ala.9 | | |
| 1A7.Ala.10 | | |
| 1A7.Ala.11 | | |
| 1A7.Ala.12 | | |
| 1A7.Ala.13 | | |
| 1A7.Ala.14 | | |
| 1A7.Ala.15 | | |
| 1A7.Ala.16 | | |
| HVR-L3-1A7.gr.1 | QQGHTLPPT | 7 |
| 1A7.gr.2 | | |
| 1A7.gr.3 | | |
| 1A7.gr.4 | | |
| 1A7.gr.5 | | |
| 1A7.gr.6 | | |
| 1A7.gr.7 | | |
| 1A7.gr.DA | | |
| 1A7.gr.ES | | |
| 1A7.gr.NADS | | |
| 1A7.gr.NADA | | |
| 1A7.gr.NGDA | | |
| 1A7.gr.SGDS | | |
| 1A7.gr.NGSS | | |
| 1A7.gr.DANADA | | |
| 1A7.Ala.8 | | |
| 1A7.Ala.9 | | |
| 1A7.Ala.10 | | |
| 1A7.Ala.11 | | |
| 1A7.Ala.12 | | |
| 1A7.Ala.13 | | |
| 1A7.Ala.14 | | |
| 1A7.Ala.15 | | |
| 1A7.Ala.16 | | |
| HVR-H1-1A7.gr.DA | DAYMS | 8 |

TABLE 2-continued

Amino acid sequences

| Name | SEQUENCE | SEQ ID NO: |
|---|---|---|
| HVR-H1-1A7.gr.ES 1A7.gr.DANADA | ESYMS | 9 |
| HVR-H2-1A7.gr.NADS | DMYPDNADSSYNQKFRE | 10 |
| HVR-H2-1A7.gr.NADA 1A7.gr.DANADA | DMYPDNADASYNQKFRE | 11 |
| HVR-H2-1A7.gr.NGDA | DMYPDNGDASYNQKFRE | 12 |
| HVR-H2-1A7.gr.SGDS | DMYPDSGDSSYNQKFRE | 13 |
| HVR-H2-1A7.gr.NGSS | DMYPDNGSSSYNQKFRE | 14 |
| HVR-H3-1A7.Ala.8 | APRWYFSA | 15 |
| HVR-H3-1A7.Ala.9 | APRWYASV | 16 |
| HVR-H3-1A7.Ala.10 | APRWAFSV | 17 |
| HVR-H3-1A7.Ala.11 | APAWYFSV | 18 |
| HVR-H3-1A7.Ala.12 | APRWYFAV | 19 |
| HVR-H3-1A7.Ala.13 | APRAYFSV | 20 |
| HVR-H3-1A7.Ala.14 | AARWYFSV | 21 |
| HVR-L3-1A7.Ala.1 | QQGHTLPAT | 22 |
| HVR-L3-1A7.Ala.2 | QQGHTAPPT | 23 |
| HVR-L3-1A7.Ala.3 | QQGATLPPT | 24 |
| HVR-L3-1A7.Ala.4 | QQGHALPPT | 25 |
| HVR-L3-1A7.Ala.5 | QQAHTLPPT | 26 |
| HVR-L3-1A7.Ala.6 | QQGHTLAPT | 27 |
| HVR-L3-1A7.Ala.7 | QAGHTLPPT | 28 |
| HVR-H1-3C8.gr.1 3C8.gr.2 3C8.gr.3 3C8.gr.4 3C8.gr.5 3C8.gr.5.SG 3C8.gr.5.EG 3C8.gr.5.QG 3C9.gr.5.DQ 3C8.gr.5.DA 3C8.gr.6 | NYLIE | 29 |

TABLE 2-continued

Amino acid sequences

| Name | SEQUENCE | SEQ ID NO: |
|---|---|---|
| 3C8.gr.7 | | |
| 3C8.gr.8 | | |
| 3C8.gr.9 | | |
| 3C8.gr.10 | | |
| 3C8.gr.11 | | |
| 3C8.A.1 | | |
| 3C8.A.2 | | |
| 3C8.A.3 | | |
| 3C8.A.4 | | |
| 3C8.A.5 | | |
| 3C8.A.6 | | |
| 3C8.A.7 | | |
| 3C8.A.8 | | |
| 3C8.A.9 | | |
| 3C8.A.10 | | |
| HVR-H2-3C8.gr.1 | VINPGSGDTYYSEKFKG | 30 |
| 3C8.gr.2 | | |
| 3C8.gr.3 | | |
| 3C8.gr.4 | | |
| 3C8.gr.5 | | |
| 3C8.gr.5.SG | | |
| 3C8.gr.5.EG | | |
| 3C8.gr.5.QG | | |
| 3C8.gr.6 | | |
| 3C8.gr.7 | | |
| 3C8.gr.8 | | |
| 3C8.gr.9 | | |
| 3C8.gr.10 | | |
| 3C8.gr.11 | | |
| 3C8.A.1 | | |
| 3C8.A.2 | | |
| 3C8.A.3 | | |
| 3C8.A.4 | | |
| 3C8.A.5 | | |
| 3C8.A.6 | | |
| 3C8.A.7 | | |
| 3C8.A.8 | | |
| 3C8.A.9 | | |
| 3C8.A.10 | | |
| HVR-H2-3C8.gr.5.DA | VINPGSGDAYYSEKFKG | 31 |
| HVR-H2-3C8.gr.5.DQ | VINPGSGDQYYSEKFKG | 32 |
| HVR-H3-3C8.gr.1 | DRLDY | 33 |
| 3C8.gr.2 | | |
| 3C8.gr.3 | | |
| 3C8.gr.4 | | |
| 3C8.gr.5 | | |
| 3C8.gr.5.SG | | |
| 3C8.gr.5.EG | | |
| 3C8.gr.5.QG | | |
| 3C8.gr.5.DA | | |
| 3C8.gr.5.DQ | | |
| 3C8.gr.6 | | |
| 3C8.gr.7 | | |
| 3C8.gr.8 | | |
| 3C8.gr.9 | | |
| 3C8.gr.10 | | |
| 3C8.gr.11 | | |
| 3C8.A.1 | | |
| 3C8.A.2 | | |
| 3C8.A.3 | | |
| 3C8.A.4 | | |
| 3C8.A.5 | | |
| 3C8.A.6 | | |
| 3C8.A.7 | | |

TABLE 2-continued

Amino acid sequences

| Name | SEQUENCE | SEQ ID NO: |
|---|---|---|
| HVR-H3-3C8.A.8 | ARLDY | 34 |
| HVR-H3-3C8.A.9 | DALDY | 35 |
| HVR-H3-3C8.A.10 | DRADY | 36 |
| HVR-L1-<br>3C8.gr.1<br>3C8.gr.2<br>3C8.gr.3<br>3C8.gr.4<br>3C8.gr.5<br>3C8.gr.5.SG<br>3C8.gr.5.EG<br>3C8.gr.5.QG<br>3C8.gr.5.DA<br>3C8.gr.5.DQ<br>3C8.gr.6<br>3C8.gr.7<br>3C8.gr.8<br>3C8.gr.9<br>3C8.gr.10<br>3C8.gr.11<br>3C8.A.1<br>3C8.A.2<br>3C8.A.3<br>3C8.A.4<br>3C8.A.5<br>3C8.A.6<br>3C8.A.7<br>3C8.A.8<br>3C8.A.9<br>3C8.A.10 | HASQDISSYIV | 37 |
| HVR-L2-<br>3C8.gr.1<br>3C8.gr.2<br>3C8.gr.3<br>3C8.gr.4<br>3C8.gr.5<br>3C8.gr.5.DA<br>3C8.gr.5.DQ<br>3C8.gr.6<br>3C8.gr.7<br>3C8.gr.8<br>3C8.gr.9<br>3C8.gr.10<br>3C8.gr.11<br>3C8.A.1<br>3C8.A.2<br>3C8.A.3<br>3C8.A.4<br>3C8.A.5<br>3C8.A.6<br>3C8.A.7<br>3C8.A.8<br>3C8.A.9<br>3C8.A.10 | HGTNLED | 38 |
| HVR-L2-3C8.gr5.SG | HGTNLES | 39 |
| HVR-L2-3C8.gr.5.EG | HGTNLEE | 40 |
| HVR-L2-3C8.gr.5.QG | HGTNLEQ | 41 |
| HVR-L3 3C8.gr.1 | VHYAQFPYT | 42 |

TABLE 2-continued

Amino acid sequences

| Name | SEQUENCE | SEQ ID NO: |
|---|---|---|
| 3C8.gr.2 | | |
| 3C8.gr.3 | | |
| 3C8.gr.4 | | |
| 3C8.gr.5 | | |
| 3C8.gr.5.SG | | |
| 3C8.gr.5.EG | | |
| 3C8.gr.5.QG | | |
| 3C8.gr.5.DA | | |
| 3C8.gr.5.DQ | | |
| 3C8.gr.6 | | |
| 3C8.gr.7 | | |
| 3C8.gr.8 | | |
| 3C8.gr.9 | | |
| 3C8.gr.10 | | |
| 3C8.gr.11 | | |
| 3C8.A.8 | | |
| 3C8.A.9 | | |
| 3C8.A.10 | | |
| HVR-L3-3C8.A.1 | AHYAQFPYT | 43 |
| HVR-L3-3C8.A.2 | VAYAQFPYT | 44 |
| HVR-L3-3C8.A.3 | VHAAQFPYT | 45 |
| HVR-L3-3C8.A.4 | VHYAAFPYT | 46 |
| HVR-L3-3C8.A.5 | VHYAQAPYT | 47 |
| HVR-L3-3C8.A.6 | VHYAQFAYT | 48 |
| HVR-L3-3C8.A.7 | VHYAQFPAT | 49 |
| HVR-H1-1D2.gr.1 1D2.gr.2 1D2.gr.3 | DYGVL | 50 |
| HVR-H2-1D2.gr.1 1D2.gr.2 1D2.gr.3 | MIWSGGTTDYNAAFIS | 51 |
| HVR-H3-1D2.gr.1 1D2.gr.2 1D2.gr.3 | EEMDY | 52 |
| HVR-L1-1D2.gr.1 1D2.gr.2 1D2.gr.3 | RASQDISNFLN | 53 |
| HVR-L2-1D2.gr.1 1D2.gr.2 1D2.gr.3 | YTSRLHS | 54 |
| HVR-L3-1D2.gr.1 1D2.gr.2 1D2.gr.3 | QQGNTLPWT | 55 |
| 1A7.gr.1 $V_H$ | EVQLVQSGAEVKKPGASVKVSCKASGYTFTDSYMSWVRQAPGQ GLEWIGDMYPDNGDSSYNQKFRERVTITRDTSTSTAYLELSSLRS EDTAVYYCVLAPRWYFSVWGQGTLVTVSS | 56 |

TABLE 2-continued

Amino acid sequences

| Name | SEQUENCE | SEQ ID NO: |
|---|---|---|
| 1A7.gr.1 $V_L$ | DIQMTQSPSSLSASVGDRVTITCRASQDISNYLNWYQQKPGKAPK LLIYYTSRLRSGVPSRFSGSGSGTDFTLTISSLQPEDFATYYCQQG HTLPPTFGQGTKVEIK | 57 |
| 1A7.gr.2 $V_H$ | EVQLVQSGAEVKKPGASVKVSCKASGYTFTDSYMSWVRQAPGQ GLEWIGDMYPDNGDSSYNQKFRERVTITVDTSTSTAYLELSSLRS EDTAVYYCVLAPRWYFSVWGQGTLVTVSS | 58 |
| 1A7.gr.2 $V_L$ | DIQMTQSPSSLSASVGDRVTITCRASQDISNYLNWYQQKPGKAPK LLIYYTSRLRSGVPSRFSGSGSGTDFTLTISSLQPEDFATYYCQQG HTLPPTFGQGTKVEIK | 59 |
| 1A7.gr.3 $V_H$ | EVQLVQSGAEVKKPGASVKVSCKASGYTFTDSYMSWVRQAPGQ GLEWIGDMYPDNGDSSYNQKFRERVTLTVDTSTSTAYLELSSLRS EDTAVYYCVLAPRWYFSVWGQGTLVTVSS | 60 |
| 1A7.gr.3 $V_L$ | DIQMTQSPSSLSASVGDRVTITCRASQDISNYLNWYQQKPGKAPK LLIYYTSRLRSGVPSRFSGSGSGTDFTLTISSLQPEDFATYYCQQG HTLPPTFGQGTKVEIK | 61 |
| 1A7.gr.4 $V_H$ | EVQLVQSGAEVKKPGASVKVSCKASGYTFTDSYMSWVRQAPGQ GLEWIGDMYPDNGDSSYNQKFRERVTITVDTSTSTAYLELSSLRS EDTAVYYCVLAPRWYFSVWGQGTLVTVSS | 62 |
| 1A7.gr.4 $V_L$ | DIQMTQSPSSLSASVGDRVTITCRASQDISNYLNWYQQKPGKTVK LLIYYTSRLRSGVPSRFSGSGSGTDFTLTISSLQPEDFATYYCQQG HTLPPTFGQGTKVEIK | 63 |
| 1A7.gr.5 $V_H$ | EVQLVQSGAEVKKPGASVKVSCKASGYTFTDSYMSWVRQAPGQ GLEWIGDMYPDNGDSSYNQKFRERVTITVDTSTSTAYLELSSLRS EDTAVYYCVLAPRWYFSVWGQGTLVTVSS | 64 |
| 1A7.gr.5 $V_L$ | DIQMTQSPSSLSASVGDRVTITCRASQDISNYLNWYQQKPGKTVK LLIYYTSRLRSGVPSRFSGSGSGTDFTLTISSLQPEDFATYYCQQG HTLPPTFGQGTKVEIK | 65 |
| 1A7.gr.6 $V_H$ | EVQLVQSGAEVKKPGASVKVSCKASGYTFTDSYMSWVRQAPGQ GLEWIGDMYPDNGDSSYNQKFRERVTITVDTSTSTAYLELSSLRS EDTAVYYCVLAPRWYFSVWGQGTLVTVSS | 66 |
| 1A7.gr.6 $V_L$ | DIQMTQSPSSLSASVGDRVTITCRASQDISNYLNWYQQKPGKTVK LLIYYTSRLRSGVPSRFSGSGSGKDYTLTISSLQPEDFATYFCQQG HTLPPTFGQGTKVEIK | 67 |
| 1A7.gr.7 $V_H$ | EVQLVQSGAEVKKPGASVKVSCKASGYTFTDSYMSWVRQAPGQ GLEWIGDMYPDNGDSSYNQKFRERVTITVDTSTSTAYLELSSLRS EDTAVYYCVLAPRWYFSVWGQGTLVTVSS | 68 |
| 1A7.gr.7 $V_L$ | DIQMTQSPSSLSASVGDRVTITCRASQDISNYLNWYQQKPGKTVK LLIYYTSRLRSGVPSRFSGSGSGKDYTLTISSLQPEDFATYFCQQG HTLPPTFGQGTKVEIK | 69 |
| 1A7.gr.DA $V_H$ | EVQLVQSGAEVKKPGASVKVSCKASGYTFTDAYMSWVRQAPGQ GLEWIGDMYPDNGDSSYNQKFRERVTIRDTSTSTAYLELSSLRS EDTAVYYCVLAPRWYFSVWGQGTLVTVSS | 70 |
| 1A7.gr.DA $V_L$ | DIQMTQSPSSLSASVGDRVTITCRASQDISNYLNWYQQKPGKAPK LLIYYTSRLRSGVPSRFSGSGSGTDFTLTISSLQPEDFATYYCQQG HTLPPTFGQGTKVEIK | 71 |
| 1A7.gr.ES $V_H$ | EVQLVQSGAEVKKPGASVKVSCKASGYTFTESYMSWVRQAPGQ GLEWIGDMYPDNGDSSYNQKFRERVTIRDTSTSTAYLELSSLRS EDTAVYYCVLAPRWYFSVWGQGTLVTVSS | 72 |
| 1A7.gr.ES $V_L$ | DIQMTQSPSSLSASVGDRVTITCRASQDISNYLNWYQQKPGKAPK LLIYYTSRLRSGVPSRFSGSGSGTDFTLTISSLQPEDFATYYCQQG HTLPPTFGQGTKVEIK | 73 |
| 1A7.gr.NADS $V_H$ | EVQLVQSGAEVKKPGASVKVSCKASGYTFTDSYMSWVRQAPGQ GLEWIGDMYPDNADSSYNQKFRERVTIRDTSTSTAYLELSSLRS EDTAVYYCVLAPRWYFSVWGQGTLVTVSS | 74 |

TABLE 2-continued

Amino acid sequences

| Name | SEQUENCE | SEQ ID NO: |
|---|---|---|
| 1A7.gr.NADS $V_L$ | DIQMTQSPSSLSASVGDRVTITCRASQDISNYLNWYQQKPGKAPK LLIYYTSRLRSGVPSRFSGSGSGTDFTLTISSLQPEDFATYYCQQG HTLPPTFGQGTKVEIK | 75 |
| 1A7.gr.NADA $V_H$ | EVQLVQSGAEVKKPGASVKVSCKASGYTFTDSYMSWVRQAPGQ GLEWIGDMYPDNADASYNQKFRERVTITRDTSTSTAYLELSSLRS EDTAVYYCVLAPRWYFSVWGQGTLVTVSS | 76 |
| 1A7.gr.NADA $V_L$ | DIQMTQSPSSLSASVGDRVTITCRASQDISNYLNWYQQKPGKAPK LLIYYTSRLRSGVPSRFSGSGSGTDFTLTISSLQPEDFATYYCQQG HTLPPTFGQGTKVEIK | 77 |
| 1A7.gr.NGDA $V_H$ | EVQLVQSGAEVKKPGASVKVSCKASGYTFTDSYMSWVRQAPGQ GLEWIGDMYPDNGDASYNQKFRERVTITRDTSTSTAYLELSSLRS EDTAVYYCVLAPRWYFSVWGQGTLVTVSS | 78 |
| 1A7.gr.NGDA $V_L$ | DIQMTQSPSSLSASVGDRVTITCRASQDISNYLNWYQQKPGKAPK LLIYYTSRLRSGVPSRFSGSGSGTDFTLTISSLQPEDFATYYCQQG HTLPPTFGQGTKVEIK | 79 |
| 1A7.gr.SGDS $V_H$ | EVQLVQSGAEVKKPGASVKVSCKASGYTFTDSYMSWVRQAPGQ GLEWIGDMYPDSGDSSYNQKFRERVTITRDTSTSTAYLELSSLRSE DTAVYYCVLAPRWYFSVWGQGTLVTVSS | 80 |
| 1A7.gr.SGDS $V_L$ | DIQMTQSPSSLSASVGDRVTITCRASQDISNYLNWYQQKPGKAPK LLIYYTSRLRSGVPSRFSGSGSGTDFTLTISSLQPEDFATYYCQQG HTLPPTFGQGTKVEIK | 81 |
| 1A7.gr.NGSS $V_H$ | EVQLVQSGAEVKKPGASVKVSCKASGYTFTDSYMSWVRQAPGQ GLEWIGDMYPDNGSSSYNQKFRERVTITRDTSTSTAYLELSSLRSE DTAVYYCVLAPRWYFSVWGQGTLVTVSS | 82 |
| 1A7.gr.NGSS $V_L$ | DIQMTQSPSSLSASVGDRVTITCRASQDISNYLNWYQQKPGKAPK LLIYYTSRLRSGVPSRFSGSGSGTDFTLTISSLQPEDFATYYCQQG HTLPPTFGQGTKVEIK | 83 |
| 1A7.gr.DANADA $V_H$ | EVQLVQSGAEVKKPGASVKVSCKASGYTFTDAYMSWVRQAPGQ GLEWIGDMYPDNADASYNQKFRERVTITRDTSTSTAYLELSSLRS EDTAVYYCVLAPRWYFSVWGQGTLVTVSS | 84 |
| 1A7.gr.DANADA $V_L$ | DIQMTQSPSSLSASVGDRVTITCRASQDISNYLNWYQQKPGKAPK LLIYYTSRLRSGVPSRFSGSGSGTDFTLTISSLQPEDFATYYCQQG HTLPPTFGQGTKVEIK | 85 |
| 1A7.Ala.1 $V_H$ | EVQLVQSGAEVKKPGASVKVSCKASGYTFTDSYMSWVRQAPGQ GLEWIGDMYPDNGDSSYNQKFRERVTITRDTSTSTAYLELSSLRS EDTAVYYCVLAPRWYFSVWGQGTLVTVSS | 86 |
| 1A7.Ala.1 $V_L$ | DIQMTQSPSSLSASVGDRVTITCRASQDISNYLNWYQQKPGKAPK LLIYYTSRLRSGVPSRFSGSGSGTDFTLTISSLQPEDFATYYCQQG HTLPATFGQGTKVEIK | 87 |
| 1A7.Ala.2 $V_H$ | EVQLVQSGAEVKKPGASVKVSCKASGYTFTDSYMSWVRQAPGQ GLEWIGDMYPDNGDSSYNQKFRERVTITRDTSTSTAYLELSSLRS EDTAVYYCVLAPRWYFSVWGQGTLVTVSS | 88 |
| 1A7.Ala.2 $V_L$ | DIQMTQSPSSLSASVGDRVTITCRASQDISNYLNWYQQKPGKAPK LLIYYTSRLRSGVPSRFSGSGSGTDFTLTISSLQPEDFATYYCQQG HTAPPTFGQGTKVEIK | 89 |
| 1A7.Ala.3 $V_H$ | EVQLVQSGAEVKKPGASVKVSCKASGYTFTDSYMSWVRQAPGQ GLEWIGDMYPDNGDSSYNQKFRERVTITRDTSTSTAYLELSSLRS EDTAVYYCVLAPRWYFSVWGQGTLVTVSS | 90 |
| 1A7.Ala.3 $V_L$ | DIQMTQSPSSLSASVGDRVTITCRASQDISNYLNWYQQKPGKAPK LLIYYTSRLRSGVPSRFSGSGSGTDFTLTISSLQPEDFATYYCQQG ATLPPTFGQGTKVEIK | 91 |
| 1A7.Ala.4 $V_H$ | EVQLVQSGAEVKKPGASVKVSCKASGYTFTDSYMSWVRQAPGQ GLEWIGDMYPDNGDSSYNQKFRERVTITRDTSTSTAYLELSSLRS EDTAVYYCVLAPRWYFSVWGQGTLVTVSS | 92 |

TABLE 2-continued

Amino acid sequences

| Name | SEQUENCE | SEQ ID NO: |
|---|---|---|
| 1A7.Ala.4 $V_L$ | DIQMTQSPSSLSASVGDRVTITCRASQDISNYLNWYQQKPGKAPK LLIYYTSRLRSGVPSRFSGSGSGTDFTLTISSLQPEDFATYYCQQG HALPPTFGQGTKVEIK | 93 |
| 1A7.Ala.5 $V_H$ | EVQLVQSGAEVKKPGASVKVSCKASGYTFTDSYMSWVRQAPGQ GLEWIGDMYPDNGDSSYNQKFRERVTITRDTSTSTAYLELSSLRS EDTAVYYCVLAPRWYFSVWGQGTLVTVSS | 94 |
| 1A7.Ala.5 $V_L$ | DIQMTQSPSSLSASVGDRVTITCRASQDISNYLNWYQQKPGKAPK LLIYYTSRLRSGVPSRFSGSGSGTDFTLTISSLQPEDFATYYCQQA HTLPPTFGQGTKVEIK | 95 |
| 1A7.Ala.6 $V_H$ | EVQLVQSGAEVKKPGASVKVSCKASGYTFTDSYMSWVRQAPGQ GLEWIGDMYPDNGDSSYNQKFRERVTITRDTSTSTAYLELSSLRS EDTAVYYCVLAPRWYFSVWGQGTLVTVSS | 96 |
| 1A7.Ala.6 $V_L$ | DIQMTQSPSSLSASVGDRVTITCRASQDISNYLNWYQQKPGKAPK LLIYYTSRLRSGVPSRFSGSGSGTDFTLTISSLQPEDFATYYCQQG HTLAPTFGQGTKVEIK | 97 |
| 1A7.Ala.7 $V_H$ | EVQLVQSGAEVKKPGASVKVSCKASGYTFTDSYMSWVRQAPGQ GLEWIGDMYPDNGDSSYNQKFRERVTITRDTSTSTAYLELSSLRS EDTAVYYCVLAPRWYFSVWGQGTLVTVSS | 98 |
| 1A7.Ala.7 $V_L$ | DIQMTQSPSSLSASVGDRVTITCRASQDISNYLNWYQQKPGKAPK LLIYYTSRLRSGVPSRFSGSGSGTDFTLTISSLQPEDFATYYCQAG HTLPPTFGQGTKVEIK | 99 |
| 1A7.Ala.8 $V_H$ | EVQLVQSGAEVKKPGASVKVSCKASGYTFTDSYMSWVRQAPGQ GLEWIGDMYPDNGDSSYNQKFRERVTITRDTSTSTAYLELSSLRS EDTAVYYCVLAPRWYFSAWGQGTLVTVSS | 100 |
| 1A7.Ala.8 $V_L$ | DIQMTQSPSSLSASVGDRVTITCRASQDISNYLNWYQQKPGKAPK LLIYYTSRLRSGVPSRFSGSGSGTDFTLTISSLQPEDFATYYCQQG HTLPPTFGQGTKVEIK | 101 |
| 1A7.Ala.9 $V_H$ | EVQLVQSGAEVKKPGASVKVSCKASGYTFTDSYMSWVRQAPGQ GLEWIGDMYPDNGDSSYNQKFRERVTITRDTSTSTAYLELSSLRS EDTAVYYCVLAPRWYASVWGQGTLVTVSS | 102 |
| 1A7.Ala.9 $V_L$ | DIQMTQSPSSLSASVGDRVTITCRASQDISNYLNWYQQKPGKAPK LLIYYTSRLRSGVPSRFSGSGSGTDFTLTISSLQPEDFATYYCQQG HTLPPTFGQGTKVEIK | 103 |
| 1A7.Ala.10 $V_H$ | EVQLVQSGAEVKKPGASVKVSCKASGYTFTDSYMSWVRQAPGQ GLEWIGDMYPDNGDSSYNQKFRERVTITRDTSTSTAYLELSSLRS EDTAVYYCVLAPRWAFSVWGQGTLVTVSS | 104 |
| 1A7.Ala.10 $V_L$ | DIQMTQSPSSLSASVGDRVTITCRASQDISNYLNWYQQKPGKAPK LLIYYTSRLRSGVPSRFSGSGSGTDFTLTISSLQPEDFATYYCQQG HTLPPTFGQGTKVEIK | 105 |
| 1A7.Ala.11 $V_H$ | EVQLVQSGAEVKKPGASVKVSCKASGYTFTDSYMSWVRQAPGQ GLEWIGDMYPDNGDSSYNQKFRERVTITRDTSTSTAYLELSSLRS EDTAVYYCVLAPAWYFSVWGQGTLVTVSS | 106 |
| 1A7.Ala.11 $V_L$ | DIQMTQSPSSLSASVGDRVTITCRASQDISNYLNWYQQKPGKAPK LLIYYTSRLRSGVPSRFSGSGSGTDFTLTISSLQPEDFATYYCQQG HTLPPTFGQGTKVEIK | 107 |
| 1A7.Ala.12 $V_H$ | EVQLVQSGAEVKKPGASVKVSCKASGYTFTDSYMSWVRQAPGQ GLEWIGDMYPDNGDSSYNQKFRERVTITRDTSTSTAYLELSSLRS EDTAVYYCVLAPRWYFAVWGQGTLVTVSS | 108 |
| 1A7.Ala.12 $V_L$ | DIQMTQSPSSLSASVGDRVTITCRASQDISNYLNWYQQKPGKAPK LLIYYTSRLRSGVPSRFSGSGSGTDFTLTISSLQPEDFATYYCQQG HTLPPTFGQGTKVEIK | 109 |
| 1A7.Ala.13 $V_H$ | EVQLVQSGAEVKKPGASVKVSCKASGYTFTDSYMSWVRQAPGQ GLEWIGDMYPDNGDSSYNQKFRERVTITRDTSTSTAYLELSSLRS EDTAVYYCVLAPRAYFSVWGQGTLVTVSS | 110 |

TABLE 2-continued

Amino acid sequences

| Name | SEQUENCE | SEQ ID NO: |
|---|---|---|
| 1A7.Ala.13 V_L | DIQMTQSPSSLSASVGDRVTITCRASQDISNYLNWYQQKPGKAPK LLIYYTSRLRSGVPSRFSGSGSGTDFTLTISSLQPEDFATYYCQQG HTLPPTFGQGTKVEIK | 111 |
| 1A7.Ala.14 V_H | EVQLVQSGAEVKKPGASVKVSCKASGYTFTDSYMSWVRQAPGQ GLEWIGDMYPDNGDSSYNQKFRERVTITRDTSTSTAYLELSSLRS EDTAVYYCVLAARWYFSVWGQGTLVTVSS | 112 |
| 1A7.Ala.14 V_L | DIQMTQSPSSLSASVGDRVTITCRASQDISNYLNWYQQKPGKAPK LLIYYTSRLRSGVPSRFSGSGSGTDFTLTISSLQPEDFATYYCQQG HTLPPTFGQGTKVEIK | 113 |
| 1A7.Ala.15 V_H | EVQLVQSGAEVKKPGASVKVSCKASGYTFTDSYMSWVRQAPGQ GLEWIGDMYPDNGDSSYNQKFRERVTITRDTSTSTAYLELSSLRS EDTAVYYCALAPRWYFSVWGQGTLVTVSS | 114 |
| 1A7.Ala.15 V_L | DIQMTQSPSSLSASVGDRVTITCRASQDISNYLNWYQQKPGKAPK LLIYYTSRLRSGVPSRFSGSGSGTDFTLTISSLQPEDFATYYCQQG HTLPPTFGQGTKVEIK | 115 |
| 1A7.Ala.16 V_H | EVQLVQSGAEVKKPGASVKVSCKASGYTFTDSYMSWVRQAPGQ GLEWIGDMYPDNGDSSYNQKFRERVTITRDTSTSTAYLELSSLRS EDTAVYYCVAAPRWYFSVWGQGTLVTVSS | 116 |
| 1A7.Ala.16 V_L | DIQMTQSPSSLSASVGDRVTITCRASQDISNYLNWYQQKPGKAPK LLIYYTSRLRSGVPSRFSGSGSGTDFTLTISSLQPEDFATYYCQQG HTLPPTFGQGTKVEIK | 117 |
| 3C8.gr.1 V_H | EVQLVQSGAEVKKPGASVKVSCKASGYAFTNYLIEWVRQAPGQ GLEWIGVINPGSGDTYYSEKFKGRVTITRDTSTSTAYLELSSLRSE DTAVYYCARDRLDYWGQGTLVTVSS | 118 |
| 3C8.gr.1 V_L | DIQMTQSPSSLSASVGDRVTITCHASQDISSYIVWYQQKPGKAPK LLIYHGTNLEDGVPSRFSGSGSGTDFTLTISSLQPEDFATYYCVHY AQFPYTFGQGTKVEIK | 119 |
| 3C8.gr.2 V_H | EVQLVQSGAEVKKPGASVKVSCKASGYAFTNYLIEWVRQAPGQ GLEWIGVINPGSGDTYYSEKFKGRVTITADTSTSTAYLELSSLRSE DTAVYYCARDRLDYWGQGTLVTVSS | 120 |
| 3C8.gr.2 V_L | DIQMTQSPSSLSASVGDRVTITCHASQDISSYIVWYQQKPGKAPK LLIYHGTNLEDGVPSRFSGSGSGTDFTLTISSLQPEDFATYYCVHY AQFPYTFGQGTKVEIK | 121 |
| 3C8.gr.3 V_H | EVQLVQSGAEVKKPGASVKVSCKASGYAFTNYLIEWVRQAPGQ GLEWIGVINPGSGDTYYSEKFKGRVTLTADTSTSTAYLELSSLRSE DTAVYYCARDRLDYWGQGTLVTVSS | 122 |
| 3C8.gr.3 V_L | DIQMTQSPSSLSASVGDRVTITCHASQDISSYIVWYQQKPGKAPK LLIYHGTNLEDGVPSRFSGSGSGTDFTLTISSLQPEDFATYYCVHY AQFPYTFGQGTKVEIK | 123 |
| 3C8.gr.4 V_H | EVQLVQSGAEVKKPGASVKVSCKASGYAFTNYLIEWVRQAPGQ GLEWIGVINPGSGDTYYSEKFKGRVTITADTSTSTAYLELSSLRSE DTAVYYCARDRLDYWGQGTLVTVSS | 124 |
| 3C8.gr.4 V_L | DIQMTQSPSSLSASVGDRVTITCHASQDISSYIVWYQQKPGKSFKG LIYHGTNLEDGVPSRFSGSGSGTDFTLTISSLQPEDFATYYCVHYA QFPYTFGQGTKVEIK | 125 |
| 3C8.gr.5 V_H | EVQLVQSGAEVKKPGASVKVSCKASGYAFTNYLIEWVRQAPGQ GLEWIGVINPGSGDTYYSEKFKGRVTLTADTSTSTAYLELSSLRSE DTAVYYCARDRLDYWGQGTLVTVSS | 126 |
| 3C8.gr.5 V_L | DIQMTQSPSSLSASVGDRVTITCHASQDISSYIVWYQQKPGKSFKG LIYHGTNLEDGVPSRFSGSGSGTDFTLTISSLQPEDFATYYCVHYA QFPYTFGQGTKVEIK | 127 |
| 3C8.gr.5.SG V_H | EVQLVQSGAEVKKPGASVKVSCKASGYAFTNYLIEWVRQAPGQ GLEWIGVINPGSGDTYYSEKFKGRVTLTADTSTSTAYLELSSLRSE DTAVYYCARDRLDYWGQGTLVTVSS | 128 |

TABLE 2-continued

Amino acid sequences

| Name | SEQUENCE | SEQ ID NO: |
|---|---|---|
| 3C8.gr.5.SG $V_L$ | DIQMTQSPSSLSASVGDRVTITCHASQDISSYIVWYQQKPGKSFKG LIYHGTNLESGVPSRFSGSGSGTDFTLTISSLQPEDFATYYCVHYA QFPYTFGQGTKVEIK | 129 |
| 3C8.gr.5.EG $V_H$ | EVQLVQSGAEVKKPGASVKVSCKASGYAFTNYLIEWVRQAPGQ GLEWIGVINPGSGDTYYSEKFKGRVTLTADTSTSTAYLELSSLRSE DTAVYYCARDRLDYWGQGTLVTVSS | 130 |
| 3C8.gr.5.EG $V_L$ | DIQMTQSPSSLSASVGDRVTITCHASQDISSYIVWYQQKPGKSFKG LIYHGTNLEEGVPSRFSGSGSGTDFTLTISSLQPEDFATYYCVHYA QFPYTFGQGTKVEIK | 131 |
| 3C8.gr.5.QG $V_H$ | EVQLVQSGAEVKKPGASVKVSCKASGYAFTNYLIEWVRQAPGQ GLEWIGVINPGSGDTYYSEKFKGRVTLTADTSTSTAYLELSSLRSE DTAVYYCARDRLDYWGQGTLVTVSS | 132 |
| 3C8.gr.5.QG $V_L$ | DIQMTQSPSSLSASVGDRVTITCHASQDISSYIVWYQQKPGKSFKG LIYHGTNLEQGVPSRFSGSGSGTDFTLTISSLQPEDFATYYCVHYA QFPYTFGQGTKVEIK | 133 |
| 3C8.gr.6 $V_H$ | EVQLVQSGAEVKKPGASVKVSCKASGYAFTNYLIEWVRQAPGQ GLEWIGVINPGSGDTYYSEKFKGRVTITADTSTSTAYLELSSLRSE DTAVYYCARDRLDYWGQGTLVTVSS | 134 |
| 3C8.gr.6 $V_L$ | DIQMTQSPSSLSASVGDRVTITCHASQDISSYIVWYQQKPGKSFKG LIYHGTNLEDGVPSRFSGSGSGADYTLTISSLQPEDFATYYCVHY AQFPYTFGQGTKVEIK | 135 |
| 3C8.gr.7 $V_H$ | EVQLVQSGAEVKKPGASVKVSCKASGYAFTNYLIEWVRQAPGQ GLEWIGVINPGSGDTYYSEKFKGRVTLTADTSTSTAYLELSSLRSE DTAVYYCARDRLDYWGQGTLVTVSS | 136 |
| 3C8.gr.7 $V_L$ | DIQMTQSPSSLSASVGDRVTITCHASQDISSYIVWYQQKPGKSFKG LIYHGTNLEDGVPSRFSGSGSGADYTLTISSLQPEDFATYYCVHY AQFPYTFGQGTKVEIK | 137 |
| 3C8.gr.8 $V_H$ | EVQLVQSGAEVKKPGASVKVSCKASGYAFTNYLIEWVRQAPGQ GLEWIGVINPGSGDTYYSEKFKGRVTLTRDTSTSTAYLELSSLRSE DTAVYYCARDRLDYWGQGTLVTVSS | 138 |
| 3C8.gr.8 $V_L$ | DIQMTQSPSSLSASVGDRVTITCHASQDISSYIVWYQQKPGKSFKG LIYHGTNLEDGVPSRFSGSGSGTDFTLTISSLQPEDFATYYCVHYA QFPYTFGQGTKVEIK | 139 |
| 3C8.gr.9 $V_H$ | EVQLVQSGAEVKKPGASVKVSCKASGYAFTNYLIEWVRQAPGQ GLEWIGVINPGSGDTYYSEKFKGRVTLTRDTSTSTAYLELSSLRSE DTAVYYCARDRLDYWGQGTLVTVSS | 140 |
| 3C8.gr.9 $V_L$ | DIQMTQSPSSLSASVGDRVTITCHASQDISSYIVWYQQKPGKSPKL LIYHGTNLEDGVPSRFSGSGSGTDFTLTISSLQPEDFATYYCVHYA QFPYTFGQGTKVEIK | 141 |
| 3C8.gr.10 $V_H$ | EVQLVQSGAEVKKPGASVKVSCKASGYAFTNYLIEWVRQAPGQ GLEWIGVINPGSGDTYYSEKFKGRVTLTRDTSTSTAYLELSSLRSE DTAVYYCARDRLDYWGQGTLVTVSS | 142 |
| 3C8.gr.10 $V_L$ | DIQMTQSPSSLSASVGDRVTITCHASQDISSYIVWYQQKPGKAFK LLIYHGTNLEDGVPSRFSGSGSGTDFTLTISSLQPEDFATYYCVHY AQFPYTFGQGTKVEIK | 143 |
| 3C8.gr.11 $V_H$ | EVQLVQSGAEVKKPGASVKVSCKASGYAFTNYLIEWVRQAPGQ GLEWIGVINPGSGDTYYSEKFKGRVTLTRDTSTSTAYLELSSLRSE DTAVYYCARDRLDYWGQGTLVTVSS | 144 |
| 3C8.gr.11 $V_L$ | DIQMTQSPSSLSASVGDRVTITCHASQDISSYIVWYQQKPGKAPK GLIYHGTNLEDGVPSRFSGSGSGTDFTLTISSLQPEDFATYYCVHY AQFPYTFGQGTKVEIK | 145 |
| 3C8.A.1 $V_H$ | EVQLVQSGAEVKKPGASVKVSCKASGYAFTNYLIEWVRQAPGQ GLEWIGVINPGSGDTYYSEKFKGRVTLTADTSTSTAYLELSSLRSE DTAVYYCARDRLDYWGQGTLVTVSS | 146 |

TABLE 2-continued

Amino acid sequences

| Name | SEQUENCE | SEQ ID NO: |
|---|---|---|
| 3C8.A.1 $V_L$ | DIQMTQSPSSLSASVGDRVTITCHASQDISSYIVWYQQKPGKSFKG LIYHGTNLEDGVPSRFSGSGSGTDFTLTISSLQPEDFATYYCAHYA QFPYTFGQGTKVEIK | 147 |
| 3C8.A.2 $V_H$ | EVQLVQSGAEVKKPGASVKVSCKASGYAFTNYLIEWVRQAPGQ GLEWIGVINPGSGDTYYSEKFKGRVTLTADTSTSTAYLELSSLRSE DTAVYYCARDRLDYWGQGTLVTVSS | 148 |
| 3C8.A.2 $V_L$ | DIQMTQSPSSLSASVGDRVTITCHASQDISSYIVWYQQKPGKSFKG LIYHGTNLEDGVPSRFSGSGSGTDFTLTISSLQPEDFATYYCVAYA QFPYTFGQGTKVEIK | 149 |
| 3C8.A.3 $V_H$ | EVQLVQSGAEVKKPGASVKVSCKASGYAFTNYLIEWVRQAPGQ GLEWIGVINPGSGDTYYSEKFKGRVTLTADTSTSTAYLELSSLRSE DTAVYYCARDRLDYWGQGTLVTVSS | 150 |
| 3C8.A.3 $V_L$ | DIQMTQSPSSLSASVGDRVTITCHASQDISSYIVWYQQKPGKSFKG LIYHGTNLEDGVPSRFSGSGSGTDFTLTISSLQPEDFATYYCVHAA QFPYTFGQGTKVEIK | 151 |
| 3C8.A.4 $V_H$ | EVQLVQSGAEVKKPGASVKVSCKASGYAFTNYLIEWVRQAPGQ GLEWIGVINPGSGDTYYSEKFKGRVTLTADTSTSTAYLELSSLRSE DTAVYYCARDRLDYWGQGTLVTVSS | 152 |
| 3C8.A.4 $V_L$ | DIQMTQSPSSLSASVGDRVTITCHASQDISSYIVWYQQKPGKSFKG LIYHGTNLEDGVPSRFSGSGSGTDFTLTISSLQPEDFATYYCVHYA AFPYTFGQGTKVEIK | 153 |
| 3C8.A.5 $V_H$ | EVQLVQSGAEVKKPGASVKVSCKASGYAFTNYLIEWVRQAPGQ GLEWIGVINPGSGDTYYSEKFKGRVTLTADTSTSTAYLELSSLRSE DTAVYYCARDRLDYWGQGTLVTVSS | 154 |
| 3C8.A.5 $V_L$ | DIQMTQSPSSLSASVGDRVTITCHASQDISSYIVWYQQKPGKSFKG LIYHGTNLEDGVPSRFSGSGSGTDFTLTISSLQPEDFATYYCVHYA QAPYTFGQGTKVEIK | 155 |
| 3C8.A.6 $V_H$ | EVQLVQSGAEVKKPGASVKVSCKASGYAFTNYLIEWVRQAPGQ GLEWIGVINPGSGDTYYSEKFKGRVTLTADTSTSTAYLELSSLRSE DTAVYYCARDRLDYWGQGTLVTVSS | 156 |
| 3C8.A.6 $V_L$ | DIQMTQSPSSLSASVGDRVTITCHASQDISSYIVWYQQKPGKSFKG LIYHGTNLEDGVPSRFSGSGSGTDFTLTISSLQPEDFATYYCVHYA QFAYTFGQGTKVEIK | 157 |
| 3C8.A.7 $V_H$ | EVQLVQSGAEVKKPGASVKVSCKASGYAFTNYLIEWVRQAPGQ GLEWIGVINPGSGDTYYSEKFKGRVTLTADTSTSTAYLELSSLRSE DTAVYYCARDRLDYWGQGTLVTVSS | 158 |
| 3C8.A.7 $V_L$ | DIQMTQSPSSLSASVGDRVTITCHASQDISSYIVWYQQKPGKSFKG LIYHGTNLEDGVPSRFSGSGSGTDFTLTISSLQPEDFATYYCVHYA QFPATFGQGTKVEIK | 159 |
| 3C8.A.8 $V_H$ | EVQLVQSGAEVKKPGASVKVSCKASGYAFTNYLIEWVRQAPGQ GLEWIGVINPGSGDTYYSEKFKGRVTLTADTSTSTAYLELSSLRSE DTAVYYCARARLDYWGQGTLVTVSS | 160 |
| 3C8.A.8 $V_L$ | DIQMTQSPSSLSASVGDRVTITCHASQDISSYIVWYQQKPGKSFKG LIYHGTNLEDGVPSRFSGSGSGTDFTLTISSLQPEDFATYYCVHYA QFPYTFGQGTKVEIK | 161 |
| 3C8.A.9 $V_H$ | EVQLVQSGAEVKKPGASVKVSCKASGYAFTNYLIEWVRQAPGQ GLEWIGVINPGSGDTYYSEKFKGRVTLTADTSTSTAYLELSSLRSE DTAVYYCARDALDYWGQGTLVTVSS | 162 |
| 3C8.A.9 $V_L$ | DIQMTQSPSSLSASVGDRVTITCHASQDISSYIVWYQQKPGKSFKG LIYHGTNLEDGVPSRFSGSGSGTDFTLTISSLQPEDFATYYCVHYA QFPYTFGQGTKVEIK | 163 |
| 3C8.A.10 $V_H$ | EVQLVQSGAEVKKPGASVKVSCKASGYAFTNYLIEWVRQAPGQ GLEWIGVINPGSGDTYYSEKFKGRVTLTADTSTSTAYLELSSLRSE DTAVYYCARDRADYWGQGTLVTVSS | 164 |

TABLE 2-continued

Amino acid sequences

| Name | SEQUENCE | SEQ ID NO: |
|---|---|---|
| 3C8.A.10 $V_L$ | DIQMTQSPSSLSASVGDRVTITCHASQDISSYIVWYQQKPGKSFKG LIYHGTNLEDGVPSRFSGSGSGTDFTLTISSLQPEDFATYYCVHYA QFPYTFGQGTKVEIK | 165 |
| 1D2.gr.1 $V_H$ | EVQLVESGPGLVKPSETLSLTCTVSGFSLTDYGVLWIRQPPGKGL EWIGMIWSGGTTDYNAAFISRVTISVDTSKNQFSLKLSSVTAADT AVYYCVREEMDYWGQGTLVTVSS | 166 |
| 1D2.gr.1 $V_L$ | DIQMTQSPSSLSASVGDRVTITCRASQDISNFLNWYQQKPGKAPK LLIYYTSRLHSGVPSRFSGSGSGTDFTLTISSLQPEDFATYYCQQG NTLPWTFGQGTKVEIK | 167 |
| 1D2.gr.2 $V_H$ | EVQLVESGPGLVKPSETLSLTCTVSGFSLTDYGVLWIRQPPGKGL EWIGMIWSGGTTDYNAAFISRVTISKDTSKNQVSLKLSSVTAADT AVYYCVREEMDYWGQGTLVTVSS | 168 |
| 1D2.gr.2 $V_L$ | DIQMTQSPSSLSASVGDRVTITCRASQDISNFLNWYQQKPGKAPK LLIYYTSRLHSGVPSRFSGSGSGTDFTLTISSLQPEDFATYYCQQG NTLPWTFGQGTKVEIK | 169 |
| 1D2.gr.3 $V_H$ | EVQLVESGPGLVKPSETLSLTCTVSGFSLTDYGVLWVRQPPGKGL EWLGMIWSGGTTDYNAAFISRLTISKDTSKNQVSLKLSSVTAADT AVYYCVREEMDYWGQGTLVTVSS | 170 |
| 1D2.gr.3 $V_L$ | DIQMTQSPSSLSASVGDRVTITCRASQDISNFLNWYQQKPGKAPK LLIYYTSRLHSGVPSRFSGSGSGTDFTLTISSLQPEDFATYYCQQG NTLPWTFGQGTKVEIK | 171 |
| CON1 (1A7) HVR-H1 | $X_1X_2$YMS, wherein $X_1$ is D or E, and $X_2$ is S or A | 172 |
| CON1 (1A7) HVR-H2 | DMYPD$X_1X_2X_3X_4$SYNQKFRE, wherein $X_1$ is N or S, $X_1$ is A or G, $X_3$ is D or S, and $X_4$ is A or S | 173 |
| CON1 (1A7) HVR-H3 | APRW$X_1X_2X_3X_4$, wherein $X_1$ is Y or A, $X_2$ is A or F, $X_3$ is S or A, and $X_4$ is A or V. | 174 |
| CON1 (1A7) HVR-L3 | Q$X_1X_2X_3X_4X_5X_6X_7$T, wherein $X_1$ is A or Q, $X_2$ is A or G, $X_3$ is A or H, $X_4$ is A or T, $X_5$ is A or L, $X_6$ is A or P, and $X_7$ is A or P. | 175 |
| CON2 (3C8) HVR-H2 | VINPGSGD$X_1$YYSEKFKG, wherein $X_1$ is T, A or Q. | 176 |
| CON2 (3C8) HVR-L2 | HGTNLE$X_1$, wherein $X_1$ is S, E, or Q. | 177 |
| CON2 (3C8) HVR-L3 | $X_1X_2$YAQFPY$X_3$, wherein $X_1$ is V or A, $X_2$ is H or A, and $X_3$ is Y or A. | 178 |
| 1A7 $V_L$ | DIQMTQTTSSLSASLGDRVTISCRASQDISNYLNWYQQKPDGTVKLL IYYTSRLSGVPSRFSGSGSGKDYFLTISNLEQEDVAAYFCQQGHTLP PTFGGGTKLEIK | 179 |
| 1A7 $V_H$ | EVQLQQSGPELVKPGASVKISCKASGYTFTDSYMSWVKQSHGKTLE WIGDMYPDNGDSSYNQKFREKVTLTVDKSSTTAYMEFRSLTSEDSA VYYCVLAPRWYFSVWGTGTTVTVSS | 180 |
| 3C8 $V_L$ | DILMTQSPSSMSVSLGDTVSITCHASQDISSYIVWLQQKPGKSFRGLI YHGTNLEDGIPSRFSGSGSGADYSLTISSLESEDFADYYCVHYAQFPY TFGGGTKLEIK | 181 |
| 3C8 $V_H$ | QVQLQQSGAELVRPGTSVKVSCKASGYAFTNYLIEWVKQRPGQGLE WIGVINPGSGDTYYSEKFKGKVTLTADKSSTAYMQLSSLTSEDSAV YFCARDRLDYWGQGTTLTVSS | 182 |
| 1A7.gr.5' $V_H$ | EVQLVQSGAEVKKPGASVKVSCKASGYTFTDSYMSWVRQAPGQGL EWIGDMYPDNGDSSYNQKFRERVTLTVDTSTSTAYLELSSLRSEDTA VYYCVLAPRWYFSVWGQGTLVTVSS | 225 |
| 1A7.gr.7' $V_H$ | EVQLVQSGAEVKKPGASVKVSCKASGYTFTDSYMSWVRQAPGQGL EWIGDMYPDNGDSSYNQKFRERVTLTVDTSTSTAYLELSSLRSEDTA VYYCVLAPRWYFSVWGQGTLVTVSS | 226 |

In some embodiments, the agonist anti-human OX40 antibody is an anti-OX40 antibody described in U.S. Pat. No. 7,550,140. In some embodiments, the agonist anti-human OX40 antibody comprises a heavy chain comprising the sequence of (SEQ ID NO: 183)
EVQLVESGGGLVQPGGSLRLSCAASGFTFSNYTMNWVRQAPGKGLEWVSA

ISGSGGSTYYADSVKGRFTISRDNSKNTLYLQMNSLRAEDTAVYYCAKDR

YSQVHYALDYWGQGTLVTVSSASTKGPSVFPLAPSSKSTSGGTAALGCLV

KDYFPEPVTVSWNSGALTSGVHTFPAVLQSSGLYSLSSVVTVPSSSLGTQ

TYICNVNHKPSNTKVDKRVEPKSCDKTHTCPPCPAPELLGGPSVFLPPPK

PKDTLMISRTPEVTCVVVDVSHEDPEVKFNWYVDGVEVHNAKTKPREEQY

NSTYRVVSVLTVLHQDWLNGKEYKCKVSNKALPAPIEKTISKAKGQPREP

QVYTLPPSREEMTKNQVSLTCLVKGFYPSDIAVEWESNGQPENNYKTTPP

VLDSDGSFFLYSKLTVDKSRWQQGNVFSCSVMHEALHNHYTQKSLSLSPG

K and/or a light chain comprising the sequence of DIVMTQSPDSLPVTPGEPASISCRSSQSLLHSNGY-NYLDWYLQKAGQSPQLLIYLGSNRASGV PDRF-SGSGSGTDFTLKISRVEAEDVGVYYCQQYYNHPTTF-GQGTKLEIKRTVAAPSVFIFPPS DEQLKSGTASVVCLLNNFYPREAKVQWKVD-NALQSGNSQESVTEQDSKDSTYSLSSTLTLS KADYEKHKVYACEVTHQGLSSPVTKSFNRGEC (SEQ ID NO:184). In some embodiments, the antibody comprises at least one, two, three, four, five or six hypervariable region (HVR) sequences of antibody 008 as described in U.S. Pat. No. 7,550,140. In some embodiments, the antibody comprises a heavy chain variable region sequence and/or a light chain variable region sequence of antibody 008 as described in U.S. Pat. No. 7,550,140.

In some embodiments, the agonist anti-human OX40 antibody is an anti-OX40 antibody described in U.S. Pat. No. 7,550,140. In some embodiments, the agonist anti-human OX40 antibody comprises the sequence of MAEVQLVESGGGLVQPGGSLRLSCAASGFTFSNYT-MNWVRQAPGKGLEWVSAISGSGGST YYADSVKGR-FTISRDNSKNTLYLQMNSLRAEDTAVYY-CAKDRYSQVHYALDYWGQGT LVTVLEGTGGSGGTGSGTGTSELDIQMTQSPD-SLPVTPGEPASISCRSSQSLLHSNGYNYL DWYLQK-AGQSPQLLIYLGSNRASGVPDRFSGSGSGTDFTLKIS-RVEAEDVGVYYCQQY YNHPTTFGQGTKLEIKRAA (SEQ ID NO:185). In some embodiments, the antibody comprises at least one, two, three, four, five or six hypervariable region (HVR) sequences of antibody SCO2008 as described in U.S. Pat. No. 7,550,140. In some embodiments, the antibody comprises a heavy chain variable region sequence and/or a light chain variable region sequence of antibody SCO2008 as described in U.S. Pat. No. 7,550,140.

In some embodiments, the agonist anti-human OX40 antibody is an anti-OX40 antibody described in U.S. Pat. No. 7,550,140. In some embodiments, the agonist anti-human OX40 antibody comprises a heavy chain comprising the sequence of EVQLVESGGGLVHPGGSLRLSCAGS-GFTFSSYAMHWVRQAPGKGLEWVSAIGTGGGTYYA DSVMGRFTISRDNSKNTLYLQMNSLRAEDTAVYY-CARYDNVMGLYWFDYWGQGTLVTVS SASTKGPS-VFPLAPSSKSTSGGTAALGCLVKDYFPEPVTVSWNS-GALTSGVHTFPAVLQSSG LYSLSSVVTVPSSSLGTQTYICNVNHKPSNTKVD-KRVEPKSCDKTHTCPPCPAPELLGGPSVF LFPPKP-KDTLMISRTPEVTCVVVDVSHEDPEVKFN-WYVDGVEVHNAKTKPREEQYNSTYRV VSVLTVLHQDWLNGKEYKCKVSNKALPAPIEK-TISKAKGQPREPQVYTLPPSREEMTKNQV SLTCLVK-GFYPSDIAVEWESNGQPENNYKTTPPVLDSDGSFFLY-SKLTVDKSRWQQGNVFSC SVMHEALHNHYTQKSLSLSPGK (SEQ ID NO:186) and/or a light chain comprising the sequence of EIVLTQS-PATLSLSPGERATLSCRASQSVSSYLAWYQQK-PGQAPRLLIYDASNRATGIPARFS GSGSGTD-FTLTISSLEPEDFAVYYCQQRSNWPPAFGGGTKVEIK RTVAAPSVFIFPPSDEQLKS GTASVVCLLNNFY-PREAKVQWKVDNALQSGNSQESVTEQDSKD-STYSLSSTLTLSKADYEK HKVY-ACEVTHQGLSSPVTKSFNRGEC (SEQ ID NO:187). In some embodiments, the antibody comprises at least one, two, three, four, five or six hypervariable region (HVR) sequences of antibody 023 as described in U.S. Pat. No. 7,550,140. In some embodiments, the antibody comprises a heavy chain variable region sequence and/or a light chain variable region sequence of antibody 023 as described in U.S. Pat. No. 7,550,140.

In some embodiments, the agonist anti-human OX40 antibody is an anti-OX40 antibody described in U.S. Pat. No. 7,960,515. In some embodiments, the agonist anti-human OX40 antibody comprises a heavy chain variable region comprising the sequence of EVQLVES-GGGLVQPGGSLRLSCAASGFTFSSYSMNWVRQAPG-KGLEWVSYISSSSSTIDYAD SVKGRFTISRD-NAKNSLYLQMNSLRDEDTAVYYCARESGWYLFDY WGQGTLVTVSS (SEQ ID NO:188) and/or a light chain variable region comprising the sequence of DIQMTQSPSSLSASVGDRVTITCRASQGISSWLAWY-QQKPEKAPKSLIYAASSLQSGVPSRFS GSGSGTD-FTLTISSLQPEDFATYYCQQYNSYPPTFGGGTKVEIK (SEQ ID NO:189). In some embodiments, the antibody comprises at least one, two, three, four, five or six hypervariable region (HVR) sequences of antibody 11D4 as described in U.S. Pat. No. 7,960,515. In some embodiments, the antibody comprises a heavy chain variable region sequence and/or a light chain variable region sequence of antibody 11D4 as described in U.S. Pat. No. 7,960,515.

In some embodiments, the agonist anti-human OX40 antibody is an anti-OX40 antibody described in U.S. Pat. No. 7,960,515. In some embodiments, the agonist anti-human OX40 antibody comprises a heavy chain comprising the sequence of EVQLVESGGGLVQPGRSLRLSCAAS-GFTFDDYAMHWVRQAPGKGLEWVSGISWNSGSIGY ADSVKGRFTISRDNAKNSLYLQMNSLRAEDTALYY-CAKDQSTADYYFYYGMDVWGQGTT VTVSSASTK-GPSVFPLAPCSRSTSESTAALGCLVKDYFPEPVT-VSWNSGALTSGVHTFPAVLQ SSGLYSLSSVVTVPSSNFGTQTYTCNVDHKPSNTK-VDKTVERKCCVECPPCPAPPVAGPSVF LFPPKP-KDTLMISRTPEVTCVVVDVSHEDPEVQFN-WYVDGVEVHNAKTKPREEQFNSTFRV VSVLTVVHQDWLNGKEYKCKVSNKGLPAPIEKTISK-TKGQPREPQVYTLPPSREEMTKNQV SLTCLVKG-FYPSDIAVEWESNGQPENNYKTTPPMLDSDGSFFLY-SKLTVDKSRWQQGNVFS CSVMHEALHNHYTQKSLSLSPGK (SEQ ID NO:190) and/or a light chain comprising the sequence of EIVVTQS-PATLSLSPGERATLSCRASQSVSSYLAWYQQK-PGQAPRLLIYDASNRATGIPARFS GSGSGTD- FTLTISSLEPEDFAVYYCQQRSNWPTFGQGTKVEIKR TVAAPSVFIFPPSDEQLKSG TASVVCLLNNFYPREAK-VQWKVDNALQSGNSQESVTEQDSKD-STYSLSSTLTLSKADYEKH KVY-ACEVTHQGLSSPVTKSFNRGEC (SEQ ID NO:191). In some embodiments, the antibody comprises at least one, two, three, four, five or six hypervariable region (HVR) sequences of antibody 18D8 as described in U.S. Pat. No. 7,960,515. In some embodiments, the antibody comprises a heavy chain variable region sequence and/or a light chain variable region sequence of antibody 18D8 as described in U.S. Pat. No. 7,960,515.

In some embodiments, the agonist anti-human OX40 antibody is an anti-OX40 antibody described in WO2012/027328. In some embodiments, the agonist anti-human OX40 antibody comprises a heavy chain variable region comprising the sequence of QVQLVQSGSELKKPGASVK-VSCKASGYTFTDYSMHWVRQAPGQGLKWMGWIN-TETGEPT YADDFKGRFVFSLDTSVSTAYLQISSLKAE-DTAVYYCANPYYDYVSYYAMDYVVGQGTTVT VSS (SEQ ID NO:192) and/or a light chain variable region comprising the sequence of DIQMTQSPSSLSAS-VGDRVTITCKASQDVSTAVAWYQQKPGKAPKWYSA-SYLYTGVPSRF SGSGSGTDFTFTISSLQPEDIATYYC-QQHYSTPRTFGQGTKLEIK (SEQ ID NO:193). In some embodiments, the antibody comprises at least one, two, three, four, five or six hypervariable region (HVR) sequences of antibody hu106-222 as described in WO2012/027328. In some embodiments, the antibody comprises a heavy chain variable region sequence and/or a light chain variable region sequence of antibody hu106-222 as described in WO2012/027328.

In some embodiments, the agonist anti-human OX40 antibody is an anti-OX40 antibody described in WO2012/027328. In some embodiments, the agonist anti-human OX40 antibody comprises a heavy chain variable region comprising the sequence of EVQLVESGGGLVQPGGSL-RLSCAASEYEFPSHDMSWVRQAPGKGLELVAAINS-DGGSTYYP DTMERRFTISRDNAKNSLYLQMNSL-RAEDTAVYYCARHYDDYYAWFAYWGQGTMVTVSS (SEQ ID NO:194) and/or a light chain variable region comprising the sequence of EIVLTQSPATLSLSPGER-ATLSCRASKSVSTSGYSYMHWYQQKPGQAPRLLI-YLASNLESGVP ARFSGSGSGTDFTLTISSLEPED-FAVYYCQHSRELPLTFGGGTKVEIK (SEQ ID NO:195). In some embodiments, the antibody comprises at least one, two, three, four, five or six hypervariable region (HVR) sequences of antibody Hu119-122 as described in WO2012/027328. In some embodiments, the antibody comprises a heavy chain variable region sequence and/or a light chain variable region sequence of antibody Hu119-122 as described in WO2012/027328.

In some embodiments, the agonist anti-human OX40 antibody is an anti-OX40 antibody described in WO2013/028231. In some embodiments, the agonist anti-human OX40 antibody comprises a heavy chain comprising the sequence of MYLGLNYVFIVFLLNGVQ-SEVKLEESGGGLVQPGGSMKLSCAASGFTFSDAWM-DWVRQSP EKGLEWVaEIRSKANNHATYYAESVNGR-FTISRDDSKSSVYLQMNSLRAEDTGIYYCTWGE VFYFDYWGQGTTLTVSSASTKGPSVFPLAPSSKST-SGGTAALGCLVKDYFPEPVTVSWNSGA LTSGVHTF-PAVLQSSGLYSLSSVVTVPSSSLGTQTYITCNVNH-KPSNTKVDKKVEPKSCDKT HTCPPCPAPELLGGPSVFLFPPKPKDTLMISRTPE-VTCVVVDVSHEDPEVKFNWYVDGVEVH NAKTK-PREEQYNSTYRVVSVLTVLHQDWLNGKEYKCK-VSNKALPAPIEKTISKAKGQPREP QVYTLPPSRDELTKNQVSLTCLVKGFYPSDIAVEW-ESNGQPENNYKTTPPVLDSDGSFFLYS KLTVDKSR-WQQGNVFSCSVMHEALHNHYTQKSLSLSPGK (SEQ ID NO:196) and/or a light chain comprising the sequence of MRPSIQFLGLLLFWLHGAQCDIQMTQSPSSLSASLG-GKVTITCKSSQDINKYIAWYQHKPGK GPRLLIHYT-STLQPGIPSRFSGSGSGRDYSFSISNLEPEDIATYY-CLQYDNLLTFGAGTKLELK RTVAAPSVFIFPPSDEQLKSGTASVVCLLNNFY-PREAKVQWKVDNALQSGNSQESVTEQDS KDSTYSLSSTLTLSKADYEKHKVY-ACEVTHQGLSSPVTKSFNRGEC (SEQ ID NO:197). In some embodiments, the anti-human OX40 agonist antibody comprises a heavy chain variable region comprising the sequence of MYLGLNYVFIVFLLNGVQ-SEVKLEESGGGLVQPGGSMKLSCAASGFTFSDAWM-DWVRQSPEKG LEWVAEIRSKANNHATYYAESVN-GRFTISRDDSKSSVYLQMNSLRAEDTGIYYCTWGEV FYFDY WGQGTTLTVSS (SEQ ID NO:198) and/or a light chain variable region comprising the sequence of MRPSIQ-FLGLLLFWLHGAQCDIQMTQSPSSLSASLGGK-VTITCKSSQDINKYIAWYQHKPGKGPR LLIHYT-STLQPGIPSRFSGSGSGRDYSFSISNLEPEDIATYYCL QYDNLLTFGAGTKLELK (SEQ ID NO:199). In some embodiments, the antibody comprises at least one, two, three, four, five or six hypervariable region (HVR) sequences of antibody Mab CH 119-43-1 as described in WO2013/028231. In some embodiments, the antibody comprises a heavy chain variable region sequence and/or a light chain variable region sequence of antibody Mab CH 119-43-1 as described in WO2013/028231.

In some embodiments, the agonist anti-human OX40 antibody is an anti-OX40 antibody described in WO2013038191. In some embodiments, the agonist anti-human OX40 antibody comprises a heavy chain variable region comprising the sequence of EVQLQQSGPELVKP-GASVKMSCKASGYTFTSYVMHWVKQKPGQGLEWI-GYINPYNDGTKY NEKFKGKATLTS-DKSSSTAYMELSSLTSEDSAVYYCANYYGSSLSMDY WGQGTSVTVSS (SEQ ID NO:200) and/or a light chain variable region comprising the sequence of DIQMTQTTSSLSASLGDRVTISCRASQDISNYLNWY-QQKPDGTVKLLIYYTSRLHSGVPSRFS GSGSGTDYS-LTISNLEQEDIATYFCQQGNTLPWTFGGGTKLEIKR (SEQ ID NO:201). In some embodiments, the antibody comprises at least one, two, three, four, five or six hypervariable region (HVR) sequences of antibody clone 20E5 as described in WO2013038191. In some embodiments, the antibody comprises a heavy chain variable region sequence and/or a light chain variable region sequence of antibody clone 20E5 as described in WO2013038191.

In some embodiments, the agonist anti-human OX40 antibody is an anti-OX40 antibody described in WO2013038191. In some embodiments, the agonist anti-human OX40 antibody comprises a heavy chain variable region comprising the sequence of EVQLQQSGPELVKP-GASVKISCKTSGYTFKDYTMHWVKQSHGKSLEWIG-GIYPNNGGSTYN QNFKDKATLTVDKSSSTAYME-FRSLTSEDSAVYYCARMGYHGPHLDFDVWGAGTTV TVSP (SEQ ID NO:202) and/or a light chain variable region comprising the sequence of DIVMTQSHKFMST-SLGDRVSITCKASQDVGAAVaWYQQKPGQSP-KLLIYWASTRHTGVPDR FTGGGSGTDFTLTISN-VQSEDLTDYFCQQYINYPLTFGGGTKLEIKR (SEQ ID NO:203). In some embodiments, the antibody comprises at least one, two, three, four, five or six hypervariable region (HVR) sequences of antibody clone 12H3 as described in WO2013038191. In some embodiments, the antibody comprises a heavy chain variable region sequence and/or a light chain variable region sequence of antibody clone 12H3 as described in WO2013038191.

In some embodiments, the agonist anti-human OX40 antibody is an anti-OX40 antibody described in WO2014148895A1. In some embodiments, the agonist anti-human OX40 antibody comprises a heavy chain variable region comprising the sequence of QVQLVQSGAEVKKPGASVKVSCKASGYTFTSYVMHWVRQAPGQRLEWMGYINPYNDGTK YNEKFKGRVTITSDTSASTAYMELSSLRSEDTAVYYCANYYGSSLSMDYWGQGTLVTVSS (SEQ ID NO:204) and/or a light chain variable region comprising the sequence of DIQMTQSPSSLSASVGDRVTITCRASQDISNYLNWYQQKPGKAPKLLIYYTSRLHSGVPSRFS GSGSGTDYTLTISSLQPEDFATYYCQQGNTLPWTFGQGTKVEIKR (SEQ ID NO:205). In some embodiments, the antibody comprises at least one, two, three, four, five or six hypervariable region (HVR) sequences of antibody clone 20E5 as described in WO2014148895A1. In some embodiments, the antibody comprises a heavy chain variable region sequence and/or a light chain variable region sequence of antibody clone 20E5 as described in WO2014148895A1.

In some embodiments, the agonist anti-human OX40 antibody is an anti-OX40 antibody described in WO2014148895A1. In some embodiments, the agonist anti-human OX40 antibody comprises a heavy chain variable region comprising the sequence of QVQLVQSGAEVKKPGASVKVSCKASGYTFTSYVMHWVRQAPGQRLEWMGYINPYNDGTK YNEKFKGRVTITSDTSASTAYMELSSLRSEDTAVYYCANYYGSSLSMDYWGQGTLVTVSS (SEQ ID NO:204) and/or a light chain variable region comprising the sequence of DIQMTQSPSSLSASVGDRVTITCRASQDISNYLNWYQQKPGKAVKLLIYYTSRLHSGVPSRFS GSGSGTDYTLTISSLQPEDFATYFCQQGNTLPWTFGQGTKVEIKR (SEQ ID NO:206). In some embodiments, the antibody comprises at least one, two, three, four, five or six hypervariable region (HVR) sequences of antibody clone 20E5 as described in WO2014148895A1. In some embodiments, the antibody comprises a heavy chain variable region sequence and/or a light chain variable region sequence of antibody clone 20E5 as described in WO2014148895A1.

In some embodiments, the agonist anti-human OX40 antibody is an anti-OX40 antibody described in WO2014148895A1. In some embodiments, the agonist anti-human OX40 antibody comprises a heavy chain variable region comprising the sequence of QVQLVQSGAEVKKPGASVKVSCKASGYTFTSYVMHWVRQAPGQRLEWIGYINPYNDGTK YNEKFKGRATITSDTSASTAYMELSSLRSEDTAVYYCANYYGSSLSMDYWGQGTLVTVSS (SEQ ID NO:207) and/or a light chain variable region comprising the sequence of DIQMTQSPSSLSASVGDRVTITCRASQDISNYLNWYQQKPGKAPKLLIYYTSRLHSGVPSRFS GSGSGTDYTLTISSLQPEDFATYYCQQGNTLPWTFGQGTKVEIKR (SEQ ID NO:205). In some embodiments, the antibody comprises at least one, two, three, four, five or six hypervariable region (HVR) sequences of antibody clone 20E5 as described in WO2014148895A1. In some embodiments, the antibody comprises a heavy chain variable region sequence and/or a light chain variable region sequence of antibody clone 20E5 as described in WO2014148895A1.

In some embodiments, the agonist anti-human OX40 antibody is an anti-OX40 antibody described in WO2014148895A1. In some embodiments, the agonist anti-human OX40 antibody comprises a heavy chain variable region comprising the sequence of QVQLVQSGAEVKKPGASVKVSCKASGYTFTSYVMHWVRQAPGQRLEWIGYINPYNDGTK YNEKFKGRATITSDTSASTAYMELSSLRSEDTAVYYCANYYGSSLSMDYWGQGTLVTVSS (SEQ ID NO:207) and/or a light chain variable region comprising the sequence of DIQMTQSPSSLSASVGDRVTITCRASQDISNYLNWYQQKPGKAVKLLIYYTSRLHSGVPSRFS GSGSGTDYTLTISSLQPEDFATYFCQQGNTLPWTFGQGTKVEIKR (SEQ ID NO:206). In some embodiments, the antibody comprises at least one, two, three, four, five or six hypervariable region (HVR) sequences of antibody clone 20E5 as described in WO2014148895A1. In some embodiments, the antibody comprises a heavy chain variable region sequence and/or a light chain variable region sequence of antibody clone 20E5 as described in WO2014148895A1.

In some embodiments, the agonist anti-human OX40 antibody is an anti-OX40 antibody described in WO2014148895A1. In some embodiments, the agonist anti-human OX40 antibody comprises a heavy chain variable region comprising the sequence of QVQLVQSGAEVKKPGASVKVSCKASGYTFTSYVMHWVRQAPGQRLEWIGYINPYNDGTK YNEKFKGRATLTSDKSASTAYMELSSLRSEDTAVYYCANYYGSSLSMDYWGQGTLVTVSS (SEQ ID NO:208) and/or a light chain variable region comprising the sequence of DIQMTQSPSSLSASVGDRVTITCRASQDISNYLNWYQQKPGKAPKLLIYYTSRLHSGVPSRFS GSGSGTDYTLTISSLQPEDFATYYCQQGNTLPWTFGQGTKVEIKR (SEQ ID NO:205). In some embodiments, the antibody comprises at least one, two, three, four, five or six hypervariable region (HVR) sequences of antibody clone 20E5 as described in WO2014148895A1. In some embodiments, the antibody comprises a heavy chain variable region sequence and/or a light chain variable region sequence of antibody clone 20E5 as described in WO2014148895A1.

In some embodiments, the agonist anti-human OX40 antibody is an anti-OX40 antibody described in WO2014148895A1. In some embodiments, the agonist anti-human OX40 antibody comprises a heavy chain variable region comprising the sequence of QVQLVQSGAEVKKPGASVKVSCKASGYTFTSYVMHWVRQAPGQRLEWIGYINPYNDGTK YNEKFKGRATLTSDKSASTAYMELSSLRSEDTAVYYCANYYGSSLSMDYWGQGTLVTVSS (SEQ ID NO:208) and/or a light chain variable region comprising the sequence of DIQMTQSPSSLSASVGDRVTITCRASQDISNYLNWYQQKPGKAVKLLIYYTSRLHSGVPSRFS GSGSGTDYTLTISSLQPEDFATYFCQQGNTLPWTFGQGTKVEIKR (SEQ ID NO:206). In some embodiments, the antibody comprises at least one, two, three, four, five or six hypervariable region (HVR) sequences of antibody clone 20E5 as described in WO2014148895A1. In some embodiments, the antibody comprises a heavy chain variable region sequence and/or a light chain variable region sequence of antibody clone 20E5 as described in WO2014148895A1.

In some embodiments, the agonist anti-human OX40 antibody is an anti-OX40 antibody described in WO2014148895A1. In some embodiments, the agonist anti-human OX40 antibody comprises a heavy chain variable region comprising the sequence of QVQLVQSGAEVKKPGSSVKVSCKASGYTFKDYTMHWVRQAPGQGLEWMGGIYPNNGGST YNQNFKDRVTITADKSTSTAYMELSSLRSEDTAVYYCARMGYHGPHLDFDVWGQGTTVTV SS (SEQ ID NO:209) and/or a light chain variable region comprising the sequence of DIQMTQSPSSLSASVGDRVTITCKASQDVGAAVaWYQQKPGKAPKLLIYWASTRHTGVPSRF SGSGSGTDFTLTISSLQPEDFATYYCQQYINYPLTFGGGTKVEIKR (SEQ ID NO:210). In some embodiments, the antibody comprises at least one, two, three, four, five or six hypervariable region (HVR) sequences of antibody clone clone 12H3 as described in WO2014148895A1. In some embodiments, the antibody comprises a heavy chain variable region sequence and/or a light chain variable region sequence of antibody clone 12H3 as described in WO2014148895A1.

In some embodiments, the agonist anti-human OX40 antibody is an anti-OX40 antibody described in WO2014148895A1. In some embodiments, the agonist antihuman OX40 antibody comprises a heavy chain variable region comprising the sequence of QVQLVQSGAEVKKPGSSVKVSCKASGYTFKDYTMHWVRQAPGQGLEWMGGIYPNNGGST YNQNFKDRVTITADKSTSTAYMELSSLRSEDTAVYYCARMGYHGPHLDFDVW GQGTTVTV SS (SEQ ID NO:209) and/or a light chain variable region comprising the sequence of DIQMTQSPSSLSASVGDRVTITCKASQDVGAAVaWYQQKPGKAPKWYWASTRHTGVPDR FSGGGSGTDFTLTISSLQPEDFATYYCQQYINYPLTFGGGTKVEIKR (SEQ ID NO:211). In some embodiments, the antibody comprises at least one, two, three, four, five or six hypervariable region (HVR) sequences of antibody clone 12H3 as described in WO2014148895A1. In some embodiments, the antibody comprises a heavy chain variable region sequence and/or a light chain variable region sequence of antibody clone 12H3 as described in WO2014148895A1.

In some embodiments, the agonist anti-human OX40 antibody is an anti-OX40 antibody described in WO2014148895A1. In some embodiments, the agonist antihuman OX40 antibody comprises a heavy chain variable region comprising the sequence of QVQLVQSGAEVKKPGSSVKVSCKASGYTFKDYTMHWVRQAPGQGLEWIGGIYPNNGGSTY NQNFKDRVTLTADKSTSTAYMELSSLRSEDTAVYYCARMGYHGPHLDFDVW GQGTTVTVS S (SEQ ID NO:212) and/or a light chain variable region comprising the sequence of DIQMTQSPSSLSASVGDRVTITCKASQDVGAAVaWYQQKPGKAPKWYWASTRHTGVPSRF SGSGSGTDFTLTISSLQPEDFATYYCQQYINYPLTFGGGTKVEIKR (SEQ ID NO:210). In some embodiments, the antibody comprises at least one, two, three, four, five or six hypervariable region (HVR) sequences of antibody clone 12H3 as described in WO2014148895A1. In some embodiments, the antibody comprises a heavy chain variable region sequence and/or a light chain variable region sequence of antibody clone 12H3 as described in WO2014148895A1.

In some embodiments, the agonist anti-human OX40 antibody is an anti-OX40 antibody described in WO2014148895A1. In some embodiments, the agonist antihuman OX40 antibody comprises a heavy chain variable region comprising the sequence of QVQLVQSGAEVKKPGSSVKVSCKASGYTFKDYTMHWVRQAPGQGLEWIGGIYPNNGGSTY NQNFKDRVTLTADKSTSTAYMELSSLRSEDTAVYYCARMGYHGPHLDFDVW GQGTTVTVS S (SEQ ID NO:212) and/or a light chain variable region comprising the sequence of DIQMTQSPSSLSASVGDRVTITCKASQDVGAAVaWYQQKPGKAPKWYWASTRHTGVPDR FSGGGSGTDFTLTISSLQPEDFATYYCQQYINYPLTFGGGTKVEIKR (SEQ ID NO:211). In some embodiments, the antibody comprises at least one, two, three, four, five or six hypervariable region (HVR) sequences of antibody clone 12H3 as described in WO2014148895A1. In some embodiments, the antibody comprises a heavy chain variable region sequence and/or a light chain variable region sequence of antibody clone 12H3 as described in WO2014148895A1.

In some embodiments, the agonist anti-human OX40 antibody is an anti-OX40 antibody described in WO2014148895A1. In some embodiments, the agonist antihuman OX40 antibody comprises a heavy chain variable region comprising the sequence of QVQLVQSGAEVKKPGSSVKVSCKASGYTFKDYTMHWVRQAPGQGLEWIGGIYPNNGGSTY NQNFKDRATLTVDKSTSTAYMELSSLRSEDTAVYYCARMGYHGPHLDFDVW GQGTTVTVS S (SEQ ID NO:213) and/or a light chain variable region comprising the sequence of DIQMTQSPSSLSASVGDRVTITCKASQDVGAAVaWYQQKPGKAPKWYWASTRHTGVPSRF SGSGSGTDFTLTISSLQPEDFATYYCQQYINYPLTFGGGTKVEIKR (SEQ ID NO:210). In some embodiments, the antibody comprises at least one, two, three, four, five or six hypervariable region (HVR) sequences of antibody clone 12H3 as described in WO2014148895A1. In some embodiments, the antibody comprises a heavy chain variable region sequence and/or a light chain variable region sequence of antibody clone 12H3 as described in WO2014148895A1.

In some embodiments, the agonist anti-human OX40 antibody is an anti-OX40 antibody described in WO2014148895A1. In some embodiments, the agonist antihuman OX40 antibody comprises a heavy chain variable region comprising the sequence of QVQLVQSGAEVKKPGSSVKVSCKASGYTFKDYTMHWVRQAPGQGLEWIGGIYPNNGGSTY NQNFKDRATLTVDKSTSTAYMELSSLRSEDTAVYYCARMGYHGPHLDFDVW GQGTTVTVS S (SEQ ID NO:213) and/or a light chain variable region comprising the sequence of DIQMTQSPSSLSASVGDRVTITCKASQDVGAAVaWYQQKPGKAPKWYWASTRHTGVPDR FSGGGSGTDFTLTISSLQPEDFATYYCQQYINYPLTFGGGTKVEIKR (SEQ ID NO:211). In some embodiments, the antibody comprises at least one, two, three, four, five or six hypervariable region (HVR) sequences of antibody clone 12H3 as described in WO2014148895A1. In some embodiments, the antibody comprises a heavy chain variable region sequence and/or a light chain variable region sequence of antibody clone 12H3 as described in WO2014148895A1.

In some embodiments, the agonist anti-human OX40 antibody is L106 BD (Pharmingen Product #340420). In some embodiments, the antibody comprises at least one, two, three, four, five or six hypervariable region (HVR) sequences of antibody L106 (BD Pharmingen Pduct #340420). In some embodiments, the antibody comprises a heavy chain variable region sequence and/or a light chain variable region sequence of antibody L106 (BD Pharmingen Product #340420).

In some embodiments, the agonist anti-human OX40 antibody is ACT35 (Santa Cruz Biotechnology, Catalog #20073). In some embodiments, the antibody comprises at least one, two, three, four, five or six hypervariable region (HVR) sequences of antibody ACT35 (Santa Cruz Biotechnology, Catalog #20073). In some embodiments, the antibody comprises a heavy chain variable region sequence and/or a light chain variable region sequence of antibody ACT35 (Santa Cruz Biotechnology, Catalog #20073).

In some embodiments, the agonist anti-human OX40 antibody is MEDI6469. In some embodiments, the antibody comprises at least one, two, three, four, five or six hypervariable region (HVR) sequences of antibody MEDI6469. In some embodiments, the antibody comprises a heavy chain variable region sequence and/or a light chain variable region sequence of antibody MEDI6469.

In some embodiments, the agonist anti-human OX40 antibody is MEDI0562. In some embodiments, the antibody comprises at least one, two, three, four, five or six hypervariable region (HVR) sequences of antibody MEDI0562. In some embodiments, the antibody comprises a heavy chain variable region sequence and/or a light chain variable region sequence of antibody MEDI0562.

Other OX40 Agonists

OX40 agonists useful for the methods described herein are in no way intended to be limited to antibodies. Non-antibody OX40 agonists are contemplated and well known in the art.

As described above, OX40L (also known as CD134L) serves as a ligand for OX40. As such, agonists that present part or all of OX40L may serve as OX40 agonists. In some embodiments, an OX40 agonist may include one or more extracellular domains of OX40L. Examples of extracellular domains of OX40L may include OX40-binding domains. In some embodiments, an OX40 agonist may be a soluble form of OX40L that includes one or more extracellular domains of OX40L but lacks other, insoluble domains of the protein, e.g., transmembrane domains. In some embodiments, an OX40 agonist is a soluble protein that includes one or more extracellular domains of OX40L able to bind OX40L. In some embodiments, an OX40 agonist may be linked to another protein domain, e.g., to increase its effectiveness, half-life, or other desired characteristics. In some embodiments, an OX40 agonist may include one or more extracellular domains of OX40L linked to an immunoglobulin Fc domain.

In some embodiments, an OX40 agonist may be any one of the OX40 agonists described in U.S. Pat. No. 7,696,175.

In some embodiments, an OX40 agonist may be an oligomeric or multimeric molecule. For example, an OX40 agonist may contain one or more domains (e.g., a leucine zipper domain) that allows proteins to oligomerize. In some embodiments, an OX40 agonist may include one or more extracellular domains of OX40L linked to one or more leucine zipper domains.

In some embodiments, an OX40 agonist may be any one of the OX40 agonists described in European Patent No. EP0672141 B1.

In some embodiments, an OX40 agonist may be a trimeric OX40L fusion protein. For example, an OX40 agonist may include one or more extracellular domains of OX40L linked to an immunoglobulin Fc domain and a trimerization domain (including without limitation an isoleucine zipper domain).

In some embodiments, an OX40 agonist may be any one of the OX40 agonists described in International Publication No. WO2006/121810. In some embodiments, the OX40 agonist is MEDI6383.

In a further aspect, an anti-OX40 agonist and/or antibody according to any of the above embodiments may incorporate any of the features, singly or in combination, as described below.

1. Antibody Affinity

In certain embodiments, an antibody provided herein has a dissociation constant (Kd) of ≤1 μM, ≤100 nM, ≤10 nM, ≤1 nM, ≤0.1 nM, ≤0.01 nM, or ≤0.001 nM (e.g. 10−8 M or less, e.g. from 10−8 M to 10−13 M, e.g., from 10−9 M to 10−13 M).

In one embodiment, Kd is measured by a radiolabeled antigen binding assay (RIA). In one embodiment, an RIA is performed with the Fab version of an antibody of interest and its antigen. For example, solution binding affinity of Fabs for antigen is measured by equilibrating Fab with a minimal concentration of (125I)-labeled antigen in the presence of a titration series of unlabeled antigen, then capturing bound antigen with an anti-Fab antibody-coated plate (see, e.g., Chen et al., J. Mol. Biol. 293:865-881 (1999)). To establish conditions for the assay, MICROTITER® multi-well plates (Thermo Scientific) are coated overnight with 5 μg/ml of a capturing anti-Fab antibody (Cappel Labs) in 50 mM sodium carbonate (pH 9.6), and subsequently blocked with 2% (w/v) bovine serum albumin in PBS for two to five hours at room temperature (approximately 23° C.). In a non-adsorbent plate (Nunc #269620), 100 pM or 26 pM [125I]-antigen are mixed with serial dilutions of a Fab of interest (e.g., consistent with assessment of the anti-VEGF antibody, Fab-12, in Presta et al., Cancer Res. 57:4593-4599 (1997)). The Fab of interest is then incubated overnight; however, the incubation may continue for a longer period (e.g., about 65 hours) to ensure that equilibrium is reached. Thereafter, the mixtures are transferred to the capture plate for incubation at room temperature (e.g., for one hour). The solution is then removed and the plate washed eight times with 0.1% polysorbate 20 (TWEEN-20®) in PBS. When the plates have dried, 150 μl/well of scintillant (MICROSCINT-20 ™; Packard) is added, and the plates are counted on a TOPCOUNT™ gamma counter (Packard) for ten minutes. Concentrations of each Fab that give less than or equal to 20% of maximal binding are chosen for use in competitive binding assays.

According to another embodiment, Kd is measured using a BIACORE® surface plasmon resonance assay. For example, an assay using a BIACORE®-2000 or a BIACORE®-3000 (BIAcore, Inc., Piscataway, N.J.) is performed at 25° C. with immobilized antigen CM5 chips at ~10 response units (RU). In one embodiment, carboxymethylated dextran biosensor chips (CM5, BIACORE, Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, to 5 μg/ml (~0.2 μM) before injection at a flow rate of 5 μl/minute to achieve approximately 10 response units (RU) of coupled protein. Following the injection of antigen, 1 M ethanolamine is injected to block unreacted groups. For kinetics measurements, two-fold serial dilutions of Fab (0.78 nM to 500 nM) are injected in PBS with 0.05% polysorbate 20 (TWEEN-20™) surfactant (PBST) at 25° C. at a flow rate of approximately 25 μl/min. Association rates (kon) and dissociation rates (koff) are calculated using a simple one-to-one Langmuir binding model (BIACORE® Evaluation Software version 3.2) by simultaneously fitting the association and dissociation sensorgrams. The equilibrium dissociation constant (Kd) is calculated as the ratio koff/kon. See, e.g., Chen et al., J. Mol. Biol. 293:865-881 (1999). If the on-rate exceeds 106 M-1 s-1 by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophotometer (Aviv Instruments) or a 8000-series SLM-AMINCO™ spectrophotometer (ThermoSpectronic) with a stirred cuvette.

2. Antibody Fragments

In certain embodiments, an antibody provided herein is an antibody fragment. Antibody fragments include, but are not limited to, Fab, Fab', Fab'-SH, F(ab')2, Fv, and scFv fragments, and other fragments described below. For a review of certain antibody fragments, see Hudson et al. Nat. Med. 9:129-134 (2003). For a review of scFv fragments, see, e.g., Pluckthün, in The Pharmacology of Monoclonal Antibodies, vol. 113, Rosenburg and Moore eds., (Springer-Verlag, New York), pp. 269-315 (1994); see also WO 93/16185; and U.S. Pat. Nos. 5,571,894 and 5,587,458. For discussion of Fab and F(ab')2 fragments comprising salvage receptor binding epitope residues and having increased in vivo half-life, see U.S. Pat. No. 5,869,046.

Diabodies are antibody fragments with two antigen-binding sites that may be bivalent or bispecific. See, for example, EP 404,097; WO 1993/01161; Hudson et al., Nat. Med. 9:129-134 (2003); and Hollinger et al., Proc. Natl. Acad. Sci. USA 90: 6444-6448 (1993). Triabodies and tetrabodies are also described in Hudson et al., Nat. Med. 9:129-134 (2003).

Single-domain antibodies are antibody fragments comprising all or a portion of the heavy chain variable domain or all or a portion of the light chain variable domain of an antibody. In certain embodiments, a single-domain antibody is a human single-domain antibody (Domantis, Inc., Waltham, Mass.; see, e.g., U.S. Pat. No. 6,248,516 B1).

Antibody fragments can be made by various techniques, including but not limited to proteolytic digestion of an intact antibody as well as production by recombinant host cells (e.g. *E. coli* or phage), as described herein.

3. Chimeric and Humanized Antibodies

In certain embodiments, an antibody provided herein is a chimeric antibody. Certain chimeric antibodies are described, e.g., in U.S. Pat. No. 4,816,567; and Morrison et al., Proc. Natl. Acad. Sci. USA, 81:6851-6855 (1984)). In one example, a chimeric antibody comprises a non-human variable region (e.g., a variable region derived from a mouse, rat, hamster, rabbit, or non-human primate, such as a monkey) and a human constant region. In a further example, a chimeric antibody is a "class switched" antibody in which the class or subclass has been changed from that of the parent antibody. Chimeric antibodies include antigen-binding fragments thereof.

In certain embodiments, a chimeric antibody is a humanized antibody. Typically, a non-human antibody is humanized to reduce immunogenicity to humans, while retaining the specificity and affinity of the parental non-human antibody. Generally, a humanized antibody comprises one or more variable domains in which HVRs, e.g., CDRs, (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the HVR residues are derived), e.g., to restore or improve antibody specificity or affinity.

Humanized antibodies and methods of making them are reviewed, e.g., in Almagro and Fransson, Front. Biosci. 13:1619-1633 (2008), and are further described, e.g., in Riechmann et al., Nature 332:323-329 (1988); Queen et al., Proc. Nat'l Acad. Sci. USA 86:10029-10033 (1989); U.S. Pat. Nos. 5,821,337, 7,527,791, 6,982,321, and 7,087,409; Kashmiri et al., Methods 36:25-34 (2005) (describing specificity determining region (SDR) grafting); Padlan, Mol. Immunol. 28:489-498 (1991) (describing "resurfacing"); Dall'Acqua et al., Methods 36:43-60 (2005) (describing "FR shuffling"); and Osbourn et al., Methods 36:61-68 (2005) and Klimka et al., Br. J. Cancer, 83:252-260 (2000) (describing the "guided selection" approach to FR shuffling).

Human framework regions that may be used for humanization include but are not limited to: framework regions selected using the "best-fit" method (see, e.g., Sims et al. J. Immunol. 151:2296 (1993)); framework regions derived from the consensus sequence of human antibodies of a particular subgroup of light or heavy chain variable regions (see, e.g., Carter et al. Proc. Natl. Acad. Sci. USA, 89:4285 (1992); and Presta et al. J. Immunol., 151:2623 (1993)); human mature (somatically mutated) framework regions or human germline framework regions (see, e.g., Almagro and Fransson, Front. Biosci. 13:1619-1633 (2008)); and framework regions derived from screening FR libraries (see, e.g., Baca et al., J. Biol. Chem. 272:10678-10684 (1997) and Rosok et al., J. Biol. Chem. 271:22611-22618 (1996)).

4. Human Antibodies

In certain embodiments, an antibody provided herein is a human antibody. Human antibodies can be produced using various techniques known in the art. Human antibodies are described generally in van Dijk and van de Winkel, Curr. Opin. Pharmacol. 5: 368-74 (2001) and Lonberg, Curr. Opin. Immunol. 20:450-459 (2008).

Human antibodies may be prepared by administering an immunogen to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic mice, the endogenous immunoglobulin loci have generally been inactivated. For review of methods for obtaining human antibodies from transgenic animals, see Lonberg, Nat. Biotech. 23:1117-1125 (2005). See also, e.g., U.S. Pat. Nos. 6,075,181 and 6,150,584 describing XENO-MOUSE™ technology; U.S. Pat. No. 5,770,429 describing HuMab® technology; U.S. Pat. No. 7,041,870 describing K-M MOUSE® technology, and U.S. Patent Application Publication No. US 2007/0061900, describing VelociMouse® technology). Human variable regions from intact antibodies generated by such animals may be further modified, e.g., by combining with a different human constant region.

Human antibodies can also be made by hybridoma-based methods. Human myeloma and mouse-human heteromyeloma cell lines for the production of human monoclonal antibodies have been described. (See, e.g., Kozbor J. Immunol., 133: 3001 (1984); Brodeur et al., Monoclonal Antibody Production Techniques and Applications, pp. 51-63 (Marcel Dekker, Inc., New York, 1987); and Boerner et al., J. Immunol., 147: 86 (1991).) Human antibodies generated via human B-cell hybridoma technology are also described in Li et al., Proc. Natl. Acad. Sci. USA, 103:3557-3562 (2006). Additional methods include those described, for example, in U.S. Pat. No. 7,189,826 (describing production of monoclonal human IgM antibodies from hybridoma cell lines) and Ni, Xiandai Mianyixue, 26(4):265-268 (2006) (describing human-human hybridomas). Human hybridoma technology (Trioma technology) is also described in Vollmers and Brandlein, Histology and Histopathology, 20(3):927-937 (2005) and Vollmers and Brandlein, Methods and Findings in Experimental and Clinical Pharmacology, 27(3):185-91 (2005).

Human antibodies may also be generated by isolating Fv clone variable domain sequences selected from human-derived phage display libraries. Such variable domain sequences may then be combined with a desired human constant domain. Techniques for selecting human antibodies from antibody libraries are described below.

5. Library-Derived Antibodies

Antibodies of the invention may be isolated by screening combinatorial libraries for antibodies with the desired activity or activities. For example, a variety of methods are known in the art for generating phage display libraries and screening such libraries for antibodies possessing the desired binding characteristics. Such methods are reviewed, e.g., in Hoogenboom et al. in Methods in Molecular Biology 178: 1-37 (O'Brien et al., ed., Human Press, Totowa, N.J., 2001) and further described, e.g., in the McCafferty et al., Nature 348:552-554; Clackson et al., Nature 352: 624-628 (1991); Marks et al., J. Mol. Biol. 222: 581-597 (1992); Marks and Bradbury, in Methods in Molecular Biology 248:161-175 (Lo, ed., Human Press, Totowa, N.J., 2003); Sidhu et al., J. Mol. Biol. 338(2): 299-310 (2004); Lee et al., J. Mol. Biol. 340(5): 1073-1093 (2004); Fellouse, Proc. Natl. Acad. Sci. USA 101(34): 12467-12472 (2004); and Lee et al., J. Immunol. Methods 284(1-2): 119-132 (2004).

In certain phage display methods, repertoires of VH and VL genes are separately cloned by polymerase chain reaction (PCR) and recombined randomly in phage libraries, which can then be screened for antigen-binding phage as described in Winter et al., Ann. Rev. Immunol., 12: 433-455 (1994). Phage typically display antibody fragments, either as single-chain Fv (scFv) fragments or as Fab fragments. Libraries from immunized sources provide high-affinity antibodies to the immunogen without the requirement of constructing hybridomas. Alternatively, the naive repertoire can be cloned (e.g., from human) to provide a single source of antibodies to a wide range of non-self and also self antigens without any immunization as described by Griffiths et al., EMBO J, 12: 725-734 (1993). Finally, naive libraries can also be made synthetically by cloning unrearranged V-gene segments from stem cells, and using PCR primers containing random sequence to encode the highly variable CDR3 regions and to accomplish rearrangement in vitro, as described by Hoogenboom and Winter, J. Mol. Biol., 227: 381-388 (1992). Patent publications describing human antibody phage libraries include, for example: U.S. Pat. No. 5,750,373, and US Patent Publication Nos. 2005/0079574, 2005/0119455, 2005/0266000, 2007/0117126, 2007/0160598, 2007/0237764, 2007/0292936, and 2009/0002360.

Antibodies or antibody fragments isolated from human antibody libraries are considered human antibodies or human antibody fragments herein.

6. Multispecific Antibodies

In certain embodiments, an antibody provided herein is a multispecific antibody, e.g. a bispecific antibody. Multispecific antibodies are monoclonal antibodies that have binding specificities for at least two different sites. In certain embodiments, one of the binding specificities is for OX40 and the other is for any other antigen. In certain embodiments, bispecific antibodies may bind to two different epitopes of OX40. Bispecific antibodies may also be used to localize cytotoxic agents to cells which express OX40. Bispecific antibodies can be prepared as full length antibodies or antibody fragments.

Techniques for making multispecific antibodies include, but are not limited to, recombinant co-expression of two immunoglobulin heavy chain-light chain pairs having different specificities (see Milstein and Cuello, Nature 305: 537 (1983)), WO 93/08829, and Traunecker et al., EMBO J. 10: 3655 (1991)), and "knob-in-hole" engineering (see, e.g., U.S. Pat. No. 5,731,168). Multi-specific antibodies may also be made by engineering electrostatic steering effects for making antibody Fc-heterodimeric molecules (WO 2009/089004A1); cross-linking two or more antibodies or fragments (see, e.g., U.S. Pat. No. 4,676,980, and Brennan et al., Science, 229: 81 (1985)); using leucine zippers to produce bi-specific antibodies (see, e.g., Kostelny et al., J. Immunol., 148(5):1547-1553 (1992)); using "diabody" technology for making bispecific antibody fragments (see, e.g., Hollinger et al., Proc. Natl. Acad. Sci. USA, 90:6444-6448 (1993)); and using single-chain Fv (sFv) dimers (see, e.g. Gruber et al., J. Immunol., 152:5368 (1994)); and preparing trispecific antibodies as described, e.g., in Tutt et al. J. Immunol. 147: 60 (1991).

Engineered antibodies with three or more functional antigen binding sites, including "Octopus antibodies," are also included herein (see, e.g. US 2006/0025576A1).

The antibody or fragment herein also includes a "Dual Acting FAb" or "DAF" comprising an antigen binding site that binds to OX40 as well as another, different antigen (see, US 2008/0069820, for example).

7. Antibody Variants

In certain embodiments, amino acid sequence variants of the antibodies provided herein are contemplated. For example, it may be desirable to improve the binding affinity and/or other biological properties of the antibody. Amino acid sequence variants of an antibody may be prepared by introducing appropriate modifications into the nucleotide sequence encoding the antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, e.g., antigen-binding.

a) Substitution, Insertion, and Deletion Variants

In certain embodiments, antibody variants having one or more amino acid substitutions are provided. Sites of interest for substitutional mutagenesis include the HVRs and FRs. Conservative substitutions are shown in Table A under the heading of "preferred substitutions." More substantial changes are provided in Table A under the heading of "exemplary substitutions," and as further described below in reference to amino acid side chain classes. Amino acid substitutions may be introduced into an antibody of interest and the products screened for a desired activity, e.g., retained/improved antigen binding, decreased immunogenicity, or improved ADCC or CDC.

TABLE A

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |

TABLE A-continued

| Original Residue | Exemplary Substitutions | Preferred Substitutions |
|---|---|---|
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped according to common side-chain properties:
(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe.

Non-conservative substitutions will entail exchanging a member of one of these classes for another class.

One type of substitutional variant involves substituting one or more hypervariable region residues of a parent antibody (e.g. a humanized or human antibody). Generally, the resulting variant(s) selected for further study will have modifications (e.g., improvements) in certain biological properties (e.g., increased affinity, reduced immunogenicity) relative to the parent antibody and/or will have substantially retained certain biological properties of the parent antibody. An exemplary substitutional variant is an affinity matured antibody, which may be conveniently generated, e.g., using phage display-based affinity maturation techniques such as those described herein. Briefly, one or more HVR residues are mutated and the variant antibodies displayed on phage and screened for a particular biological activity (e.g. binding affinity).

Alterations (e.g., substitutions) may be made in HVRs, e.g., to improve antibody affinity. Such alterations may be made in HVR "hotspots," i.e., residues encoded by codons that undergo mutation at high frequency during the somatic maturation process (see, e.g., Chowdhury, Methods Mol. Biol. 207:179-196 (2008)), and/or residues that contact antigen, with the resulting variant VH or VL being tested for binding affinity. Affinity maturation by constructing and reselecting from secondary libraries has been described, e.g., in Hoogenboom et al. in Methods in Molecular Biology 178:1-37 (O'Brien et al., ed., Human Press, Totowa, N.J., (2001).) In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity. Another method to introduce diversity involves HVR-directed approaches, in which several HVR residues (e.g., 4-6 residues at a time) are randomized. HVR residues involved in antigen binding may be specifically identified, e.g., using alanine scanning mutagenesis or modeling. CDR-H3 and CDR-L3 in particular are often targeted.

In certain embodiments, substitutions, insertions, or deletions may occur within one or more HVRs so long as such alterations do not substantially reduce the ability of the antibody to bind antigen. For example, conservative alterations (e.g., conservative substitutions as provided herein) that do not substantially reduce binding affinity may be made in HVRs. Such alterations may, for example, be outside of antigen contacting residues in the HVRs. In certain embodiments of the variant VH and VL sequences provided above, each HVR either is unaltered, or contains no more than one, two or three amino acid substitutions.

A useful method for identification of residues or regions of an antibody that may be targeted for mutagenesis is called "alanine scanning mutagenesis" as described by Cunningham and Wells (1989) Science, 244:1081-1085. In this method, a residue or group of target residues (e.g., charged residues such as arg, asp, his, lys, and glu) are identified and replaced by a neutral or negatively charged amino acid (e.g., alanine or polyalanine) to determine whether the interaction of the antibody with antigen is affected. Further substitutions may be introduced at the amino acid locations demonstrating functional sensitivity to the initial substitutions. Alternatively, or additionally, a crystal structure of an antigen-antibody complex to identify contact points between the antibody and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g. for ADEPT) or a polypeptide which increases the serum half-life of the antibody.

b) Glycosylation Variants

In certain embodiments, an antibody provided herein is altered to increase or decrease the extent to which the antibody is glycosylated. Addition or deletion of glycosylation sites to an antibody may be conveniently accomplished by altering the amino acid sequence such that one or more glycosylation sites is created or removed.

Where the antibody comprises an Fc region, the carbohydrate attached thereto may be altered. Native antibodies produced by mammalian cells typically comprise a branched, biantennary oligosaccharide that is generally attached by an N-linkage to Asn297 of the CH2 domain of the Fc region. See, e.g., Wright et al. TIBTECH 15:26-32 (1997). The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in an antibody of the invention may be made in order to create antibody variants with certain improved properties.

In one embodiment, antibody variants are provided having a carbohydrate structure that lacks fucose attached (directly or indirectly) to an Fc region. For example, the amount of fucose in such antibody may be from 1% to 80%, from 1% to 65%, from 5% to 65% or from 20% to 40%. The amount of fucose is determined by calculating the average amount of fucose within the sugar chain at Asn297, relative to the sum of all glycostructures attached to Asn 297 (e. g. complex, hybrid and high mannose structures) as measured by MALDI-TOF mass spectrometry, as described in WO 2008/077546, for example. Asn297 refers to the asparagine residue located at about position 297 in the Fc region (Eu numbering of Fc region residues); however, Asn297 may also be located about ±3 amino acids upstream or downstream of position 297, i.e., between positions 294 and 300, due to minor sequence variations in antibodies. Such fucosylation variants may have improved ADCC function. See, e.g., US Patent Publication Nos. US 2003/0157108 (Presta, L.); US 2004/0093621 (Kyowa Hakko Kogyo Co., Ltd). Examples of publications related to "defucosylated" or "fucose-deficient" antibody variants include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO2005/053742; WO2002/031140; Okazaki et al. J. Mol. Biol. 336:1239-1249 (2004); Yamane-Ohnuki et al. Biotech. Bioeng. 87: 614 (2004). Examples of cell lines capable of producing defucosylated antibodies include Lec13 CHO cells deficient in protein fucosylation (Ripka et al. Arch. Biochem. Biophys. 249: 533-545 (1986); US Pat Appl No US 2003/0157108 A1, Presta, L; and WO 2004/056312 A1, Adams et al., especially at Example 11), and knockout cell lines, such as alpha-1,6-fucosyltransferase gene, FUT8, knockout CHO cells (see, e.g., Yamane-Ohnuki et al. Biotech. Bioeng. 87: 614 (2004); Kanda, Y. et al., Biotechnol. Bioeng., 94(4):680-688 (2006); and WO2003/085107).

Antibodies variants are further provided with bisected oligosaccharides, e.g., in which a biantennary oligosaccharide attached to the Fc region of the antibody is bisected by GlcNAc. Such antibody variants may have reduced fucosylation and/or improved ADCC function. Examples of such antibody variants are described, e.g., in WO 2003/011878 (Jean-Mairet et al.); U.S. Pat. No. 6,602,684 (Umana et al.); and US 2005/0123546 (Umana et al.). Antibody variants with at least one galactose residue in the oligosaccharide attached to the Fc region are also provided. Such antibody variants may have improved CDC function. Such antibody variants are described, e.g., in WO 1997/30087 (Patel et al.); WO 1998/58964 (Raju, S.); and WO 1999/22764 (Raju, S.).

c) Fc Region Variants

In certain embodiments, one or more amino acid modifications may be introduced into the Fc region of an antibody provided herein, thereby generating an Fc region variant. The Fc region variant may comprise a human Fc region sequence (e.g., a human IgG1, IgG2, IgG3 or IgG4 Fc region) comprising an amino acid modification (e.g. a substitution) at one or more amino acid positions.

In certain embodiments, the invention contemplates an antibody variant that possesses some but not all effector functions, which make it a desirable candidate for applications in which the half life of the antibody in vivo is important yet certain effector functions (such as complement and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC, NK cells, express Fc(RIII only, whereas monocytes express Fc(RI, Fc(RII and Fc(RIII. FcR expression on hematopoietic cells is summarized in Table 3 on page 464 of Ravetch and Kinet, Annu. Rev. Immunol. 9:457-492 (1991). Non-limiting examples of in vitro assays to assess ADCC activity of a molecule of interest is described in U.S. Pat. No. 5,500,362 (see, e.g. Hellstrom, I. et al. Proc. Nat'l Acad. Sci. USA 83:7059-7063 (1986)) and Hellstrom, I et al., Proc. Nat'l Acad. Sci. USA 82:1499-1502 (1985); U.S. Pat. No. 5,821,337 (see Bruggemann, M. et al., J. Exp. Med. 166:1351-1361 (1987)). Alternatively, non-radioactive assays methods may be employed (see, for example, ACTI™ non-radioactive cytotoxicity assay for flow cytometry (CellTechnology, Inc. Mountain View, Calif.; and CytoTox 96® non-radioactive cytotoxicity assay (Promega, Madison, Wis.). Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al. Proc. Nat'l Acad. Sci. USA 95:652-656 (1998). C1q binding assays may also be carried out to confirm that the antibody is unable to bind C1q and hence lacks CDC activity. See, e.g., C1q and C3c binding ELISA in WO 2006/029879 and WO 2005/100402. To assess complement activation, a CDC assay may be performed (see, for example, Gazzano-Santoro et al., J. Immunol. Methods 202:163 (1996); Cragg, M. S. et al., Blood 101:1045-1052 (2003); and Cragg, M. S. and M. J. Glennie, Blood 103:2738-2743 (2004)). FcRn binding and in vivo clearance/half life determinations can also be performed using methods known in the art (see, e.g., Petkova, S. B. et al., Int'l. Immunol. 18(12):1759-1769 (2006)).

In some embodiments, an antibody includes an Fc region with a mutation that decreases binding to an Fc receptor. Antibodies with reduced effector function include without limitation those with substitution of one or more of Fc region residues 238, 265, 269, 270, 297, 327 and 329 (U.S. Pat. No. 6,737,056). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581).

Certain antibody variants with improved or diminished binding to FcRs are described. (See, e.g., U.S. Pat. No. 6,737,056; WO 2004/056312, and Shields et al., J. Biol. Chem. 9(2): 6591-6604 (2001).)

In certain embodiments, an antibody variant comprises an Fc region with one or more amino acid substitutions which improve ADCC, e.g., substitutions at positions 298, 333, and/or 334 of the Fc region (EU numbering of residues).

In some embodiments, alterations are made in the Fc region that result in altered (i.e., either improved or diminished) C1q binding and/or Complement Dependent Cytotoxicity (CDC), e.g., as described in U.S. Pat. No. 6,194,551, WO 99/51642, and Idusogie et al. J. Immunol. 164: 4178-4184 (2000).

Antibodies with increased half lives and improved binding to the neonatal Fc receptor (FcRn), which is responsible for the transfer of maternal IgGs to the fetus (Guyer et al., J. Immunol. 117:587 (1976) and Kim et al., J. Immunol. 24:249 (1994)), are described in US2005/0014934A1 (Hinton et al.). Those antibodies comprise an Fc region with one or more substitutions therein which improve binding of the Fc region to FcRn. Such Fc variants include those with substitutions at one or more of Fc region residues: 238, 256, 265, 272, 286, 303, 305, 307, 311, 312, 317, 340, 356, 360, 362, 376, 378, 380, 382, 413, 424 or 434, e.g., substitution of Fc region residue 434 (U.S. Pat. No. 7,371,826).

See also Duncan & Winter, Nature 322:738-40 (1988); U.S. Pat. Nos. 5,648,260; 5,624,821; and WO 94/29351 concerning other examples of Fc region variants.

d) Cysteine Engineered Antibody Variants

In certain embodiments, it may be desirable to create cysteine engineered antibodies, e.g., "thioMAbs," in which one or more residues of an antibody are substituted with cysteine residues. In particular embodiments, the substituted residues occur at accessible sites of the antibody. By substituting those residues with cysteine, reactive thiol groups are thereby positioned at accessible sites of the antibody and may be used to conjugate the antibody to other moieties, such as drug moieties or linker-drug moieties, to create an immunoconjugate, as described further herein. In certain embodiments, any one or more of the following residues may be substituted with cysteine: V205 (Kabat numbering) of the light chain; A118 (EU numbering) of the heavy chain; and S400 (EU numbering) of the heavy chain Fc region. Cysteine engineered antibodies may be generated as described, e.g., in U.S. Pat. No. 7,521,541.

e) Antibody Derivatives

In certain embodiments, an antibody provided herein may be further modified to contain additional nonproteinaceous moieties that are known in the art and readily available. The moieties suitable for derivatization of the antibody include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone) polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer are attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

In another embodiment, conjugates of an antibody and nonproteinaceous moiety that may be selectively heated by exposure to radiation are provided. In one embodiment, the nonproteinaceous moiety is a carbon nanotube (Kam et al., Proc. Natl. Acad. Sci. USA 102: 11600-11605 (2005)). The radiation may be of any wavelength, and includes, but is not limited to, wavelengths that do not harm ordinary cells, but which heat the nonproteinaceous moiety to a temperature at which cells proximal to the antibody-nonproteinaceous moiety are killed.

Recombinant Methods and Compositions

Antibodies may be produced using recombinant methods and compositions, e.g., as described in U.S. Pat. No. 4,816,567. In one embodiment, isolated nucleic acid encoding an anti-OX40 antibody described herein is provided. Such nucleic acid may encode an amino acid sequence comprising the VL and/or an amino acid sequence comprising the VH of the antibody (e.g., the light and/or heavy chains of the antibody). In a further embodiment, one or more vectors (e.g., expression vectors) comprising such nucleic acid are provided. In a further embodiment, a host cell comprising such nucleic acid is provided. In one such embodiment, a host cell comprises (e.g., has been transformed with): (1) a vector comprising a nucleic acid that encodes an amino acid sequence comprising the VL of the antibody and an amino acid sequence comprising the VH of the antibody, or (2) a first vector comprising a nucleic acid that encodes an amino acid sequence comprising the VL of the antibody and a second vector comprising a nucleic acid that encodes an amino acid sequence comprising the VH of the antibody. In one embodiment, the host cell is eukaryotic, e.g. a Chinese Hamster Ovary (CHO) cell or lymphoid cell (e.g., Y0, NS0, Sp20 cell). In one embodiment, a method of making an anti-OX40 antibody is provided, wherein the method comprises culturing a host cell comprising a nucleic acid encoding the antibody, as provided above, under conditions suitable for expression of the antibody, and optionally recovering the antibody from the host cell (or host cell culture medium).

For recombinant production of an anti-OX40 antibody, nucleic acid encoding an antibody, e.g., as described above, is isolated and inserted into one or more vectors for further cloning and/or expression in a host cell. Such nucleic acid may be readily isolated and sequenced using conventional procedures (e.g., by using oligonucleotide probes that are capable of binding specifically to genes encoding the heavy and light chains of the antibody).

Suitable host cells for cloning or expression of antibody-encoding vectors include prokaryotic or eukaryotic cells described herein. For example, antibodies may be produced in bacteria, in particular when glycosylation and Fc effector function are not needed. For expression of antibody fragments and polypeptides in bacteria, see, e.g., U.S. Pat. Nos. 5,648,237, 5,789,199, and 5,840,523. (See also Charlton, Methods in Molecular Biology, Vol. 248 (B. K. C. Lo, ed., Humana Press, Totowa, N.J., 2003), pp. 245-254, describing expression of antibody fragments in *E. coli*.) After expression, the antibody may be isolated from the bacterial cell paste in a soluble fraction and can be further purified.

In addition to prokaryotes, eukaryotic microbes such as filamentous fungi or yeast are suitable cloning or expression hosts for antibody-encoding vectors, including fungi and yeast strains whose glycosylation pathways have been "humanized," resulting in the production of an antibody with a partially or fully human glycosylation pattern. See Gerngross, Nat. Biotech. 22:1409-1414 (2004), and Li et al., Nat. Biotech. 24:210-215 (2006).

Suitable host cells for the expression of glycosylated antibody are also derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells.

Plant cell cultures can also be utilized as hosts. See, e.g., U.S. Pat. Nos. 5,959,177, 6,040,498, 6,420,548, 7,125,978, and 6,417,429 (describing PLANTIBODIES™ technology for producing antibodies in transgenic plants).

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293 cells as described, e.g., in Graham et al., J. Gen Virol. 36:59 (1977)); baby hamster kidney cells (BHK); mouse sertoli cells (TM4 cells as described, e.g., in Mather, Biol. Reprod. 23:243-251 (1980)); monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TRI cells, as described, e.g., in Mather et al., Annals N.Y. Acad. Sci. 383:44-68 (1982); MRC 5 cells; and FS4 cells. Other useful mammalian host cell lines include Chinese hamster ovary (CHO) cells, including DHFR− CHO cells (Urlaub et al., Proc. Natl. Acad. Sci. USA 77:4216 (1980)); and myeloma cell lines such as Y0, NS0 and Sp2/0. For a review of certain mammalian host cell lines suitable for antibody production, see, e.g., Yazaki and Wu, Methods in Molecular Biology, Vol. 248 (B. K. C. Lo, ed., Humana Press, Totowa, N.J.), pp. 255-268 (2003).

Assays

Anti-OX40 antibodies provided herein may be identified, screened for, or characterized for their physical/chemical properties and/or biological activities by various assays known in the art.

1. Binding Assays and Other Assays

In one aspect, an antibody of the invention is tested for its antigen binding activity, e.g., by known methods such as ELISA, Western blot, etc. OX40 binding may be determined using methods known in the art and exemplary methods are disclosed herein. In one embodiment, binding is measured using radioimmunoassay. An exemplary radioimmunassay is exemplified in the Examples. OX40 antibody is iodinated, and competition reaction mixtures are prepared containing a fixed concentration of iodinated antibody and decreasing concentrations of serially diluted, unlabeled OZ X40 antibody. Cells expressing OX40 (e.g., BT474 cells stably transfected with human OX40) are added to the reaction mixture. Following an incubation, cells are washed to separate the free iodinated OX40 antibody from the OX40 antibody bound to the cells. Level of bound iodinated OX40 antibody is determined, e.g., by counting radioactivity associated with cells, and binding affinity determined using standard methods. In another embodiment, ability of OX40 antibody to bind to surface-expressed OX40 (e.g., on T cell subsets) is assessed using flow cytometry. Peripheral white blood cells are obtained (e.g., from human, cynomolgus monkey, rat or mouse) and cells are blocked with serum. Labeled OX40 antibody is added in serial dilutions, and T cells are also stained to identify T cell subsets (using methods known in the art). Following incubation of the samples and washing, the cells are sorted using flow cytometer, and data analyzed using methods well known in the art. In another embodiment, OX40 binding may be analyzed using surface plasmon resonance. An exemplary surface plasmon resonance method is exemplified in the Examples.

In another aspect, competition assays may be used to identify an antibody that competes with any of the anti-OX40 antibodies disclosed herein for binding to OX40. In certain embodiments, such a competing antibody binds to the same epitope (e.g., a linear or a conformational epitope) that is bound by any of the anti-OX40 antibodies disclosed herein. Detailed exemplary methods for mapping an epitope to which an antibody binds are provided in Morris (1996) "Epitope Mapping Protocols," in Methods in Molecular Biology vol. 66 (Humana Press, Totowa, N.J.). A competition assay is exemplified in the Examples.

In an exemplary competition assay, immobilized OX40 is incubated in a solution comprising a first labeled antibody that binds to OX40 (e.g., mab 1A7.gr.1, mab 3C8.gr5) and a second unlabeled antibody that is being tested for its ability to compete with the first antibody for binding to OX40. The second antibody may be present in a hybridoma supernatant. As a control, immobilized OX40 is incubated in a solution comprising the first labeled antibody but not the second unlabeled antibody. After incubation under conditions permissive for binding of the first antibody to OX40, excess unbound antibody is removed, and the amount of label associated with immobilized OX40 is measured. If the amount of label associated with immobilized OX40 is substantially reduced in the test sample relative to the control sample, then that indicates that the second antibody is competing with the first antibody for binding to OX40. See Harlow and Lane (1988) Antibodies: A Laboratory Manual ch. 14 (Cold Spring Harbor Laboratory, Cold Spring Harbor, N.Y.).

2. Activity Assays

In one aspect, assays are provided for identifying anti-OX40 antibodies thereof having biological activity. Biological activity may include, e.g., binding OX40 (e.g., binding human and/or cynomolgus OX40), increasing OX40-mediated signal transduction (e.g., increasing NFkB-mediated transcription), depleting cells that express human OX40 (e.g., T cells), depleting cells that express human OX40 by ADCC and/or phagocytosis, enhancing T effector cell function (e.g., CD4+ effector T cell), e.g., by increasing effector T cell proliferation and/or increasing cytokine production (e.g., gamma interferon) by effector T cells, enhancing memory T cell function (e.g., CD4+ memory T cell), e.g., by increasing memory T cell proliferation and/or increasing cytokine production by memory T cells (e.g., gamma interferon), inhibiting regulatory T cell function (e.g., by decreasing Treg suppression of effector T cell function (e.g., CD4+ effector T cell function), binding human effector cells. Antibodies having such biological activity in vivo and/or in vitro are also provided.

In certain embodiments, an antibody of the invention is tested for such biological activity.

T cell costimulation may be assayed using methods known in the art and exemplary methods are disclosed herein. For example, T cells (e.g., memory or effector T cells) may be obtained from peripheral white blood cells (e.g., isolated from human whole blood using Ficoll gradient centrifugation). Memory T cells (e.g., CD4+ memory T cells) or effector T cells (e.g. CD4+ Teff cells) may be isolated from PBMC using methods known in the art. For example, the Miltenyi CD4+ memory T cell isolation kit or Miltenyi naïve CD4+ T cell isolation kit may be used. Isolated T cells are cultured in the presence of antigen presenting cells (e.g., irradiated L cells that express CD32 and CD80), and activated by addition of anti-CD3 antibody in the presence or absence of OX40 agonist antibody. Effect of agonist OX40 antibody of T cell proliferation may be measured using methods well known in the art. For example, the CellTiter Glo kit (Promega) may be used, and results read on a Multilabel Reader (Perkin Elmer). Effect of agonist OX40 antibody on T cell function may also be determined by analysis of cytokines produced by the T cell. In one embodiment, production of interferon gamma by CD4+ T cells is determined, e.g., by measurement of interferon gamma in cell culture supernatant. Methods for measuring interferon gamma are well-known in the art.

Treg cell function may be assayed using methods known in the art and exemplary methods are disclosed herein. In one example, the ability of Treg to suppress effector T cell proliferation is assayed. T cells are isolated from human whole blood using methods known in the art (e.g., isolating memory T cells or naïve T cells). Purified CD4+ naïve T cells are labeled (e.g., with CFSE) and purified Treg cells are labeled with a different reagent. Irradiated antigen presenting cells (e.g., L cells expressing CD32 and CD80) are co-cultured with the labeled purified naïve CD4+ T cells and purified Tregs. The co-cultures are activated using anti-CD3 antibody and tested in the presence or absence of agonist OX40 antibody. Following a suitable time (e.g., 6 days of coculture), level of CD4+ naïve T cell proliferation is tracked by dye dilution in reduced label staining (e.g., reduced CFSE label staining) using FACS analysis.

OX40 signaling may be assayed using methods well known in the art and exemplary methods are disclosed herein. In one embodiment, transgenic cells are generated that express human OX40 and a reporter gene comprising the NFkB promoter fused to a reporter gene (e.g., beta luciferase). Addition of OX40 agonist antibody to the cells results in increased NFkB transcription, which is detected using an assay for the reporter gene.

Phagocytosis may be assayed, e.g., by using monocyte-derived macrophages, or U937 cells (a human histiocytic lymphoma cells line with the morphology and characteristics of mature macrophages). OX40 expressing cells are added to the monocyte-derived macrophages or U937 cells in the presence or absence of anti-OX40 agonist antibody. Following culturing of the cells for a suitable period of time, the percentage of phagocytosis is determined by examining percentage of cells that double stain for markers of 1) the macrophage or U937 cell and 2) the OX40 expressing cell, and dividing this by the total number of cells that show markers of the OX40 expressing cell (e.g., GFP). Analysis may be done by flow cytometry. In another embodiment, analysis may be done by fluorescent microscopy analysis.

ADCC may be assayed, e.g., using methods well known in the art. Exemplary methods are described in the definition section and an exemplary assay is disclosed in the Examples. In some embodiments, level of OX40 is characterized on an OX40 expressing cell that is used for testing in an ADCC assay. The cell may be stained with a detectably labeled anti-OX40 antibody (e.g., PE labeled), then level of fluorescence determined using flow cytometry, and results presented as median fluorescence intensity (MFI). In another embodiment, ADCC may be analyzed by CellTiter Glo assay kit and cell viability/cytotoxicity may be determined by chemioluminescence.

The binding affinities of various antibodies to FcγRIA, FcγRIIA, FcγRIIB, and two allotypes of FcγRIIIA (F158 and V158) may be measured in ELISA-based ligand-binding assays using the respective recombinant Fcγ receptors. Purified human Fcγ receptors are expressed as fusion proteins containing the extracellular domain of the receptor γ chain linked to a Gly/6×His/glutathione S-transferase (GST) polypeptide tag at the C-terminus. The binding affinities of antibodies to those human Fcγ receptors are assayed as follows. For the low-affinity receptors, i.e. FcγRIIA (CD32A), FcγRIIB (CD32B), and the two allotypes of FcγRIIIA (CD16), F-158 and V-158, antibodies may be tested as multimers by cross-linking with a F(ab')2 fragment of goat anti-human kappa chain (ICN Biomedical; Irvine, Calif.) at an approximate molar ratio of 1:3 antibody:cross-linking F(ab')2. Plates are coated with an anti-GST antibody (Genentech) and blocked with bovine serum albumin (BSA). After washing with phosphate-buffered saline (PBS) containing 0.05% Tween-20 with an ELx405™ plate washer (Biotek Instruments; Winooski, Vt.), Fcγ receptors are added to the plate at 25 ng/well and incubated at room temperature for 1 hour. After the plates are washed, serial dilutions of test antibodies are added as multimeric complexes and the plates were incubated at room temperature for 2 hours. Following plate washing to remove unbound antibodies, the antibodies bound to the Fcγ receptor are detected with horseradish peroxidase (HRP)-conjugated F(ab')2 fragment of goat anti-human F(ab')2 (Jackson ImmunoResearch Laboratories; West Grove, Pa.) followed by the addition of substrate, tetramethylbenzidine (TMB) (Kirkegaard & Perry Laboratories; Gaithersburg, Md.). The plates are incubated at room temperature for 5-20 minutes, depending on the Fcγ receptors tested, to allow color development. The reaction is terminated with 1 M H3PO4 and absorbance at 450 nm was measured with a microplate reader (SpectraMax®190, Molecular Devices; Sunnyvale, Calif.). Dose-response binding curves are generated by plotting the mean absorbance values from the duplicates of antibody dilutions against the concentrations of the antibody. Values for the effective concentration of the antibody at which 50% of the maximum response from binding to the Fcγ receptor is detected (EC50) were determined after fitting the binding curve with a four-parameter equation using SoftMax Pro (Molecular Devices).

To select for antibodies which induce cell death, loss of membrane integrity as indicated by, e.g., propidium iodide (PI), trypan blue or 7AAD uptake may be assessed relative to control. A PI uptake assay can be performed in the absence of complement and immune effector cells. OX40 expressing cells are incubated with medium alone or medium containing of the appropriate monoclonal antibody at e.g., about 10 μg/ml. The cells are incubated for a time period (e.g., 1 or 3 days). Following each treatment, cells are washed and aliquoted. In some embodiments, cells are aliquoted into 35 mm strainer-capped 12×75 tubes (1 ml per tube, 3 tubes per treatment group) for removal of cell clumps. Tubes then receive PI (10 μg/ml). Samples may be analyzed using a FACSCAN™ flow cytometer and FACSCONVERT™ CellQuest software (Becton Dickinson).

Cells for use in any of the above in vitro assays include cells or cell lines that naturally express OX40 or that have been engineered to express OX40. Such cells include activated T cells, Treg cells and activated memory T cells that naturally express OX40. Such cells also include cell lines that express OX40 and cell lines that do not normally express OX40 but have been transfected with nucleic acid encoding OX40. Exemplary cell lines provided herein for use in any of the above in vitro assays include transgenic BT474 cells (a human breast cancer cell line) that express human OX40

It is understood that any of the above assays may be carried out using an immunoconjugate of the invention in place of or in addition to an anti-OX40 antibody.

It is understood that any of the above assays may be carried out using anti-OX40 antibody and an additional therapeutic agent.

Immunoconjugates

The invention also provides immunoconjugates comprising an anti-OX40 antibody herein conjugated to one or more cytotoxic agents, such as chemotherapeutic agents or drugs, growth inhibitory agents, toxins (e.g., protein toxins, enzymatically active toxins of bacterial, fungal, plant, or animal origin, or fragments thereof), or radioactive isotopes.

In one embodiment, an immunoconjugate is an antibody-drug conjugate (ADC) in which an antibody is conjugated to one or more drugs, including but not limited to a maytansinoid (see U.S. Pat. Nos. 5,208,020, 5,416,064 and European Patent EP 0 425 235 B1); an auristatin such as monomethylauristatin drug moieties DE and DF (MMAE and MMAF) (see U.S. Pat. Nos. 5,635,483 and 5,780,588, and 7,498,298); a dolastatin; a calicheamicin or derivative thereof (see U.S. Pat. Nos. 5,712,374, 5,714,586, 5,739,116, 5,767,285, 5,770,701, 5,770,710, 5,773,001, and 5,877,296; Hinman et al., Cancer Res. 53:3336-3342 (1993); and Lode et al., Cancer Res. 58:2925-2928 (1998)); an anthracycline such as daunomycin or doxorubicin (see Kratz et al., Current Med. Chem. 13:477-523 (2006); Jeffrey et al., Bioorganic & Med. Chem. Letters 16:358-362 (2006); Torgov et al., Bioconj. Chem. 16:717-721 (2005); Nagy et al., Proc. Natl. Acad. Sci. USA 97:829-834 (2000); Dubowchik et al., Bioorg. & Med.

Chem. Letters 12:1529-1532 (2002); King et al., J. Med. Chem. 45:4336-4343 (2002); and U.S. Pat. No. 6,630,579); methotrexate; vindesine; a taxane such as docetaxel, paclitaxel, larotaxel, tesetaxel, and ortataxel; a trichothecene; and CC1065.

In another embodiment, an immunoconjugate comprises an antibody as described herein conjugated to an enzymatically active toxin or fragment thereof, including but not limited to diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin, and the tricothecenes.

In another embodiment, an immunoconjugate comprises an antibody as described herein conjugated to a radioactive atom to form a radioconjugate. A variety of radioactive isotopes are available for the production of radioconjugates. Examples include At211, I131, I125, Y90, Re186, Re188, Sm153, Bi212, P32, Pb212 and radioactive isotopes of Lu. When the radioconjugate is used for detection, it may comprise a radioactive atom for scintigraphic studies, for example tc99m or I123, or a spin label for nuclear magnetic resonance (NMR) imaging (also known as magnetic resonance imaging, mri), such as iodine-123 again, iodine-131, indium-111, fluorine-19, carbon-13, nitrogen-15, oxygen-17, gadolinium, manganese or iron.

Conjugates of an antibody and cytotoxic agent may be made using a variety of bifunctional protein coupling agents such as N-succinimidyl-3-(2-pyridyldithio) propionate (SPDP), succinimidyl-4-(N-maleimidomethyl) cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., Science 238:1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026. The linker may be a "cleavable linker" facilitating release of a cytotoxic drug in the cell. For example, an acid-labile linker, peptidase-sensitive linker, photolabile linker, dimethyl linker or disulfide-containing linker (Chari et al., Cancer Res. 52:127-131 (1992); U.S. Pat. No. 5,208,020) may be used.

The immunuoconjugates or ADCs herein expressly contemplate, but are not limited to such conjugates prepared with cross-linker reagents including, but not limited to, BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate) which are commercially available (e.g., from Pierce Biotechnology, Inc., Rockford, Ill., U.S.A).

IV. Predictive and Prognostic Methods

Provided herein are methods for determining the prognosis of a subject having cancer by measuring the number of CD4+ OX40+ Foxp3+ lymphocytes in a sample containing cancer cells and lymphocytes obtained from the subject; and determining the prognosis of the subject based on the number of CD4+ OX40+ Foxp3+ lymphocytes in the sample, as compared with a reference, wherein an increased number of CD4+ OX40+ Foxp3+ lymphocytes in the sample indicates that the subject may have an improved prognosis. These methods are based in part on the discovery described herein that increased prevalence of CD4+ OX40+ Foxp3+ lymphocytes (i.e., OX40+ Treg cells) in a tumor sample correlates with improved patient prognosis. Further provided herein are methods for determining the prognosis of a subject having cancer by measuring the number of CD4+, OX40+, CD4+ OX40+ Foxp3+, or CD4+ OX40+ Foxp3− lymphocytes in a sample containing metastatic cancer cells and lymphocytes obtained from the subject; and determining the prognosis of the subject based on the number of OX40+, CD4+ OX40+ Foxp3+, or CD4+ OX40+ Foxp3− lymphocytes in the sample, as compared with a reference, wherein an increased number of OX40+, CD4+ OX40+ Foxp3+, or CD4+ OX40+ Foxp3− lymphocytes in the sample indicates that the subject may have an improved prognosis. These methods are based in part on the discovery described herein that increased prevalence of CD4+ lymphocytes, total OX40+ lymphocytes, CD4+ OX40+ Foxp3+ lymphocytes (i.e., OX40+ Treg cells), or CD4+ OX40+ Foxp3− lymphocytes (i.e., OX40+ Teff cells) in a tumor sample correlates with improved patient prognosis, and that the prevalence of each of these lymphocyte subtypes is strongly correlated in matched primary tumor and metastatic samples from a subject.

Certain aspects of the present disclosure relate to measuring the number of OX40+, CD4+OX40+ Foxp3+, or CD4+ OX40+ Foxp3− lymphocytes in a sample comprising cancer cells and lymphocytes obtained from the subject. In some embodiments, a sample may include cancer cells and lymphocytes. For example, the sample may be a tumor sample. A tumor sample may include cancer cells, lymphocytes, leukocytes, stroma, blood vessels, connective tissue, basal lamina, and any other cell type in association with the tumor. A sample may be obtained from a subject by any method known in the art, including without limitation a biopsy, endoscopy, or surgical procedure. In some embodiments, a sample may be prepared by methods such as freezing, fixation (e.g., by using formalin or a similar fixative), and/or embedding in paraffin wax. In some embodiments, a sample may be sectioned.

In some embodiments, the number of OX40+, CD4+ OX40+ Foxp3+, or CD4+ OX40+ Foxp3− lymphocytes in a tumor is measured. In some embodiments, the number of OX40+, CD4+OX40+ Foxp3+, or CD4+ OX40+ Foxp3− lymphocytes in a metastatic tumor is measured. In any or all of the above cases, the lymphocytes may be tumor-infiltrating lymphocytes. As used herein, any lymphocyte associated with a tumor may be a tumor-infiltrating lymphocyte. In some embodiments, the tumor-infiltrating lymphocyte may be associated with cancer cells in the tumor. In some embodiments, the tumor-infiltrating lymphocyte may be associated with the tumor stroma.

As used herein, a CD4+ OX40+ Foxp3+ cell (e.g., a lymphocyte or leukocyte) may refer to any cell that has increased expression of CD4 as compared with a reference, increased expression of OX40 as compared with a reference, and increased expression of Foxp3 as compared with a reference. As used herein, a CD4+ OX40+ Foxp3− cell (e.g., a lymphocyte or leukocyte) may refer to any cell that has increased expression of CD4 as compared with a reference, increased expression of OX40 as compared with a reference, and decreased expression of Foxp3 as compared with a reference. As used herein, an OX40+ cell (e.g., a lymphocyte or leukocyte) may refer to any cell that has increased expression of OX40 as compared with a reference. The phrases "compared with" and "compared to" may be used interchangeably herein. In some embodiments, expression may refer to protein expression. In some embodiments, expression may refer to mRNA expression.

In some embodiment, tumor may refer to a physical mass containing a plurality of cancer cells, e.g., cells showing the characteristics of any of the cancers described herein. Examples of tumors may include primary tumors of any of the above types of cancer or metastatic tumors at a second site derived from any of the above types of cancer. In some embodiments, a tumor may contain cancer cells as well as tumor stroma.

In some embodiments, within a tumor section, a region of interest may be identified. A region of interest may refer to any subset of a tumor section selected for analysis. In some embodiments, a region of interest may include a portion of a tumor section, which may include cancer cells, lymphocytes, and, optionally, tumor stroma. Lymphocytes may be associated with cancer cells and/or tumor stroma. In some embodiments, more than one region of interest from a sample may be analyzed (e.g., if a main tumor mass and satellite mass are observed).

The level of expression of CD4, OX40, and/or Foxp3 may be compared with a reference. Many methods for comparing the expression level of a gene or protein of interest to a reference are known in the art. For example, in some embodiments, a reference may be expression level of a tumor with a known responsiveness to a treatment (e.g., with an OX40 agonist) or prognosis, a control (e.g., expression level of a housekeeping biomarker), or a reference number (e.g., a set threshold level of expression, such as a threshold based on clinical outcome data). In some embodiments, a comparison with a reference may refer to a comparison with a reference number (e.g., a predetermined level of expression) or a comparison with a reference sample.

In some embodiments, the expression level of a gene or protein of interest (e.g., CD4, OX40, and/or Foxp3) in a cell may be compared with the expression level of the gene of interest in other cells in the sample. For example, the sample may be assayed for the expression level of a gene or protein of interest (e.g., CD4, OX40, and/or Foxp3), and cells that show increased expression of the gene or protein of interest relative to other cells in the sample may be considered "positive" for expression of the gene or protein of interest. In some embodiments, the sample may be assayed for the expression level of a gene or protein of interest (e.g., CD4, OX40, and/or Foxp3), and a global threshold for expression level may be applied. Cells that show expression at or above the global threshold may be considered "positive" for expression of the gene or protein of interest, whereas cells that show expression below the global threshold may be considered "negative" for expression of the gene or protein of interest. In some embodiments, the expression level of a gene or protein of interest (e.g., CD4, OX40, and/or Foxp3) in a cell may be compared with the expression level of the gene of interest in other cells in the region of interest.

Many methods for assaying the expression level of a gene or protein of interest are known in the art. For example, in some embodiments, expression level may be assayed by immunofluorescence staining, immunohistochemistry, imaging (e.g., microscopic imaging, such as fluorescence microscopy), flow cytometry, in situ hybridization, immunoprecipitation, and the like. In some embodiments, lymphocytes showing CD4 expression, OX40 expression, and Foxp3 expression are labeled by immunofluorescence staining Exemplary methods for immunofluorescence staining are described herein.

In some embodiments, expression level may refer to a median or mean expression level detected for a cell in a sample. In some embodiments, expression level may refer to the maximum expression level detected for a cell. For example, if assayed by immunofluorescence staining and immunofluorescence imaging, expression level of a gene or protein of interest in a cell may be based on the median fluorescence intensity detected in the area corresponding to the cell (e.g., as defined by morphology, membrane staining, and/or a nuclear staining).

In some embodiments, an absolute number of cells of interest (e.g., OX40+, CD4+ OX40+ Foxp3+, or CD4+ OX40+ Foxp3− cells) may be measured and used. In some embodiments, a relative number of cells of interest (e.g., OX40+, CD4+ OX40+ Foxp3+, or CD4+ OX40+ Foxp3− cells) may be measured or used. For example, the number of CD4+ OX40+ Foxp3+ cells may be normalized to the total amount of cells detected in a sample, or in a region of interest from the sample. In some embodiments, the number of cells of interest may be an average, mean, or median of number of cells of interest in different regions of interest of a sample or different samples from the subject.

Certain aspects of the present disclosure relate to determining the prognosis of the subject based on the number of CD4+ OX40+ Foxp3+ lymphocytes in the sample, as compared with a reference of the present disclosure. In some embodiments, an increased number (e.g., absolute or normalized number) of cells of interest (e.g., e.g., OX40+, CD4+ OX40+ Foxp3+, or CD4+ OX40+ Foxp3− cells) as compared with a reference of the present disclosure may indicate an improved prognosis. Certain aspects of the present disclosure relate to determining the prognosis of the subject based on the number of CD4+ OX40+ Foxp3− lymphocytes in the sample, as compared with a reference of the present disclosure. In some embodiments, an increased number (e.g., absolute or normalized number) of cells of interest (e.g., CD4+ OX40+ Foxp3− cells) as compared with a reference of the present disclosure may indicate an improved prognosis. Certain aspects of the present disclosure relate to determining the prognosis of the subject based on the number of OX40+ lymphocytes in the sample, as compared with a reference of the present disclosure. In some embodiments, an increased number (e.g., absolute or normalized number) of cells of interest (e.g., OX40+ cells) as compared with a reference of the present disclosure may indicate an improved prognosis.

In some embodiments, prognosis may refer to overall survival and/or progression-free survival. In some embodiments, an improved prognosis may predict increased overall survival. In some embodiments, an improved prognosis may predict increased progression-free survival. In some embodiments, an improved prognosis may predict increased overall survival and increased progression-free survival. In some embodiments, other factors may additionally be considered to determine a prognosis, including without limitation, age, the type and/or location of a cancer, stage, cancer grade, overall health, family history, and so forth.

In some embodiments, a reference of the present disclosure may refer to a number of cells of interest (e.g., OX40+, CD4+ OX40+ Foxp3+, or CD4+ OX40+ Foxp3− cells) in a sample comprising cancer cells and lymphocytes obtained from a cancer having the same type and/or stage as the cancer of the subject. For example, if the subject presents with stage I colorectal cancer, the sample from the patient may be compared with a reference sample from another patient or patients with stage I colorectal cancer. An increased number of CD4+ OX40+ Foxp3+ cells in the patient sample as compared with the reference sample may indicate an improved prognosis. It is a discovery of the present disclosure that the numbers of OX40+ Treg and OX40+ Teff are correlated with prognosis (e.g., overall survival) when the analyses are adjusted for factors such as age, gender, and cancer stage.

In some embodiments, the reference is based on the number of CD4+ OX40+ Foxp3+ lymphocytes in a sample comprising cancer cells and lymphocytes obtained from a cancer having the same type and/or stage as the cancer of the subject. In some embodiments, the reference is based on the number of CD4+ OX40+ Foxp3− lymphocytes in a sample comprising metastatic cancer cells and lymphocytes obtained from a cancer having the same type and/or stage as the cancer of the subject. In some embodiments, the reference is based on the number of OX40+ lymphocytes in a sample comprising metastatic cancer cells and lymphocytes obtained from a cancer having the same type and/or stage as the cancer of the subject. For example, a set of samples obtained from cancers having a shared characteristic (e.g., the same cancer type and/or stage) may be studied from a population, such as with a clinical outcome study. This set may be used to derive a reference, e.g., a reference number, to which a subject's sample may be compared. As such, the number of OX40+, CD4+OX40+ Foxp3+, or OX40+, CD4+ OX40+ Foxp3− lymphocytes in a sample may be correlated to clinical outcome. Therefore, a reference number of OX40+, CD4+ OX40+ Foxp3+, or OX40+, CD4+ OX40+ Foxp3− lymphocytes may be used for comparison with a subject's sample to predict responsiveness of a subject to an OX40 agonist treatment and/or determine the prognosis of a subject.

In some embodiments, the reference is the mean number of OX40+, CD4+ OX40+ Foxp3+, or OX40+, CD4+ OX40+ Foxp3− lymphocytes in samples obtained from cancers having the same type and/or stage as the cancer of the subject. In some embodiments, the reference is the median number of OX40+, CD4+ OX40+ Foxp3+, or OX40+, CD4+ OX40+ Foxp3− lymphocytes in samples obtained from cancers having the same type and/or stage as the cancer of the subject. In some embodiments, the reference is the average number of OX40+, CD4+ OX40+ Foxp3+, or OX40+, CD4+ OX40+ Foxp3− lymphocytes in samples obtained from cancers having the same type and/or stage as the cancer of the subject.

Provided herein are methods for predicting responsiveness of a subject having cancer to an OX40 agonist treatment by measuring the number of CD4+ OX40+ Foxp3+ lymphocytes in a sample containing cancer cells and lymphocytes obtained from the subject; and classifying the subject as a responsive or non-responsive subject based on the number of CD4+ OX40+ Foxp3+ lymphocytes in the sample, as compared with a reference, where an increased number of CD4+ OX40+ Foxp3+ lymphocytes in the sample indicates a responsive subject, as compared with a subject whose sample has a decreased number of CD4+ OX40+ Foxp3+ lymphocytes. Further provided herein are methods for predicting responsiveness of a subject having cancer to an OX40 agonist treatment by measuring the number of OX40+, CD4+ OX40+ Foxp3+, or CD4+ OX40+ Foxp3− lymphocytes in a sample containing metastatic cancer cells and lymphocytes obtained from the subject; and classifying the subject as a responsive or non-responsive subject based on the number of OX40+, CD4+ OX40+ Foxp3+, or CD4+ OX40+ Foxp3− lymphocytes in the sample, as compared with a reference, where an increased number of OX40+, CD4+ OX40+ Foxp3+, or CD4+ OX40+ Foxp3− lymphocytes in the sample indicates a responsive subject, as compared with a subject whose sample has a decreased number of OX40+, CD4+ OX40+ Foxp3+, or CD4+ OX40+ Foxp3− lymphocytes. Without wishing to be bound to theory, it is thought that patients having tumors with increased numbers of OX40+, CD4+ OX40+ Foxp3+, and/or CD4+ OX40+ Foxp3− lymphocytes may be more likely to respond to OX40 agonist treatment, compared to patients whose tumors have fewer such cells. Predicting a patient's responsiveness to a treatment may be highly advantageous in selecting a treatment option with the greatest likelihood of producing a successful clinical outcome, either by positively selecting a treatment option that is deemed more likely to work, or by eliminating a treatment option that is deemed less likely to work. Any of the methods herein for measuring OX40+, CD4+ OX40+ Foxp3+ or CD4+ OX40+ Foxp3− lymphocytes of the present disclosure may find use in these methods.

In some embodiments, a subject is classified as responsive or non-responsive based on the number of OX40+, CD4+ OX40+ Foxp3+, or CD4+ OX40+ Foxp3− lymphocytes in a sample, as compared with a reference. Any of the references described herein may be used. For example, the number of CD4+ OX40+ Foxp3+ lymphocytes in a patient sample may be compared to a reference number (e.g., one based on clinical outcome studies), or a sample with known responsiveness to treatment.

In some embodiments, responsiveness to treatment may refer to any one or more of: extending survival (including overall survival and progression free survival); resulting in an objective response (including a complete response or a partial response); or improving signs or symptoms of cancer. In some embodiments, responsiveness may refer to improvement of one or more factors according to the published set of RECIST or Immune-Related Response Criteria guidelines for determining the status of a tumor in a cancer patient, i.e., responding, stabilizing, or progressing. For a more detailed discussion of these guidelines, see Eisenhauer et al., *Eur J Cancer* 2009; 45: 228-47; Topalian et al., *N Engl J Med* 2012; 366:2443-54; Wolchok et al., *Clin Can Res* 2009; 15:7412-20; and Therasse, P., et al. *J. Natl. Cancer Inst.* 92:205-16 (2000). A responsive subject may refer to a subject whose tumor(s) show improvement, e.g., according to one or more factors based on RECIST or Immune-Related Response criteria. A non-responsive subject may refer to a subject whose tumor(s) do not show improvement, e.g., according to one or more factors based on RECIST or Immune-Related Response criteria. In some embodiments, responsiveness may include immune activation. In some embodiments, responsiveness may include treatment efficacy. In some embodiments, responsiveness may include immune activation and treatment efficacy.

Conventional response criteria may not be adequate to characterize the anti-tumor activity of immunotherapeutic agents, which can produce delayed responses that may be preceded by initial apparent radiological progression, including the appearance of new lesions. Therefore, modified response criteria have been developed that account for the possible appearance of new lesions and allow radiological progression to be confirmed at a subsequent assessment. Accordingly, in some embodiments, responsiveness may refer to improvement of one of more factors according to immune-related response criteria2(irRC). See, e.g., Wolchok et al., Clin Can Res 2009; 15:7412-20. In some embodiments, new lesions are added into the defined tumor burden and followed, e.g., for radiological progression at a subsequent assessment. In some embodiments, presence of non-target lesions are included in assessment of complete response and not included in assessment of radiological progression. In some embodiments, radiological progression may be determined only on the basis of measurable disease and/or may be confirmed by a consecutive assessment ≥4 weeks from the date first documented.

Certain aspects of the present disclosure relate to methods for measuring the number of CD4+ OX40+ Foxp3+ lymphocytes in a sample comprising cancer cells and lymphocytes obtained from a subject. In some embodiments, the methods include: (a) labeling lymphocytes that show CD4 expression in the sample; (b) labeling lymphocytes that show OX40 expression in the sample after step (a); (c) labeling lymphocytes that show Foxp3 expression in the sample after step (b); and (d) measuring the number of CD4+ OX40+ Foxp3+ lymphocytes in the sample after step (c). These methods may find use in any of the other methods described herein, e.g., methods for predicting responsiveness of a subject having cancer to an OX40 agonist treatment, methods for determining the prognosis of a subject having cancer by measuring the number of CD4+ OX40+ Foxp3+ lymphocytes in a sample containing cancer cells and lymphocytes obtained from the subject, and/or methods for treating or delaying progression of cancer in a subject.

In some embodiments, lymphocytes that show expression of CD4, OX40, and/or Foxp3 are labeled. Any suitable method known in the art and/or described herein for labeling a cell that shows expression of a marker may be used. In some embodiments, lymphocytes that show expression of CD4, OX40, and/or Foxp3 are labeled using an antibody that specifically binds to CD4, OX40, or Foxp3. For example, such antibodies may be used for assays including without limitation immunofluorescence staining, flow cytometry, immunoprecipitation, and the like. In some embodiments, lymphocytes showing CD4 expression, OX40 expression, and Foxp3 expression are labeled by immunofluorescence staining. In some embodiments, lymphocytes that show expression of CD4, OX40, and/or Foxp3 are labeled for in situ hybridization using a probe that specifically binds to CD4, OX40, or Foxp3 transcripts. In some embodiments, expression of CD4, OX40, and/or Foxp3 may be labeled using the same technique. In some embodiments, expression of CD4, OX40, and/or Foxp3 may be labeled using multiple techniques.

In some embodiments, imaging techniques are used to quantify expression of CD4, OX40, and/or Foxp3 corresponding to labeled lymphocytes. For example, fluorescence microscopy may be used to measure the amount of CD4, OX40, and/or Foxp3 expression in a sample. Image analysis techniques, such as those described above, may be used to quantify expression of each marker on a cell-by-cell basis, enabling the enumeration of cells of interest (e.g., CD4+ OX40+ Foxp3+ lymphocytes).

In some embodiments, lymphocytes that show CD4 expression in a sample are labeled first, followed by lymphocytes that show OX40 expression in the sample, followed by lymphocytes that show Foxp3 expression in the sample. In some embodiments, detection of CD4 expression may occur before detection of OX40 expression, and/or detection of OX40 expression may occur before detection of Foxp3 expression. In some embodiments, each marker may be labeled in succession, but the detection of all three markers may be performed at the same time (e.g., by multichannel fluorescence microscopy). It is to be noted that detection of three separate fluorophores may not occur simultaneously; rather, "at the same time" may encompass successive imaging of a sample using a first channel, then a second channel, then a third channel, to create a composite, three-color image of a sample showing expression levels of CD4, OX40, and Foxp3.

In some embodiments, antigen retrieval techniques are used between labeling steps. Antigen retrieval techniques are widely known and used in the art to improve specific binding of antibodies to antigens. Without wishing to be bound to theory, these techniques are thought to uncover and/or recover antigenic sites by breaking cross-linkages or otherwise altering protein conformation. Antigen retrieval techniques often include heat, chemical, and/or enzymatic treatment of samples, such as fixed and/or paraffin-embedded samples.

In some embodiments, a sample may be treated with a solution containing an effective amount of an antigen retrieval agent between labeling lymphocytes that show CD4 expression in the sample and labeling lymphocytes that show OX40 expression in the sample and/or between labeling lymphocytes that show OX40 expression in the sample and labeling lymphocytes that show Foxp3 expression in the sample. In some embodiments, a sample may be heated while being treated with an antigen retrieval agent.

In some embodiments, the antigen retrieval agent contains EDTA. In some embodiments, the antigen retrieval agent includes an EDTA buffer. Effective amounts of various antigen retrieval agents may be determined empirically, such as by assaying the effectiveness of staining with a particular antibody, and effective amounts of many antigen retrieval agents are known in the art. For example, a sample may be treated with 1 mM EDTA buffer. In some embodiments, the EDTA buffer may be at pH 8.0, pH 8.5, or pH 9.0.

In some embodiments, the antigen retrieval agent contains a citrate buffer. For example, DAKO® Target Retrieval Solution or sodium citrate buffer may be used. Effective amounts of various antigen retrieval agents may be determined empirically, such as by assaying the effectiveness of staining with a particular antibody, and effective amounts of many antigen retrieval agents are known in the art. For example, a sample may be treated with 10 mM sodium citrate buffer. In some embodiments, the citrate buffer may be at pH 6.0.

It is known in the art that different primary antibodies used for immunofluorescence staining may have different effective dilutions. In some embodiments, an anti-CD4 antibody in concentrated form may be diluted between 1:50-1:500 for use. In some embodiments, an anti-CD4 antibody in concentrated form may be diluted 1:50 for use. In some embodiments, the anti-CD4 antibody may be clone 4B12 (Fisher Scientific, Waltham, Mass.). In some embodiments, an anti-OX40 antibody in concentrated form may be diluted between 1:200-1:600 for use. In some embodiments, an anti-OX40 antibody in concentrated form may be diluted 1:400 for use. In some embodiments, the anti-OX40 antibody may be 1A7. In some embodiments, an anti-Foxp3 antibody in concentrated form may be diluted between 1:100-1:500 for use. In some embodiments, an anti-Foxp3 antibody in concentrated form may be diluted 1:100 for use. In some embodiments, the anti-Foxp3 antibody may be clone 236A/E7 (Abcam, Cambridge, UK).

Various antibodies known in the art that specifically bind to OX40 may be used in the detection assays described herein. In some embodiments, lymphocytes that show expression of OX40 are labeled by one of the antibodies described herein. In some embodiments, lymphocytes that show expression of OX40 are labeled by an antibody comprising (a) HVR-H1 comprising the amino acid sequence of SEQ ID NO:2; (b) HVR-H2 comprising the amino acid sequence of SEQ ID NO:3; (c) HVR-H3 comprising the amino acid sequence of SEQ ID NO:4; (d) HVR-L1 comprising the amino acid sequence of SEQ ID NO:5; (e) HVR-L2 comprising the amino acid sequence of SEQ ID NO:6; and (f) HVR-L3 comprising an amino acid sequence selected from SEQ ID NO:7.

In some embodiments, lymphocytes that show expression of OX40 are labeled by antibody clone 1A7. In some embodiments, lymphocytes that show expression of OX40 are labeled by an antibody comprising a heavy chain variable region comprising the amino acid sequence of EVQLQQSGPELVKPGASVKISCKASGYTFTDSYM-SWVKQSHGKTLEWIGDMYPDNGDSSY NQKFREK-VTLTVDKSSTTAYMEFRSLTSEDSAVYYCVL-APRWYFSVWGTGTTVTVSS (SEQ ID NO:) and/or a light chain variable region comprising the amino acid sequence of

```
                                        (SEQ ID NO:  )
DIQMTQTTSSLSASLGDRVTISCRASQDISNYLNWYQQKPDGTVKLLIYY

TSRLRSGVPSRFSGSGSGKDYFLTISNLEQEDVAAYFCQQGHTLPPTFGG

GTKLEIK.
```

In some embodiments, the anti-OX40 antibody for use in a method of diagnosis or detection is an anti-human OX40 antibody comprising at least one, two, three, four, five, or six HVRs selected from (a) HVR-H1 comprising the amino acid sequence of SEQ ID NO:2; (b) HVR-H2 comprising the amino acid sequence of SEQ ID NO:3; (c) HVR-H3 comprising the amino acid sequence of SEQ ID NO:4; (d) HVR-L1 comprising the amino acid sequence of SEQ ID NO:5; (e) HVR-L2 comprising the amino acid sequence of SEQ ID NO:6; and (f) HVR-L3 comprising the amino acid sequence of SEQ ID NO:7. In some embodiments, the anti-OX40 antibody comprises (a) a VH domain comprising at least one, at least two, or all three VH HVR sequences selected from (i) HVR-H1 comprising the amino acid sequence of SEQ ID NO:2, (ii) HVR-H2 comprising the amino acid sequence of SEQ ID NO:3, and (iii) HVR-H3 comprising an amino acid sequence selected from SEQ ID NO:4; and (b) a VL domain comprising at least one, at least two, or all three VL HVR sequences selected from (i) HVR-L1 comprising the amino acid sequence of SEQ ID NO:5, (ii) HVR-L2 comprising the amino acid sequence of SEQ ID NO:6, and (c) HVR-L3 comprising the amino acid sequence of SEQ ID NO:7. In some embodiments, the OX40 antibody comprises (a) HVR-H1 comprising the amino acid sequence of SEQ ID NO:2; (b) HVR-H2 comprising the amino acid sequence of SEQ ID NO:3; (c) HVR-H3 comprising the amino acid sequence of SEQ ID NO:4; (d) HVR-L1 comprising the amino acid sequence of SEQ ID NO:5; (e) HVR-L2 comprising the amino acid sequence of SEQ ID NO:6; and (f) HVR-L3 comprising an amino acid sequence selected from SEQ ID NO:7. In some embodiments, the antibody comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO:179. In certain embodiments, a VH sequence having at least 90%, 91%, 92%, 93%, 94%, 95%, 96%, 97%, 98%, or 99% sequence identity contains substitutions (e.g., conservative substitutions), insertions, or deletions relative to the reference sequence, but an anti-human OX40 agonist antibody comprising that sequence retains the ability to bind to OX40. In certain embodiments, a total of 1 to 10 amino acids have been substituted, inserted and/or deleted in SEQ ID NO:179. In certain embodiments, substitutions, insertions, or deletions occur in regions outside the HVRs (i.e., in the FRs). Optionally, the anti-human OX40 agonist antibody comprises the VH sequence in SEQ ID NO:179, including post-translational modifications of that sequence. In a particular embodiment, the VH comprises one, two or three HVRs selected from: (a) HVR-H1 comprising the amino acid sequence of SEQ ID NO:2, (b) HVR-H2 comprising the amino acid sequence of SEQ ID NO:3, and (c) HVR-H3 comprising the amino acid sequence of SEQ ID NO:4. In some embodiments, the antibody comprises a light chain variable domain (VL) having at least 90%, 91%, 92%, 93%, 94%, 95%, 96%, 97%, 98%, 99%, or 100% sequence identity to the amino acid sequence of SEQ ID NO:180. In certain embodiments, a VL sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-human OX40 agonist antibody comprising that sequence retains the ability to bind to OX40. In certain embodiments, a total of 1 to 10 amino acids have been substituted, inserted and/or deleted in SEQ ID NO: 180. In certain embodiments, the substitutions, insertions, or deletions occur in regions outside the HVRs (i.e., in the FRs). Optionally, the anti-human OX40 agonist antibody comprises the VL sequence in SEQ ID NO: 180, including post-translational modifications of that sequence. In a particular embodiment, the VL comprises one, two or three HVRs selected from (a) HVR-L1 comprising the amino acid sequence of SEQ ID NO:5; (b) HVR-L2 comprising the amino acid sequence of SEQ ID NO:6; and (c) HVR-L3 comprising the amino acid sequence of SEQ ID NO:7.

In some embodiments, the anti-OX40 antibody used in the method of diagnosis or detection is an anti-human OX40 antibody comprising at least one, two, three, four, five, or six HVRs selected from (a) HVR-H1 comprising the amino acid sequence of SEQ ID NO:29; (b) HVR-H2 comprising the amino acid sequence of SEQ ID NO:30; (c) HVR-H3 comprising the amino acid sequence of SEQ ID NO:31; (d) HVR-L1 comprising the amino acid sequence of SEQ ID NO:37; (e) HVR-L2 comprising the amino acid sequence of SEQ ID NO:39; and (f) HVR-L3 comprising the amino acid sequence of SEQ ID NO:42. In some embodiments, the anti-OX40 antibody comprises (a) a VH domain comprising at least one, at least two, or all three VH HVR sequences selected from (i) HVR-H1 comprising the amino acid sequence of SEQ ID NO:29, (ii) HVR-H2 comprising the amino acid sequence of SEQ ID NO:30, and (iii) HVR-H3 comprising an amino acid sequence selected from SEQ ID NO:31; and (b) a VL domain comprising at least one, at least two, or all three VL HVR sequences selected from (i) HVR-L1 comprising the amino acid sequence of SEQ ID NO:37, (ii) HVR-L2 comprising the amino acid sequence of SEQ ID NO:39, and (c) HVR-L3 comprising the amino acid sequence of SEQ ID NO:42. In some embodiments, the anti-OX40 antibody comprises (a) HVR-H1 comprising the amino acid sequence of SEQ ID NO:29; (b) HVR-H2 comprising the amino acid sequence of SEQ ID NO:30; (c) HVR-H3 comprising the amino acid sequence of SEQ ID NO:31; (d) HVR-L1 comprising the amino acid sequence of SEQ ID NO:37; (e) HVR-L2 comprising the amino acid sequence of SEQ ID NO:39; and (f) HVR-L3 comprising an amino acid sequence selected from SEQ ID NO:42. In some embodiment, the anti-OX40 antibody comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO:181. In certain embodiments, a VH sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-human OX40 agonist antibody comprising that sequence retains the ability to bind to OX40. In certain embodiments, a total of 1 to 10 amino acids have been substituted, inserted and/or deleted in SEQ ID NO:181. In certain embodiments, substitutions, insertions, or deletions occur in regions outside the HVRs (i.e., in the FRs). Optionally, the anti-human OX40 agonist antibody comprises the VH sequence in SEQ ID NO:181, including post-translational modifications of that sequence. In a particular embodiment, the VH comprises one, two or three HVRs selected from: (a) HVR-H1 comprising the amino acid sequence of SEQ ID NO:29, (b) HVR-H2 comprising the amino acid sequence of SEQ ID NO:30, and (c) HVR-H3 comprising the amino acid sequence of SEQ ID NO:31. In some embodiments, the anti-OX40 antibody comprises a light chain variable domain (VL) having at least 90%, 91%, 92%, 93%, 94%, 95%, 96%, 97%, 98%, 99%, or 100% sequence identity to the amino acid sequence of SEQ ID NO:182. In certain embodiments, a VL sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-human OX40 agonist antibody comprising that sequence retains the ability to bind to OX40. In certain embodiments, a total of 1 to 10 amino acids have been substituted, inserted and/or deleted in SEQ ID NO: 182. In certain embodiments, the substitutions, insertions, or deletions occur in regions outside the HVRs (i.e., in the FRs). Optionally, the anti-human OX40 agonist antibody comprises the VL sequence in SEQ ID NO: 182, including post-translational modifications of that sequence. In a particular embodiment, the VL comprises one, two or three HVRs selected from (a) HVR-L1 comprising the amino acid sequence of SEQ ID NO:37; (b) HVR-L2 comprising the amino acid sequence of SEQ ID NO:39; and (c) HVR-L3 comprising the amino acid sequence of SEQ ID NO:42.

In some embodiments, the anti-OX40 antibody comprises a VH sequence of SEQ ID NO: 179. In some embodiments, the anti-OX40 antibody comprises a VL sequence of SEQ ID NO: 180. In some embodiments, the anti-OX40 antibody comprises a VH sequence of SEQ ID NO:179 and a VL sequence of SEQ ID NO: 180. In some embodiments, the anti-OX40 antibody comprises a VH sequence of SEQ ID NO: 181. In some embodiments, the anti-OX40 antibody comprises a VL sequence of SEQ ID NO: 182. In some embodiments, the anti-OX40 antibody comprises a VH sequence of SEQ ID NO:181 and a VL sequence of SEQ ID NO: 182.

V. Methods of Treatment

In one aspect, provided herein are methods for treating or delaying progression of cancer in an individual comprising administering to the individual an effective amount of an OX40 agonist. The methods of this disclosure may find use, inter alia, in treating conditions where enhanced immunogenicity is desired such as increasing tumor immunogenicity for the treatment of cancer or T cell dysfunctional disorders. A variety of cancers may be treated, or their progression may be delayed, by these methods.

Certain aspects of the present disclosure relate to methods for treating or delaying progression of cancer in a subject. In some embodiments, the methods include measuring the number of CD4+ OX40+ Foxp3+ lymphocytes in a sample containing cancer cells and lymphocytes obtained from the subject; determining the number of CD4+ OX40+ Foxp3+ lymphocytes in the sample, as compared with a reference; and if the number of CD4+ OX40+ Foxp3+ lymphocytes in the sample is higher than the reference, administering to the subject an effective amount of an OX40 agonist. In some embodiments, the methods include administering to the subject an effective amount of an OX40 agonist, where a sample comprising cancer cells and lymphocytes obtained from the subject has an increased number of CD4+ OX40+ Foxp3+ lymphocytes, as compared with a reference. In some embodiments, the methods include measuring the number of CD4+ OX40+ Foxp3− lymphocytes in a sample containing cancer cells (e.g., metastatic cancer cells) and lymphocytes obtained from the subject; determining the number of CD4+ OX40+ Foxp3-lymphocytes in the sample, as compared with a reference; and if the number of CD4+ OX40+ Foxp3− lymphocytes in the sample is higher than the reference, administering to the subject an effective amount of an OX40 agonist. In some embodiments, the methods include administering to the subject an effective amount of an OX40 agonist, where a sample comprising (e.g., metastatic cancer cells) cancer cells and lymphocytes obtained from the subject has an increased number of CD4+ OX40+ Foxp3− lymphocytes, as compared with a reference. In some embodiments, the methods include measuring the number of OX40+ lymphocytes in a sample containing metastatic cancer cells and lymphocytes obtained from the subject; determining the number of OX40+ lymphocytes in the sample, as compared with a reference; and if the number of OX40+ lymphocytes in the sample is higher than the reference, administering to the subject an effective amount of an OX40 agonist. In some embodiments, the methods include administering to the subject an effective amount of an OX40 agonist, where a sample comprising metastatic cancer cells and lymphocytes obtained from the subject has an increased number of OX40+ lymphocytes, as compared with a reference. Any of the methods described herein for measuring the number of OX40+ lymphocytes in a sample may be used.

In some embodiments, the OX40 agonist is administered to a subject wherein a sample containing cancer cells (including metastatic cancer cells) and lymphocytes from the subject have been detected for having increase number of OX40+, CD4+ OX40+ Foxp3+, and/or CD4+ OX40+ Foxp3− lymphocytes in the sample as compared to a reference. In some embodiments, the increase may be one that is considered increased to a skilled person. For example, such increase may be at least about 0.5 fold, at least about 1 fold, at least about 2 fold, or at least about 5 fold relative to the reference.

In some embodiments, a cancer to be treated by the methods of the present disclosure includes, but is not limited to, squamous cell cancer (e.g., epithelial squamous cell cancer), lung cancer including small-cell lung cancer, non-small cell lung cancer, adenocarcinoma of the lung and squamous carcinoma of the lung, cancer of the peritoneum, hepatocellular cancer, gastric or stomach cancer including gastrointestinal cancer and gastrointestinal stromal cancer, pancreatic cancer, glioblastoma, cervical cancer, ovarian cancer, liver cancer, bladder cancer, cancer of the urinary tract, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, melanoma, superficial spreading melanoma, lentigo maligna melanoma, acral lentiginous melanomas, nodular melanomas, multiple myeloma and B-cell lymphoma; chronic lymphocytic leukemia (CLL); acute lymphoblastic leukemia (ALL); hairy cell leukemia; chronic myeloblastic leukemia; and post-transplant lymphoproliferative disorder (PTLD), as well as abnormal vascular proliferation associated with phakomatoses, edema (such as that associated with brain tumors), Meigs' syndrome, brain, as well as head and neck cancer, and associated metastases. In some embodiments, the cancer is colorectal cancer. In some embodiments, the cancer is selected from non-small cell lung cancer, glioblastoma, neuroblastoma, renal cell carcinoma, bladder cancer, ovarian cancer, melanoma, breast carcinoma, gastric cancer, and hepatocellular carcinoma. In some embodiments, the cancer is triple-negative breast carcinoma. In some embodiments, the cancer may be an early stage cancer or a late stage cancer. In some embodiments, the cancer may be a primary tumor. In some embodiments, the cancer may be a metastatic tumor at a second site derived from any of the above types of cancer.

In some embodiments, examples of cancer further include, but are not limited to, B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia); chronic lymphocytic leukemia (CLL); acute lymphoblastic leukemia (ALL); Hairy cell leukemia; chronic myeloblastic leukemia; and post-transplant lymphoproliferative disorder (PTLD), as well as abnormal vascular proliferation associated with phakomatoses, edema (such as that associated with brain tumors), B-cell proliferative disorders, and Meigs' syndrome. More specific examples include, but are not limited to, relapsed or refractory NHL, front line low grade NHL, Stage III/IV NHL, chemotherapy resistant NHL, precursor B lymphoblastic leukemia and/or lymphoma, small lymphocytic lymphoma, B-cell chronic lymphocytic leukemia and/or prolymphocytic leukemia and/or small lymphocytic lymphoma, B-cell prolymphocytic lymphoma, immunocytoma and/or lymphoplasmacytic lymphoma, lymphoplasmacytic lymphoma, marginal zone B-cell lymphoma, splenic marginal zone lymphoma, extranodal marginal zone—MALT lymphoma, nodal marginal zone lymphoma, hairy cell leukemia, plasmacytoma and/or plasma cell myeloma, low grade/follicular lymphoma, intermediate grade/follicular NHL, mantle cell lymphoma, follicle center lymphoma (follicular), intermediate grade diffuse NHL, diffuse large B-cell lymphoma, aggressive NHL (including aggressive front-line NHL and aggressive relapsed NHL), NHL relapsing after or refractory to autologous stem cell transplantation, primary mediastinal large B-cell lymphoma, primary effusion lymphoma, high grade immunoblastic NHL, high grade lymphoblastic NHL, high grade small non-cleaved cell NHL, bulky disease NHL, Burkitt's lymphoma, precursor (peripheral) large granular lymphocytic leukemia, mycosis fungoides and/or Sezary syndrome, skin (cutaneous) lymphomas, anaplastic large cell lymphoma, angiocentric lymphoma.

In some embodiments, examples of cancer further include, but are not limited to, B-cell proliferative disorders, which further include, but are not limited to, lymphomas (e.g., B-Cell Non-Hodgkin's lymphomas (NHL)) and lymphocytic leukemias. Such lymphomas and lymphocytic leukemias include e.g. a) follicular lymphomas, b) Small Non-Cleaved Cell Lymphomas/Burkitt's lymphoma (including endemic Burkitt's lymphoma, sporadic Burkitt's lymphoma and Non-Burkitt's lymphoma), c) marginal zone lymphomas (including extranodal marginal zone B-cell lymphoma (Mucosa-associated lymphatic tissue lymphomas, MALT), nodal marginal zone B-cell lymphoma and splenic marginal zone lymphoma), d) Mantle cell lymphoma (MCL), e) Large Cell Lymphoma (including B-cell diffuse large cell lymphoma (DLCL), Diffuse Mixed Cell Lymphoma, Immunoblastic Lymphoma, Primary Mediastinal B-Cell Lymphoma, Angiocentric Lymphoma-Pulmonary B-Cell Lymphoma), f) hairy cell leukemia, g) lymphocytic lymphoma, Waldenstrom's macroglobulinemia, h) acute lymphocytic leukemia (ALL), chronic lymphocytic leukemia (CLL)/small lymphocytic lymphoma (SLL), B cell prolymphocytic leukemia, i) plasma cell neoplasms, plasma cell myeloma, multiple myeloma, plasmacytoma, and/or j) Hodgkin's disease.

In some embodiments of any of the methods, the cancer is a B-cell proliferative disorder. In some embodiments, the B-cell proliferative disorder is lymphoma, non-Hodgkins lymphoma (NHL), aggressive NHL, relapsed aggressive NHL, relapsed indolent NHL, refractory NHL, refractory indolent NHL, chronic lymphocytic leukemia (CLL), small lymphocytic lymphoma, leukemia, hairy cell leukemia (HCL), acute lymphocytic leukemia (ALL), or mantle cell lymphoma. In some embodiments, the B-cell proliferative disorder is NHL, such as indolent NHL and/or aggressive NHL. In some embodiments, the B-cell proliferative disorder is indolent follicular lymphoma or diffuse large B-cell lymphoma.

It is a discovery of the present disclosure that the OX40+ status of immune infiltrates found on primary tumors and metastases are strongly correlated. That is to say, matched samples representing a primary tumor and a metastatic site from the same patient strongly correlate with respect to the number of OX40+ cells present (e.g., CD4+ OX40+ Foxp3+ Treg or CD4+ OX40+ Foxp3− Teff cells). Advantageously, this allows a clinician to sample a metastatic lesion for OX40+ status and determine the likely OX40+ status of the primary tumor, or vice versa. Certain aspects of the present disclosure relate to samples comprising cancer cells and lymphocytes. Therefore, in some embodiments, the cancer cells may be from a primary tumor, while in other embodiments, the cancer cells may be from a metastasis.

In some embodiments, the individual has cancer or is at risk of developing cancer. In some embodiments, the treatment results in a sustained response in the individual after cessation of the treatment. In some embodiments, the individual has cancer that may be at early stage or late stage. In some embodiments, the individual is a human. In some embodiments, the individual is a mammal, such as domesticated animals (e.g., cows, sheep, cats, dogs, and horses), primates (e.g., humans and non-human primates such as monkeys), rabbits, and rodents (e.g., mice and rats).

In some embodiments, provided is a method for treating or delaying progression of cancer in an individual comprising administering to the individual an effective amount of an OX40 agonist, and further comprising administering an additional therapy. The additional therapy may be radiation therapy, surgery (e.g., lumpectomy and a mastectomy), chemotherapy, gene therapy, DNA therapy, viral therapy, RNA therapy, immunotherapy, bone marrow transplantation, nanotherapy, monoclonal antibody therapy, or a combination of the foregoing. The additional therapy may be in the form of adjuvant or neoadjuvant therapy. In some embodiments, the additional therapy is the administration of small molecule enzymatic inhibitor or anti-metastatic agent. In some embodiments, the additional therapy is the administration of side-effect limiting agents (e.g., agents intended to lessen the occurrence and/or severity of side effects of treatment, such as anti-nausea agents, etc.). In some embodiments, the additional therapy is radiation therapy. In some embodiments, the additional therapy is surgery. In some embodiments, the additional therapy is a combination of radiation therapy and surgery. In some embodiments, the additional therapy is gamma irradiation. In some embodiments, the additional therapy is therapy targeting PI3K/AKT/mTOR pathway, HSP90 inhibitor, tubulin inhibitor, apoptosis inhibitor, and/or chemopreventative agent. The additional therapy may be one or more of the chemotherapeutic agents described hereabove.

Such combination therapies noted above encompass combined administration (where two or more therapeutic agents are included in the same or separate formulations), and separate administration, in which case, administration of the OX40 agonist of the invention can occur prior to, simultaneously, and/or following, administration of the additional therapeutic agent or agents. In one embodiment, administration of the OX40 agonist and administration of an additional therapeutic agent occur within about one month, or within about one, two or three weeks, or within about one, two, three, four, five, or six days, of each other. OX40 agonists of the invention can also be used in combination with radiation therapy.

In some embodiments, an anti-human OX40 agonist may be administered in conjunction with a chemotherapy or chemotherapeutic agent. In some embodiments, an anti-human OX40 agonist may be administered in conjunction with a radiation therapy or radiotherapeutic agent. In some embodiments, an anti-human OX40 agonist may be administered in conjunction with a targeted therapy or targeted therapeutic agent. In some embodiments, an anti-human OX40 agonist may be administered in conjunction with an immunotherapy or immunotherapeutic agent, for example a monoclonal antibody.

In some embodiments, an OX40 agonist (e.g., an anti-human OX40 agonist antibody) may be administered in conjunction with in combination with a PD-1 axis binding antagonist. A PD-1 axis binding antagonist includes but is not limited to a PD-1 binding antagonist, a PD-L1 binding antagonist and a PD-L2 binding antagonist. Alternative names for "PD-1" include CD279 and SLEB2. Alternative names for "PD-L1" include B7-H 1, B7-4, CD274, and B7-H. Alternative names for "PD-L2" include B7-DC, Btdc, and CD273. In some embodiments, PD-1, PD-L1, and PD-L2 are human PD-1, PD-L1 and PD-L2. In some embodiments, the PD-1 binding antagonist is a molecule that inhibits the binding of PD-1 to its ligand binding partners. In a specific aspect the PD-1 ligand binding partners are PD-L1 and/or PD-L2. In another embodiment, a PD-L1 binding antagonist is a molecule that inhibits the binding of PD-L1 to its binding partners. In a specific aspect, PD-L1 binding partners are PD-1 and/or B7-1. In another embodiment, the PD-L2 binding antagonist is a molecule that inhibits the binding of PD-L2 to its binding partners. In a specific aspect, a PD-L2 binding partner is PD-1. The antagonist may be an antibody, an antigen binding fragment thereof, an immunoadhesin, a fusion protein, or oligopeptide. In some embodiment, the PD-1 binding antagonist is an anti-PD-1 antibody (e.g., a human antibody, a humanized antibody, or a chimeric antibody). In some embodiments, the anti-PD-1 antibody is selected from the group consisting of MDX-1 106, Merck 3475 and CT-011. In some embodiments, the PD-1 binding antagonist is an immunoadhesin (e.g., an immunoadhesin comprising an extracellular or PD-1 binding portion of PD-L1 or PD-L2 fused to a constant region (e.g., an Fc region of an immunoglobulin sequence). In some embodiments, the PD-1 binding antagonist is AMP-224. In some embodiments, the PD-L1 binding antagonist is an anti-PD-L1 antibody. In some embodiments, the anti-PD-L1 binding antagonist is selected from the group consisting of YW243.55.S70, MPDL3280A (atezolizumab), MEDI4736 (durvalumab), MDX-1105, and MSB0010718C (avelumab). MDX-1 105, also known as BMS-936559, is an anti-PD-L1 antibody described in WO2007/005874. Antibody YW243.55.S70 (heavy and light chain variable region sequences shown in SEQ ID Nos. 20 and 21, respectively) is an anti-PD-L1 described in WO 2010/077634 A1. MDX-1 106, also known as MDX-1 106-04, ONO-4538 or BMS-936558, is an anti-PD-1 antibody described in WO2006/121168. Merck 3745, also known as MK-3475, SCH-900475, pembrolizumab, and KEYTRUDA®, is an anti-PD-1 antibody described in WO2009/114335. CT-011, also known as hBAT, hBAT-1, and pidilizumab, is an anti-PD-1 antibody described in WO2009/101611. AMP-224, also known as B7-DCIg, is a PD-L2-Fc fusion soluble receptor described in WO2010/027827 and WO2011/066342. In some embodiments, the anti-PD-1 antibody is MDX-1106. Alternative names for "MDX-1106" include MDX-1 106-04, ONO-4538, BMS-936558, Nivolumab, or OPDIVO®. In some embodiments, the anti-PD-1 antibody is Nivolumab (CAS Registry Number: 946414-94-4). In some embodiments, the anti-PD-1 antibody is selected from the group consisting of MDX-1106 (nivolumab, OPDIVO®), Merck 3475 (MK-3475, pembrolizumab, KEYTRUDA®), CT-011 (Pidilizumab), MEDI-0680 (AMP-514), PDR001, REGN2810, BGB-108, and BGB-A317.

In some embodiments, an OX40 agonist (e.g., an anti-human OX40 agonist antibody) may be administered in conjunction with an antagonist directed against CTLA-4 (also known as CD152), e.g., a blocking antibody. In some embodiments, an OX40 agonist (e.g., an anti-human OX40 agonist antibody) may be administered in conjunction with ipilimumab (also known as MDX-010, MDX-101, or Yervoy®). In some embodiments, an OX40 agonist (e.g., an anti-human OX40 agonist antibody) may be administered in conjunction with tremelimumab (also known as ticilimumab or CP-675,206). In some embodiments, an OX40 agonist (e.g., an anti-human OX40 agonist antibody) may be administered in conjunction with an antagonist directed against B7-H3 (also known as CD276), e.g., a blocking antibody. In some embodiments, an OX40 agonist (e.g., an anti-human OX40 agonist antibody) may be administered in conjunction with MGA271. In some embodiments, an OX40 agonist (e.g., an anti-human OX40 agonist antibody) may be administered in conjunction with an antagonist directed against a TGF beta, e.g., metelimumab (also known as CAT-192), fresolimumab (also known as GC1008), or LY2157299.

In some embodiments, an OX40 agonist (e.g., an anti-human OX40 agonist antibody) may be administered in conjunction with a treatment comprising adoptive transfer of a T cell (e.g., a cytotoxic T cell or CTL) expressing a chimeric antigen receptor (CAR). In some embodiments, an OX40 agonist (e.g., an anti-human OX40 agonist antibody) may be administered in conjunction with a treatment comprising adoptive transfer of a T cell comprising a dominant-negative TGF beta receptor, e.g, a dominant-negative TGF beta type II receptor. In some embodiments, an OX40 agonist (e.g., an anti-human OX40 agonist antibody) may be administered in conjunction with a treatment comprising a HERCREEM protocol (see, e.g., ClinicalTrials.gov Identifier NCT00889954).

In some embodiments, an OX40 agonist (e.g., an anti-human OX40 agonist antibody) may be administered in conjunction with an agonist directed against CD137 (also known as TNFRSF9, 4-1BB, or ILA), e.g., an activating antibody. In some embodiments, an OX40 agonist (e.g., an anti-human OX40 agonist antibody) may be administered in conjunction with urelumab (also known as BMS-663513). In some embodiments, an OX40 agonist (e.g., an anti-human OX40 agonist antibody) may be administered in conjunction with an agonist directed against CD40, e.g., an activating antibody. In some embodiments, an OX40 agonist (e.g., an anti-human OX40 agonist antibody) may be administered in conjunction with CP-870893. In some embodiments, an OX40 agonist (e.g., an anti-human OX40 agonist antibody) may be administered in conjunction with an agonist directed against OX40 (also known as CD134), e.g., an activating antibody. In some embodiments, an OX40 agonist (e.g., an anti-human OX40 agonist antibody) may be administered in conjunction with a different anti-OX40 antibody (e.g., AgonOX). In some embodiments, an OX40 agonist (e.g., an anti-human OX40 agonist antibody) may be administered in conjunction with an agonist directed against CD27, e.g., an activating antibody. In some embodiments, an OX40 agonist (e.g., an anti-human OX40 agonist antibody) may be administered in conjunction with CDX-1127. In some embodiments, an OX40 agonist (e.g., an anti-human OX40 agonist antibody) may be administered in conjunction with an antagonist directed against indoleamine-2,3-dioxygenase (IDO). In some embodiments, with the IDO antagonist is 1-methyl-D-tryptophan (also known as 1-D-MT).

In some embodiments, an OX40 agonist (e.g., an anti-human OX40 agonist antibody) may be administered in conjunction with an antibody-drug conjugate. In some embodiments, the antibody-drug conjugate comprises mertansine or monomethyl auristatin E (MMAE). In some embodiments, an OX40 agonist (e.g., an anti-human OX40 agonist antibody) may be administered in conjunction with and anti-NaPi2b antibody-MMAE conjugate (also known as DNIB0600A or RG7599). In some embodiments, an OX40 agonist (e.g., an anti-human OX40 agonist antibody) may be administered in conjunction with trastuzumab emtansine (also known as T-DM1, ado-trastuzumab emtansine, or KADCYLA®, Genentech). In some embodiments, an OX40 agonist (e.g., an anti-human OX40 agonist antibody) may be administered in conjunction with DMUC5754A. In some embodiments, an OX40 agonist (e.g., an anti-human OX40 agonist antibody) may be administered in conjunction with an antibody-drug conjugate targeting the endothelin B receptor (EDNBR), e.g., an antibody directed against EDNBR conjugated with MMAE.

In some embodiments, an OX40 agonist (e.g., an anti-human OX40 agonist antibody) may be administered in conjunction with an angiogenesis inhibitor. In some embodiments, an OX40 agonist (e.g., an anti-human OX40 agonist antibody) may be administered in conjunction with an antibody directed against a VEGF, e.g., VEGF-A. In some embodiments, an OX40 agonist (e.g., an anti-human OX40 agonist antibody) may be administered in conjunction with bevacizumab (also known as AVASTIN®, Genentech). In some embodiments, an OX40 agonist (e.g., an anti-human OX40 agonist antibody) may be administered in conjunction with an antibody directed against angiopoietin 2 (also known as Ang2). In some embodiments, an OX40 agonist (e.g., an anti-human OX40 agonist antibody) may be administered in conjunction with MEDI3617.

In some embodiments, an OX40 agonist (e.g., an anti-human OX40 agonist antibody) may be administered in conjunction with an antineoplastic agent. In some embodiments, an OX40 agonist (e.g., an anti-human OX40 agonist antibody) may be administered in conjunction with an agent targeting CSF-1R (also known as M-CSFR or CD115). In some embodiments, an OX40 agonist (e.g., an anti-human OX40 agonist antibody) may be administered in conjunction with anti-CSF-1R (also known as IMC-CS4). In some embodiments, an OX40 agonist (e.g., an anti-human OX40 agonist antibody) may be administered in conjunction with an interferon, for example interferon alpha or interferon gamma. In some embodiments, an OX40 agonist (e.g., an anti-human OX40 agonist antibody) may be administered in conjunction with Roferon-A (also known as recombinant Interferon alpha-2a). In some embodiments, an OX40 agonist (e.g., an anti-human OX40 agonist antibody) may be administered in conjunction with GM-CSF (also known as recombinant human granulocyte macrophage colony stimulating factor, rhu GM-CSF, sargramostim, or Leukine®). In some embodiments, an OX40 agonist (e.g., an anti-human OX40 agonist antibody) may be administered in conjunction with IL-2 (also known as aldesleukin or Proleukin®). In some embodiments, an OX40 agonist (e.g., an anti-human OX40 agonist antibody) may be administered in conjunction with IL-12. In some embodiments, an OX40 agonist (e.g., an anti-human OX40 agonist antibody) may be administered in conjunction with an antibody targeting CD20. In some embodiments, the antibody targeting CD20 is obinutuzumab (also known as GA101 or Gazyva®) or rituximab. In some embodiments, an OX40 agonist (e.g., an anti-human OX40 agonist antibody) may be administered in conjunction with an antibody targeting GITR. In some embodiments, the antibody targeting GITR is TRX518.

In some embodiments, an OX40 agonist (e.g., an anti-human OX40 agonist antibody) may be administered in conjunction with a cancer vaccine. In some embodiments, the cancer vaccine is a peptide cancer vaccine, which in some embodiments is a personalized peptide vaccine. In some embodiments the peptide cancer vaccine is a multivalent long peptide, a multi-peptide, a peptide cocktail, a hybrid peptide, or a peptide-pulsed dendritic cell vaccine (see, e.g., Yamada et al., Cancer Sci, 104:14-21, 2013). In some embodiments, an OX40 agonist (e.g., an anti-human OX40 agonist antibody) may be administered in conjunction with an adjuvant. In some embodiments, an OX40 agonist (e.g., an anti-human OX40 agonist antibody) may be administered in conjunction with a treatment comprising a TLR agonist, e.g., Poly-ICLC (also known as Hiltonol®), LPS, MPL, or CpG ODN. In some embodiments, an OX40 agonist (e.g., an anti-human OX40 agonist antibody) may be administered in conjunction with tumor necrosis factor (TNF) alpha. In some embodiments, an OX40 agonist (e.g., an anti-human OX40 agonist antibody) may be administered in conjunction with IL-1. In some embodiments, an OX40 agonist (e.g., an anti-human OX40 agonist antibody) may be administered in conjunction with HMGB1. In some embodiments, an OX40 agonist (e.g., an anti-human OX40 agonist antibody) may be administered in conjunction with an IL-10 antagonist. In some embodiments, an OX40 agonist (e.g., an anti-human OX40 agonist antibody) may be administered in conjunction with an IL-4 antagonist. In some embodiments, an OX40 agonist (e.g., an anti-human OX40 agonist antibody) may be administered in conjunction with an IL-13 antagonist. In some embodiments, an OX40 agonist (e.g., an anti-human OX40 agonist antibody) may be administered in conjunction with an HVEM antagonist. In some embodiments, an OX40 agonist (e.g., an anti-human OX40 agonist antibody) may be administered in conjunction with an ICOS agonist, e.g., by administration of ICOS-L, or an agonistic antibody directed against ICOS. In some embodiments, an OX40 agonist (e.g., an anti-human OX40 agonist antibody) may be administered in conjunction with a treatment targeting CX3CL1. In some embodiments, an OX40 agonist (e.g., an anti-human OX40 agonist antibody) may be administered in conjunction with a treatment targeting CXCL9. In some embodiments, an OX40 agonist (e.g., an anti-human OX40 agonist antibody) may be administered in conjunction with a treatment targeting CXCL10. In some embodiments, an OX40 agonist (e.g., an anti-human OX40 agonist antibody) may be administered in conjunction with a treatment targeting CCL5. In some embodiments, an OX40 agonist (e.g., an anti-human OX40 agonist antibody) may be administered in conjunction with an LFA-1 or ICAM1 agonist. In some embodiments, an OX40 agonist (e.g., an anti-human OX40 agonist antibody) may be administered in conjunction with a Selectin agonist.

In some embodiments, an OX40 agonist (e.g., an anti-human OX40 agonist antibody) may be administered in conjunction with a targeted therapy. In some embodiments, an OX40 agonist (e.g., an anti-human OX40 agonist antibody) may be administered in conjunction with an inhibitor of B-Raf. In some embodiments, an OX40 agonist (e.g., an anti-human OX40 agonist antibody) may be administered in conjunction with vemurafenib (also known as Zelboraf®). In some embodiments, an OX40 agonist (e.g., an anti-human OX40 agonist antibody) may be administered in conjunction with dabrafenib (also known as Tafinlar®). In some embodiments, an OX40 agonist (e.g., an anti-human OX40 agonist antibody) may be administered in conjunction with erlotinib (also known as Tarceva®). In some embodiments, an OX40 agonist (e.g., an anti-human OX40 agonist antibody) may be administered in conjunction with an inhibitor of a MEK, such as MEK1 (also known as MAP2K1) or MEK2 (also known as MAP2K2). In some embodiments, an OX40 agonist (e.g., an anti-human OX40 agonist antibody) may be administered in conjunction with cobimetinib (also known as GDC-0973 or XL-518). In some embodiments, an OX40 agonist (e.g., an anti-human OX40 agonist antibody) may be administered in conjunction with trametinib (also known as Mekinist®). In some embodiments, an OX40 agonist (e.g., an anti-human OX40 agonist antibody) may be administered in conjunction with an inhibitor of K-Ras. In some embodiments, an OX40 agonist (e.g., an anti-human OX40 agonist antibody) may be administered in conjunction with an inhibitor of c-Met. In some embodiments, an OX40 agonist (e.g., an anti-human OX40 agonist antibody) may be administered in conjunction with onartuzumab (also known as MetMAb). In some embodiments, an OX40 agonist (e.g., an anti-human OX40 agonist antibody) may be administered in conjunction with an inhibitor of Alk. In some embodiments, an OX40 agonist (e.g., an anti-human OX40 agonist antibody) may be administered in conjunction with AF802 (also known as CH5424802 or alectinib). In some embodiments, an OX40 agonist (e.g., an anti-human OX40 agonist antibody) may be administered in conjunction with an inhibitor of a phosphatidylinositol 3-kinase (PI3K). In some embodiments, an OX40 agonist (e.g., an anti-human OX40 agonist antibody) may be administered in conjunction with BKM120. In some embodiments, an OX40 agonist (e.g., an anti-human OX40 agonist antibody) may be administered in conjunction with idelalisib (also known as GS-1101 or CAL-101). In some embodiments, an OX40 agonist (e.g., an anti-human OX40 agonist antibody) may be administered in conjunction with perifosine (also known as KRX-0401). In some embodiments, an OX40 agonist (e.g., an anti-human OX40 agonist antibody) may be administered in conjunction with an inhibitor of an Akt. In some embodiments, an OX40 agonist (e.g., an anti-human OX40 agonist antibody) may be administered in conjunction with MK2206. In some embodiments, an OX40 agonist (e.g., an anti-human OX40 agonist antibody) may be administered in conjunction with GSK690693. In some embodiments, an OX40 agonist (e.g., an anti-human OX40 agonist antibody) may be administered in conjunction with GDC-0941. In some embodiments, an OX40 agonist (e.g., an anti-human OX40 agonist antibody) may be administered in conjunction with an inhibitor of mTOR. In some embodiments, an OX40 agonist (e.g., an anti-human OX40 agonist antibody) may be administered in conjunction with sirolimus (also known as rapamycin). In some embodiments, an OX40 agonist (e.g., an anti-human OX40 agonist antibody) may be administered in conjunction with temsirolimus (also known as CCI-779 or Torisel®). In some embodiments, an OX40 agonist (e.g., an anti-human OX40 agonist antibody) may be administered in conjunction with everolimus (also known as RAD001). In some embodiments, an OX40 agonist (e.g., an anti-human OX40 agonist antibody) may be administered in conjunction with ridaforolimus (also known as AP-23573, MK-8669, or deforolimus). In some embodiments, an OX40 agonist (e.g., an anti-human OX40 agonist antibody) may be administered in conjunction with OSI-027. In some embodiments, an OX40 agonist (e.g., an anti-human OX40 agonist antibody) may be administered in conjunction with AZD8055. In some embodiments, an OX40 agonist (e.g., an anti-human OX40 agonist antibody) may be administered in conjunction with INK128. In some embodiments, an OX40 agonist (e.g., an anti-human OX40 agonist antibody) may be administered in conjunction with a dual PI3K/mTOR inhibitor. In some embodiments, an OX40 agonist (e.g., an anti-human OX40 agonist antibody) may be administered in conjunction with XL765. In some embodiments, an OX40 agonist (e.g., an anti-human OX40 agonist antibody) may be administered in conjunction with GDC-0980. In some embodiments, an OX40 agonist (e.g., an anti-human OX40 agonist antibody) may be administered in conjunction with BEZ235 (also known as NVP-BEZ235). In some embodiments, an OX40 agonist (e.g., an anti-human OX40 agonist antibody) may be administered in conjunction with BGT226. In some embodiments, an OX40 agonist (e.g., an anti-human OX40 agonist antibody) may be administered in conjunction with GSK2126458. In some embodiments, an OX40 agonist (e.g., an anti-human OX40 agonist antibody) may be administered in conjunction with PF-04691502. In some embodiments, an OX40 agonist (e.g., an anti-human OX40 agonist antibody) may be administered in conjunction with PF-05212384 (also known as PKI-587).

An OX40 agonist of the invention (and any additional therapeutic agent) can be administered by any suitable means, including parenteral, intrapulmonary, and intranasal, and, if desired for local treatment, intralesional administration. Parenteral infusions include intramuscular, intravenous, intraarterial, intraperitoneal, or subcutaneous administration. Dosing can be by any suitable route, e.g. by injections, such as intravenous or subcutaneous injections, depending in part on whether the administration is brief or chronic. Various dosing schedules including but not limited to single or multiple administrations over various timepoints, bolus administration, and pulse infusion are contemplated herein.

OX40 agonists of the invention would be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The antibody need not be, but is optionally formulated with one or more agents currently used to prevent or treat the disorder in question. The effective amount of such other agents depends on the amount of antibody present in the formulation, the type of disorder or treatment, and other factors discussed above. These are generally used in the same dosages and with administration routes as described herein, or about from 1 to 99% of the dosages described herein, or in any dosage and by any route that is empirically/clinically determined to be appropriate.

For the prevention or treatment of disease, the appropriate dosage of an OX40 agonist of the invention (when used alone or in combination with one or more other additional therapeutic agents) will depend on the type of disease to be treated, the type of antibody, the severity and course of the disease, whether the antibody is administered for preventive or therapeutic purposes, previous therapy, the patient's clinical history and response to the antibody, and the discretion of the attending physician. The antibody is suitably administered to the patient at one time or over a series of treatments. Depending on the type and severity of the disease, about 1 µg/kg to 40 mg/kg of antibody can be an initial candidate dosage for administration to the patient, whether, for example, by one or more separate administrations, or by continuous infusion. One typical daily dosage might range from about 1 µg/kg to 100 mg/kg or more, depending on the factors mentioned above. For repeated administrations over several days or longer, depending on the condition, the treatment would generally be sustained until a desired suppression of disease symptoms occurs. Such doses may be administered intermittently, e.g. every week or every three weeks (e.g. such that the patient receives from about two to about twenty, or e.g. about six doses of the antibody). An initial higher loading dose, followed by one or more lower doses may be administered. However, other dosage regimens may be useful. The progress of this therapy is easily monitored by conventional techniques and assays.

In some embodiments of the methods of the present disclosure, the cancer has elevated levels of T cell infiltration. As used herein, T cell infiltration of a cancer may refer to the presence of T cells, such as tumor-infiltrating lymphocytes (TILs), within or otherwise associated with the cancer tissue. It is known in the art that T cell infiltration may be associated with improved clinical outcome in certain cancers (see, e.g., Zhang et al., N. Engl. J. Med. 348(3): 203-213 (2003)). In some embodiments, the TILs may be OX40+. In some embodiments, the TILs may be CD4+ OX40+ Foxp3+ Treg or CD4+ OX40+ Foxp3− Teff cells.

The specification is considered to be sufficient to enable one skilled in the art to practice the invention. Various modifications of the invention in addition to those shown and described herein will become apparent to those skilled in the art from the foregoing description and fall within the scope of the appended claims.

VI. Kits and Articles of Manufacture

For use in the methods described above and herein, kits or articles of manufacture are also provided. Such kits may comprise at least one reagent specific for detecting CD4+, OX40+, CD4+ OX40+ Foxp3+, or CD4+ OX40+ Foxp3− lymphocytes in a sample comprising cancer cells and lymphocytes from a subject. In some embodiments, kits or articles of manufacture comprises an antibody that binds to human CD4 (e.g., NeoMarkers clone 4B12), an antibody that binds to human OX40 (e.g., antibody 1A7), and/or an antibody that binds to FoxP3 (e.g., Abcam clone 236A/E7). In some embodiments, the kits or articles of manufacture further comprise an OX40 agonist (e.g., an anti-OX40 agonist antibody) described herein. In some embodiments, the kits or articles of manufacture further comprise other reagents and/or buffers, such as bacteriostatic water for injection (BWFI), phosphate-buffered saline, Ringer's solution and dextrose solution. It may further include other materials desirable from a commercial and user standpoint, including other buffers, diluents, filters, needles, and syringes. The reagents and antibodies may be in a container. Suitable containers include, for example, bottles, vials, syringes, IV solution bags, etc. The containers may be formed from a variety of materials such as glass or plastic. In some embodiments, the kits and article of manufactures further comprise a label or packages insert (that may be on or associated with a container) providing instructions to use the reagents and/or antibodies in methods described herein.

All publications, patents, and patent applications cited herein are hereby incorporated by reference in their entirety for all purposes.

EXAMPLES

The invention can be further understood by reference to the following examples, which are provided by way of illustration and are not meant to be limiting.

Example 1: Inverse Correlation Between T-Cell Subsets and Cancer Stage

Increased numbers of OX40+ T cells in the tumor microenvironment of colorectal cancer (CRC) patients have been associated with improved outcome (Petty, J. K., et al. (2002) Am. J. Surg. 183(5):512-8). However, the OX40+ T cell population is heterogeneous and includes, among others, CD4+ Foxp3+ regulatory T cells (Tregs) as well as CD4+ Foxp3− effector T cells (Teff).

To study the functional significance of these T cell subsets, a multiplex immunofluorescence assay was developed to evaluate the expression of OX40 in certain CD4+ T cell subsets. This assay was utilized to determine whether OX40+ cell subsets and clinical outcome are associated in colorectal cancer (CRC) patients.

Materials and Methods

Case Selection

Formalin-fixed paraffin-embedded (FFPE) CRC specimens including primary site (n=48) and matched metastases (n=19) were included from a collection annotated with treatment histories and survival outcomes. Patient ages ranged from 26-85 yrs. and Stage I (4), Stage II (12), Stage III (17) and Stage IV (8) disease were represented. Cases were included well- or moderately-differentiated adenocarcinoma (n=36) with additional cases with either poorly-differentiated (n=4) or mucinous features (8).

Immunofluorescence Staining

A sequential approach was followed for all immunolabelings, including the double and triple round of immunofluorescence staining. CD4 (NeoMarkers clone 4B12), FoxP3 (Abcam clone 236A/E7), and OX40 (Clone 1A7) antibodies were used.

Formalin fixed, paraffin embedded human tissue sections were cut at 4 um, deparaffinized and rehydrated through a graded series of alcohols. Sections were then pre-treated for antigen retrieval by incubation in a PT Module (Thermo Scientific, Waltham, Mass.) using EDTA Retrieval (Lab Vision, Fremont, Calif.) at 65° C. Sections were then heated to 99° C. for 20 minutes, followed by 20 minutes of cooling. After pretreatment with EDTA Retrieval, endogenous peroxidase activity was quenched by incubating sections in 3% $H_2O_2$ at room temperature for 4 minutes.

Sections were then stained using antigen retrieval techniques. As such, sections were stained first using the anti-CD4 primary antibody (diluted 1:50 in 10% normal horse serum, NHS), then the anti-OX40 primary antibody (diluted to 10 µg/mL in 10% NHS), and finally the anti-Foxp3 primary antibody (diluted to 10 µg/mL in 10% NHS). Sections were treated with antigen retrieval agent between anti-CD4 and anti-OX40 incubation, as well as between anti-OX40 and anti-Foxp3 incubation, as described below.

For each primary antibody staining step, sections were blocked for avidin/biotin using an Avidin/Biotin Blocking Kit (Vector Laboratories, Burlingame, Calif.) according to manufacturer's instructions. Sections were then rinsed and subsequently blocked for non-specific binding sites with 10% Horse serum/3% BSA/PBS. Sections were incubated in primary antibody solution for 60 minutes at room temperature, followed by incubation with a biotinylated horse-anti-mouse (Vector Labs). Sections were subsequently incubated with Vector Elite ABC-HRP reagent (Vector Labs). After rinsing, sections were stained with secondary antibody solution per manufacturer's instructions. The following secondary antibodies were used: Alexa 488-tyramide conjugate (CD4), Alexa 555-tyramide conjugate (Foxp3), or Alexa 647-tyramide conjugate (OX40) (Life Technologies, Grand Island, N.Y.).

Between primary antibody staining steps, after incubation with secondary antibody solution, sections were incubated in EDTA buffer (Thermo Scientific, Waltham, Mass.) or DAKO target retrieval solution (Dako North America, Carpinteria, Calif.) per manufacturer's instructions at 99° C. for 20 minutes, followed by 20 minutes cooling. After the last secondary antibody incubation, slides were counter-stained with DAPI and cover-slipped with ProLong Gold Antifade Mountant (Life Technologies). For negative controls, sections were incubated with appropriate naïve isotype controls for each marker in place of the primary antibody.

Digital Imaging and Analysis

Images were acquired by the Ariol SL-50 automated slide scanning platform (Leica Microsystems, Buffalo Grove, Ill.) at 100× final magnification using standard fluorescence filters. The entire tiled image was exported and analyzed in the Matlab software package (ver. R2012b, Mathworks, Natick, Mass.).

For each tumor section, at least one region of interest was manually identified and subjected to analysis. For some tumors, multiple regions of interest were selected (e.g., if both a main tumor mass and satellite mass were observed on the slide). Within each region of interest, individual cell nuclei were segmented using a radial symmetry based method applied to the DAPI channel (Veta, M., et al. (2013) PLoS ONE 8(7):e70221), and then scored by the presence of signal above a global intensity threshold in the nucleus (FoxP3), or the area immediately surrounding each nucleus (CD4 and OX40). The global threshold for each marker was determined empirically such that false positive calls of obviously negative cells, in samples with and without being exposed to the primary labeling antibody, were less than 0.5% of all cells identified.

Statistical Analysis

Overall survival was calculated from the date of diagnosis to the date of death from any cause; data for patients still alive were censored at the date the patient was last known to be alive. Association between level of tumor-associated T cell subsets (dichotomized by median) and overall survival was evaluated using log-rank tests. To assess the association between tumor-associated T cell subsets and TNM stage at diagnosis, Kruskal-Wallis tests were employed. No multiple testing correction was applied.

A multivariate Cox regression model was employed to assess the strength of association between overall survival and OX40 expression (dichotomized at median) adjusted for age (>=60 vs <60), gender (male vs female) and stage (IV vs III vs I/II).

Results

Tumors from 48 CRC patients including primary site (n=48) and matched metastases (n=19) were stained and digitally imaged.

Figure 1A:
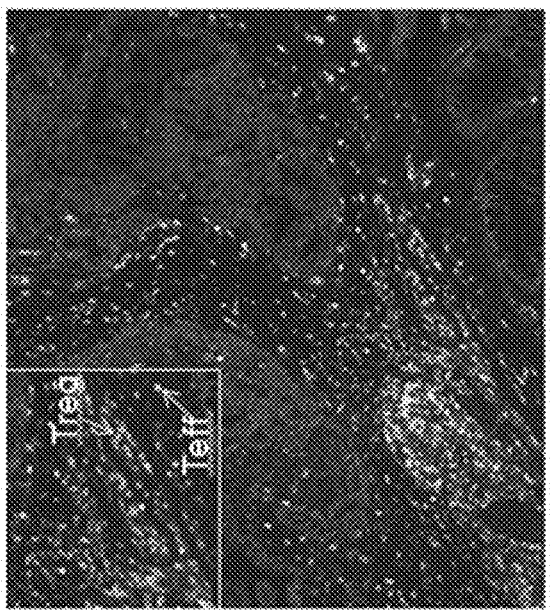
FIGS. 1A-1C show representative images of triple immunofluorescence staining for expression of CD4 (green), OX40 (white), and Foxp3 (red) on stage I colorectal cancer samples. Cell nuclei are counter-stained using DAPI (blue). Exemplary Treg and Teff cells are labeled.
Figure 1B:
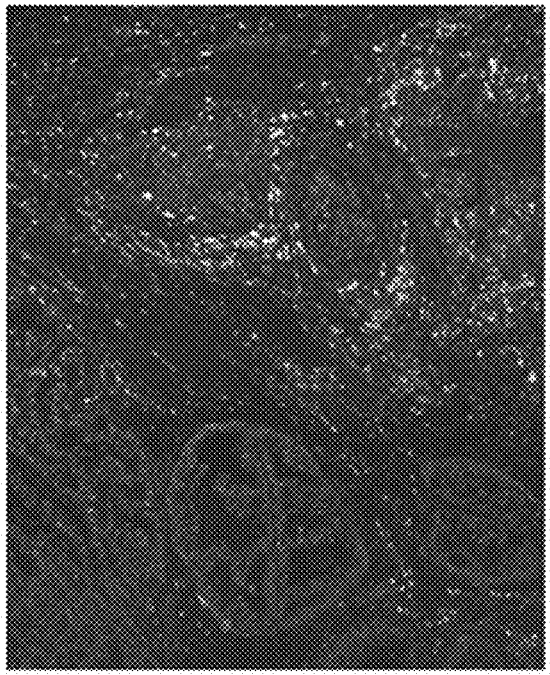
Figure 1C:
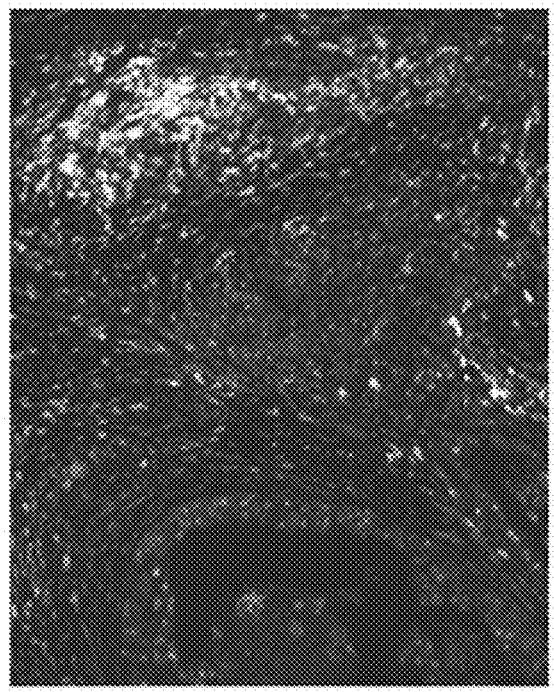
Figure 2A:
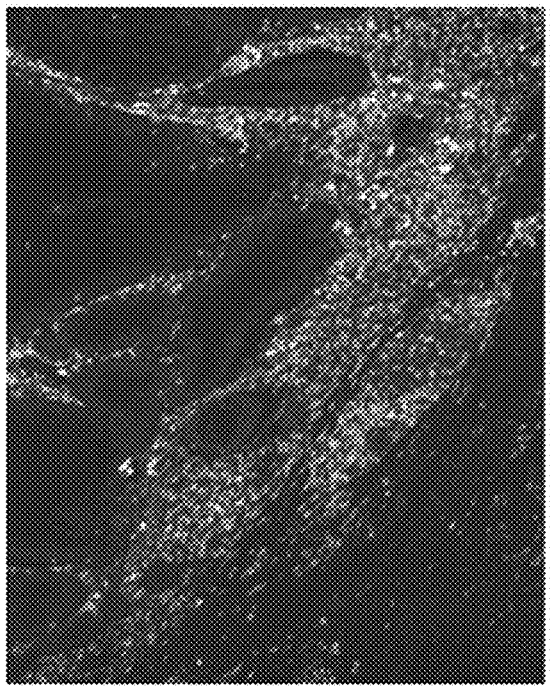
FIGS. 2A-2C show representative images of triple immunofluorescence staining for expression of CD4 (green), OX40 (white), and Foxp3 (red) on stage II colorectal cancer samples. Cell nuclei are counter-stained using DAPI (blue).
Figure 2B:
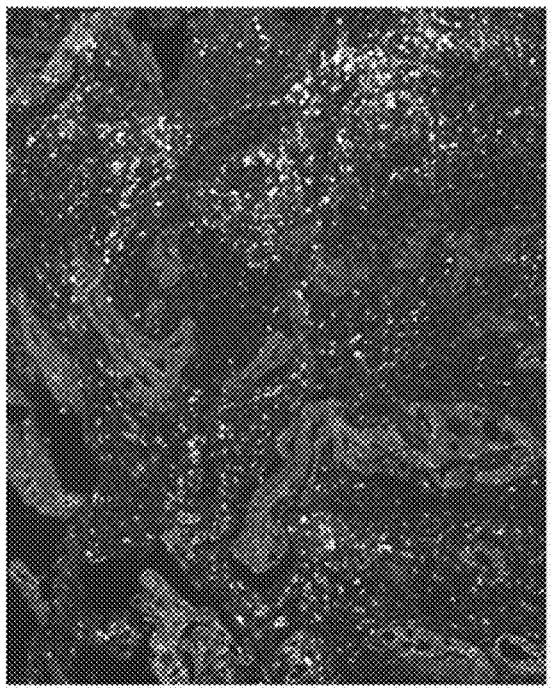
Figure 2C:
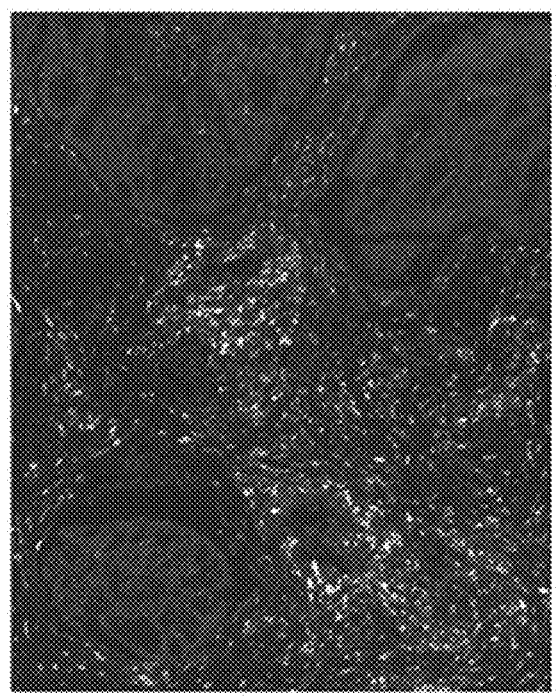
Figure 3A:
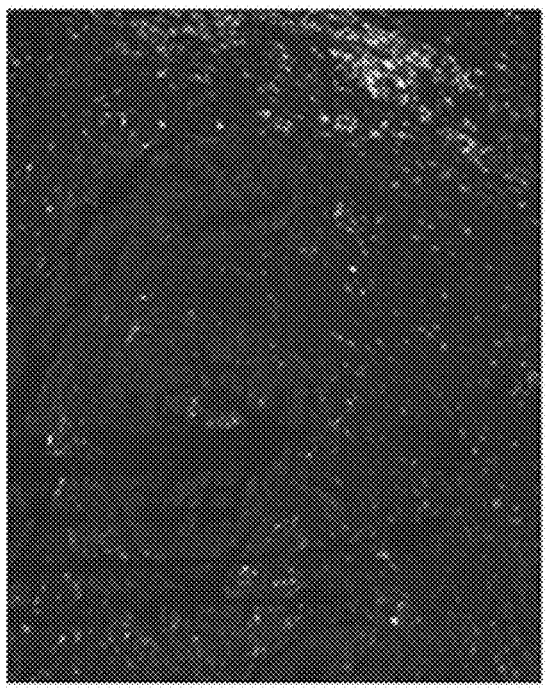
FIGS. 3A-3C show representative images of triple immunofluorescence staining for expression of CD4 (green), OX40 (white), and Foxp3 (red) on stage III colorectal cancer samples. Cell nuclei are counter-stained using DAPI (blue).
Figure 3B:
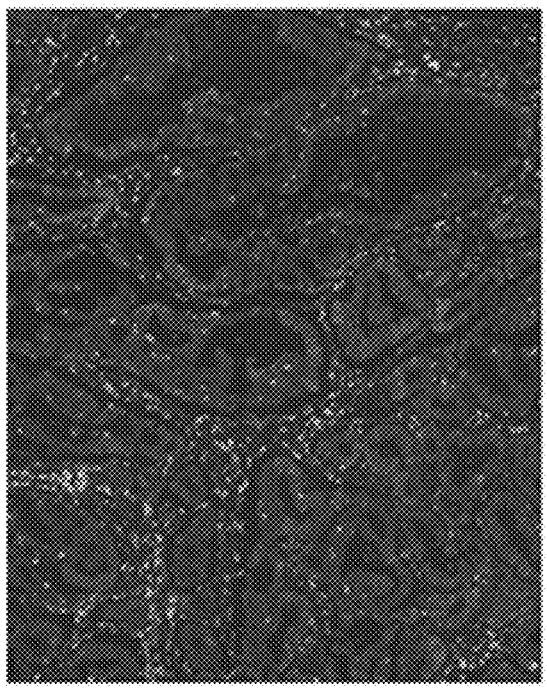
Figure 3C:
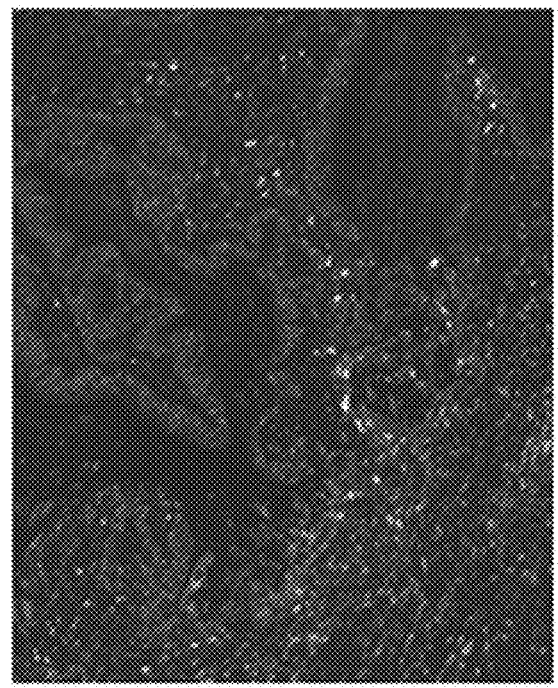
Figure 4A:
FIGS. 4A-4C show representative images of triple immunofluorescence staining for expression of CD4 (green), OX40 (white), and Foxp3 (red) on stage IV colorectal cancer samples. Cell nuclei are counter-stained using DAPI (blue).
Figure 4B:
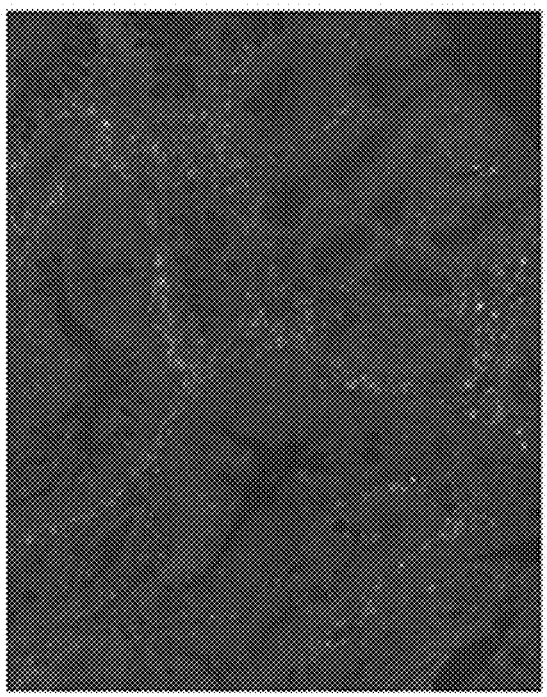
Figure 4C:
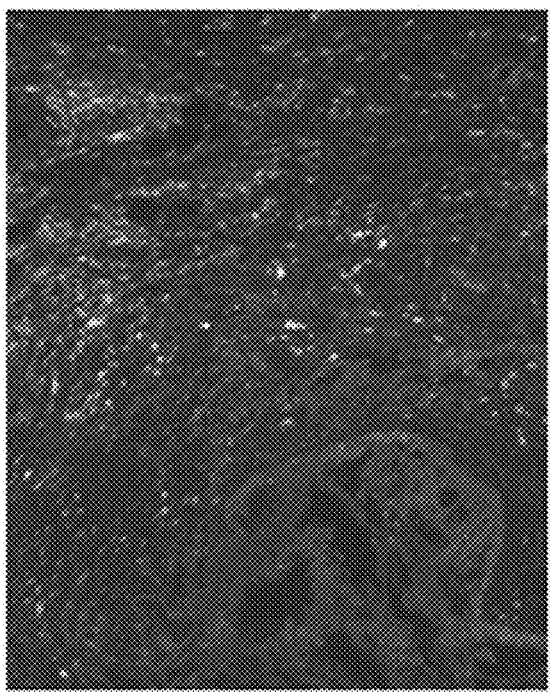
Figure 5A:
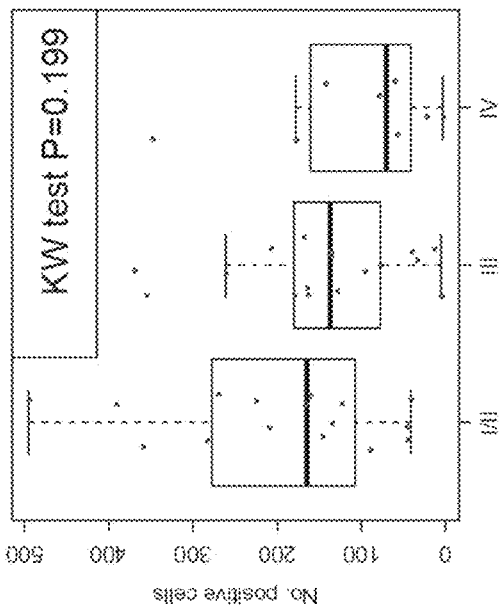
FIGS. 5A-5C show the correlation between the number of cells in a sample showing expression of specific marker(s) and cancer stage at diagnosis. Mean counts of cells that are positive for expression of specific markers are provided as follows: CD4+ (FIG. 5A), Foxp3+ (FIG. 5B), and OX40+ (FIG. 5C).
Figure 5B:
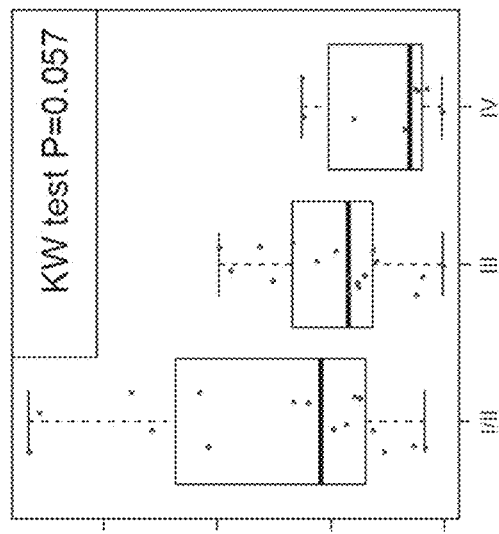
Figure 5C:
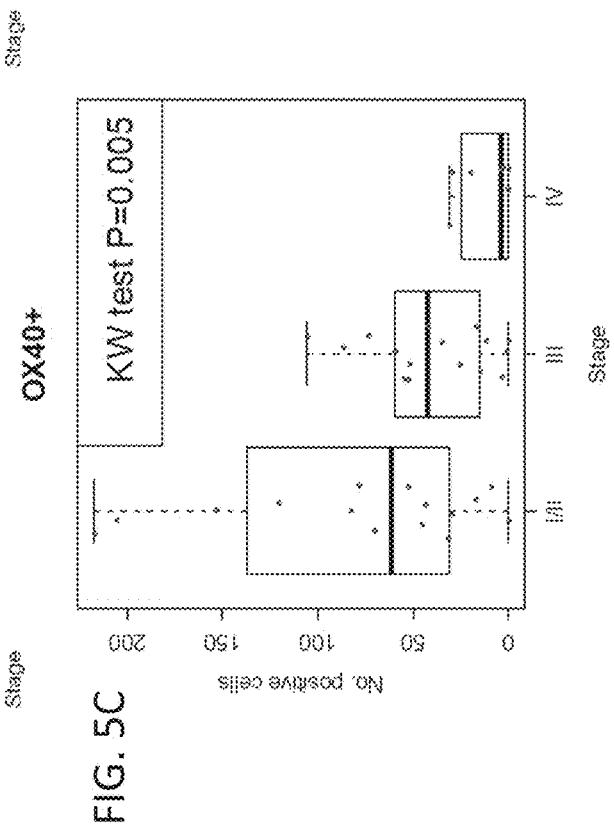

FIGS. 1A-1C show representative immunofluorescence images of stage I CRC samples that were stained for expression of CD4, OX40, and Foxp3. These images demonstrate the presence of CD4+ OX40+ Foxp3+ Treg cells as well as CD4+ OX40+ Foxp3– Teff cells. Representative immunofluorescence images of stage II (FIGS. 2A-2C), stage III (FIGS. 3A-3C), and stage IV (FIGS. 4A-4C) CRC samples were also captured. To summarize these data, decreased numbers of total OX40+ cells, as well as CD4+ OX40+ Foxp3+ Treg cells, were observed in stage IV samples, compared to stage I-III samples.

Figure 6A:
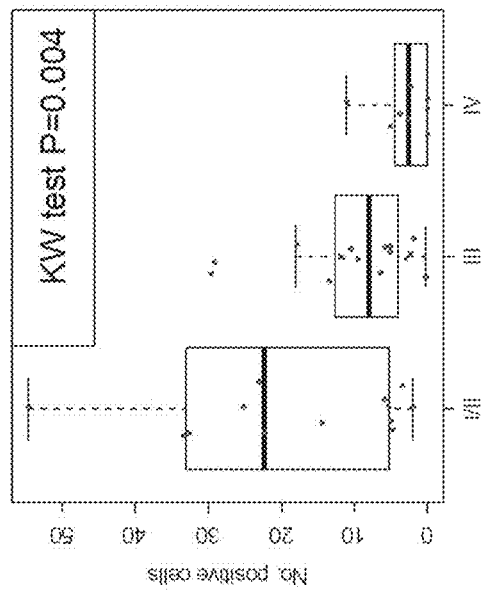
FIGS. 6A-6D show the correlation between the number of cells in a sample showing expression of specific marker(s) and cancer stage at diagnosis. Mean counts of cells that are positive for specific markers are provided as follows: OX40+CD4+ (FIG. 6A), OX40+CD4− (FIG. 6B), OX40+CD4+ Foxp3+ (FIG. 6C), and OX40+CD4+ Foxp3− (FIG. 6D).
Figure 6C:
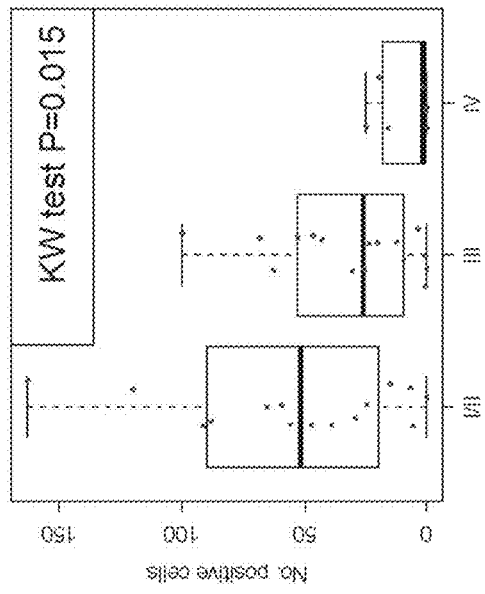
Figure 6B:
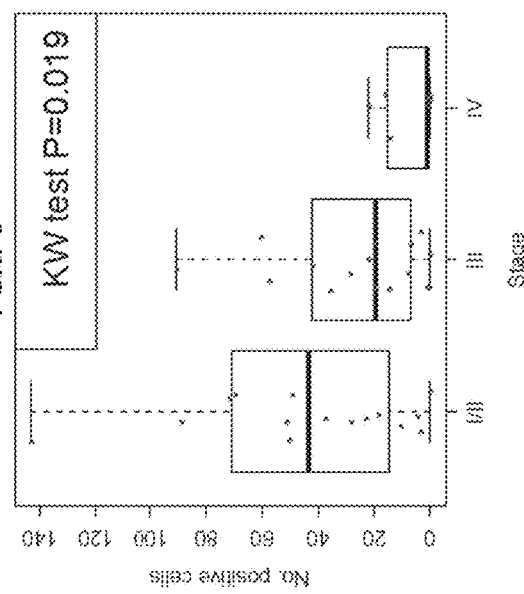
Figure 6D:
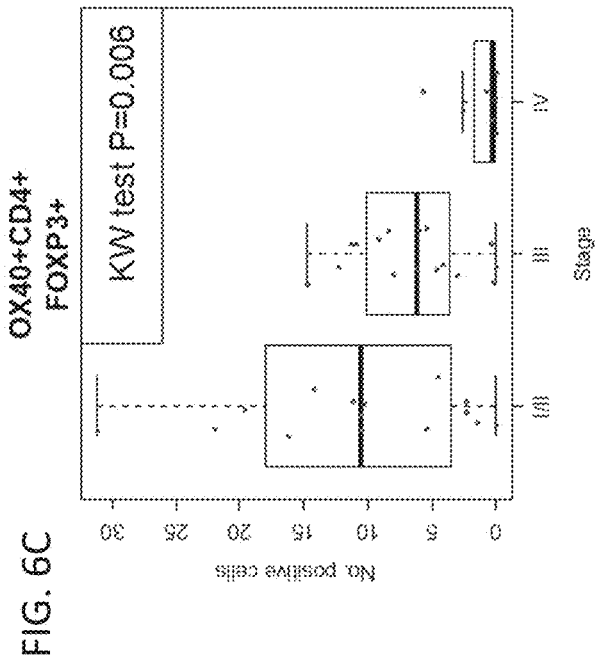
Figure 7A:
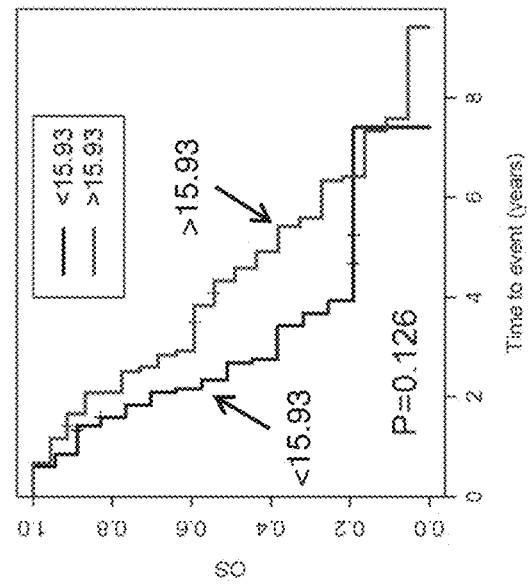
FIGS. 7A-7C show the correlation between overall survival and the number of cells in a sample showing expression of specific marker(s). Overall survival is shown for patients whose samples contained greater than or less than the median count (as labeled) of the following cell types: CD4+ (FIG. 7A), Foxp3+ (FIG. 7B), and OX40+ (FIG. 7C).
Figure 7B:
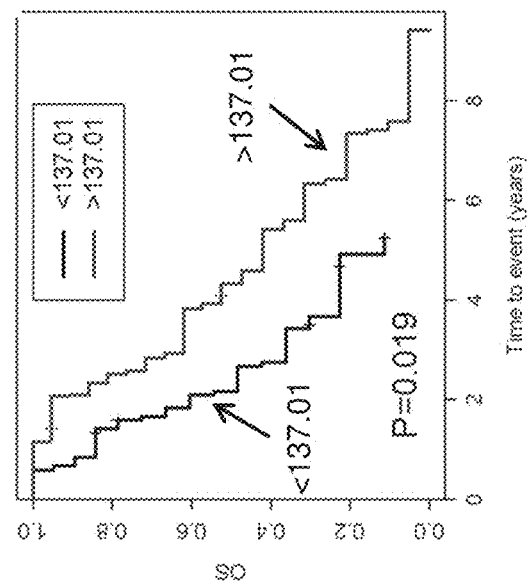
Figure 7C:
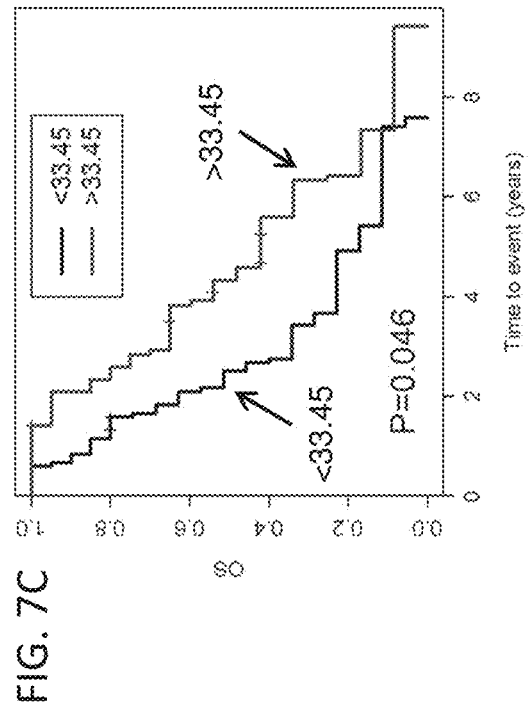

From these images, tumor-associated T cell subsets were enumerated. The correlation between the number of cells corresponding to specific tumor-associated T cell subsets and tumor stage was analyzed as described above. FIGS. 5A-6D show the results of these correlation analyses, with the T cell subsets selected for study provided as follows: CD4+ (FIG. 5A), Foxp3+ (FIG. 5B), OX40+ (FIG. 5C), OX40+CD4+ (FIG. 6A), OX40+CD4– (FIG. 6B), OX40+ CD4+ Foxp3+ (FIG. 6C), and OX40+CD4+ Foxp3– (FIG. 6D).

These results indicate statistically significant inverse correlations of OX40+ cells, OX40+ Treg cells, and OX40+ Teff cells with increased stage at diagnosis. These associations remained statistically significant when counts were normalized to total cells. Total CD4+ or Foxp3+ cells did not show significant association with stage.

Example 2: Presence of Increased OX40+ Lymphocytes is Associated with Improved Survival Because of the observed correlations between OX40+ T cell subsets and cancer stage described above, the presence of these T cell subsets was next analyzed with respect to prognosis.

The prevalence of T cell subsets in the tumor samples described above was analyzed to determine potential association with patient prognosis (e.g., overall survival). FIGS. 7A-8D show the results of these correlation analyses, with the T cell subsets selected for study provided as follows: CD4+ (FIG. 7A), Foxp3+ (FIG. 7B), OX40+ (FIG. 7C), OX40+CD4+ (FIG. 8A), OX40+CD4– (FIG. 8B), OX40+ CD4+ Foxp3+ (FIG. 8C), and OX40+CD4+ Foxp3– (FIG. 8D). Overall survival was plotted for patients whose samples showed expression of the labeled marker(s) above or below the median of all samples, as indicated in each plot.

These analyses indicated that increased prevalence of CD4+ (p=0.019), total OX40+(p=0.046), and OX40+ Treg (p=0.022) cells correlated with improved overall survival. Higher prevalence of OX40+ Teff cells also showed a trend of improved overall survival, but did not reach statistical significance. When normalized to total number of cells, CD4+ (p=0.02) and total OX40+(p=0.041) cells remained statistically significant. Treg number showed a closer correlation to survival than did Teff (p=0.265), though neither achieved statistical significance.

Figure 11A:
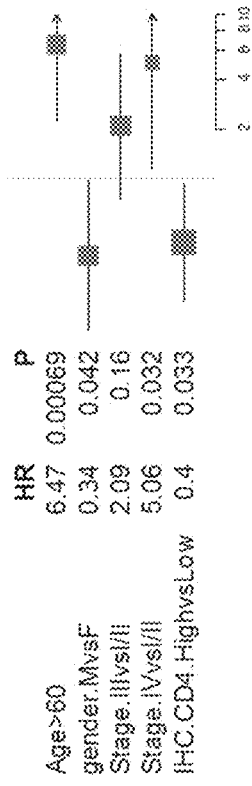
Figure 11B:
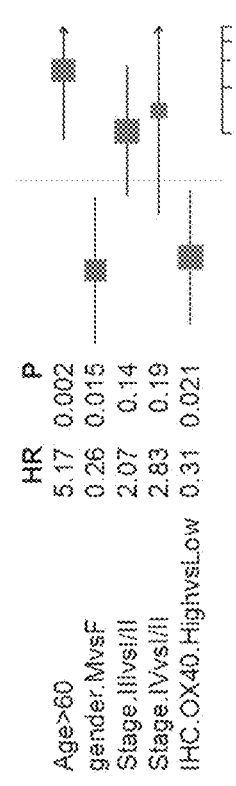
Figure 11C:
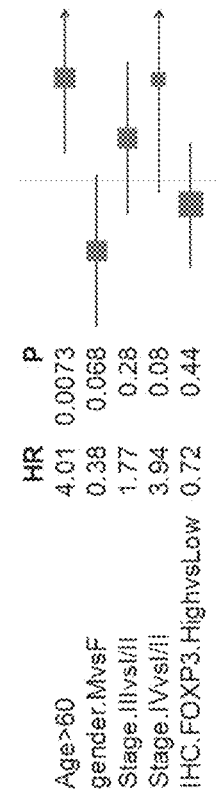
Figure 11D:
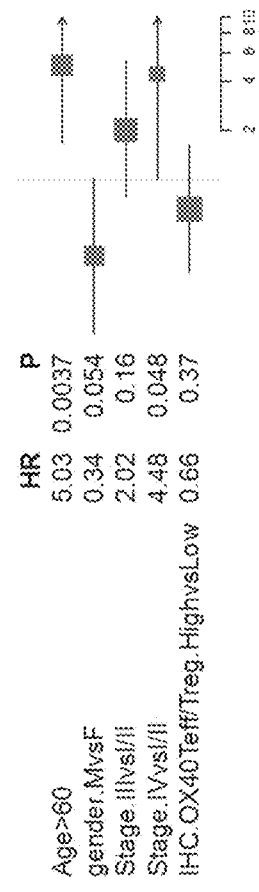

Importantly, CD4, OX40, and Foxp3 IHC staining remained significantly associated with overall survival in a multivariate Cox PH model, adjusting for age, gender and stage. FIGS. 11A-11D provide the results of these analyses of CD4 expression (FIG. 11A), OX40 expression (FIG. 11B), Foxp3 expression (FIG. 11C), and the ratio of OX40+ Teff cells to OX40+ Treg cells (FIG. 11D). These results indicate that these markers remain prognostic even after adjusting for baseline characteristics (e.g., age, gender, and stage).

These results demonstrate that higher numbers of total OX40+ cells and OX40+ Treg cells are associated with improved prognosis in CRC.

Example 3: Correlation Between OX40+ Status of Immune Infiltrates of Primary Tumors and Metastases Given the correlations observed between OX40+ cells found in tumor samples and tumor stage and patient survival, OX40+ T cell subsets were next analyzed in paired primary and metastatic tumor samples.

FIGS. 9A-10D show the results of these correlation analyses, with the T cell subsets selected for study provided as follows: CD4+ (FIG. 9A), Foxp3+ (FIG. 9B), OX40+ (FIG. 9C), OX40+CD4+ (FIG. 10A), OX40+CD4− (FIG. 10B), OX40+CD4+ Foxp3+ (FIG. 10C), and OX40+CD4+ Foxp3− (FIG. 10D).

Analysis of paired primary and metastatic samples (n=19) showed strong correlations between positive cell counts for CD4 (r=0.75), total OX40+ (r=0.84), OX40+ Treg (0.52), and OX40+ Teff (r=0.85) subsets in primary and metastatic samples. These associations remained strong when counts were normalized to total cells. These results show that the OX40+ status of immune infiltrates of primary tumors and metastases are strongly correlated.

Taken together, these results demonstrate that higher numbers of total OX40+ cells and OX40+ Treg cells are associated with improved prognosis in CRC. The triple immunofluorescence assay described herein may be useful in characterizing associations between OX40+ Treg and Teff cell subsets and clinical outcome in multiple solid tumor types. Moreover, incorporating this assay into clinical trials may help identify patients and indications that are likely to respond to therapeutics targeting OX40.

All patents, patent applications, documents, and articles cited herein are herein incorporated by reference in their entireties.

---

What is claimed is:

1. A method for treating or delaying progression of cancer in a subject, comprising:

(a) measuring the number of CD4+OX40+Foxp3+ lymphocytes in a sample comprising cancer cells and lymphocytes obtained from the subject;

(b) determining the number of CD4+OX40+Foxp3+ lymphocytes in the sample, as compared with a reference; and (c) if the number of CD4+OX40+Foxp3+ lymphocytes in the sample is higher than the reference, administering to the subject an effective amount of an agonist antihuman OX40 antibody, wherein the antibody comprises (a) HVR-H1 comprising the amino acid sequence of SEQ ID NO:2, 8 or 9; (b) HVR-H2 comprising the amino acid sequence of SEQ ID NO:3, 10, 11, 12, 13, or 14; (c) HVR-H3 comprising the amino acid sequence of SEQ ID NO:4, 15 or 19; (d) HVR-L1 comprising the amino acid sequence of SEQ ID NO:5; (e) HVR-L2 comprising the amino acid sequence of SEQ ID NO:6; and (f) HVR-L3 comprising the amino acid sequence of SEQ ID NO:7, 22, 23, 24, 25, 26, 27 or 28.

2. The method of claim 1, wherein the number of CD4+OX40+Foxp3+ lymphocytes is a median, mean or average number of CD4+OX40+Foxp3+ lymphocytes in different regions of interest of the sample from the subject.

3. The method of claim 2, wherein the number of CD4+OX40+Foxp3+ lymphocytes is normalized to total cells in the region of interest of the sample.

4. The method of any claim 1, wherein the reference is based on the number of CD4+OX40+Foxp3+ lymphocytes in a sample comprising cancer cells and lymphocytes obtained from a cancer having the same type and/or stage as the cancer of the subject.

5. The method of claim 4, wherein the reference is a median, mean, or average number of CD4+OX40+Foxp3+ lymphocytes in samples obtained from cancers having the same type and/or stage as the cancer of the subject.

6. The method of claim 1, wherein the cancer is selected from the group consisting of non-small cell lung cancer, renal cell carcinoma, bladder cancer, ovarian cancer, glioblastoma, neuroblastoma, melanoma, triple-negative breast carcinoma, gastric cancer, colorectal cancer, and hepatocellular carcinoma.

7. A method for treating or delaying progression of cancer in a subject, comprising:
   (a) measuring the number of OX40+, CD4+OX40+Foxp3+, or CD4+OX40+Foxp3− lymphocytes in a sample comprising metastatic cancer cells and lymphocytes obtained from the subject;
   (b) determining the number of OX40+, CD4+OX40+Foxp3+, or CD4+OX40+Foxp3− lymphocytes in the sample, as compared with a reference; and
   (c) if the number of OX40+, CD4+OX40+Foxp3+, or CD4+OX40+Foxp3-lymphocytes in the sample is higher than the reference, administering to the subject an effective amount of an agonist anti-human OX40 antibody, wherein the antibody comprises (a) HVR-H1 comprising the amino acid sequence of SEQ ID NO:2, 8 or 9; (b) HVR-H2 comprising the amino acid sequence of SEQ ID NO:3, 10, 11, 12, 13, or 14; (c) HVR-H3 comprising the amino acid sequence of SEQ ID NO:4, 15 or 19; (d) HVR-L1 comprising the amino acid sequence of SEQ ID NO:5; (e) HVR-L2 comprising the amino acid sequence of SEQ ID NO:6; and (f) HVR-L3 comprising the amino acid sequence of SEQ ID NO:7, 22, 23, 24, 25, 26, 27 or 28.

8. The method of claim 7, wherein the number of OX40+, CD4+OX40+Foxp3+, or CD4+OX40+Foxp3− lymphocytes is a median, mean or average number of OX40+, CD4+OX40+Foxp3+, or CD4+OX40+Foxp3− lymphocytes in different regions of interest in the sample from the subject.

9. The method of claim 8, wherein the number of OX40+, CD4+OX40+Foxp3+, or CD4+OX40+Foxp3− lymphocytes is normalized to total cells in the region in the sample.

10. The method of claim 7, wherein the reference is based on the number of OX40+, CD4+OX40+Foxp3+, or CD4+OX40+Foxp3− lymphocytes in a sample comprising metastatic cancer cells and lymphocytes obtained from a cancer having the same type and/or stage as the cancer of the subject.

11. The method of claim 10, wherein the reference is a median, mean, or average number of CD4+OX40+Foxp3+ lymphocytes in samples obtained from cancers having the same type and/or stage as the cancer of the subject.

12. The method of claim 7, wherein the cancer is selected from the group consisting of non-small cell lung cancer, renal cell carcinoma, bladder cancer, ovarian cancer, glioblastoma, neuroblastoma, melanoma, triple-negative breast carcinoma, gastric cancer, colorectal cancer, and hepatocellular carcinoma.

* * * * *